United States Patent
van Haastert et al.

(10) Patent No.: US 10,201,556 B2
(45) Date of Patent: Feb. 12, 2019

(54) COMBINATION FOR USE IN TREATING DISEASES OR CONDITIONS ASSOCIATED WITH MELANOMA, OR TREATING DISEASES OR CONDITIONS ASSOCIATED WITH ACTIVATED B-RAF PATHWAY

(71) Applicant: InteRNA Technologies B.V., Nijmegen (NL)

(72) Inventors: Rick Jan van Haastert, Amersfoort (NL); Petronella Innocentia van Noort, Megen (NL); Grégoire Pierre André Prevost, Antony (FR); Willemijn Maria Gommans, Voorschoten (NL); Roeland Quirinus Jozef Schaapveld, Bussum (NL); Matheus Maria De Gunst, Woudenberg (NL); Iman Johannes Schultz, Nijmegen (NL); Eugene Berezikov, Bedum (NL)

(73) Assignee: INTERNA TECHNOLOGIES B.V., Nijmegen (NL)

( * ) Notice: Subject to any disclaimer, the term of this patent is extended or adjusted under 35 U.S.C. 154(b) by 217 days.

(21) Appl. No.: 14/440,826

(22) PCT Filed: Nov. 6, 2013

(86) PCT No.: PCT/EP2013/073192
§ 371 (c)(1),
(2) Date: May 5, 2015

(87) PCT Pub. No.: WO2014/072357
PCT Pub. Date: May 15, 2014

(65) Prior Publication Data
US 2015/0297626 A1 Oct. 22, 2015

Related U.S. Application Data

(60) Provisional application No. 61/722,861, filed on Nov. 6, 2012.

(30) Foreign Application Priority Data

Nov. 6, 2012 (EP) .................................. 12191392

(51) Int. Cl.
C12N 15/11 (2006.01)
A61K 48/00 (2006.01)
(Continued)

(52) U.S. Cl.
CPC ........ *A61K 31/713* (2013.01); *A61K 31/4184* (2013.01); *A61K 31/437* (2013.01);
(Continued)

(58) Field of Classification Search
CPC .............. A61K 31/7088; C12N 15/111; C12N 15/113; C12N 2310/141; C12N 2320/31
(Continued)

(56) References Cited

FOREIGN PATENT DOCUMENTS

WO WO 2012/005572 1/2012

OTHER PUBLICATIONS

Bollag et al. (Nature Reviews, published online Oct. 12, 2012, vol. 11:873-886).*
(Continued)

*Primary Examiner* — Terra C Gibbs
(74) *Attorney, Agent, or Firm* — Polsinelli PC; Christopher M. Cabral

(57) ABSTRACT

The invention relates to the therapeutic use of a combination in a disease and condition associated with melanoma or a disease or a condition associated with activated BRAF pathway.

10 Claims, 20 Drawing Sheets
Specification includes a Sequence Listing.

(51) Int. Cl.
    *C07H 21/02* (2006.01)
    *C07H 21/04* (2006.01)
    *A61K 31/713* (2006.01)
    *A61K 31/4184* (2006.01)
    *A61K 31/437* (2006.01)
    *A61K 31/506* (2006.01)
    *A61K 31/519* (2006.01)
    *C12N 15/113* (2010.01)

(52) U.S. Cl.
    CPC .......... *A61K 31/506* (2013.01); *A61K 31/519* (2013.01); *C12N 15/1135* (2013.01); *C12N 2310/113* (2013.01); *C12N 2310/141* (2013.01); *C12N 2320/10* (2013.01); *C12N 2320/31* (2013.01); *C12N 2330/10* (2013.01)

(58) Field of Classification Search
    USPC .......................... 514/44; 536/23.1, 24.3, 24.5
    See application file for complete search history.

(56) References Cited

OTHER PUBLICATIONS

Aird, K., et al., "Suppression of Nucleotide Metabolism Underlies the Establishment and Maintenance of Oncogene-Induced Senesence," Cell Rep., vol. 3, No. 4, (Apr. 25, 2013).

Atefi, M., et al., "Reversing Melanoma Cross-Resistance to BRAF and MEK Inhibitors by Co-Targeting the AKT/mTOR Pathway," PLoS One, vol. 6, Issue 12, p. e28973 (Dec. 2011).

Balch, C. et al., "Final Version of the American Joint Committee on Cancer Staging System for Cutaneous Melanoma," Journal of Clinical Oncology, vol. 19, No. 16, pp. 3635-3648 (Aug. 15, 2001).

Balch, C., et al., "Prognostic Factors Analysis of 17,600 Melanoma Patients: Validation of the American Joint Committee on Cancer Melanoma Staging System," Journal of Clinical Oncology, vol. 19, No. 16, pp. 3622-3634 (Aug. 15, 2001).

Bonet, C., et al., "Aurora B is Regulted by the Mitogen-Activated Protein Kinase/Extracellular Sigal-Regulated Kinase (MAPK/ERK) Signaling Pathway and is a Valuable Potential Target in Melanoma Cells" The Journal of Biological Chemistry, vol. 287, No. 35, pp. 29887-29898 (Jul. 5, 2012).

Dassie, J., et al., "Systemic Administration of Optimized Aptamer-siRA Chimeras Promotes Regression of PSMA-Expressing Tumors," NIH Public Access Author Manuscript, Nat. Biotechnol., vol. 27, No. 9, pp. 839-849 (Sep. 2009).

de Saint-Hubert, M., et al., "Molecular Imaging of Cell Death," Methods, vol. 48, pp. 178-187 (Apr. 9, 2009).

Dhomen, N., et al., "BRAF Signaling and Targeted Therapies in Melanoma," Hematol. Oncol. Cli. N. Am., vol. 23, pp. 529-545 (Apr. 2009).

Duxbury, M., et al., "RNA Interference Targeting the M2 Subunit of Ribonucleotide Reductase Enhances Pancreatic Adenocarcinoma Chemosensitivity to Gemcitabine," Onogene, vol. 23, pp. 1539-1548 (Dec. 8, 2003).

Dweep, H., et al., "miRWalk—Database: Prediction of Possible miRNA inding Sites by 'Walking' the Genes of Three Genomes," Journal of Biomedical Informatics, vol. 44, pp. 839-847 (May 14, 2011).

Felicetti, F., et al., "The Promyelocytic Leukemia Zinc Finger-MicroRNA-221/-222 Pathway Controls elanoma Progression Through Multiple Oncogenic Mechanisms," Cancer Res., vol. 68, No. 8, pp. 2745-2754 (Apr. 15, 2008).

Garbe, C., et al., "Melanoma Epidemiology and Trends," Clinics in Dermatology, vol. 27, Issue 1, pp. 3-9 (Jan.-Feb. 2009).

Hafekamp, S., et al., "Vemurafenib Induces Senescence Features in Melanoma Cells," Journal of Investigative Dermatology, vol. 133, pp. 1601-1609 (Feb. 14, 2013).

Hingorani, S., et al., "Suppression of BRAF$^{V599E}$ in Human Melanoma Abrogats Transformation," Cancer Research, vol. 63, pp. 5198-5202 (Sep. 1, 2003).

Houben, R., et al., "Constitutive Activation of the Ras-Raf Signaling Pathway in Metastatic Melanoma is Associated with Poor Prognosis," Journal of Carcinogenesis, vol. 3, No. 6, pp. 1-13 (Mar. 26, 2004).

Ikenoue, T., et al., "Functional Analysis of utatiaons Within the Kinase Activation Segment of B-Raf in Human Colorectal Tumors," Cancer Research, vol. 63, pp. 8132-8137 (Dec. 1, 2003).

Jalili, A., et al., "Dual Suppression of the Cyclin-Dependent Kinase Inhibitors CDKN2C and CDKN1A in Human Melanoma," J. Natl. Cancer Inst., vol. 104, pp. 1673-1679 (Sep. 20, 2012).

Ji, Z., et al., "Vemurafenib Synergizes with Nutlin-3 to Deplete Survivin and Suppresses Melanoma Viability and Tumor Growth," Clin Cancer Res., vol. 19, No. 16, pp. 4383-4391 (Jun. 27, 2013).

Karasarides, M., et al., "B-RAF is a Therapeutic Target in Melanoma," Oncogene, vol. 23, pp. 6292-6298 (Jun. 21, 2004).

Madhunapantula, S., et al., "The PTEN-AKT3 Signaling Cascade as a Therapeutic Target in Melanoma," NIH Public Access Author Manuscript, Pigment Cell Melanoma Res., vol. 22, No. 4, pp. 400-419 (Aug. 2009).

Millington, G.W.M., Mutations of the BRAF Gene in Human Cancer, Clinical and Experimental Dematology, vol. 38, pp. 222-223 (Feb. 12, 2013).

Mraz-Gernard, S., et al., "Prediction of Sentinel Lymph Node Micrometastasis by Histological Features in Primary Cutaneous Malignant Melanoma," Arch Dermatol., vol. 134, pp. 983-987 (Aug. 1998).

Obad, S., et al., "Silencing of microRNA Families by Seed-Targeting Tiny LNAs," Nature Genetics, vol. 43, No. 4, pp. 371-378 (Apr. 2011).

Parkin, D. Max, et al, "Global Cancer Statistics, 2002," Cancer J Clin, vol. 55, No. 2, pp. 75-108 (Mar./Apr. 2005).

Poell, J., et al., "A Functional Screen Identifies Specific MicroRNAs Capble of Inhibition Human Melanoma Cell Viability," PLOS ONCE, vol. 7, No. 8, pp. e 3569 (Apr. 22, 2012).

Schutters, K., et al., "Phosphatidylserin Targeting for Diagnosis and Treatment of Human Disease," Apoptosis, vol. 15, pp. 1072-1082 (May 4, 2010).

Smalley, KSM, et al., "CRAF Inhibition Induces Apoptosis in Melanoma Cells with Non-V600E BRAF Mutations," Oncogene, vol. 28, pp. 85-94 (Sep. 15, 2008).

Steeper, J.R., et al., "A Rapid Assay for CDP Reductase Activity in Mammalian Cell Extracts," Analytical Biochemistry, vol. 34, Issue 1, pp. 123-130 (Mar. 1970).

Steffen, P., et al., "RNAshapes: an Integrated RNA Analysis Package Based on Abstract Shapes," Bioinformatics, vol. 22, No. 4, pp. 500-503 (Dec. 15, 2005).

Wong, Kwong-Kwok, "Recent Developments in Anti-Cancer Agents Targeting the Ras/Raf/MEK/ERK Pathway," Recent Patents on Anti-Cancer Drug Discovery, vol. 4, pp. 28-35 ( Jan. 2009).

Xu, N., et al., "FoxM1 Mediated Resistance to gefitinib in Non-Small-Cell Lung Cancer Cells," Acta Pharmacologica Sinica, vol. 33, pp. 675-681 (Mar. 26, 2012).

Zhou, B., et al., "A Small-Molecule Blocking Ribonucleotide Reductase Holoenzyme Formation Inhibits Cancer Cell Growth and Overcomes Drug Resistance," Cancer Res., vol. 73, No. 21, pp. 6484-6493 (Sep. 26, 2013).

Gopal, Y.N. Vashisht, et al., "Basal and Treatment-Induced Activation of AKT Mediates Resistance to Cell Death by AZD6244 (ARRY-142886) in Braf-Mutant Human Cutaneous Melanoma Cells," Cancer Research, vol. 70, No. 21, pp. 8736-8747 (Oct. 19, 2010).

International Search Report of PCT/EP2013/073192 dated Mar. 20, 2014.

Jiang, C.C., et al., "MEK-Independent Survival of B-RAF$^{V600E}$ Melanoma Cells Selected for Resistance to Apoptosis Induced by the RAF Inhibitor PLX4720," Clinical Cancer Research, vol. 17, No. 4, pp. 721-730 (Feb. 15, 2011).

Lin, X., et al., "Seed Analysis of Off-Target siRNAs Reveals an Essential Role of Mcl-1 in Resistance to the Small-Molecule Bcl-2/Bcl-X$_L$ Inhibitor ABT-737," Oncogene, vol. 26, No. 27, pp. 3972-3979 (Jun. 7, 2007).

(56) References Cited

OTHER PUBLICATIONS

Liu, Shujing, et al., "miR-200c Inhibits Melanoma Progression and Drug Resistance through Down-Regulation of Bmi-1," American Journal of Pathology, vol. 181, No. 5, pp. 1823-1835 (Sep. 13, 2012).

Martin, A. P., et al., "BCL-2 Family Inhibitors Enhance Histone Deacetylase Inhibitor and Sorafenib Lethality via Autophagy and Overcome Blockade of the Extrinsic Pathway to Facilitate Killing," Molecular Pharmacology, vol. 76, No. 2, pp. 327-341 (May 29, 2009).

Villanueva, Jessie, et al., "Acquired Resistance to BRAF Inhibitors Mediated by a RAF Kinase Switch in Melanoma Can Be Overcome by Cotargeting MEK and IGF-1R/PI3K," Cancer Cell, vol. 18, No. 6, pp. 683-695 (Dec. 14, 2010).

Niehr, F., et al., "Combination Therapy with Vemurafenib (PLX4032/RG7204) and Metformin in Melanoma Cell Lines with Distinct Driver Mutations," Journal of Translational Medicine, vol. 9, pp. 76 (May 2011).

\* cited by examiner a

ERK1 3'UTR:   3' ucugacgugaucggACCGACUu 5' hsa-miR-3157 *(SEQ ID NO:6)*
                           ||||||
              5' uagagaugugucuaUGGCUGAa 3' ERK1 *(SEQ ID NO:297)*

RRM2 3'UTR:   3' ucugACGUGAUCGGACCGACUu 5' hsa-miR-3157 *(SEQ ID NO:6)*
                     ||| || |:|||||||
              5' gaugUGCCCUUACUUGGCUGAu 3' RRM2 *(SEQ ID NO:298)*

AURKB 3'UTR:  3' ucugacgugaucggaCCGACUu 5' hsa-miR-3157 *(SEQ ID NO:6)*
                                ||||||
              5' ccuuuguuuaauaaaGGCUGAa 3' AURKB *(SEQ ID NO:299)*

B

C

COMBINATION FOR USE IN TREATING DISEASES OR CONDITIONS ASSOCIATED WITH MELANOMA, OR TREATING DISEASES OR CONDITIONS ASSOCIATED WITH ACTIVATED B-RAF PATHWAY

CROSS REFERENCE TO RELATED APPLICATIONS

The present application is the 35 U.S.C. 371 National Stage of International Application Number PCT/EP2013/073192, filed Nov. 6, 2013, which claims the benefit of U.S. Provisional Application No. 61/722,861, filed Nov. 6, 2012 and claims priority from European patent application no. 12191392.5, filed Nov. 6, 2012, the contents of each of which are incorporated herein by reference.

SEQUENCE LISTING SUBMISSION VIA EFS-WEB

A computer readable text file, entitled "105811-5019US-Revised-Sequence-Listing" created on or about Jun. 12, 2017, with a file size of about 62 KB contains the sequence listing for this application and is hereby incorporated by reference in its entirety.

FIELD OF THE INVENTION

The invention relates to the therapeutic use of a first combination of at least two compounds, at least one compound being taken from the first list and at least one compound being taken from the second list:
a) at least one miRNA molecule selected from a miRNA-96-5p, miRNA-10b-3p, miRNA-129-5p, miRNA-3157-5p, miRNA-200c-5p, miRNA-182-3p, miRNA-16-5p, miRNA-497-5p, miRNA-518b and/or a miRNA-7-5p molecule, an equivalent, or a source thereof, or a composition comprising at least one of said miRNA, equivalent or source thereof and
b) at least one B-raf and/or MEK inhibitor, preferably said B-raf inhibitor is vemurafenib and/or dabrafenib and/or preferably said MEK inhibitor is trametinib and/or selumetinib, or a composition comprising said at least one B-raf and/or MEK inhibitor.

BACKGROUND OF THE INVENTION

Melanoma is a common cancer of the skin resulting in high morbidity and mortality. Melanomas are malignancies of melanocytes, the specialized pigment cells of the skin, located at the basal layer of the epidermis and which originate from neural crest. Melanoma is one of the most aggressive cancer types in human. Melanoma accounts for only about 4% of skin cancer cases but for as many as 74% of all skin cancer deaths. In 2002, the WHO estimated 160,000 new cases of malignant melanoma worldwide and reported 41,000 deaths caused by this dreadful disease (Parkin D. M. et al). It is the cancer type with the highest increase in incidence: of all cancer in the United States, cutaneous melanoma ranks fifth in incidence among men and seventh among women and is the second leading cause of lost productive years. Recent estimates suggest a doubling of melanoma incidence every 10-20 years (Garbe C. et al). If melanoma can be diagnosed early, it can be cured by surgical excision and this is what occurs in appr. 80% of the cases. However, metastatic melanoma is refractory to current therapies and has a very poor prognosis with a median survival rate of 6 months. Both due to the high propensity to metastisize as well as resistance to available therapies, melanoma represents a great problem for oncology.

Several genes have been implicated in the development of melanoma. The most common tumor suppressor gene involved in melanoma is p16ink4a, encoded by the CDKN2A locus. The CDKN2A locus on human chromosome 9p21 encodes two proteins, p16ink4a and p14ARF, that mainly regulate cell cycle progression and cell survival via the pRb and p53 pathways, respectively. Loss of p16 is accomplished through deletion, mutation or promoter methylation. Mutations in the p14ARF tumor suppressor gene also play a role in melanoma, independent of the effect of the p16ink4a gene. The most commonly mutated oncogenes in melanoma are BRAF and N-RAS (Q61K/R), which are generally mutually exclusive. Interestingly, BRAF is mutated in ~70% of malignant melanomas, papillary thyroid cancer (36-53%), serous ovarian cancer (~30%) and colorectal cancer (5-22%), of which the majority is the V600E mutation. In addition, other BRAF mutations have also been detected in, serous ovarian cancer (30%) and lung cancer (3%) (Garnett M. J. et al). However, there are in at least 35 other amino acids within the BRAF protein that are targets for mutations in melanoma (Dhomen N. et al). The V600E mutation results in constitutively active BRAF and has been shown to act as an oncogene in melanocytes. As a consequence of the somatic mutations of BRAF and N-RAS, the RAS-RAF-MEK-ERK MAPK signal transduction pathway, that controls a variety of biological responses, including proliferation and survival, is constitutively active. The aberrant activation of this pathway results in increased proliferation and survival, but also represents an attractive molecular target for melanoma treatment. The importance of MAPK activation in melanoma was shown by inhibiting BRAF with RNAi and inhibiting BRAF or MEK with small molecule inhibitors (Hingorani S. R. et al., Karasarides M. et al.,). Such treatments block cell proliferation, survival, induce apoptosis and inhibit anchorage independent growth. Additional pathways that are aberrantly activated in melanoma are the PI3K/PTEN/Akt pathways. The phosphoinositide-3-kinase (PI3K) and mitogen-activated protein (MAP) kinase pathways are two key signaling cascades that have been found to play prominent roles in melanoma development. Therefore, members of the PI3K signaling pathway may also function as interesting targets for therapeutic intervention (Madhunapantula S. V. et al).

At present, enormous efforts are taken to unravel the molecular mechanisms that lead to changes in cellular processes and the resulting malignant behaviour of transformed melanocytes. One family of molecules involved in the genesis and progression of melanoma cells, the miRNAs, is currently attracting a lot of attention.

miRNAs are naturally occurring single-stranded, non-coding small RNA molecules that control gene expression by binding to complementary sequences in their target mRNAs, thereby inhibiting translation or inducing mRNA degradation. miRNAs have recently emerged as key regulators of gene expression during development and are frequently misexpressed in human disease states, in particular cancer. Recently, WO2012/005572 described several miRNA molecules that could be used for treating diseases or conditions associated with activated BRAF pathway in a subject.

There is currently no effective known medicament that may be used for specifically preventing, treating, regressing, curing and/or delaying a disease or condition associated with melanoma or for diseases or conditions associated with activated BRAF pathway in a subject. The only standard treatments comprise chemotherapy, radiotherapy, surgery. Therefore, there is still a need for new treatments of disease or conditions associated with melanoma.

DESCRIPTION OF THE INVENTION

The invention encompasses several uses of a combination, a miRNA molecule, equivalent, mimic, isomiR or antagomir or source thereof as identified herein. The invention also encompasses each of the newly identified miRNA molecules, equivalent, mimic, isomiR or antagomir per se.

The invention relates to several possible compounds/treatments that could be used for preventing, treating, regressing, curing and/or delaying a disease or condition associated with melanoma or for diseases or conditions associated with activated BRAF pathway in a subject:

A first combination of the invention as defined herein ("a first combination"),

A miRNA-518b molecule, equivalent and/or source thereof ("a miRNA-518b-based compound") or a composition comprising or consisting of said miRNA molecule, equivalent and/or source thereof, At least one miRNA molecule, equivalent or source thereof selected from the following list ("at least one miRNA, equivalent, source from a first list"): a miRNA-96-5p, miRNA-10b, miRNA-129-5p, miRNA-3157-5p, miRNA-200c-5p, miRNA-182-3p, miRNA-16-5p, miRNA-497-5p, miRNA-518b and/or a miRNA-7-5p molecule, an equivalent or a source thereof, or a composition comprising at least one of said miRNA, equivalent or source thereof that could be used in a subject resistant for a B-raf and/or a MEK inhibitor.

All embodiments disclosed herein and relating to the prevention, treatment, regression, curing and/or delay of a disease or condition associated with melanoma or for diseases or conditions associated with activated BRAF pathway in a subject apply for all three types of compounds/treatments defined above unless otherwise indicated.

The invention also relates to a second combination that could be used for preventing, treating, regressing, curing and/or delaying a cancer that acquired resistance to a cancer drug and is accompanied by an upregulation/increase of RRM2 and/or AURKB in a subject.

The invention also relates to a miRNA-3157 molecule, equivalent, mimic, isomiR or source thereof (also called "stand alone/sole therapy using miRNA-3157") for preventing, treating, regressing, curing and/or delaying a disease or condition associated with an increased expression of RRM2 and/or AURKB.

The invention relates to a first combination of at least two compounds, at least one compound being taken from the first list and at least one compound being taken from the second list:

a) at least one miRNA molecule selected from a miRNA-96-5p, miRNA-10b, miRNA-129-5p, miRNA-3157-5p, miRNA-200c-5p, miRNA-182-3p, miRNA-16-5p, miRNA-497-5p, miRNA-518b and/or a miRNA-7-5p molecule, an equivalent or a source thereof, or a composition comprising at least one of said miRNA, equivalent or source thereof and b) at least one B-raf and/or MEK inhibitor, preferably said B-raf inhibitor is vemurafenib and/or dabrafenib, and/or preferably said MEK inhibitor is trametinib and/or selumetinib, or a composition comprising said at least one B-raf and/or MEK inhibitor.

Surprisingly, it has been found that the compounds/treatment present in said "first combination", "miRNA-518b-based compound" and the "at least one miRNA molecule, equivalent or source from a first list" as defined above are highly attractive for use as a medicament for preventing, treating, regressing, curing and/or delaying a disease or a condition associated with melanoma and/or a disease or a condition associated with activated BRAF pathway.

This "first combination" and this "at least one miRNA molecule, equivalent or source from a first list" preferably allow to delay or prevent a resistance to B-raf and/or MEK inhibitors such as B-raf inhibitors vemurafenib and/or dabrafenib and/or such as MEK inhibitor trametinib and/or selumetinib.

This "first combination" and this "at least one miRNA molecule, equivalent or source from a first list" preferably optimize the therapeutic activity/application of B-raf and/or MEK inhibitors such as B-raf inhibitors vemurafenib and/or dafrafenib, and/or such as MEK inhibitor trametinib and/or selumetinib. This is possible since this "first combination" and this "at least one miRNA molecule, equivalent or source from a first list" are expected to sensitisize a subject towards B-raf and/or MEK inhibitors.

This "first combination" and this "at least one miRNA molecule, equivalent or source from a first list" may be expected to lead to synergistic effects at least on inhibition of tumor cell (preferably melanocytes) proliferation or tumor cell (preferably melanocytes) survival as explained later herein.

Accordingly, in a preferred embodiment, said "first combination" and said "at least one miRNA molecule, equivalent or source from a first list" of the invention are such that:

a) resistance to at least one B-raf and/or MEK inhibitor, preferably vemurafenib and/or dabrafenib, trametinib and/or selumetinib, is at least overcome, circumvented or delayed, and/or b) the therapeutic effect of at least one B-raf and/or MEK inhibitor, preferably vemurafenib and/or dabrafenib and/or trametinib and/or selumetinib is optimized, and/or c) sensitization of a subject to at least one B-raf and/or MEK inhibitor is promoted.

All these specific advantages (i.e. overcome, circumvent or delay of resistance, optimization of a therapeutic effect and sensitisize) are later herein defined.

Below we first defined the "at least one compound" from the first list that is present in said "first combination" and in said "at least one miRNA molecule, equivalent or source from a first list". The compound present in said "miRNA-518b-based compound" is also identified below. Subsequently, we will define the "at least one compound" from the second list present in said "first combination".

As indicated above, the invention also relates to a second combination that could be used for preventing, treating, regressing, curing and/or delaying a cancer that acquired resistance to a drug and is accompanied by an upregulation of RRM2 (ribonucleotide reductase small subunit or ribonucleoside-diphosphate reductase subunit M2) and/or AURKB (Aurora B kinase) in a subject. This second combination of at least two compounds is such that it comprises the compound present in the first list and at least one compound from the second list below:

a) a miRNA molecule miRNA-3157-5p, an equivalent or a source thereof, or a composition comprising said miRNA, equivalent or source thereof and b) at least one cancer drug, preferably selected from the list of chemotherapeutic in the part dedicated to the general definition. Preferably said cancer drug comprises at least one RNR inhibitor and/or at least one AURKB inhibitor. Within the context of the second combination but also within the context of the "stand alone therapy using miRNA-3157" a RNR inhibitor may be a RRM2 inhibitor.

An even more preferred RNR inhibitor is selected from the group consisting of gemcitabine, hydroxyurea, clolar clofarabine and triapine.

Surprisingly, it has been found that the compounds/ treatment present in said "second combination" are highly attractive for use as a medicament for preventing, treating, regressing, curing and/or delaying a cancer that acquired resistance to a drug and is accompanied by an upregulation of RRM2 and/or AURKB (Aurora B kinase) in a subject.

This "second combination" preferably allows to delay or prevent or reverse or overcome a resistance to such a cancer drug. More preferably, such second combination allows to delay or prevent or reverse or overcome a resistance to such a RNR inhibitor and/or an AURKB inhibitor, preferably to a RNR inhibitor and/or a AURKB inhibitor as defined herein.

This "second combination" preferably optimizes the therapeutic activity/application of such a cancer drug, preferably to such a RNR inhibitor and/or a AURKB inhibitor, preferably to a RNR inhibitor and/or a AURKB inhibitor as defined herein. This is possible since this "second combination" is expected to sensitisize a subject towards such a cancer drug, preferably to such RNR inhibitors and/or AURKB inhibitors.

This "second combination" may be expected to lead to synergistic effects at least on inhibition of tumor cell (preferably melanocytes and other cancer cells as defined herein) proliferation or tumor cell (preferably melanocytes and other cancer cells as defined herein) survival as explained later herein.

Accordingly, in a preferred embodiment, said "second combination" is such that:
a) resistance to at least one cancer drug, preferably to a RNR inhibitor and/or a AURKB inhibitor (preferably to at least one the inhibitors defined herein) is at least overcome, circumvented or delayed, and/or
b) the therapeutic effect of at least one cancer drug, preferably a RNR inhibitor and/or a AURKB inhibitor (preferably to at least one of the inhibitors as defined herein), preferably is optimized, and/or
c) sensitization of a subject to at least one cancer drug, preferably at least one RNR inhibitor and/or a AURKB inhibitor (preferably to at least one of the inhibitors as defined herein), is promoted.

All these specific advantages (i.e. overcome, circumvent or delay of resistance, optimization of a therapeutic effect and sensitisize) are later herein defined.

MicroRNAs (miRNAs) are small RNAs of 17-25 nucleotides, which function as regulators of gene expression in eukaryotes. miRNAs are initially expressed in the nucleus as part of long primary transcripts called primary miRNAs (pri-miRNAs). Inside the nucleus, pri-miRNAs are partially digested by the enzyme Drosha, to form 65-120 nucleotide-long hairpin precursor miRNAs (pre-miRNAs) that are exported to the cytoplasm for further processing by Dicer into shorter, mature miRNAs, which are the active molecules. In animals, these short RNAs comprise a 5' proximal "seed" region (nucleotides 2 to 8) which appears to be the primary determinant of the pairing specificity of the miRNA to the 3' untranslated region (3'-UTR) of a target mRNA. A more detailed explanation is given in the part dedicated to general definitions.

Each of the definitions given below concerning a miRNA molecule, a miRNA equivalent or a miRNA source is to be used for each of the identified miRNAs or miRNA equivalent or miRNA sources of this application: miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p, equivalents and sources thereof. Preferred mature (as identified in Table 1), seed (as identified in Table 4) or source sequences (as identified in Tables 2 (RNA precursor) or 3 (DNA encoding an RNA precursor)) or isomiR sequences (as identified in Table 5) of said miRNA molecule or equivalent thereof respectively are identified in corresponding tables. A DNA or RNA molecule encoding a RNA precursor of a miRNA molecule may be identified as a hsa-miR-X (see for example Table 3 and Table 2) being a DNA or precursor of miRNA-X. A hsa-miR-X is a *Homo sapiens* miR-X. A hsa-mir-X is a *Homo sapiens* precursor of a *Homo sapiens* miR-X. Within the context of the invention, more preferred miRNA molecules, equivalents or precursors are *Homo sapiens* molecules.

Within the whole text of the application unless otherwise indicated, a miRNA may also be named a miRNA molecule, a miR, or an equivalent thereof or a source or a precursor thereof. It is to be noted that some miRNA molecule are encoded by several precursors. For example hsa-miRNA-7-5p is encoded by hsa-mir-7-1, hsa-mir-7-2 or hsa-mir-7-3. As another example, miRNA-129-5p is encoded by hsa-mir-129-1 or hsa-mir-129-2. As another example, miRNA-16-5p is encoded by hsa-mir-16-1 or hsa-mir-16-2. It is also possible that one precursor may lead to several mature miRNA molecule. An example is hsa-mir10b which may lead to hsa-miR-10b-5p and hsa-miR-10-3p (also known as hsa-miR-10b*). Each sequence identified herein may be identified as being SEQ ID NO as used in the text of the application or as seq in the sequence listing.

MiRNA-221 and miRNA-222 are also referred to in the present invention. They are the only miRNA molecules of this invention whose expression is not to be upregulated/ overexpressed/increased in order to be used in therapeutic applications for treatment of diseases or conditions associated with melanoma, or in diseases or conditions associated with activated BRAF pathway. In contrast, the endogenous expression of these two miRNA molecules needs to be downregulated/decreased to obtain a therapeutically desirable effect. This is preferably carried out as explained later herein using an antagomir. Therefore, in the invention when reference is made to these two miRNA molecules in a therapeutic use, one always refers to a use of an antagomir of a miRNA-221 or miRNA-222 molecule or of an equivalent of an antagomir of miRNA-221 or miRNA-222 molecule or a source of an antagomir of miRNA-221 or miRNA-222 molecule. Accordingly, when one refers to an antagomir one always refers to a use of an antagomir of a miRNA-221 or miRNA-222 molecule or an equivalent thereof or a source thereof. Each definition given herein concerning a given antagomir of a miRNA molecule also holds for other antagomir of distinct miRNA molecule all as defined herein.

In the context of the invention, a miRNA molecule or an equivalent or a mimic or an antogomir or an isomiR thereof may be a synthetic or natural or recombinant or mature or part of a mature miRNA or a human miRNA or derived from a human miRNA as further defined in the part dedicated to the general definitions. A human miRNA molecule is a miRNA molecule which is found in a human cell, tissue, organ or a body fluid (i.e. endogenous human miRNA molecule). A human miRNA molecule may also be a human miRNA molecule derived from an endogenous human miRNA molecule by substitution, deletion and/or addition of a nucleotide. A miRNA molecule or an equivalent or a mimic or an antagomir thereof may be a single stranded or double stranded RNA molecule.

In an embodiment, each of the miRNA molecules or equivalents or mimics or antagomirs or isomiRs or precursors thereof identified herein may be modified compared to the corresponding miRNA molecules or equivalents or mimics or antagomirs or precursors thereof occurring in nature. In this embodiment, each of these miRNA molecules or equivalents or mimics or antagomirs or isomiRs or precursors thereof are identified as modified miRNA molecules or equivalents or mimics or antagomirs or isomiRs or precursors thereof or as derivatives or as analogs of the naturally occurring miRNA molecule, equivalent, mimic, antagomir or precursors. Therefore in this embodiment, each of the miRNA molecules or equivalents or mimics or antagomirs or isomiRs or precursors thereof identified herein is not identical with its natural counterpart. Such modified miRNA molecules or equivalents or mimics or antagomirs or isomiRs or precursors thereof may be modified in the sense that:

One, 2, 3, 4 or 5 or at least 20%, 30%, 40%, 50%, 60%, 70%, 80%, or at least 90% or 100% of their nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of their nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

In an embodiment, a miRNA molecule or an equivalent, or a mimic or an antagomir thereof can be from 6 to 30 or 12 to 30 nucleotides in length, preferably 15 to 28 nucleotides in length, more preferably a miRNA molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA molecule, equivalent, mimic, or antagomir thereof is a modified miRNA molecule or equivalent or mimic or antagomir or isomiR thereof and more preferably said modified miRNA molecule or equivalent or mimic or antagomir or isomiR thereof is not identical with its natural counterpart. Preferred modified miRNA molecule, equivalent, mimic, or antagomir thereof are such that:

One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Preferably an antagomir of a miRNA molecule is from 8 to 30 nucleotides in length, preferably 10 to 30 nucleotides in length, preferably 12 to 28 nucleotides in length, more preferably said molecule has a length of at least 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-96-5p molecule or equivalent or mimic or isomiR thereof is represented by a sequence comprising SEQ ID NO: 3 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA-96-5p molecule, equivalent or mimic or isomiR thereof is a modified miRNA-96-5p molecule or equivalent or mimic or isomiR thereof and more preferably said modified miRNA-96-5p molecule or equivalent or mimic or isomiR thereof is not identical with its natural counterpart. Preferred modified miRNA-96-5p molecule, equivalent, mimic or isomiR thereof is such that:

One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred miRNA-10b-3p molecule or equivalent or mimic or isomiR thereof is represented by a sequence comprising SEQ ID NO: 2 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA-10b-3p molecule, equivalent or mimic or isomiR thereof is a modified miRNA molecule or equivalent or mimic or isomiR thereof and more preferably said modified miRNA-10b-3p molecule or equivalent or mimic or isomiR thereof is not identical with its natural counterpart. Preferred modified miRNA-10b-3p molecule, equivalent, mimic or isomiR thereof is such that:

One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred miRNA-129-5p molecule or equivalent or mimic or isomiR thereof is represented by a sequence comprising SEQ ID NO: 4 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA-129-5p molecule, equivalent or mimic or isomiR thereof is a modified miRNA molecule or equivalent or mimic or isomiR thereof and more preferably said modified miRNA-129-5p molecule or equivalent or mimic or isomiR thereof is not identical with its natural counterpart. Preferred modified miRNA-129-5p molecule, equivalent, mimic or isomiR thereof is such that:
  One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or
  One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred miRNA-3157-5p molecule or equivalent or mimic or isomiR thereof is represented by a sequence comprising SEQ ID NO: 6 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA-3157-5p molecule, equivalent or mimic or isomiR thereof is a modified miRNA molecule or equivalent or mimic or isomiR thereof and more preferably said modified miRNA-3157-5p molecule or equivalent or mimic or isomiR thereof is not identical with its natural counterpart. Preferred modified miRNA-3157-5p molecule, equivalent, mimic or isomiR thereof is such that:
  One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or
  One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred miRNA-200c-5p molecule or equivalent or mimic or isomiR thereof is represented by a sequence comprising SEQ ID NO: 9 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA-200c-5p molecule, equivalent or mimic or isomiR thereof is a modified miRNA molecule or equivalent or mimic or isomiR thereof and more preferably said modified miRNA-200c-5p molecule or equivalent or mimic or isomiR thereof is not identical with its natural counterpart. Preferred modified miRNA-200c-5p molecule, equivalent, mimic or isomiR thereof is such that:
  One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or
  One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred miRNA-182-3p molecule or equivalent or mimic or isomiR thereof is represented by a sequence comprising SEQ ID NO: 10 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA-182-3p molecule, equivalent or mimic or isomiR thereof is a modified miRNA molecule or equivalent or mimic or isomiR thereof and more preferably said modified miRNA-182-3p molecule or equivalent or mimic or isomiR thereof is not identical with its natural counterpart. Preferred modified miRNA-182-3p molecule, equivalent, mimic or isomiR thereof is such that:
  One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or
  One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred miRNA-16-5p molecule or equivalent or mimic or isomiR thereof is represented by a sequence comprising SEQ ID NO: 7 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA-16-5p molecule, equivalent or mimic or isomiR thereof is a modified miRNA molecule or equivalent or mimic or isomiR thereof and more preferably said modified miRNA-16-5p molecule or equivalent or mimic or isomiR thereof is not identical with its natural counterpart. Preferred modified miRNA-16-5p molecule, equivalent, mimic or isomiR thereof is such that:

One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred miRNA-497-5p molecule or equivalent or mimic or isomiR thereof is represented by a sequence comprising SEQ ID NO: 8 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA-497-5p molecule, equivalent or mimic or isomiR thereof is a modified miRNA molecule or equivalent or mimic or isomiR thereof and more preferably said modified miRNA-497-5p molecule or equivalent or mimic or isomiR thereof is not identical with its natural counterpart. Preferred modified miRNA-497-5p molecule, equivalent, mimic or isomiR thereof is such that:

One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred miRNA-518b molecule or equivalent or mimic or isomiR thereof is represented by a sequence comprising SEQ ID NO: 5 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA-518b molecule, equivalent or mimic or isomiR thereof is a modified miRNA molecule or equivalent or mimic or isomiR thereof and more preferably said modified miRNA-518b molecule or equivalent or mimic or isomiR thereof is not identical with its natural counterpart. Preferred modified miRNA-518b molecule, equivalent, mimic or isomiR thereof is such that:

One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred miRNA-7-5p molecule or equivalent or mimic or isomiR thereof is represented by a sequence comprising SEQ ID NO: 1 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA7-5p molecule, equivalent or mimic or isomiR thereof is a modified miRNA molecule or equivalent or mimic or isomiR thereof and more preferably said modified miRNA-7-5p molecule or equivalent or mimic or isomiR thereof is not identical with its natural counterpart. Preferred modified miRNA-7-5p molecule, equivalent, mimic or isomiR thereof is such that:

One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

For each of the miRNA molecule identified above, a part of a SEQ ID NO as identified may be at least 19 nucleotides of this SEQ ID NO.

In an embodiment, a miRNA molecule or equivalent or a mimic or an isomiR thereof comprises at least 6 of the 7 nucleotides present in the seed sequence of said miRNA molecule or equivalent or mimic or isomiR thereof (Table 4 shows preferred seed sequence of each of the miRNAs molecule identified herein). Preferably in this embodiment, a miRNA molecule or an equivalent or a mimic or isomiR thereof is from 6 to 30 nucleotides in length and more preferably comprises at least 6 of the 7 nucleotides present in the seed sequence of said miRNA molecule or equivalent thereof. Even more preferably a miRNA molecule or an equivalent or a mimic or isomiR thereof is from 15 to 28 nucleotides in length and more preferably comprises at least 6 of the 7 nucleotides present in the seed sequence, even more preferably a miRNA molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-96-5p molecule or equivalent or mimic or isomiR thereof comprises at least 6 of the 7 nucleotides present in the seed sequence identified as SEQ ID NO: 41 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-10b-3p molecule or equivalent or mimic or isomiR thereof comprises at least 6 of the 7 nucleotides present in the seed sequence identified as SEQ ID NO: 40 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-129-5p molecule or equivalent or mimic or isomiR thereof comprises at least 6 of the 7 nucleotides present in the seed sequence identified as SEQ ID NO: 42 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-3157-5p molecule or equivalent or mimic or isomiR thereof comprises at least 6 of the 7 nucleotides present in the seed sequence identified as SEQ ID NO: 44 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-200c-5p molecule or equivalent or mimic or isomiR thereof comprises at least 6 of the 7 nucleotides present in the seed sequence identified as SEQ ID NO: 47 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-182-3p molecule or equivalent or mimic or isomiR thereof comprises at least 6 of the 7 nucleotides present in the seed sequence identified as SEQ ID NO: 48 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-16-5p molecule or equivalent or mimic or isomiR thereof comprises at least 6 of the 7 nucleotides present in the seed sequence identified as SEQ ID NO: 45 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-497-5p molecule or equivalent or mimic or isomiR thereof comprises at least 6 of the 7 nucleotides present in the seed sequence identified as SEQ ID NO: 46 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-518b molecule or equivalent or mimic or isomiR thereof comprises at least 6 of the 7 nucleotides present in the seed sequence identified as SEQ ID NO: 43 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-7-5p molecule or equivalent or mimic or isomiR thereof comprises at least 6 of the 7 nucleotides present in the seed sequence identified as SEQ ID NO: 39 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

For each of the miRNA molecule identified above, a part of a SEQ ID NO as identified may be at least 19 nucleotides of this SEQ ID NO.

In another preferred embodiment, a miRNA molecule or an equivalent or a mimic thereof comprises at least 6 of the 7 nucleotides present in a given seed sequence and has at least 70% identity over the whole mature sequence (Table 1 shows preferred mature sequences of each of the miRNAs identified herein and Table 5 shows preferred IsomiR equivalents of each of the mature miRNAs identified). Preferably, identity is at least 75%, 80%, 85%, 90%, 95% or higher. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-96-5p molecule or equivalent or mimic or isomiR thereof comprises at least 6 of the 7 nucleotides present in the seed sequence identified as SEQ ID NO: 41 or a part thereof and/or has at least 70%, 75%, 80%, 85%, 90%, 95%, 97%, 98%, 99% or 100% identity over SEQ ID NO: 3 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-10b-3p molecule or equivalent or mimic or isomiR thereof comprises at least 6 of the 7 nucleotides present in the seed sequence identified as SEQ ID NO: 40 or a part thereof and/or has at least 70%, 75%, 80%, 85%, 90%, 95%, 97%, 98%, 99% or 100% identity over SEQ ID NO: 2 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-129-5p molecule or equivalent or mimic or isomiR thereof comprises at least 6 of the 7 nucleotides present in the seed sequence identified as SEQ ID NO: 42 or a part thereof and/or has at least 70%, 75%, 80%, 85%, 90%, 95%, 97%, 98%, 99% or 100% identity over SEQ ID NO: 4 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-3157-5p molecule or equivalent or mimic or isomiR thereof comprises at least 6 of the 7 nucleotides present in the seed sequence identified as SEQ ID NO: 44 or a part thereof and/or has at least 70%, 75%, 80%, 85%, 90%, 95%, 97%, 98%, 99% or 100% identity over SEQ ID NO: 6 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-200c-5p molecule or equivalent or mimic or isomiR thereof comprises at least 6 of the 7 nucleotides present in the seed sequence identified as SEQ ID NO: 47 or a part thereof and/or has at least 70%, 75%, 80%, 85%, 90%, 95%, 97%, 98%, 99% or 100% identity over SEQ ID NO: 9 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-182-3p molecule or equivalent or mimic or isomiR thereof comprises at least 6 of the 7 nucleotides present in the seed sequence identified as SEQ ID NO: 48 or a part thereof and/or has at least 70%, 75%, 80%, 85%, 90%, 95%, 97%, 98%, 99% or 100% identity over SEQ ID NO: 10 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-16-5p molecule or equivalent or mimic or isomiR thereof comprises at least 6 of the 7 nucleotides present in the seed sequence identified as SEQ ID NO: 45 or a part thereof and/or has at least 70%, 75%, 80%, 85%, 90%, 95%, 97%, 98%, 99% or 100% identity over SEQ ID NO: 7 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-497-5p molecule or equivalent or mimic or isomiR thereof comprises at least 6 of the 7 nucleotides present in the seed sequence identified as SEQ ID NO: 46 or a part thereof and/or has at least 70%, 75%, 80%, 85%, 90%, 95%, 97%, 98%, 99% or 100% identity over SEQ ID NO: 8 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-518b molecule or equivalent or mimic or isomiR thereof comprises at least 6 of the 7 nucleotides present in the seed sequence identified as SEQ ID NO: 43 or a part thereof and/or has at least 70%, 75%, 80%, 85%, 90%, 95%, 97%, 98%, 99% or 100% identity over SEQ ID NO: 5 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-7-5p molecule or equivalent or mimic or isomiR thereof comprises at least 6 of the 7 nucleotides present in the seed sequence identified as SEQ ID NO: 39 or a part thereof and/or has at least 70%, 75%, 80%, 85%, 90%, 95%, 97%, 98%, 99% or 100% identity over SEQ ID NO: 1 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In another preferred embodiment, an isomiR of a miRNA molecule has at least 70% identity over the whole isomiR sequence (Table 5 shows preferred isomiR of each of the mature miRNAs identified as SEQ ID NO: 1-10). Preferably, identity is at least 75%, 80%, 85%, 90%, 95% or higher. Preferably in this embodiment, an isomiR of a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In a preferred embodiment, an isomiR is a modified miRNA molecule or equivalent thereof and more preferably said modified miRNA molecule or equivalent thereof is not identical with its natural counterpart. Preferred modified isomiR thereof is such that:
   One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or
   One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred isomiR of a miRNA-96-5p molecule or equivalent thereof comprises at least 6 of the 7 nucleotides present in the seed sequence identified as SEQ ID NO: 62, 63, 64, 65, 66 or 67 or a part thereof and/or has at least 70%, 75%, 80%, 85%, 90%, 95%, 97%, 98%, 99% or 100% identity over SEQ ID NO: 159, 160, 161, 162, 163, 164, 165, 166, 167, 168, 169, 170, 171, 172, 173 or 174 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a preferred embodiment, an isomiR of a miRNA-96-5p molecule or equivalent thereof is a modified miRNA molecule or equivalent thereof and more preferably said modified miRNA molecule or equivalent thereof is not identical with its natural counterpart. Preferred modified isomiR thereof is such that:
   One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or
   One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred isomiR of a miRNA-10b-3p molecule or equivalent thereof comprises at least 6 of the 7 nucleotides present in the seed sequence identified as SEQ ID NO: 58, 59, 60 or 61 or a part thereof and/or has at least 70%, 75%, 80%, 85%, 90%, 95%, 97%, 98%, 99% or 100% identity over SEQ ID NO: 147, 148, 149, 150, 151, 152, 153, 154, 155, 156, 157 or 158 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a preferred embodiment, an isomiR of a miRNA-10b-3p molecule or equivalent thereof is a modified miRNA molecule or equivalent thereof and more preferably said modified miRNA molecule or equivalent thereof is not identical with its natural counterpart. Preferred modified isomiR thereof is such that:
   One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or
   One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred isomiR of a miRNA-129-5p molecule or equivalent thereof comprises at least 6 of the 7 nucleotides present in the seed sequence identified as SEQ ID NO: 68, 69, 70, 71 or 72 or a part thereof and/or has at least 70%, 75%, 80%, 85%, 90%, 95%, 97%, 98%, 99% or 100% identity over SEQ ID NO: 175, 176, 177, 178, 179, 180, 181, 182, 183, 184, 185 or 186 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a preferred embodiment, an isomiR of a miRNA-129-5p molecule or equivalent thereof is a modified miRNA molecule or equivalent thereof and more preferably said modified miRNA molecule or equivalent thereof is not identical with its natural counterpart. Preferred modified isomiR thereof is such that:

One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred isomiR of a miRNA-3157-5p molecule or equivalent thereof comprises at least 6 of the 7 nucleotides present in the seed sequence identified as SEQ ID NO: 75 or 76 or a part thereof and/or has at least 70%, 75%, 80%, 85%, 90%, 95%, 97%, 98%, 99% or 100% identity over SEQ ID NO: 192, 193 or 194 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a preferred embodiment, an isomiR of a miRNA-3157-5p molecule or equivalent thereof is a modified miRNA molecule or equivalent thereof and more preferably said modified miRNA molecule or equivalent thereof is not identical with its natural counterpart. Preferred modified isomiR thereof is such that:

One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred isomiR of a miRNA-200c-5p molecule or equivalent thereof comprises at least 6 of the 7 nucleotides present in the seed sequence identified as SEQ ID NO: 92 or a part thereof and/or has at least 70%, 75%, 80%, 85%, 90%, 95%, 97%, 98%, 99% or 100% identity over SEQ ID NO: 265 or 266 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a preferred embodiment, an isomiR of a miRNA-200c-5p molecule or equivalent thereof is a modified miRNA molecule or equivalent thereof and more preferably said modified miRNA molecule or equivalent thereof is not identical with its natural counterpart. Preferred modified isomiR thereof is such that:

One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred isomiR of a miRNA-182-3p molecule or equivalent thereof comprises at least 6 of the 7 nucleotides present in the seed sequence identified as SEQ ID NO: 93, 94 or 95 or a part thereof and/or has at least 70%, 75%, 80%, 85%, 90%, 95%, 97%, 98%, 99% or 100% identity over SEQ ID NO: 267, 268, 269, 270 or 271 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a preferred embodiment, an isomiR of a miRNA-182-3p molecule or equivalent thereof is a modified miRNA molecule or equivalent thereof and more preferably said modified miRNA molecule or equivalent thereof is not identical with its natural counterpart. Preferred modified isomiR thereof is such that:

One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Accordingly a preferred isomiR of a miRNA-16-5p molecule or equivalent thereof comprises at least 6 of the 7 nucleotides present in the seed sequence identified as SEQ ID NO: 77, 78, 79, 80, 81, 82, 83, 84, 85, or 86 or a part thereof and/or has at least 70%, 75%, 80%, 85%, 90%, 95%, 97%, 98%, 99% or 100% identity over SEQ ID NO: 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240 or 241 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a preferred embodiment, an isomiR of a miRNA-16-5p molecule or equivalent thereof is a modified miRNA molecule or equivalent thereof and more preferably said modified miRNA molecule or equivalent thereof is not identical with its natural counterpart. Preferred modified isomiR thereof is such that:
  One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or
  One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.
  In the part of the application dedicated to the definitions, preferred nucleotides, nucleosides, nucleobases, nucleobases linker moiety and backbone moiety have been disclosed.

Accordingly a preferred isomiR of a miRNA-497-5p molecule or equivalent thereof comprises at least 6 of the 7 nucleotides present in the seed sequence identified as SEQ ID NO: 87, 88, 89, 90 or 91 or a part thereof and/or has at least 70%, 75%, 80%, 85%, 90%, 95%, 97%, 98%, 99% or 100% identity over SEQ ID NO: 242, 243, 244, 245, 246, 247, 248, 249, 250, 251, 252, 253, 254, 255, 256, 257, 258, 259, 260, 261, 262, 263 or 264 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a preferred embodiment, an isomiR of a miRNA-497-5p molecule or equivalent thereof is a modified miRNA molecule or equivalent thereof and more preferably said modified miRNA molecule or equivalent thereof is not identical with its natural counterpart. Preferred modified isomiR thereof is such that:
  One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or
  One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.
  In the part of the application dedicated to the definitions, preferred nucleotides, nucleosides, nucleobases, nucleobases linker moiety and backbone moiety have been disclosed.

Accordingly a preferred isomiR of a miRNA-518b molecule or equivalent thereof comprises at least 6 of the 7 nucleotides present in the seed sequence identified as SEQ ID NO: 73 or 74 or a part thereof and/or has at least 70%, 75%, 80%, 85%, 90%, 95%, 97%, 98%, 99% or 100% identity over SEQ ID NO: 187, 188, 189, 190, or 191 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a preferred embodiment, an isomiR of a miRNA-518b molecule or equivalent thereof is a modified miRNA molecule or equivalent thereof and more preferably said modified miRNA molecule or equivalent thereof is not identical with its natural counterpart. Preferred modified isomiR thereof is such that:
  One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or
  One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.
  In the part of the application dedicated to the definitions, preferred nucleotides, nucleosides, nucleobases, nucleobases linker moiety and backbone moiety have been disclosed.

Accordingly a preferred isomiR of a miRNA-7-5p molecule or equivalent thereof comprises at least 6 of the 7 nucleotides present in the seed sequence identified as SEQ ID NO: 49, 50, 51, 52, 53, 54, 55, 56 or 57 or a part thereof and/or has at least 70%, 75%, 80%, 85%, 90%, 95%, 97%, 98%, 99% or 100% identity over SEQ ID NO: 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145 or 146 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

In a preferred embodiment, an isomiR of a miRNA-7-5p molecule or equivalent thereof is a modified miRNA molecule or equivalent thereof and more preferably said modified miRNA molecule or equivalent thereof is not identical with its natural counterpart. Preferred modified isomiR thereof is such that:
  One, 2, 3, 4 or 5 or at least 20%, 30%, 40%, 50%, 60%, 70%, 80%, or at least 90% or 100% of its nucleotides has been deleted or added compared to the corresponding nucleotide present in the naturally occurring molecule, and/or
  One, 2, 3, 4 or 5 or at least 20%, 30%, 40%, 50%, 60%, 70%, 80%, or at least 90% or 100% of its nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.
  In the part of the application dedicated to the definitions, preferred nucleotides, nucleosides, nucleobases, nucleobases linker moiety and backbone moiety have been disclosed.

For each of the miRNA molecules identified above, a part of a SEQ ID NO as identified may be at least 19 nucleotides of this SEQ ID NO.

Each of the miRNA molecules or equivalents or mimics thereof as identified herein has an acceptable level of an activity of a given miRNA they derive from.

A preferred miRNA molecule or equivalent or a mimic thereof is derived from a given seed sequence (Table 4 or 5) or from a given mature sequence (Table 1) or from a given isomiR sequence (Table 5) or from a precursor sequence (Table 2) or from a DNA encoding an RNA precursor (Table 3) by substitution, deletion and/or addition of 1, 2, 3 or more nucleotides and has still an acceptable activity.

Another preferred miRNA molecule or equivalent or mimic thereof has at least 60% identity with a seed sequence (as identified in Table 4 or 5) or with a mature sequence (as identified in Table 1) or with a precursor sequence (as identified in Table 2) or with a DNA encoding an RNA precursor (as identified in Table 3) or with an isomiR sequence (as identified in Table 5). Identity may be at least 65%, 70%, 75%, 80%, 85%, 90%, 95%, 99% or 100%. Identity is preferably assessed on the whole SEQ ID NO as identified in a given Table. However, identity may also be assessed on part of a given SEQ ID NO. Part may mean at least 50% of the length of the SEQ ID NO, at least 60%, at least 70%, at least 80%, at least 90% or 100%.

An equivalent of a miRNA molecule may be an isomiR or a mimic. A precursor sequence may result in more than one isomiR sequences depending on the maturation process (see for example miRNA-7-5p, where in certain tissues multiple isomiRs have been identified (Table 5). A mimic is a molecule which has a similar or identical activity with a miRNA molecule. In this context a similar activity is given the same meaning as an acceptable level of an activity. A mimic is, in a functional determination, opposed to an antagomir. An antagomir of a miRNA molecule or equivalent or source thereof is therefore a molecule which has an activity which is opposite or reverse to the one of the corresponding miRNA molecule it derives from. An antagomir of a miRNA molecule or equivalent thereof may also be defined as a molecule which is able to antagonize or silence or decrease an activity of said miRNA molecule or equivalent thereof. An activity which is opposite or reverse to the one of the corresponding miRNA molecule it derives from or an activity which is able to antagonize an activity of said miRNA molecule it derives from is preferably an activity which is able to decrease an activity of said miRNA molecule, equivalent or source thereof. In this context, decrease means at least 5%, 10%, 20%, 30%, 40%, 50%, 60%, 70%, 80%, 90%, 95% or 100% decrease of the activity of said miRNA molecule or equivalent or source thereof.

Within the context of the invention, "increasing an activity or the steady-state level of an antagomir or equivalent thereof or of said source thereof" could be replaced by "decreasing an activity or the steady-state level of the corresponding miRNA molecule or equivalent thereof".

The chemical structure of the nucleotides of an antagomir or of a miRNA molecule or of an equivalent such as a mimic or source thereof may be modified as earlier defined herein to increase stability, binding affinity and/or specificity. Said antagomir may comprise or consist of a RNA molecule or preferably a modified RNA molecule. A preferred modified RNA molecule comprises a modified sugar. One example of such modification is the introduction of a 2'-O-methyl or 2'-O-methoxyethyl group or 2'fluoride group on the nucleic acid to improve nuclease resistance and binding affinity to RNA. Another example of such modification is the introduction of a methylene bridge connecting the 2'-O atom and the 4'-C atom of the nucleic acid to lock the conformation (Locked Nucleic Acid (LNA)) to improve affinity towards complementary single-stranded RNA. A third example is the introduction of a phosphorothioate group as linker between nucleic acid in the RNA-strand to improve stability against a nuclease attack. A fourth modification is conjugation of a lipophilic moiety on the 3' end of the molecule, such as cholesterol to improve stability and cellular delivery. In a preferred embodiment, an antagomir of miRNA molecule consists of a fully LNA-modified phosphorothioate oligonucleotide, termed tiny LNA as described in Obad S., et al). An antagomir as defined herein may comprise 1, 2, 3, 4, 5, 6, 7, 8, 9, 10 or more sugar modifications. It is also encompassed by the invention to introduce more than one distinct sugar modification in one antagomir.

An acceptable level of an activity is preferably that said miRNA or equivalent thereof (miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p or an equivalent thereof) is still able to exhibit an acceptable level of said activity of said miRNA. An activity of a given miRNA (i.e. a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p) or equivalent or a mimic thereof is for example the ability to inhibit proliferation, survival, invasion and/or migration and/or to induce apoptosis and/or to interfere with the constitutively active BRAF-MEK-ERK pathway as later defined herein. An activity of a miRNA-3157-5p molecule or equivalent thereof in a second combination of the invention is for example to be able to inhibit the expression level of a RRM2 and/or of a AURKB at the protein and/or RNA level and/or to inhibit an activity of a RRM2 and/or of a AURKB or to be able to exert an anti-tumour effect as later defined herein. Please note that a RRM2 is a subunit of a RNR as later defined herein. An acceptable level of an activity is preferably at least 30%, 40%, 50%, 60%, 70%, 80%, 90%, 95% or 100% of the activity of the miRNA they derive from. An antagomir of a miRNA molecule induces a decreased activity of a miRNA molecule it derives from. For example in the context of the invention, an antagomir of a miRNA-221 or of a miRNA-222 is a molecule which induces a decreased activity of a miRNA-221 or of a miRNA-222. Preferably an antagomir of a miRNA-221 or of a miRNA-222 has the ability to inhibit proliferation, survival, invasion and/or migration and/or to induce apoptosis and/or to interfere with the constitutively active BRAF-MEK-ERK or as later described herein for a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p molecule.

Such activity may be as measured in a melanoma cell or in a relevant cancer cell of an individual or in vitro in a cell by comparison to the activity of the miRNA they derive from. The assessment of the activity may be carried out at the mRNA level, preferably using RT-qPCR. The assessment of the activity may be carried out at the protein level, preferably using assays detecting protein expression, such as Western blot analysis, ELISA, immunohistochemistry or immunofluorescence analysis of cross-sections and/or using an assay as defined later herein (proliferation test, assay for differentiation capacity of a cell, assay for assessing cell death/cell viability, assay for assessing the occurrence of metastases, assay for assessing tumor cell migration, assay for assessing tumor growth, assay for assessing patient survival). The assessment of any of these activities may be carried out using A375 cells as used in the experimental part.

A preferred activity of a miRNA molecule or equivalent or mimic thereof as identified herein (i.e. miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p or an equivalent or a mimic thereof) or of an antagomir of miRNA-221, miRNA-222 is to induce a detectable inhibition of the proliferation, survival, invasion and/or migration and/or induce apoptosis and/or to interfere with the constitutively active BRAF-MEK-ERK pathway in a subject as later defined herein. A preferred activity of a miRNA-3157-5p molecule or equivalent or mimic in a second combination of the invention is to be able to inhibit the expression level of a RRM2 and/or of a AURKB at the protein and/or RNA level and/or to inhibit an activity of a RRM2 and/or of a AURKB or to be able to exert an anti-tumour effect as later defined herein.

A preferred antagomir of miRNA-221 comprises or consists of 5'-GAAACCCAGCAGACAAUGUAGCU-3' (SEQ ID NO:272).

A preferred antagomir of miRNA-222 comprises or consists of 5'-GAGACCCAGUAGCCAGAUGUAGCU-3' (SEQ ID NO:273) (Felicetti F. et al).

Preferably, an antagomir is from 23, 24, 25, 26, 27, 28, 29, 30, 31, 32, 33, 34, 35, 36, 37, 38, 39, 40, 41, 42, 43, 44, 45, 46, 47, 48, 49, 50 nucleotides or more and has at least 60% identity with an antagomir sequence SEQ ID NO:272 or 273 as identified above. Identity may be at least 65%, 70%, 75%, 80%, 85%, 90%, 95%, 99% or 100%. Identity is preferably assessed on the whole SEQ ID NO. However, identity may also be assessed on a part of a given SEQ ID NO. A part may mean at least 50% of the length of the SEQ ID NO, at least 60%, at least 70%, at least 80%, at least 90% or 100%.

A source of a miRNA molecule or a source of an equivalent or a source of a mimic of a miRNA molecule may be any molecule which is able to induce the production of a miRNA molecule or of an equivalent thereof as identified herein and which comprises a hairpin-like structure and/or a double stranded nucleic acid molecule. The presence of a hairpin-like structure, may be assessed using the RNAshapes program (Steffen P., et al) using sliding windows of 80, 100 and 120 nt or more. The presence of a hairpin-like structure is usually present in a natural or endogenous source of a miRNA molecule whereas a double-stranded nucleic acid molecule is usually present in a recombinant or synthetic source of a miRNA molecule or of an equivalent thereof.

A source of an antagomir of a miRNA molecule or a source of an equivalent of an antagomir of a miRNA molecule may be any molecule which is able to induce the production of said antagomir. Examples of a suitable source of an antagomir are identified in Surdziel E., et al and in Scherr M., et al.

A source of a miRNA molecule or of an equivalent thereof may be a single stranded, a double stranded RNA or a partially double stranded RNA or comprise three strands, an example of which is described in WO2008/10558. In an embodiment, a single stranded miRNA molecule consists of a single stranded miRNA molecule and is therefore not a double stranded miRNA molecule. As used herein partially double stranded refers to double stranded structures that also comprise single stranded structures at the 5 'and/or at the 3' end. It may occur when each strand of a miRNA molecule does not have the same length. In general, such partial double stranded miRNA molecule may have less than 75% double stranded structure and more than 25% single stranded structure, or less than 50% double stranded structure and more than 50% single stranded structure, or more preferably less than 25%, 20% or 15% double stranded structure and more than 75%, 80%, 85% single stranded structure.

In an embodiment, each of sources or precursors of the miRNA molecules identified herein may be modified compared to the corresponding sources or precursors of miRNA molecules occurring in nature. In this embodiment, each of these sources or precursors of miRNA molecules are identified as modified sources or precursors of the miRNA molecules or as derivatives or as analogs of the naturally occurring sources or precursors of said miRNA molecule. Therefore in this embodiment, each of the sources or precursors of the miRNA molecules identified herein is not identical with its natural counterpart. Such modified sources or precursors of miRNA molecules may be modified in the sense that:

One, 2, 3, 4 or 5 or at least 20%, 30%, 40%, 50%, 60%, 70%, 80%, or at least 90% or 100% of their nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of their nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the part of the application dedicated to the definitions, preferred nucleotides, nucleosides, nucleobases, nucleobases linker moiety and backbone moiety have been disclosed.

Alternatively, a source of a miRNA molecule or of an equivalent or a mimic or an isomiR is a DNA molecule encoding a precursor of a miRNA molecule or of an equivalent or a mimic or an isomiR. Preferred DNA molecules in this context are identified in Table 3. The invention encompasses the use of a DNA molecule encoding a precursor of a miRNA molecule that has at least 70% identity with said sequence as identified in Table 3. Preferably, the identity is at least 75%, 80%, 85%, 90%, 95% or higher. Preferably in this embodiment, a DNA molecule has a length of at least 50, 55, 60, 70, 75, 80, 85, 90, 95, 100, 130, 150, 200, 250, 300, 350, 400, 450, 500 nucleotides or more and has at least 70% identity with a DNA sequence as identified in Table 3 as SEQ ID NO:25-38.

The induction of the production of a given miRNA molecule or of an equivalent or a mimic or an isomiR or an antagomir thereof is preferably obtained when said source is introduced into a cell using an assay as defined below. Cells encompassed by the present invention are later on defined.

A preferred source of a miRNA molecule or of an equivalent or a mimic or an isomiR thereof is a precursor thereof, more preferably a nucleic acid encoding said miRNA molecule or an equivalent or a mimic or an antagomir thereof or a source thereof. A preferred precursor is a naturally-occurring precursor. A precursor may be a synthetic or recombinant precursor.

A preferred precursor of a given miRNA molecule is identified in Table 2. The invention encompasses the use of a precursor of a miRNA molecule or of an equivalent thereof that has at least 70% identity with said sequence. Preferably, identity is at least 75%, 80%, 85%, 90%, 95% or higher as 97%, 98%, 99% or 100%. Preferably in this embodiment, a RNA or DNA molecule has a length of at least 50, 55, 60, 70, 75, 80, 85, 90, 95, 100, 130, 150, 200, 250, 300, 350, 400, 450, 500 nucleotides or more and has at least 70% identity with a sequence as identified in Table 2 as SEQ ID NO: 11, 12, 13, 14, 15, 16, 17, 18, 19, 20, 21, 22, 23 or 24 or a part thereof.

Accordingly, a preferred source of a miRNA-96-5p molecule has at least 70%, 75%, 80%, 85%, 90%, 95%, 97%, 98%, 99% or 100% identity with SEQ ID NO: 15 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-10b-3p molecule has at least 70%, 75%, 80%, 85%, 90%, 95%, 97%, 98%, 99% or 100% identity with SEQ ID NO: 14 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-129-5p molecule has at least 70%, 75%, 80%, 85%, 90%, 95%, 97%, 98%, 99% or 100% identity with SEQ ID NO: 16 or 17 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-3157-5p molecule has at least 70%, 75%, 80%, 85%, 90%, 95%, 97%, 98%, 99% or 100% identity with SEQ ID NO: 19 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-200c-5p molecule has at least 70%, 75%, 80%, 85%, 90%, 95%, 97%, 98%, 99% or 100% identity with SEQ ID NO: 23 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-182-3p molecule has at least 70%, 75%, 80%, 85%, 90%, 95%, 97%, 98%, 99% or 100% identity with SEQ ID NO: 24 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-16-5p molecule has at least 70%, 75%, 80%, 85%, 90%, 95%, 97%, 98%, 99% or 100% identity with SEQ ID NO: 20 or 21 and/or has a length of at least 50, 55, 60, 70, 75, 80, 85, 90, 95, 100, 130, 150, 200, 250, 300, 350, 400 nucleotides or more.

Accordingly, a preferred source of a miRNA-497-5p molecule has at least 70%, 75%, 80%, 85%, 90%, 95%, 97%, 98%, 99% or 100% identity with SEQ ID NO: 22 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-518b molecule has at least 70%, 75%, 80%, 85%, 90%, 95%, 97%, 98%, 99% or 100% identity with SEQ ID NO: 18 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-7-5p molecule has at least 70%, 75%, 80%, 85%, 90%, 95%, 97%, 98%, 99% or 100% identity with SEQ ID NO: 11, 12 or 13 or a part thereof and/or has a length of at least 50, 55, 60, 70, 75, 80, 85, 90, 95, 100, 130, 150, 200, 250, 300, 350, 400, 450, 500 nucleotides or more.

For each of the source of miRNA molecule identified above, a part of a SEQ ID NO as identified may be at least 100 or 200 nucleotides of this SEQ ID NO.

In this context, it is pointed that several precursors of a given mature miRNA molecule may lead to an identical miRNA molecule. For example, a miRNA-7-5p may originate from precursor hsa-mir-7-1, hsa-mir-7-2 or hsa-mir-7-3 (preferably identified as being SEQ ID NO: 11, 12 or 13). In a preferred embodiment, a hsa-mir-7-3 or a molecule having at least 70%, 75%, 80%, 85%, 90%, 95%, 97%, 98%, 99% or 100% identity with hsa-mir-7-3 or SEQ ID NO: 13 is used as a precursor of a miRNA-7-5p molecule.

For example, a miRNA-16-5p may originate from precursor hsa-mir-16-1 or hsa-mir-16-2 (preferably identified as being SEQ ID NO: 20 or 21). In a preferred embodiment, a hsa-mir-16-2 or a molecule having at least 70%, 75%, 80%, 85%, 90%, 95%, 97%, 98%, 99% or 100% identity with hsa-mir-16-2 or SEQ ID NO: 21 is used as a precursor of a miRNA-16-5p molecule.

For example, a miRNA-129-5p may originate from precursor hsa-mir-129-1 or hsa-mir-129-2 (preferably identified as being SEQ ID NO: 16 or 17). In a preferred embodiment, a hsa-mir-129-2 or a molecule having at least 70%, 75%, 80%, 85%, 90%, 95%, 97%, 98%, 99% or 100% identity with hsa-mir-129-2 or SEQ ID NO: 17 is used as a precursor of a miRNA-129-5p molecule.

Preferred sources or precursors have been defined later herein. A preferred source includes or comprises an expression construct comprising a nucleic acid, i.e. DNA encoding said precursor of said miRNA, more preferably said expression construct is a viral gene therapy vector selected from gene therapy vectors based on an adenovirus, an adeno-associated virus (AAV), a herpes virus, a pox virus and a retrovirus. A preferred viral gene therapy vector is an AAV or lentiviral vector. Other preferred vectors are oncolytic viral vectors. Such vectors are further described herein below.

Alternatively, a source may be a synthetic miRNA molecule or a chemical mimic or a chemical antagomir as further defined in the part dedicated to general definitions.

Within the whole invention, each time is referred to "a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p and/or an equivalent and/or a source thereof" one may further refer to the preferred subcombinations of miRNA as identified below for which best experimental results have been obtained so far:

A miRNA molecule is preferably a miRNA-3157-5p, miRNA-497-5p and/or a miRNA-129-5p and/or an equivalent and/or a source thereof.

More preferably, a miRNA molecule is:
a miRNA-3157-5p,
a miRNA-497-5p,
a miRNA-129-5p,
a miRNA-3157-5p, a miRNA-497-5p,
a miRNA-3157-5p, a miRNA-129-5p,
a miRNA-3157-5p, a miRNA-129-5p, a miRNA-497-5p,
a miRNA-497-5p, a miRNA-129-5p,
a miRNA-10b-3p, a miRNA-16-5p,
and/or an equivalent and/or a source thereof.

Below we define the "at least one compound" from the second list present in the "first combination".

B-raf inhibitors are compounds that specifically inhibit the B-raf protein, for which a mutated form of the BRAF gene encodes. Several mutations of the BRAF gene are known to cause melanoma, and specific compounds have been developed which inhibit the mutated form of the B-raf protein. B-raf inhibitors are known in the art and include, but are not limited to vemurafenib, dabrafenib, trametinib, GDC-0879, PLX-4720, sorafenib, SB590885, PLX4720, XL281 and RAF265. B-raf inhibitors are e.g. described in Wong K. K., et al, which is incorporated by reference in its entirety.

One B-raf inhibitor may be used or together with other B-raf inhibitors in a combination according to the invention. Therefore one or several distinct B-raf inhibitors may be present in a first combination of the invention. Several B-raf inhibitors is synonymous with several distinct B-raf inhibitors. Preferred B-raf inhibitors to be used in the present invention are vemurafenib, dabrafenib or a mixture of vemurafenib and dabrafenib. Vemurafenib is also known as RG7204 or N-(3-{[5-(4-chlorophenyl)-1H-pyrrolo[2,3-b]pyridin-3-yl]carbonyl}-2,4-difluorophenyl)propane-1-sulfonamide, and marketed as Zelboraf, and is represented by formula (1). Dabrafenib is also known as N-{3-[5-(2-aminopyrimidin-4-yl)-2-(1,1-dimethylethyl)thiazol-4-yl]-2-fluorophenyl}-2,6-difluorobenzenesulfonamide, and is represented by formula (2).

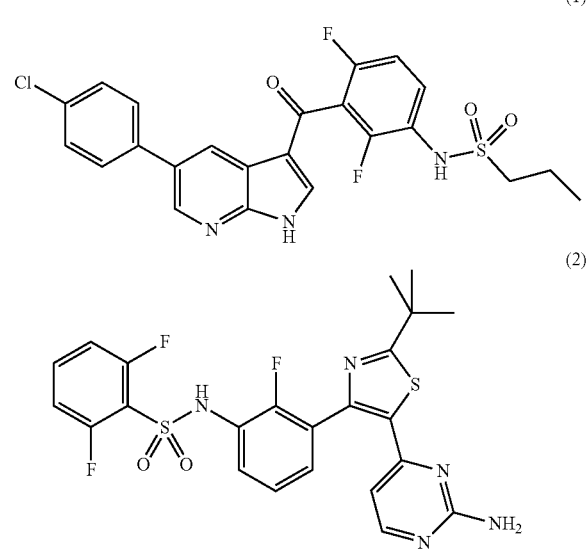

MEK inhibitors are compounds that specifically inhibit a MEK protein. Several MEK inhibitors are known in the art and include, but are not limited to trametinib (GSK1120212), selumetinib (AZD-6244), XL518, CI-1040, PD035901. Trametinib is also known as N-(3-(3-cyclopropyl-5-(2-fluoro-4-iodophenylamino)-6,8-dimethyl-2,4,7-trioxo-3,4,6,7-tetrahydropyrido[4,3-d]pyrimidin-1(2H)-yl)phenyl)acetamide. Selumetinib is also known as: 6-(4-bromo-2-chlorophenylamino)-7-fluoro-N-(2-hydroxyethoxy)-3-methyl-3H-benzo[d]imidazole-5-carboxamide. MEK inhibitors are e.g. described in Wong, K. K. et al which is incorporated by reference in its entirety.

One MEK inhibitor may be used or together with other MEK inhibitors in a first combination according to the invention. Therefore one or several distinct MEK inhibitors may be present in a first combination of the invention. Several MEK inhibitors is synonymous with several distinct MEK inhibitors. Preferred MEK inhibitors to be used in the present invention are trametinib and/or selumetinib.

Activation of the BRAF pathway in cell is characterized by a high or elevated or induction of an activation or an increase of the level of pERK1/2 (phosphorylated ERK1/2) in the cell. Activated BRAF directly phosphorylates and activates the downstream dual specificity kinase MEK, which in turn phosphorylates ERK on threonine and tyrosine residues resulting in a dramatic activation of ERK, which is characterized by a high or elevated or induction of an activation or an increase of the level of pERK1/2. To evaluate the ability of a therapeutic compound to inhibit BRAF or MEK, one can perform western blotting with p-ERK knockdown as read-out. Cells are plated in 6-well plates and treated for 72 hours at 0.01, 0.1 and 1 uM of said compound. After treatment cells are scraped into a lysis buffer as a RIPA lysis buffer. Equal amounts of protein extracts are separated by using 10% SDS-PAGE, and then transferred to a polyvinylidene difluoride membrane. After blocking for 1 hour in a Tris-buffered saline containing 0.1% Tween 20 and 5% nonfat milk, the membrane is probed with a p-ERK1/2 primary antibody, followed by a secondary antibody conjugated to horseradish peroxidase for chemiluminescent detection on film. Tubulin is used as loading control. A preferred p-ERK1/2 antibody is from Abcam (product number ab50011). This antibody recognizes T185, Y187, T202 and Y204. Another one that may be used is from Life Technologies (product number CNB0011). This antibody recognizes T185/187.

An inhibition of B-raf or MEK may therefore be assessed when a low or a decreased or a detectable decrease of the level of pERK1/2 is identified using an assay as explained above, said decrease being identified by comparison to the level of pERK when said compound is not added to the cells. A detectable decrease may be a decrease of at least 5%, 10%, 15%, 20%, 25%, 30%, 35%, 40%, 45%, 50%, 55%, 60%, 65%, 70%, 75%, 80%, 85%, 90%, 95%. Preferably no pERK is detectable.

Within the whole invention, each time is referred to "at least one B-raf and/or MEK inhibitor", one may refer to the following preferred first subcombinations as identified below:
Vemurafenib
Dabrafenib
Trametinib
Selumetinib
Vemurafenib and trametinib
Vemurafenib and selumetinib
Dabrafenib and trametinib or
Dabrafenib and selumetinib.

A preferred first combination is such that said at least one compound from the first list is a miRNA-3157-5p, and/or an equivalent and/or a source thereof or a composition comprising said miRNA-3157-5p and/or equivalent and/or source thereof and said at least one compound from the second list is vemurafenib and/or dabrafenib and/or trametinib and/or selumetinib or a composition comprising vemurafenib and/or dabrafenib and/or trametinib and/or selumetinib. A miRNA-3157-5p and/or an equivalent and/or a source thereof has been extensively defined earlier herein.

Another preferred first combination is such that said at least one compound from the first list is a miRNA-497-5p, and/or an equivalent and/or a source thereof or a composition comprising said miRNA-497-5p, and/or equivalent and/or said source thereof and said at least one compound from the second list is vemurafenib and/or dabrafenib and/or trametinib and/or selumetinib or a composition comprising vemurafenib and/or dabrafenib and/or trametinib and/or selumetinib. A miRNA-497-5p and/or an equivalent and/or a source thereof has been extensively defined earlier herein.

Another preferred first combination is such that said at least one compound from the first list is a miRNA-129-5p, and/or an equivalent and/or a source thereof or a composition comprising a miRNA-129-5p and/or equivalent and/or source thereof and said at least one compound from the second list is vemurafenib and/or dabrafenib and/or trametinib and/or selumetinib or a composition comprising vemurafenib and/or dabrafenib and/or trametinib and/or selumetinib. A miRNA-129-5p and/or an equivalent and/or a source thereof has been extensively defined earlier herein.

Another preferred first combination is such that:
a) said at least two compounds from the first list is a miRNA-16-5p and a miRNA-b-3p, and/or an equivalent and/or a source thereof or a composition comprising said miRNA-16-5p and a miRNA-10b-3p and/or an equivalent and/or a source thereof, and
b) said at least one compound from the second list is vemurafenib and/or dabrafenib trametinib and/or selumetinib or a composition comprising vemurafenib and/or dabrafenib and/or trametinib and/or selumetinib.

A miRNA-16-5p and a miRNA-10b-3p and/or an equivalent and/or a source thereof has been extensively defined earlier herein.

In a further aspect of the invention, a second combination is provided, said combination comprising at least two compounds. Said second combination is such that it comprises the compound present in the first list below and at least one compound from the second list below:
a) a miRNA molecule miRNA-3157-5p, an equivalent or a source thereof, or a composition comprising said miRNA, equivalent or source thereof and
b) at least one cancer drug as defined earlier herein, preferably a RNR inhibitor and/or AURKB inhibitor as defined herein.

The compound present in the first list has already been extensively defined herein.

Below we define the preferred at least one compound from the second list present in a second combination of the invention.

RNR and/or AURKB inhibitors are compounds that specifically inhibit RNR and/or AURKB proteins.

RNR is a ribonucleotide reductase (RNR) and as such is the only enzyme responsible for the de novo conversion of ribonucleoside diphosphate (NDP) to deoxyribonucleoside diphosphate (dNDP) (Zhou et al 2013). RNR is the key regulator of intracellular dNTP supply. Maintenance of a balanced dNTP pool is a fundamental cellular function because the consequences of imbalance in the substrates for DNA synthesis and repair include mutagenesis and cell death. Human RNR is composed of a subunits (RRM1) that contain the catalytic site and two binding sites for enzyme regulators and b subunits (RRM2) with a binuclear iron cofactor that generates the stable tyrosyl radical necessary for catalysis. An inhibitor of RNR may inhibit RRM1 and/or RRM2.

AURKB (Aurora B kinase) is a protein that functions in the attachment of the mitotic spindle to the centromere. Chromosomal segregation during mitosis as well as meiosis is regulated by kinases and phosphatases. The Aurora kinases associate with microtubules during chromosome movement and segregation. In cancerous cells, over-expression of these enzymes causes unequal distribution of genetic information, creating aneuploid cells, a hallmark of cancer.

A preferred second combination is:
a) a miRNA molecule miRNA-3157-5p, an equivalent or a source thereof, or a composition comprising said miRNA, equivalent or source thereof and
b) at least one cancer drug defined herein, preferably a RNR inhibitor preferably said RNR inhibitor is selected from the group consisting of gemcitabine, hydroxyurea, clolar clofarabine and triapine.

Another preferred second combination is:
a) a miRNA molecule miRNA-3157-5p, an equivalent or a source thereof, or a composition comprising said miRNA, equivalent or source thereof and
b) at least one cancer drug defined herein, preferably a AURKB inhibitor.

Another preferred second combination is:
a) a miRNA molecule miRNA-3157-5p, an equivalent or a source thereof, or a composition comprising said miRNA, equivalent or source thereof and
b) at least one cancer drug, preferably at least one RNR inhibitor and at least one AURKB inhibitor, more preferably said RNR inhibitor is selected from the group consisting of gemcitabine, hydroxyurea, clolar and clofarabine.

Therefore one or several distinct cancer drugs and/or one or several RNR inhibitors and/or one or several distinct AURKB inhibitors may be present in a second combination of the invention. Several RNR inhibitors is synonymous with several distinct RNR inhibitors. The same holds with several AURKB inhibitors.

A cancer drug is a drug that is able to induce or promote an anti-cancer effect as later defined herein. A preferred cancer drug is a RNR inhibitor and/or an AURKB inhibitor. Such inhibitors are compounds that specifically inhibit the RNR and/or the AURKB proteins respectively. To evaluate the ability of a therapeutic compound to inhibit RNR and/or AURKB proteins, one can perform western blotting with RNR (RRM1 and/or RRM2) or AURKB protein as read-out. Cells are plated in 6-well plates and treated for 72 hours at 0.01, 0.1 and 1 uM of said compound. After treatment cells are scraped into a lysis buffer as a RIPA lysis buffer. Equal amounts of protein extracts are separated by using 10% SDS-PAGE, and then transferred to a polyvinylidene difluoride membrane. After blocking for 1 hour in a Tris-buffered saline containing 0.1% Tween 20 and 5% nonfat milk, the membrane is probed with a RNR (i.e. RRM1 and/or RRM2) and/or a AURKB primary antibody, followed by a secondary antibody conjugated to horseradish peroxidase for chemiluminescent detection on film. Tubulin is used as loading control. A preferred RRM2 antibody used is from Santa Cruz (product#sc-10846) and/or a preferred AURKB antibody is from Cell Signalling (product#3094). The evaluation of the therapeutic ability of said RNR and/or AURKB inhibitor may also be assessed at the RNA level by carrying out a Northern blot or by PCR. It may also be possible to evaluate the ability of a therapeutic compound to inhibit RNR and/or AURKB protein by assessing an activity of RNR and/or AURKB in a CDP assay as described by Steeper et al., 1970.

An inhibition of a RNR and/or AURKB protein/RNA/activity may therefore be assessed when a low or a decreased or a detectable decrease of the level of a RNR and/or AURKB protein/RNA/activity is identified using an assay as explained above, said decrease being identified by comparison to the level of such RNR and/or AURKB protein/RNA/activity when said compound is not added to the cells. A detectable decrease may be a decrease of at least 5%, 10%, 15%, 20%, 25%, 30%, 35%, 40%, 45%, 50%, 55%, 60%, 65%, 70%, 75%, 80%, 85%, 90%, 95%. Preferably no RNR and/or AURKB protein/RNA/activity is detectable.

The detection of the presence of a miRNA molecule or of an equivalent or a mimic or an isomiR or an antagomir molecule or an equivalent thereof each as earlier defined herein may be carried out using any technique known to the skilled person. The assessment of the expression level or of the presence of a miRNA molecule or of an equivalent or a mimic or an antagomir thereof is preferably performed using classical molecular biology techniques such as (real time) qPCR, microarrays, bead arrays, RNAse protection analysis or Northern analysis. The skilled person will understand that alternatively or in combination with the quantification of a miRNA molecule or of an equivalent or a mimic or an antagomir thereof, the quantification of a substrate of a corresponding miRNA molecule or of an equivalent thereof or of any compound known to be associated with a function of said miRNA molecule or of said equivalent thereof or the quantification of a function or activity of said miRNA molecule or of said equivalent thereof using a specific assay is encompassed within the scope of the invention.

Preferred first or second combinations, compositions and formulations are all defined later herein. A miRNA molecule or an equivalent or a mimic or an isomiR or an antagomir thereof may be used as such as a naked molecule, with or without chemical modifications, or encapsulated into a particle or conjugated to a moiety. A preferred composition comprises a miRNA molecule or an equivalent or an antagomir thereof encapsulated into a nanoparticle or a liposomal structure. A miRNA molecule or equivalent or an antagomir thereof may be an aptamer-miRNA hybrid. An aptamer-miRNA is defined as a miRNA linked to a nucleic acid (RNA or DNA) oligonucleotide, the latter adopting a conformation that targets the aptamer-miRNA hybrid molecule to a cell-surface protein present on a melanoma cell or on any other type of cancer cells as defined herein. The aptamer-tagged miRNA can be linked to e.g. polyethylene glycol, which increases the chimera's circulating half-life (Dassie, J. P., et al).

Any disease or condition wherein melanoma is involved or associated or diseases or conditions associated with activated BRAF pathway may be prevented, delayed, cured, regressed and/or treated with a "first combination" or "a-miRNA-518b-based compound" or "at least one miRNA molecule, equivalent or source selected from a first list" as defined herein. In a disease or condition of the invention, melanoma may be detectable during the development of said disease or condition, i.e. after the apparition of a symptom of said disease or condition.

Accordingly, within the context of the invention, a melanoma encompasses each stage of said melanoma:
  dysplastic or benign nevi (common acquired or congenital), or
  in situ melanoma wherein melanocytes undergo radial growth phase, in which the growth expands laterally. Melanoma cells are only present in the epidermis, or
  a melanoma wherein melanoma cells have progressed to the vertical growth phase and are able to invade the dermis of the skin, usually 1 to 4 mm in depth but wherein no signs of metastasis/spreading of melanoma cells are visible, or
  a melanoma wherein melanoma cells already have metastasized either to a lymph node and/or to distant organs such as liver, lung and/or brain.

The skilled person will understand that each stage which could be considered as intermediate within each of the above identified stages is also encompassed by the present invention. Melanoma may be detected using any technique known to the skilled person. Alternatively, melanoma and any stage thereof as identified above may be diagnosed by assessing the expression of a miRNA molecule (i.e. miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p). Such assessment is preferably carried out in a tumor biopsy or section at several time points for a given subject or at one or several time points for a given subject and a healthy control. The assessment may be carried out each week, each month. The most important prognostic measure of progression is the Breslow thickness, which measures vertical thickness of the lesion: from the upper layer of the epidermis to the innermost depth of invasion (Balch C. M. et al.,). Other prognostic factors are the mitotic rate of the lesion (Scolyer R. A. et al.) and vascular invasion (Mraz-Gernhard S. et al.).

A disease or condition wherein melanoma is involved or associated could also be named cutaneous melanoma, a tumor of melanocytes, an uveal melanoma (i.e. tumor of melanocytes found in the eye), a tumor of melanocytes found in the bowel, Lentigo maligna, Lentigo maligna melanoma, superficially spreading melanoma, acral lentiginous melanoma, mucosal melanoma, modular melanoma, polypoid melanoma, desmoplastic melanoma, amelanotic melanoma, soft-tissue melanoma, melanoma with small nevus-like cells or melanoma with features of a Spitz nevus.

Within the context of the invention, a melanoma is a cancer present in or originating from melanocytes. Melanocytes are the cells that produce the skin coloring or pigment known as melanin. Melanin helps protect the deeper layers of the skin from the harmful effects of the sun.

By contrast to melanoma, there exist other types of skin cancers classified as non-melanomas skin cancer, usually starting in either basal cells or squamous cells. These cells are located at the base of the outer layer of the skin or cover the internal and external surfaces of the body. Most non-melanoma skin cancers develop on sun-exposed areas of the body, like the face, ear, neck, lips, and the backs of the hands. Depending on the type, they can be fast or slow growing, but they rarely spread to other parts of the body. Non-melanoma skin cancers may include benign, pre-malignant and malignant tumours of keratinocytes, which are the predominant type of cutaneous epithelial cells. Keratinocyte cancers include epidermal tumours such as basal cell carcinoma (BCC), squamous cell carcinoma (SCC) or a pre-malignant lesion thereof, hair follicle tumors, such as trichoblastoma, trichoepitelioma, pilomatrixoma, pilomatrixcarcinoma, trichoadenoma, trichofolliculoma; sweat gland tumors such as adnexcarcinoma, mucinous eccrin carcinoma, porocarcinoma; and premalignant lesions of the skin such as actinic keratosis, morbus Bowen, and erythroplasia Queyrat.

These two types of skin cancers (melanoma versus non-melanoma skin cancers) are totally irrelated from a biological point of view. Accordingly, preferably the invention relates to melanoma and not to non-melanoma skin cancer originating from basal or squamous cells and called BCC or SCC.

A disease or condition associated with activated BRAF pathway may be a melanoma as identified herein or papillary thyroid cancer, colorectal cancer, serous ovarian cancer or lung cancer.

The second combination of the invention is preferably used for preventing, treating, regressing, curing and/or delaying a cancer that acquired resistance to a cancer drug and is accompanied by an upregulation of RRM2 and/or AURKB in a subject. In the context of this second combination, a cancer is potentially any cancer wherein an acquired resistance to a cancer drug has been demonstrated. An acquired resistance to a cancer drug may be demonstrated by demonstrating a decrease of an anti-tumour treatment induced by said drug. Said drug is preferably an inhibitor of a RNR and/or an inhibitor of a AURKB as defined herein An upregulation of RRM2 and/or of AURKB may be assessed at the protein/RNA/activity level using techniques known to the skilled person.

A preferred cancer wherein a resistance to a cancer drug has been acquired and wherein an increase/upregulation of RRM2 occurs is ovarian cancer, acute lymphoblastic leukemia, pancreatic cancer, breast cancer, prostate cancer, colorectal cancer.

A preferred cancer wherein a resistance to a cancer drug has been acquired and wherein an increase/upregulation of AURKB occurs is NSCLC, breast cancer, colon cancer, kidney cancer, prostate cancer.

There is currently no effective known medicament that may be used for specifically preventing, treating, regressing, curing and/or delaying a disease or condition associated with melanoma or a disease or condition associated with activated BRAF pathway in a subject or a cancer associated with an acquired resistance to a cancer drug, preferably a RNR inhibitor and/or a AURKB inhibitor as defined herein and wherein an increase/regulation of RRM2 and/or of AURKB occurs. The invention encompasses to use a "first combination" or "a miRNA-518b-based compound" or "at least one miRNA molecule, equivalent or source thereof from a first list" or a "second combination" or a "stand alone therapy using miRNA-3157" depending on the type of disease and condition mentioned.

The first combination comprises or consists of at least two compounds, at least one compound being taken from the first list and at least one compound being taken from the second list:
 a) at least one miRNA molecule selected from a miRNA-96-5p, miRNA-10b-3p, miRNA-129-5p, miRNA-3157-5p, miRNA-200c-5p, miRNA-182-3p, miRNA-16-5p, miRNA-497-5p, miRNA-518b and/or a miRNA-7-5p molecule, an equivalent or a source thereof, or a composition comprising said at least one miRNA, equivalent or source thereof and
 b) at least one B-raf and/or MEK inhibitor, preferably vemurafenib and/or dabrafenib, and/or trametinib and/or selumetinib, a composition comprising said at least one said B-raf and/or MEK inhibitor.

The second combination comprises or consists of the compound present in the first list below and at least one compound from the second list below:
a) a miRNA molecule miRNA-3157-5p, an equivalent or a source thereof, or a composition comprising said miRNA, equivalent or source thereof and
b) at least one cancer drug as defined herein, preferably at least one RNR inhibitor and/or at least one AURKB inhibitor.

The invention includes increasing an activity or the steady-state level or the expression level or the amount of each compound of said first or second combination or stand alone therapy as defined herein. An activity or a steady-state level of said at least one miRNA molecule or equivalent or mimic or isomiR thereof or of said source thereof and an activity or amount of steady-state level of said at least one B-raf and/or MEK inhibitor or preferably vemurafenib and/or dabrafenib and/or trametinib and/or selumetinib or of said cancer drug (preferably a RNR inhibitor and/or an AURKB inhibitor), is increased in a subject, in a cell of said subject, in a tissue of said subject or in body fluid of said subject.

An activity or steady-state level or expression level or amount of said at least one miRNA molecule or equivalent or mimic or isomiR thereof or source thereof and of said activity or amount or steady state level of said at least one B-raf and/or MEK inhibitor, preferably vemurafenib and/or dabrafenib and/or trametinib and/or selumetinib or of said cancer drug (preferably a RNR inhibitor and/or an AURKB inhibitor), is increased in order to induce a detectable decrease of proliferation, survival, invasion and/or migration and/or to induce apoptosis and/or to induce an anti-tumour effect and/or to interfere with the constitutively active BRAF-MEK-ERK pathway in a subject, preferably in melanoma cells or tumor cells from said subject.

The assessment of the expression level of any miRNA molecule as defined herein is preferably carried out in a tumor biopsy or section at several time points for a given subject or at one or several time points for a given subject and a healthy control. The assessment may be carried out at regular time intervals, e.g. each week, each month. The increase/decrease may therefore be assessed regularly, e.g. each week, each month. A detectable decrease of proliferation and/or a detectable decrease of survival and/or a detectable increase in apoptosis and/or a detectable decrease in invasion and/or migration is preferably assessed as later explained herein to define an anti-tumor effect. In order to assess an interference with the constitutively active BRAF-MEK-ERK pathway, the activation state of this pathway is preferably assessed before treatment in melanoma or tumor cells from said subject. The activation of said pathway may be detected by direct measurement of phosphorylation of MEK and/or ERK1 and/or ERK2 in vitro and/or stimulation of ERK signalling in vivo (Davies H. et al., 2002, Ikenoue T. et al., 2003, Houben R. et al., Wan P. T. et al) or by measurement of phosphorylation of transcription factors downstream of ERK1/2. An assay has been earlier described herein for assessment of B-raf or MEK inhibition. In a preferred embodiment, there is an interference with a constitutively active BRAF-MEK-ERK pathway when MEK, ERK1/2 phosphorylation and/or activity of the ERK signalling is reduced, decreased compared to cells with an unencumbered constitutively active BRAF-MEK-ERK pathway, which consequently results in inhibition of proliferation and induction of apoptosis (Hingorani S. R. et al., and Karasarides M. et al.).

An activity or steady-state level or expression level of said at least one miRNA molecule (i.e. a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p) or equivalent or mimic or isomiR thereof or source thereof may be increased at the level of the miRNA molecule (or equivalent thereof) itself, e.g. by providing said miRNA molecule or equivalent thereof to a subject, preferably to a cell of a subject, or to a tissue of said subject, or to an organ of said subject or to said subject said miRNA molecule or equivalent thereof being from an exogenous source. For provision of a miRNA molecule or equivalent thereof from an exogenous source, said miRNA molecule or equivalent thereof may conveniently be produced by expression of a nucleic acid encoding said miRNA molecule or equivalent thereof or encoding a source of said miRNA molecule or equivalent thereof in a suitable host cell as described below or as completely synthetic molecules by chemical synthesis.

Preferably, however, an activity or steady-state level or expression level of said at least one miRNA molecule (a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p) or equivalent thereof is increased by regulating the expression level of a nucleotide sequence encoding said miRNA molecule or equivalent thereof or encoding a source of said miRNA molecule or equivalent thereof. Preferably, the expression level of a nucleotide sequence is regulated in a cell of said subject or in a tissue of said subject or in the subject. The expression level of a miRNA molecule or equivalent thereof or a source of said miRNA molecule or equivalent thereof may be increased by introduction of a miRNA, and equivalent, or a source thereof, or an expression construct (or vector) into a cell, tissue, organ or body fluid of said subject, or in the subject whereby an expression vector comprises a nucleotide sequence comprising said miRNA molecule (i.e. a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p) or equivalent thereof or comprising a source of said miRNA molecule or equivalent thereof, and whereby a nucleotide sequence is under control of a promoter capable of driving expression of a nucleotide sequence in said cell, tissue, organ, subject. The expression level of said miRNA molecule or equivalent thereof or source thereof may also be increased by introduction of an expression construct into a cell, tissue, organ, subject, whereby a construct comprises a nucleotide sequence encoding a factor capable of trans-activation of an endogenous nucleotide sequence encoding a miRNA molecule or equivalent thereof.

An activity or steady-state level or amount of said at least one B-raf inhibitor preferably vemurafenib and/or dabrafenib, is increased in a subject, in a cell of said subject, in a tissue of said subject or in body fluid of said subject by increased concentration of said at least one B-raf inhibitor, preferably vemurafenib or dabrafenib in said cell, tissue or body fluid, and/or by increased inhibition of the B-raf enzyme in said cell, tissue or body fluid, and/or by increased inhibition of the BRAF-MEK-ERK pathway, especially the B-raf/MEK step therein, in said cell, tissue or body fluid, and/or increased apoptosis of melanoma cells in said subject. The same holds for an activity or steady-state level or amount of said at least one MEK inhibitor, preferably trametinib and/or selumetinib by increased inhibition of a MEK enzyme in said cell, tissue or body fluid, and/or by increased inhibition of the BRAF-MEK-ERK pathway, especially the B-raf/MEK step therein, in said cell, tissue or body fluid, and/or increased apoptosis of melanoma cells in said subject.

An activity or steady-state level or amount of said at least one cancer drug (preferably at least one RNR inhibitor and/or at least one AURKB inhibitor preferably as earlier defined herein), is increased in a subject, in a cell of said subject, in a tissue of said subject or in body fluid of said subject by increased concentration of said at least one inhibitor in said cell, tissue or body fluid.

A first combination of the invention preferably comprises a composition comprising at least one nucleic acid construct for increasing the activity or steady state level or expression level of said at least one miRNA molecule or equivalent as defined herein (i.e. miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p) and at least one B-raf and/or MEK inhibitor, preferably vemurafenib and/or dabrafenib and/or trametinib and/or selumetinib, or a composition comprising at least one B-raf and/or MEK inhibitor. The same holds for the miRNA molecule, equivalent or source thereof present in two other compounds/treatments of the invention: the "miRNA-518b-based compound" and for the "at least one miRNA molecule, equivalent or source thereof present in the first list" and for the "stand alone/sole therapy using miRNA-3157"). A nucleic acid construct may be an expression construct as further specified herein. Preferably, an expression construct is a viral gene therapy vector selected from gene therapy vectors based on an adenovirus, an adeno-associated virus (AAV), a herpes virus, a pox virus, an oncolytic virus vector and a retrovirus. A preferred viral gene therapy vector is an AAV or lentiviral vector.

Alternatively, a first combination preferably comprises a composition comprising at least one miRNA molecule (i.e. a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p), an equivalent or a source thereof and at least one B-raf and/or MEK inhibitor, preferably vemurafenib and/or dabrafenib and/or trametinib and/or selumetinib or a composition comprising at least one B-raf and/or MEK inhibitor as defined herein. The same holds for the miRNA molecule, equivalent or source thereof present in two other compounds/treatments of the invention: the "miRNA-518b-based compound" and for the "at least one miRNA molecule, equivalent or source thereof present in the first list" and for the "stand alone/sole therapy using miRNA-3157". The same also holds for the miRNA molecule, equivalent or source thereof present in a second combination of the invention.

In the invention, a cell, a tissue, an organ or body fluid is preferably from a subject suspected to have a high risk of having a melanoma or to have a disease or condition associated with melanoma or having a disease or condition associated with activated BRAF pathway due for example to its age or its genetic background or to its diet or to the country wherein he lives or to his frequency of sun exposition or to his frequency of use of tanning salons. Alternatively, in another preferred embodiment, the invention is applied on a cell, tissue, organ or body fluid from a subject diagnosed as either having a predictive risk for developing later a disease or condition associated with melanoma or having a disease or condition associated with activated BRAF pathway. Alternatively, a cell, a tissue or organ to be treated may be selected based on risk of progression of the disease or condition associated with melanoma or having a disease or condition associated with activated BRAF pathway. Such risk of progression may be assessed using classical clinic-pathological criteria or biomarker-based prognosis known to the skilled person.

It is also encompassed by the invention to administer a first combination comprising:
  a) at least one miRNA molecule (i.e. a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p) or equivalent thereof or a source thereof, or a composition comprising said at least one miRNA molecule or equivalent thereof or source thereof and
  b) at least one B-raf and/or MEK inhibitor, preferably vemurafenib and/or dabrafenib and/or trametinib and/or selumetinib or a composition said at least one B-raf and/or MEK inhibitor,
into a tissue or organ of said subject. The same holds for the two other compounds/treatments of the invention: the "miRNA-518b-based compound" and for the "at least one miRNA molecule, equivalent or source thereof present in the first list". In the invention, a preferred cell, tissue or organ is a cell, tissue or organ that is or comprises a melanoma or skin or eye cell or tissue or is or comprises the eye or the skin as organ. In the invention, another preferred cell or tissue is a cell or tissue organ that is or comprises a tumor and that is a thyroid gland, a colon, a lung or an ovary cell or tissue, or a cell or tissue that is or comprises a tumor that is derived from a thyroid gland tumor, a colon tumor, a lung tumor or an ovary tumor. A preferred organ may be or may comprise the thyroid gland, the colon, the lung or the ovary as organ, or an organ that is or comprises a tumor that is derived from a thyroid gland tumor, a colon tumor, a lung tumor or an ovary tumor.

A treatment of a disease or condition associated with melanoma may include a treatment that prevents melanoma in a tumor cell that has not yet metastasized or regresses melanoma in a tumor cell that has already formed metastases and/or is migrating from the primary tumor to distant sites in the body.

A treatment of a disease or condition associated with activated BRAF pathway may include a treatment that regresses such diseases or conditions in a tumor cell that has already formed metastases and/or is migrating from the primary tumor to distant sites in the body.

In the invention, a cell, a tissue, an organ or body fluid is preferably from a subject suspected to have a high risk of having a disease or condition, preferably a cancer with an acquired resistance to a cancer drug (preferably to a RNR inhibitor and/or a AURKB inhibitor) and/or wherein an increase/upregulation of a RRM2 and/or of a AURKB occurs due for example to its age or its genetic background or to its diet or to the country wherein he lives or to his frequency of sun exposition or to his frequency of use of tanning salons. Alternatively, in another preferred embodiment, the invention is applied on a cell, tissue, organ or body fluid from a subject diagnosed as either having a predictive risk for developing later a disease or condition, preferably a cancer with an acquired resistance to a cancer drug (preferably to a RNR inhibitor and/or a AURKB inhibitor) and/or wherein an increase/upregulation of a RRM2 and/or of a AURKB occurs. Alternatively, a cell, a tissue or organ to be treated may be selected based on risk of progression of a disease or condition, preferably a cancer with an acquired resistance to a cancer drug (preferably to a RNR inhibitor and/or a AURKB inhibitor) and/or wherein an increase/upregulation of a RRM2 and/or of a AURKB occurs. Such risk of progression may be assessed using classical clinico-pathological criteria or biomarker-based prognosis known to the skilled person.

It is also encompassed by the invention to administer a second combination comprising:
a) a miRNA molecule miRNA-3157-5p, an equivalent or a source thereof, or a composition comprising said miRNA, equivalent or source thereof and
b) at least one cancer drug, preferably a RNR inhibitor and/or a AURKB inhibitor into a tissue or organ of said subject. In the invention, a preferred cell, tissue or organ is a cell, tissue or organ that is or comprises an ovarian cell, a blood cell, a breast cell, a prostate cell, a colorectal cell, a colon cell, a kidney cell. A preferred tissue is or comprises blood, breast, prostate, colorectal, colon or kidney. A preferred organ is or comprises ovarian organ, blood, breast, prostate, colon or kidney.

In the invention, another preferred cell or tissue is a cell or tissue organ that is or comprises a tumor.

A treatment of a disease or condition, preferably a cancer with an acquired resistance to a cancer drug (preferably to a RNR inhibitor and/or a AURKB inhibitor) and wherein an increase/upregulation of a RRM2 and/or of a AURKB occurs (more preferably ovarian cancer, acute lymphoblastic leukemia, pancreatic cancer, breast cancer, prostate cancer, colorectal cancer) may include a treatment that prevents the development of said cancer in a tumor cell that has not yet metastasized or regresses of said cancer in a tumor cell that has already formed metastases and/or is migrating from the primary tumor to distant sites in the body. A treatment of such a disease or condition may include a treatment that regresses such diseases or conditions in a tumor cell that has already formed metastases and/or is migrating from the primary tumor to distant sites in the body.

The "first or second combination" of the invention, the "miRNA-518b-based compound" and the "at least one miRNA molecule, equivalent or source thereof present in the first list" may be combined with standard treatments of disease or condition associated with melanoma or of a disease or condition associated with activated BRAF pathway or other types of cancer as defined herein for the second combination such as chemotherapy, radiotherapy or surgery. Examples of chemotherapeutic agents are exemplified later herein. The same holds for the "sole therapy using miRNA-3157" for the type of cancer concerned as indicated herein.

Although gene therapy is a possibility for preventing, treating, regressing, curing and/or delaying a condition or a disease associated with melanoma or of a disease or condition associated with activated BRAF pathway, other possible treatments may also be envisaged.

In the context of the invention, preventing, treating, regressing, curing and/or delaying a disease or condition associated with melanoma or a disease or condition associated with activated BRAF pathway or other types of cancer as defined for the second combination may mean that:
  at least a symptom of this disease or condition has been improved, and/or
  at least a parameter associated with this disease or condition has been improved.

The improvement may be measured during at least one week, one month, six months of treatment or more. A symptom may be the presence of metastases as explained below. A parameter may be the assessment of the interference with constitutive active BRAF-MEK-ERK pathway as explained herein.

In the context of the invention, preventing, treating, regressing, curing and/or delaying a disease or condition associated with melanoma or a disease or condition associated with activated BRAF pathway or preventing, treating, regressing, curing and/or delaying a cancer with an acquired resistance to a cancer drug (preferably to a RNR inhibitor and/or a AURKB inhibitor) and wherein an increase/upregulation of a RRM2 and/or of a AURKB occurs may be replaced by achieving an anti-tumor effect. Unless otherwise indicated, an anti-tumor effect is preferably assessed or detected before treatment and after at least one week, two weeks, three weeks, fours weeks, one month, two months, three months, four months, five months, six months or more in a treated subject. An anti-tumor effect is preferably identified in a subject as:
  an inhibition of proliferation or a detectable decrease of proliferation of tumor cells or a decrease in cell viability of tumor cells or melanocytes, and/or
  an increase in the capacity of differentiation of tumor cells, and/or
  an increase in tumor cell death, which is equivalent to a decrease in tumor cell survival, and/or
  a delay in occurrence of metastases and/or of tumor cell migration, and/or an inhibition or prevention or delay of the increase of a tumor weight or growth, and/or a prolongation of patient survival of at least one month, several months or more (compared to those not treated or treated with a control or compared with the subject at the onset of the treatment).

In the context of the invention, a patient may survive and may be considered as being disease free. Alternatively, the disease or condition may have been stopped or delayed or regressed. An inhibition of the proliferation of tumor cells may be at least 20%, 30%, 40%, 50%, 55%, 60%, 65%, 70% or 75% or more. Proliferation of cells may be assessed using known techniques. A decrease in cell viability of tumor cells or melanocytes may be a decrease of at least 20%, 30%, 40%, 50%, 55%, 60%, 65%, 70% or 75% or more. Such decrease may be assessed 4 days after transfection with a given miRNA molecule, equivalent or source thereof. Cell viability may be assessed via known techniques such as the MTS assay, preferably as used in the experimental part.

An induction of tumor cell death may be at least 1%, 5%, 10%, 15%, 20%, 25%, or more. A decreased in tumor cell survival may be a decrease of at least 1%, 5%, 10%, 15%, 20%, 25%, or more. Tumor cell death may be assessed by measurement of radiolabeled Annexin A5, a molecular imaging agent to measure cell death in vitro, and non-invasively in patients with cancer (Schutters K. et al.,).

Tumor growth may be inhibited at least 5%, 10%, 20%, 30%, 40%, 50%, 55%, 60%, 65%, 70% or 75%, or more. Tumor growth may be assessed using techniques known to the skilled person. Tumor growth may be assessed using MRI (Magnetic Resonance Imaging) or CT (Computer Tomography).

In certain embodiments, tumor weight increase or tumor growth may be inhibited at least 20%, 30%, 40%, 50%, 55%, 60%, 65%, 70% or 75%, or more. Tumor weight or tumor growth may be assessed using techniques known to the skilled person.

The detection of tumor growth or the detection of the proliferation of tumor cells may be assessed in vivo by measuring changes in glucose utilization by positron emission tomography with the glucose analogue 2-[18F]-fluor-2-deoxy-D-glucose (FDG-PET) or [18F]-'3-fluoro-'3-deoxy-L-thymidine PET. An ex vivo alternative may be staining of a tumor biopsy with Ki67.

A delay in occurrence of metastases and/or of tumor cell migration may be a delay of at least one week, one month, several months, one year or longer. The presence of metastases may be assessed using MRI, CT or Echography or techniques allowing the detection of circulating tumour cells (CTC). Examples of the latter tests are CellSearch CTC test (Vendex), an EpCam-based magnetic sorting of CTCs from peripheral blood.

An increase in the capacity of differentiation of tumor cells may be assessed using a specific differentiation marker and following the presence of such marker on cells treated. Preferred markers or parameters have already been identified herein, i.e. p16 (Oshie S. et al.), Trp-1 and PLZF (Felicetti F., 2004), c-Kit, MITF, Tyrosinase (Felicetti F. 2008) and Melanin. This may be done using RT-PCR, western blotting or immunohistochemistry. An increase of the capacity of differentiation may be at least a detectable increase after at least one week of treatment using any of the identified techniques. Preferably, the increase is of 1%, 5%, 10%, 15%, 20%, 25%, or more, which means that the number of differentiated cells within a given sample will increase accordingly. In certain embodiments, tumor growth may be delayed at least one week, one month, two months or more. In a certain embodiment, an occurrence of metastases is delayed at least one week, two weeks, three weeks, fours weeks, one months, two months, three months, four months, five months, six months or more.

Accordingly, in a preferred embodiment, a first combination of the invention is such that:

a) resistance to at least one B-raf and/or MEK inhibitor, preferably vemurafenib and/or dabrafenib and/or trametinib and/or selumetinib is at least overcome, circumvented or delayed, and/or b) the therapeutic effect of at least one B-raf and/or MEK inhibitor, preferably vemurafenib and/or dabrafenib and/or trametinib and/or selumetinib, is optimized and/or c) sensitization of a subject to said at least one B-raf and/or MEK inhibitor is promoted. The same holds for at least another compound/treatment of the invention: "at least one miRNA molecule, equivalent or source thereof present in the first list" and most probably also for the "miRNA-518b-based compound".

Sensitivity of cells to a B-raf or MEK inhibitor is associated with a concentration dependent decrease of pERK1/2 protein levels after treatment of cells with a B-raf or MEK inhibitor at concentrations varying from 0.01 to 10 µM. The assessment of pERK1/2 has already been explained earlier herein.

Resistance of cells to a B-raf or MEK inhibitor is associated with a concentration independent constant level of pERK1/2 protein after treatment of cells with a B-raf or MEK inhibitor at concentrations varying from 0.01 to 10 µM. It means that at a concentration of 10 µM the pERK1/2 level is approximately equal to the level that is observed at a concentration of 0.01 µM. In this context, "approximately equal" may mean that a difference of 20% or less in terms of pERK1/2 level is detected, or a difference of 15% or less, 10% or less, 5% or less or 2% or less. Such resistance to a B-raf and/or a MEK inhibitor may therefore be at least delayed, overcome, circumvented when such resistance is not seen at the onset of a treatment with such a B-raf and/or MEK inhibitor. Resistance may also be delayed, overcome, circumvented when such resistance is not seen at least during the first 3, 4, 5, 6, 7, 8, 9, 10, 11, 12, 13, 14, 15, 16, 17, 18, 19, 20 months of treatment with such a B-raf and/or a MEK inhibitor. Resistance may also be delayed, prevented, overcome or circumvented if it is not seen at least during the first 20, 21, 22, 23, 24, 25, 26, 27, 28, 29, 30 months of treatment with such a B-raf and/or a MEK inhibitor. The invention provides a "combination" and "at least one miRNA molecule, equivalent or source thereof present in the first list" as defined herein that are expected to at least overcome, delay, circumvent and possibly prevent such resistance to a B-raf and/or MEK inhibitor.

The therapeutic effect of a B-raf and/or MEK inhibitor may be optimized when an optimal or maximum or synergistic effect is expected to be obtained at least on the inhibition of proliferation and/or survival and/or a detectable decrease of pERK1/2 of tumor cells or melanocytes. It is expected that a stronger inhibition of proliferation and/or of survival and/or a detectable decrease of pERK1/2 of tumor cells or melanocytes will be obtained using a combination of the invention than when using a compound from the first list or a compound from the second list. The assessment of the inhibition of the proliferation and/or survival and/or a detectable decrease of pERK1/2 of tumor cells has been defined herein. It may be carried out as described in the experimental part.

An inhibition of proliferation and/or of survival of tumor cells or melanocytes may be optimal or maximum when such inhibition is increased when using a combination of the invention compared to said inhibition when using a compound of the first list or a compound of the second list. Preferably said increase is at least 5%, 10%, 15%, 20%, 25%, 30%, 35%, 40%, 45%, 50%, 55%, 60%, 65%, 70%, 75%, 80%, 85%, 90%, 95%, 100%.

A detectable decrease of the level of pERK1/2 may be optimal or maximum when such detectable decrease is increased when using a combination of the invention compared to said detectable decrease when using a compound of the first list or a compound of the second list. Preferably said detectable decrease is at least 5%, 10%, 15%, 20%, 25%, 30%, 35%, 40%, 45%, 50%, 55%, 60%, 65%, 70%, 75%, 80%, 85%, 90%, 95%, 100% more than said detectable decrease when using a compound of the first list or a compound of the second list. Sensitization of cells that are resistant to a B-raf or MEK inhibitors is associated with a re-appearance of a concentration dependent decrease in pERK1/2 protein level after treatment of cells with a re-sensitizing drug, preferably a compound of the first list as identified herein and subsequent or combined treatment with a B-raf or MEK inhibitor at concentrations varying from 0.01 to 10 µM. It is also encompassed that a combination of the invention will promote a sensitization of tumor cells or melanocytes to a B-raf and/or MEK inhibitor.

In a further preferred embodiment, there is provided a "first combination", "miRNA-518b-based compound" and "at least one miRNA molecule equivalent or source from a first list" further comprising another miRNA molecule selected from:
a) at least one of miRNA-13, Let-7 and Let-7a and/or an equivalent or a source thereof, and/or
b) at least one antagomir of miRNA-221 and miRNA-222 and/or an equivalent or a source thereof.

Since not each of the identified miRNAs molecules or equivalents thereof is expected to have the same target genes, in a preferred embodiment of the invention it is assumed that the use of a "first combination" comprising at least one miRNA molecule selected from a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p or equivalent thereof of source thereof (or a composition comprising said at least one miRNA molecule, equivalent or source thereof) and at least one B-raf and/or MEK inhibitor, preferably vemurafenib and/or dabrafenib and/or trametinib and/or selumetinib or a composition comprising said at least one B-raf and/or MEK inhibitor optionally combined with at least one of the miRNA molecules, or equivalents thereof or sources thereof identified above under a) and/or b) allows an even more effective treatment of a disease or condition associated with melanoma or of a disease or condition associated with activated BRAF pathway. A tumor treated by a combination comprising at least one miRNA-molecule selected from a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p, or equivalent or source thereof (or a composition comprising said at least one miRNA molecule, equivalent or source thereof) and at least one B-raf and/or MEK inhibitor, preferably vemurafenib and/or dabrafenib and/or trametinib and/or selumetinib or a composition comprising said at least one B-raf and/or MEK inhibitor is expected to have fewer possibilities to escape or to resist said treatment. In a further preferred embodiment, it is encompassed to diagnose the expression of each of the miRNA molecules or of their target genes as identified herein and depending on the outcome to adapt the identity of the miRNA molecules used for the treatment. The same holds for other compounds/treatment defined herein: a "miRNA-518b-based compound" and "at least one miRNA molecule equivalent or source from a first list.

Since the invention preferably relates to a first combination of:
at least one miRNA molecule, equivalent or source thereof, or a composition comprising said at least one miRNA molecule, equivalent or source thereof and
at least one B-raf and/or MEK inhibitor, preferably vemurafenib and/or dabrafenib and/or trametinib and/or selumetinib or a composition comprising said at least one B-raf and/or MEK inhibitor,
each of the at least one miRNA molecules, equivalent, source thereof as defined herein may be combined with at least one B-raf and/or MEK inhibitor, preferably vemurafenib or dabrafenib and/or trametinib and/or selumetinib, or a composition comprising said at least one B-raf and/or MEK inhibitor as defined herein. It is also encompassed by the present invention to use a combination of at least one miRNA molecule being "miRNA-based" (i.e. miRNA, equivalent, mimic, antagomir as identified herein) with at least one B-raf and/or MEK inhibitor, preferably vemurafenib and/or dabrafenib and/or trametinib and/or selumetinib or a composition comprising said at least one B-raf and/or MEK inhibitor. It is also encompassed by the present invention to use a first combination of at least one miRNA molecule being "source-based" (i.e. DNA and/or RNA precursors of a miRNA, molecule as identified herein) with at least one B-raf and/or MEK inhibitor, preferably vemurafenib and/or dabrafenib and/or trametinib and/or selumetinib or a composition comprising at least one of said Braf inhibitor and/or MEK inhibitor.

Within the context of the invention, the word "first combination" means that
at least one miRNA molecule, equivalent or source thereof, or a composition comprising said at least one miRNA molecule, equivalent or source thereof and
at least one B-raf and/or MEK inhibitor, preferably vemurafenib and/or dabrafenib and/or trametinib and/or selumetinib or a composition comprising said at least one B-raf and/or MEK inhibitor,
are contemplated and encompassed.
Each of
at least one miRNA molecule, equivalent or source thereof, or a composition comprising said at least one miRNA molecule, equivalent or source thereof and
at least one B-raf and/or MEK inhibitor, preferably vemurafenib and/or dabrafenib and/or trametinib and/or selumetinib or a composition comprising said at least one B-raf and/or MEK inhibitor,
may be together or present together or combined together or physically in contact with the other at least one compound forming one single composition.

Each at least one compound (at least one miRNA molecule, equivalent or source thereof and at least one B-raf and/or MEK inhibitor, preferably vemurafenib and/or dabrafenib and/or trametinib and/or selumetinib, or a composition comprising said at least one B-raf and/or MEK inhibitor) may alternatively be comprised within one distinct composition. However, the invention provides the insight that both types of compounds are needed or are used in order to get an optimal or maximum effect as defined herein. If each type of compound is not present in a same composition, each type of compound may be used sequentially or simultaneously. In an embodiment, a first combination is provided wherein
   at least one miRNA molecule, equivalent or source thereof, or a composition a comprising said at least one miRNA molecule, equivalent or source thereof and
   at least one B-raf and/or MEK inhibitor, preferably vemurafenib and/or dabrafenib and/or trametinib and/or selumetinib or a composition comprising said at least one B-raf and/or MEK inhibitor,
are present in one single composition or wherein at least one miRNA molecule, equivalent or source thereof (or a composition comprising said at least one miRNA molecule, equivalent or source thereof) is present in one composition and at least one B-raf and/or MEK inhibitor, preferably vemurafenib and/or dabrafenib and/or trametinib and/or selumetinib or a composition comprising said at least one B-raf and/or MEK inhibitor is present in a distinct composition. Composition will be defined later herein.

Accordingly, in a preferred embodiment, a second combination of the invention is such that:
a) resistance to at least one cancer drug (preferably to a RNR inhibitor and/or to a AURKB inhibitor, preferably as earlier defined herein) is at least overcome, circumvented or delayed, and/or
b) the therapeutic effect of at least one cancer drug (preferably of a RNR inhibitor and/or of a AURKB inhibitor, preferably as earlier defined herein) is optimized and/or
c) sensitization of a subject to said at least one cancer drug (preferably to a RNR inhibitor and/or to a AURKB inhibitor is promoted).

Sensitivity of cells to a RNR inhibitor and/or AURKB inhibitor is associated with the capacity of the cells to downregulate/reduce RRM2 and/or AURKB at the protein/RNA level as earlier explained herein. Alternatively an activity of RRM2 and/or of AURKB may be downregulated/decreased.

Resistance of cells to a RNR inhibitor and/or AURKB inhibitor is associated with the capacity of the cells to upregulate/increase RRM2 and/or AURKB at the protein/RNA level as earlier explained herein. Alternatively an activity of RRM2 and/or of AURKB may be upregulated/increased.

Such resistance to a cancer drug (preferably to a RNR inhibitor and/or to a AURKB inhibitor) may therefore be at least delayed, overcome, circumvented when such resistance is not seen at the onset of a treatment with such an inhibitor. Resistance may also be delayed, overcome, circumvented when such resistance is not seen at least during the first 3, 4, 5, 6, 7, 8, 9, 10, 11, 12, 13, 14, 15, 16, 17, 18, 19, 20 months of treatment with such an inhibitor. Resistance may also be delayed, prevented, overcome or circumvented if it is not seen at least during the first 20, 21, 22, 23, 24, 25, 26, 27, 28, 29, 30 months of treatment with such an inhibitor.

The invention provides a "second combination" as defined herein that is expected to at least overcome, delay, circumvent and possibly prevent such resistance to such inhibitor.

The therapeutic effect of such a cancer drug (preferably a RNR inhibitor and/or a AURKB inhibitor) may be optimized when an optimal or maximum or synergistic effect is expected to be obtained at least on the inhibition of proliferation and/or survival/viability and/or a detectable decrease of viability of tumor cells. It is expected that a stronger inhibition of proliferation and/or of survival and/or a detectable decrease of viability of tumor cells will be obtained using a second combination of the invention than when using a compound from the second list alone. The assessment of the inhibition of the proliferation and/or survival and/or a detectable decrease of viability of tumor cells has been defined herein.

An inhibition of proliferation and/or of survival of tumor cells may be optimal or maximum when such inhibition is increased when using a second combination of the invention compared to said inhibition when using the compound of the first list or a compound of the second list. Preferably said increase is at least 5%, 10%, 15%, 20%, 25%, 30%, 35%, 40%, 45%, 50%, 55%, 60%, 65%, 70%, 75%, 80%, 85%, 90%, 95%, 100%.

A detectable decrease of the level of viability of tumour cells may be optimal or maximum when such detectable decrease is increased when using a second combination of the invention compared to said detectable decrease when using the compound of the first list or a compound of the second list. Preferably said detectable decrease is at least 5%, 10%, 15%, 20%, 25%, 30%, 35%, 40%, 45%, 50%, 55%, 60%, 65%, 70%, 75%, 80%, 85%, 90%, 95%, 100% more than said detectable decrease when using the compound of the first list or a compound of the second list.

Sensitization of cells that are resistant to a cancer drug (preferably a RNR inhibitor and/or a AURKB inhibitor) is associated with a re-appearance of a concentration dependent decrease in tumour cell viability after treatment of cells with a re-sensitizing drug, preferably the compound of the first list as identified herein and subsequent or combined treatment with a cancer drug (preferably a RNR inhibitor and/or a AURKB inhibitor) at concentrations varying from 0.01 to 10 µM. It is also encompassed that a second combination of the invention will promote a sensitization of tumor cells to a cancer drug (preferably a RNR inhibitor and/or a AURKB inhibitor).

Each of
a) a miRNA molecule miRNA-3157-5p, an equivalent or a source thereof, or a composition comprising said miRNA, equivalent or source thereof and
b) at least one cancer drug (preferably at least one RNR inhibitor and at least one AURKB inhibitor, more preferably as defined herein)
may be together or present together or combined together or physically in contact with the forming one single composition.

Each compound (a miRNA-3157 molecule, equivalent or source thereof) and at least one cancer drug (preferably at least one RNR inhibitor and/or at least one drug cancer) may alternatively be comprised within one distinct composition. However, the invention provides the insight that both types of compounds are needed or are used in order to get an optimal or maximum effect as defined herein. If each type of compound is not present in a same composition, each type of compound may be used sequentially or simultaneously.

A first or second combination comprises at least two compounds (at least one from the first list or the one from the first list and at least one from the second list), it is therefore encompassed that each compound may be present each in a separate composition preferably within a kit of parts, each composition being sequentially or simultaneously administered to a subject. Alternatively, it is also encompassed that more than one compound is present in a composition as defined herein.

Accordingly, a first or second combination of the invention is such that said at least one compound from the first list or the one from the first list and said at least one compound from the second list are:

(i) combined in a single composition; or
(ii) present in a kit of parts comprising at least two separate compositions for sequential or simultaneous administered to a subject.

When the invention relates to a "first or second combination" or to "at least one miRNA molecule, equivalent or source thereof from the first list" or to a "miRNA-518b-based compound" comprising more than one miRNA molecule or equivalent thereof or source thereof (or a composition comprising said more than one miRNA molecule or equivalent or source thereof) as defined herein, it is encompassed that each miRNA molecule or equivalent thereof or source thereof (or a composition comprising each miRNA molecule or equivalent thereof or source thereof) may be present each in a separate composition preferably within a kit of parts, each composition being sequentially or simultaneously administered to a subject. Alternatively, it is also encompassed that more than one miRNA molecules or equivalents thereof or sources thereof is present in a combination as defined herein.

The first or second combination according to the invention may take the form of a single composition comprising the at least one compound from the first list and the at least one compound from the second list. Alternatively, the first or second combination according to the invention may take the form of a kit of part comprising at least two separate compositions for sequential or simultaneous administered to a subject. In a preferred embodiment, the combination according to the invention is in the form of a single composition.

In said kit of parts, it is preferred that a first composition comprises the at least one compound from the first list and a second composition comprises the at least one compound from the second list. If the first or second combination according to the invention comprises more than two compounds, e.g. more than one compound from the first list or the one from the first list, and/or more than one compound from the second list, and/or further components as described herein, the more than one compounds for the same list may be present in the same composition, or in different compositions. Preferably, the more than one compounds for the same list are present in the same composition. The further components, which may optionally be present in the combination according to the invention, may be present in said first composition, and/or said second composition, and/or in a further composition.

In said kit of parts, the separate compositions are preferably present in separate containers or holders, which are linked together via physical packaging (i.e. the separate containers comprised in the kit of parts are present within a single packaging, such as in a single tray or wrapped together via physical means, such as a plastic foil), or via instructions or indices on their labels or in the accompanying manual. Such instructions indicate that the different compositions are to be administered sequentially or simultaneously to a subject. Preferably, the kit of parts comprises at least two separate compositions which are linked via physical packaging.

In a further aspect, there is provided the use of a first combination comprising:
at least one miRNA molecule selected from a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p, an equivalent or a source thereof, or a composition comprising said at least one miRNA molecule, an equivalent or a source thereof, and
at least one B-raf and/or MEK inhibitor, preferably vemurafenib and/or dabrafenib and/or trametinib and/or selumetinib or a composition comprising said at least one B-raf and/or MEK inhibitor,
for the manufacture of a medicament for preventing, treating, regressing, curing and/or delaying a disease or a condition associated with melanoma or a disease or condition associated with activated BRAF pathway. Each feature of this further aspect has already been described herein.

In a further aspect, there is provided a method for preventing, treating, regressing, curing and/or delaying a condition or disease associated with melanoma or a disease or condition associated with activated BRAF pathway by administering a first combination comprising:
At least one miRNA molecule selected from a miRNA-10b-3p, miRNA-96-5p, miRNA-129-5p, miRNA-3157-5p, miRNA-200c-5p, miRNA-182-3p, miRNA-16-5p, miRNA-497-5p, miRNA-518b and/or a miRNA-7-5p or equivalent thereof or source thereof, or a composition comprising said at least one miRNA molecule, equivalent or source thereof as earlier defined herein and
at least one B-raf and/or MEK inhibitor, preferably vemurafenib and/or dabrafenib and/or trametinib and/or selumetinib or a composition comprising said at least one B-raf and/or MEK inhibitor,
to a subject in the need thereof. Each feature of this further aspect has already been described herein.

In a further aspect, there is provided the use of a second combination comprising:
a) a miRNA molecule miRNA-3157-5p, an equivalent or a source thereof, or a composition comprising said miRNA, equivalent or source thereof and
b) at least one cancer drug (preferably at least one RNR inhibitor and at least one AURKB inhibitor) for the manufacture of a medicament for preventing, treating, regressing, curing and/or delaying a cancer with acquired resistance to a cancer drug (preferably a RNR inhibitor and/or a AURKB inhibitor as defined herein) wherein RRM2 and/or AURKB has been upregulated/increased.

Each feature of this further aspect has already been described herein.

In a further aspect, there is provided a method for preventing, treating, regressing, curing and/or delaying a condition or disease associated with acquired resistance to a cancer drug (preferably a RNR inhibitor and/or a AURKB inhibitor as defined herein) wherein RRM2 and/or AURKB has been upregulated/increased and comprising administering a second combination comprising:
a) a miRNA molecule miRNA-3157-5p, an equivalent or a source thereof, or a composition comprising said miRNA, equivalent or source thereof and
b) at least one cancer drug (preferably at least one RNR inhibitor and at least one AURKB inhibitor as defined herein), to a subject in the need thereof. Each feature of this further aspect has already been described herein.

In addition, in a further aspect, the invention provides the insight to prevent, treat, regress, cure and/or delay a disease or a condition associated with melanoma and/or a disease or a condition associated with activated BRAF pathway in a subpopulation of subjects who are resistant to a B-raf and/or MEK inhibitor administering at least one compound from the first list as identified herein. This subpopulation of subject may have been first treated with such B-raf and/or MEK inhibitor. However, this subpopulation may also not yet have been treated with such B-raf and/or MEK inhibitor. This subpopulation is no longer sensitive or is not sensitive for said B-raf and/or MEK inhibitor. Usually before deciding to start the treatment, said subject will be tested to assess whether he is sensitive or resistant to such B-raf and/or MEK inhibitor as defined herein. Preferred miRNA molecules, equivalents, sources thereof are the same as those that have already been defined herein in the context of the combination. All features of this additional aspect of the invention have already been defined herein in previous aspects of the invention.

In addition, in a further aspect, the invention provides the insight to prevent, treat, regress, cure and/or delay a cancer with acquired resistance to a cancer drug (preferably a RNR inhibitor and/or a AURKB inhibitor as defined herein) in a subpopulation of cancer subjects who are resistant to said cancer drug administering the compound from the first list as identified herein (i.e. a miRNA-3157 molecule, an equivalent, mimic, isomiR or source thereof). This subpopulation of subject may have been first treated with said cancer drug (preferably said RNR inhibitor and/or said AURKB inhibitor). However, this subpopulation may also not yet have been treated with such cancer drug (preferably said RNR inhibitor and/or said AURKB inhibitor as defined herein). This subpopulation is no longer sensitive or is not sensitive for said cancer drug (preferably said RNR inhibitor and/or said AURKB inhibitor as defined herein). Usually before deciding to start the treatment, said subject will be tested to assess whether it is sensitive or resistant to such cancer drug (preferably such RNR inhibitor and/or such AURKB inhibitor as defined herein). Preferred miRNA molecules, equivalents, sources thereof are the same as those that have already been defined herein in the context of the combination. All features of this additional aspect of the invention have already been defined herein in previous aspects of the invention.

In a further aspect, there is provided a miRNA-518b molecule, an equivalent or a source thereof or a composition comprising or consisting of said miRNA molecule, said equivalent or said source thereof for use as a medicament for preventing, treating, regressing, curing and/or delaying a disease or a condition associated with melanoma or for diseases or conditions associated with activated BRAF pathway. In this aspect, said miRNA molecule, equivalent or source thereof is preferably used as a sole active compound or as stand alone therapy in a subject as identified herein. This subject may be resistant to a B-raf and/or MEK inhibitor. However, this subject may be sensitive to a B-raf and/or MEK inhibitor. This subject may have already been treated with a B-raf and/or MEK inhibitor. However, this subject may have not already been treated with a B-raf and/or MEK inhibitor. In a later stage, such subject may be treated with a first combination of the invention as earlier defined herein. All features of this additional aspect of the invention have already been defined herein in previous aspects of the invention (i.e. miRNA molecule, equivalent, source, composition, disease or condition associated with melanoma or activated BRAF pathway, effect of the miRNA molecule on the subject). Said miRNA-518b molecule, equivalent or a source thereof may be used in combination with at least one miRNA molecule selected from a miRNA-10b-3p, miRNA-96-5p, miRNA-129-5p, miRNA-3157-5p, miRNA-200c-5p, miRNA-182-3p, miRNA-16-5p, miRNA-497-5p and/or a miRNA-7-5p or equivalent thereof or source thereof, or a composition comprising said at least one miRNA molecule, equivalent or source thereof as earlier defined herein.

In a further aspect, there is provided a miRNA-3157 molecule, an equivalent or a source thereof or a composition comprising or consisting of said miRNA molecule, said equivalent or said source thereof for use as a medicament for preventing, treating, regressing, curing and/or delaying a disease or a condition, preferably a cancer associated with an upregulation/increase of RRM2 and/or of AURKB. In this aspect, said miRNA molecule, equivalent or source thereof is preferably used as a sole active compound or as stand alone therapy in a subject as identified herein. This subject may be resistant to a cancer drug, preferably a RNR and/or to an AURKB inhibitor as defined herein. However, this subject may be sensitive to a cancer drug, preferably a RNR and/or AURKB inhibitor as defined herein. This subject may have already been treated with a cancer drug, preferably a RNR and/or a AURKB inhibitor as defined herein. However, this subject may have not already been treated with a cancer drug, preferably a RNR and/or AURKB inhibitor as defined herein. In a later stage, such subject may be treated with a second combination of the invention as earlier defined herein. Most features of this additional aspect of the invention have already been defined herein in previous aspects of the invention (i.e. miRNA molecule, equivalent, source, composition, upregulation/increase of RRM2 and/or of AURKB).

A disease or a condition associated with an upregulation/increase of RRM2 is preferably a cancer, more preferably pancreatic cancer, colorectal cancer, ovarian cancer, hepatocellular cancer, gastric cancer, bladder cancer, breast cancer, osteosarcoma.

A disease or a condition associated with an upregulation/increase of AURKB is preferably a cancer, more preferably breast cancer, colorectal cancer, kidney cancer, non small cell lung cancer, thyroid cancer, prostate cancer, glioblastoma.

The efficacy of said miRNA-3157 molecule, equivalent, source thereof or a composition comprising or consisting of said miRNA molecule, said equivalent or said source thereof may be carried out by the assessment of the presence of an anti-tumour effect as earlier defined herein and/or by the assessment of the level of RRM2 and/or AURKB in a treated subject. Said assessment of said RRM2 and/or AURKB may be carried out at the protein/RNA level as earlier defined herein. Alternatively, said assessment may be carried out by measuring an activity of said RRM2 and/or AURKB.

General Definitions and General Technologies Referred to Herein

MicroRNA molecules ("miRNAs") are generally 21 to 22 nucleotides in length, though lengths of 17 and up to 25 nucleotides have been reported. Any length of 17, 18, 19, 20, 21, 22, 23, 24, 25 is therefore encompassed within the present invention. The miRNAs are each processed from a longer precursor RNA molecule ("precursor miRNA"). Precursor miRNAs are generally transcribed from non-protein-encoding genes. Occasionally, introns of protein coding genes are the source of miRNA transcription. A precursor may have a length of at least 70, 75, 80, 85 nucleotides. The precursor miRNAs have two regions of complementarity that enables them to form a stem-loop- or fold-back-like structure, which is cleaved by enzymes called Dicer and Drosha in animals. Dicer and Drosha are ribonuclease III-like nucleases. The processed miRNA is typically a portion of the stem.

The processed miRNA (also referred to as "mature miRNA") becomes part of a large complex, known as the RNA-Induced Silencing Complex (RISC) complex, to (down)-regulate a particular target gene. Examples of animal miRNAs include those that perfectly or imperfectly basepair with the mRNA target, resulting in either mRNA degradation or inhibition of translation respectively (Olsen et al, 1999; Seggerson et al, 2002). SiRNA molecules also are processed by Dicer, but from a long, double-stranded RNA molecule. SiRNAs are not naturally found in animal cells, but they can function in such cells in a RNA-induced silencing complex (RISC) to direct the sequence-specific cleavage of an mRNA target (Denli et al, 2003).

The study of endogenous miRNA molecules is described in U.S. Patent Application 60/575,743, which is hereby incorporated by reference in its entirety. A miRNA is apparently active in the cell when the mature, single-stranded RNA is bound by a protein complex that regulates the translation of mRNAs that hybridize to the miRNA. Introducing exogenous RNA molecules that affect cells in the same way as endogenously expressed miRNAs requires that a single-stranded RNA molecule of the same sequence as the endogenous mature miRNA be taken up by the protein complex that facilitates translational control. A variety of RNA molecule designs have been evaluated. Three general designs that maximize uptake of the desired single-stranded miRNA by the miRNA pathway have been identified. An RNA molecule with a miRNA sequence having at least one of the three designs may be referred to as a synthetic miRNA.

miRNA molecules of the invention can replace or supplement the gene silencing activity of an endogenous miRNA. An example of such molecules, preferred characteristics and modifications of such molecules and compositions comprising such molecules is described in WO2009/091982, which is hereby incorporated by reference in its entirety.

miRNA molecules of the invention or equivalents or source thereof comprise, in some embodiments, two RNA molecules wherein one RNA is identical to a naturally occurring, mature miRNA. The RNA molecule that is identical to a mature miRNA is referred to as the active strand. The second RNA molecule, referred to as the complementary strand, is at least partially complementary to the active strand. The active and complementary strands are hybridized to create a double-stranded RNA, that is similar to the naturally occurring miRNA precursor that is bound by the protein complex immediately prior to miRNA activation in the cell. Maximizing activity of said miRNA requires maximizing uptake of the active strand and minimizing uptake of the complementary strand by the miRNA protein complex that regulates gene expression at the level of translation. The molecular designs that provide optimal miRNA activity involve modifications of the complementary strand. Two designs incorporate chemical modifications of the complementary strand. The first modification involves creating a complementary RNA with a group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules including NH2, NHCOCH3, biotin, and others. The second chemical modification strategy that significantly reduces uptake of the complementary strand by the miRNA pathway is incorporating nucleotides with sugar modifications in the first 2-6 nucleotides of the complementary strand. It should be noted that the sugar modifications consistent with the second design strategy can be coupled with 5' terminal modifications consistent with the first design strategy to further enhance miRNA activities.

The third miRNA design involves incorporating nucleotides in the 3' end of the complementary strand that are not complementary to the active strand. Hybrids of the resulting active and complementary RNAs are very stable at the 3' end of the active strand but relatively unstable at the 5' end of the active strand. Studies with siRNAs indicate that 5' hybrid stability is a key indicator of RNA uptake by the protein complex that supports RNA interference, which is at least related to the miRNA pathway in cells. The inventors have found that the judicious use of mismatches in the complementary RNA strand significantly enhances the activity of said miRNA.

miRNAs are contemplated to be made primarily of RNA, though in some embodiments, they may be RNA, nucleotide analogs, such as Locked nucleic acids (LNA) or Unlocked nucleic acids (UNA), DNA, or any combination of DNA, RNA, nucleotide analogs, and PNAs. Accordingly, it is understood that the library contains one or more nucleic acids for these different miRNAs. In specific embodiments, the library is specific to human miRNAs, though libraries for multiple organisms are contemplated.

An RNA molecule of the invention has or comprises or consists of a miRNA region. In specific embodiments, a miRNA molecule or equivalent thereof has a sequence that derives from any of SEQ ID NOs: 1-10 (as identified in Table 1) or from any of SEQ ID NO: 96-271 (as identified in Table 5).

A miRNA molecule or equivalent thereof will include a sequence that extends at least 1 to 5 nucleotides of coding sequence upstream and/or downstream of the predicted miRNA sequence. In some embodiments, molecules have up to 1, 2, 3, 4, 5, 6, 7, or more contiguous nucleotides, or any range derivable therein, that flank the sequence encoding the predominant processed miRNA on one or both sides (5' and/or 3' end).

It is encompassed by the present invention that each of the miRNA molecules or equivalents or mimics or antagomirs or isomiRs or precursors thereof identified herein may be modified compared to the corresponding miRNA molecules or equivalents or mimics or antagomirs or precursors thereof occurring in nature. In this embodiment, each of these miRNA molecules or equivalents or mimics or antagomirs or isomiRs or precursors thereof are identified as modified miRNA molecules or equivalents or mimics or antagomirs or isomiRs or precursors thereof or as derivatives or as analogs of the naturally occurring miRNA molecule, equivalent, mimic, antagomir or precursors. Therefore in this embodiment, each of the miRNA molecules or equivalents or mimics or antagomirs or isomiRs or precursors thereof identified herein is not identical with its natural counterpart. Such modified miRNA molecules or equivalents or mimics or antagomirs or isomiRs or precursors thereof may be modified in the sense that:

One, 2, 3, 4 or 5 or at least 20%, 30%, 40%, 50%, 60%, 70%, 80%, or at least 90% or 100% of their nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of their nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

Below, preferred nucleotides, nucleosides, nucleobases, nucleobases linker moiety and backbone moiety have been disclosed. Some of them correspond to naturally occurring nucleotides, nucleosides, nucleobases, nucleobases linker moiety and backbone moiety. Some of them do not occur in nature as explained below.

Nucleic Acids

The present invention concerns nucleic acid molecules also called sources or precursors of miRNAs that can introduce miRNAs in cultured cells or into a subject. The nucleic acids may have been produced in cells or in vitro by purified enzymes though they are preferentially produced by chemical synthesis. They may be crude or purified. The term "miRNA," unless otherwise indicated, refers to the processed miRNA, after it has been cleaved from its precursor. Table 2 indicates which SEQ ID NO corresponds to a particular precursor sequence of a miRNA (SEQ ID NO:11-24 and Table 1 which SEQ ID NO corresponds to the mature sequence of a miRNA (SEQ ID NO: 1-10). Table 3 identifies the cloned DNA sequences into the lentiviral vector (SEQ ID NO: 25-38), which were used in the functional screen as described in the examples. Table 4 identifies the preferred seed sequence of each of the mature miRNAs of Table 2 (SEQ ID NO:39-48). Table 5 shows preferred IsomiR equivalents of each of the mature miRNAs identified (SEQ ID NO:96-271). The name of the miRNA is often abbreviated and referred to without the prefix and will be understood as such, depending on the context. Unless otherwise indicated, miRNAs referred to in the application are human sequences identified as mir-X or let-X, where X is a number and/or letter.

It is understood that a miRNA is derived from genomic sequences or a non-coding gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "recombinant" may be used and this generally refers to a molecule that has been manipulated in vitro or that is the replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary.

As used herein, "hybridization", "hybridizes" or "capable of hybridizing" is understood to mean the forming of a double or triple stranded molecule or a molecule with partial double or triple stranded nature using techniques known to the skilled person such as southern blotting procedures. The term "anneal" as used herein is synonymous with "hybridize." The term "hybridization", "hybridize(s)" or "capable of hybridizing" may mean "low", "medium" or "high" hybridization conditions as defined below.

Low to medium to high stringency conditions means prehybridization and hybridization at 42° C. in 5×SSPE, 0.3% SDS, 200 pg/ml sheared and denatured salmon sperm DNA, and either 25% 35% or 50% formamide for low to medium to high stringencies respectively. Subsequently, the hybridization reaction is washed three times for 30 minutes each using 2×SSC, 0.2% SDS and either 55° C., 65° C., or 75° C. for low to medium to high stringencies.

Nucleic acids or derivatives thereof of the invention will comprise, in some embodiments the miRNA sequence of any miRNA described in SEQ ID NOs: 1-10 or are described in SEQ ID NO: 11-24 or in SEQ ID NO: 25-38 or in SEQ ID NO: 39-48 or in SEQ ID NO: 49-95 or in SEQ ID NO: 96-271. It is contemplated that nucleic acids sequences of the invention derived from SEQ ID NO: 1-10 can have, have at least, or have at most 5, 6, 7, 8, 9, 10, 11, 12, 13, 14, 15, 16, 17, 18, 19, 20, 21, 22, 23, contiguous nucleotides from SEQ ID NOs: 1-10 (or any range derivable therein). In other embodiments, nucleic acids are, are at least, or are at most 80, 81, 82, 83, 84, 85, 86, 87, 88, 89, 90, 91, 92, 93, 94, 95, 96, 97, 98, 99, 100% identical to the miRNA sequence of SEQ ID NOs: 1-10 or to the precursor sequence of any of SEQ ID NO: 11-24 or any combination or range derivable therein.

Nucleobases (or Bases)

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moeity. Preferred alkyl (e.g., alkyl, carboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652,099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified T-deoxyfuranosyl moieties) used in nucleic acid detection; U.S. Pat. No. 5,446,137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2' or 3' carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240, which describe oligonucleotides with three or four atom linker moiety replacing phosphodiester backbone moiety used for improved nuclease resistance, cellular uptake and regulating RNA expression; U.S. Pat. No. 5,858,988, which describes hydrophobic carrier agent attached to the 2'-0 position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and WO98/39352, WO99/14226, WO2003/95467 and WO2007/085485, which describe modified RNA nucleotides of which the ribose moiety is modified with an extra bridge connecting the 2' oxygen and 4' carbon. The locked ribose significantly increases the binding affinity and specificity; and WO2008/147824, which describes modified RNA nucleotides termed UNA (unlocked nucleic acid). UNA are acyclic analogues of RNA in which the bond between the C2' and C3' atoms has been cleaved, decreasing binding affinity towards a complementary strand. UNA are compatible with RNase H recognition and RNA cleavage and improves siRNA mediated gene silencing; WO2008/036127 which describes Morpholino nucleic acid analogues, which contain both uncharged and cationic intersubunit linkages; WO/2007/069092 and EP2075342 which describe Zip Nucleic Acids (ZNA), containing conjugating spermine derivatives as cationic moieties (Z units) to an oligonucleotide; U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and U.S. Pat. No. 5,480,980 (7-deaza-2'-deoxyguanosine nucleotides and nucleic acid analogs thereof).

The use of other analogs is specifically contemplated for use in the context of the present invention. Such analogs may be used in synthetic nucleic acid molecules of the invention, both throughout the molecule or at selected nucleotides. They include, but are not limited to, 1) ribose modifications (such as 2'F, 2' NH2, 2'N3,4'thio, or 2' O—CH3) and 2) phosphate modifications (such as those found in phosphorothioates, methyl phosphonates, and phosphoroborates).

Such analogs have been created to confer stability on RNAs by reducing or eliminating their capacity to be cleaved by ribonucleases. When these nucleotide analogs are present in RNAs, they can have profoundly positive effects on the stability of the RNAs in animals. It is contemplated that the use of nucleotide analogs can be used alone or in conjunction with any of the design modifications of a synthetic miRNA for any nucleic acid of the invention.

Modified Nucleotides miRNAs of the invention specifically contemplate the use of nucleotides that are modified to enhance their activities. Such nucleotides include those that are at the 5' or 3' terminus of the RNA as well as those that are internal within the molecule. Modified nucleotides used in the complementary strands of said miRNAs either block the 5'OH or phosphate of the RNA or introduce internal sugar modifications that enhance uptake of the active strand of the miRNA. Modifications for the miRNAs include internal sugar modifications that enhance hybridization as well as stabilize the molecules in cells and terminal modifications that further stabilize the nucleic acids in cells. Further contemplated are modifications that can be detected by microscopy or other methods to identify cells that contain the synthetic miRNAs.

Preparation of Nucleic Acids

A nucleic acid may be made by any technique known to one of ordinary skill in the art, such as for example, chemical synthesis, enzymatic production or biological production. Though miRNAs according to the invention could be produced using recombinant methods, it is preferred to produce miRNAs by chemical synthesis or enzymatic production. miRNAs can be produced by a number of methods, including methods involving recombinant DNA technology.

Nucleic acid synthesis is performed according to standard methods. See, for example, Itakura and Riggs (1980). Additionally, U.S. Pat. No. 4,704,362, U.S. Pat. No. 5,221,619, and U.S. Pat. No. 5,583,013 each describe various methods of preparing nucleic acids. Non-limiting examples of a nucleic acid (e.g., a oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference.

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

Diester Method

The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester Method

The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purifications are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide Phosphorylase Method.

This is an enzymatic method of DNA synthesis that can be used to synthesize many useful oligonucleotides (Gillam et al., 1978; Gillam et al, 1979). Under controlled conditions, polynucleotide phosphorylase adds predominantly a single nucleotide to a short oligonucleotide.

Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-Phase Methods.

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant Methods.

Recombinant methods for producing nucleic acids in a cell are well known to those of skill in the art. These include the use of vectors, plasmids, cosmids, and other vehicles for delivery a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference. In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

Design of miRNAs miRNAs typically comprise two strands, an active strand that is identical in sequence to the mature miRNA that is being studied and a complementary strand that is at least partially complementary to the active strand. The active strand is the biologically relevant molecule and should be preferentially taken up by the complex in cells that modulates translation either through mRNA degradation or translational control. Preferential uptake of the active strand has two profound results: (1) the observed activity of said miRNA increases dramatically and (2) non-intended effects induced by uptake and activation of the complementary strand are essentially eliminated. According to the invention, several miRNA designs can be used to ensure the preferential uptake of the active strand.

5' Blocking Agent.

The introduction of a stable moiety other than phosphate or hydroxyl at the 5' end of the complementary strand impairs its activity in the miRNA pathway. This ensures that only the active strand of the miRNA will be used to regulate translation in the cell. 5' modifications include, but are not limited to, NH2, biotin, an amine group, a lower alkylamine group, an acetyl group, 2' O-Me, DMTO, fluoroscein, a thiol, or acridine or any other group with this type of functionality.

Other sense strand modifications. The introduction of nucleotide modifications like 2'-OMe, 2'-deoxy, T-deoxy-2'-fluoro, 2'-O-methyl, 2'-O-methoxyethyl (2'-0-MOE), 2'-O-aminopropyl (2'-0-AP), 2'-O-dimethylaminoethyl (2'-0-DMAOE), 2'-O-dimethylaminopropyl (2'-0-DMAP), 2'-O-dimethylaminoethyloxyethyl (2'-0-DMAEOE), or 2'-O—N-methylacetamido (2'-0-NMA), NH2, biotin, an amine group, a lower alkylamine group, an acetyl group, DMTO, fluoroscein, a thiol, or acridine or any other group with this type of functionality in the complementary strand of the miRNA can eliminate the activity of the complementary strand and enhance uptake of the active strand of the miRNA.

Base mismatches in the sense strand. As with siRNAs (Schwarz 2003), the relative stability of the 5' and 3' ends of the active strand of the miRNA apparently determines the uptake and activation of the active by the miRNA pathway. Destabilizing the 5' end of the active strand of the miRNA by the strategic placement of base mismatches in the 3' end of the complementary strand of the synthetic miRNA enhances the activity of the active strand and essentially eliminates the activity of the complementary strand.

Host Cells and Target Cells

The cells wherein a miRNA or source thereof is introduced or wherein the presence of a miRNA is assessed may be derived from or contained in any organism. Preferably, the cell is a vertebrate cell. More preferably, the cell is a mammalian cell. Even more preferably, the cell is a human cell.

A mammalian cell may be from the germ line or somatic, totipotent or pluripotent, dividing or non-dividing, epithelium, immortalized or transformed, or the like. The cell may be an undifferentiated cell, such as a stem cell, or a differentiated cell, such as from a cell of an organ or tissue. Alternatively, cells may be qualified as epithelial cells, brain, breast, cervix, colon, gastrointestinal tract, heart, kidney, large intestine, liver, lung, ovary, pancreas, heart, prostate, bladder, small intestine, stomach, testes or uterus.

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a small, interfering RNA or a template construct encoding a reporter gene has been introduced. Therefore, recombinant cells are distinguishable from naturally occurring cells that do not contain a recombinantly introduced nucleic acid.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to brain, stem cells, liver, lung, bone, breast, cervix, colon, endometrium, epithelial, esophagus, goblet cells, kidney, ovaries, pancreas, prostate, bladder, skin, small intestine, stomach, testes, heart.

In certain embodiments, the host cell or tissue may be comprised in at least one organism. In certain embodiments, the organism may be a mammal, a human, a primate or murine. One of skill in the art would further understand the conditions under which to incubate all of the above described host cells to maintain them and to permit their division to form progeny.

Delivery Methods

The present invention involves in some embodiments delivering a nucleic acid into a cell. This may be done as part of a therapeutic application.

RNA molecules may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, lentivirus, and plant viruses), and artificial chromosomes (e.g., YACs). One of skill in the art would be well equipped to construct a vector through standard recombinant techniques, which are described in Sambrook et al, 1989 and Ausubel et al, 1996, both incorporated herein by reference. In addition to encoding a modified polypeptide such as modified gelonin, a vector may encode non-modified polypeptide sequences such as a tag or targeting molecule. A targeting molecule is one that directs the desired nucleic acid to a particular organ, tissue, cell, or other location in a subject's body.

The term "expression vector" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described.

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986). The expression vectors may contain an RNAi expression cassette comprising one promoter and one or more stem-loop structures separated by one or more spacer regions (WO2006/084209). Another way of introducing expression vectors into cells, using avidin fusion proteins is described in U.S. Pat. No. 6,287,792.

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al, 1988) adeno-associated virus (AAV) (Ridgeway, 1988; Baichwal and Sugden, 1986; Hermonat and Muzycska, 1984), lentivirus (WO2008/071959, WO2004/054512), Hemaglutinating Virus of Japan (WO2004/035779), Baculovirus (WO2006/048662) and herpesviruses may be employed. They offer several attractive features for various mammalian cells (Friedmann, 1989; Ridgeway, 1988; Baichwal and Sugden, 1986; Coupar et al, 1988; Horwich et al, 1990).

Other suitable methods for nucleic acid delivery to affect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al, 1987); by liposome mediated transfection (Nicolau and Sene, 1982; Fraley et al., 1979; Nicolau et al, 1987; Wong et al, 1980; Kaneda et al., 1989; Kato et al., 1991); by photochemical internalization (WO2008/007073); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al, 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

A review provides several ways of formulating a RNA molecule in order to optimize its internalisation into a cell (Kim S S., et al, Trends Mol. Med., (2009), 15: 491-500). The following other publications discloses alternative ways of formulating a RNA molecule in order to improve its internalisation into a cell, each incorporated herein by reference: WO 2007/095152, describing the use of PTD-DRBD (Peptide transduction domains linked to double stranded binding domain) for delivery of oligonucleotides, WO 2009/086558, describing the use of SNALP (Stable Nucleic Acid Lipid Particles) particles, comprising a mixture of cationic and fusogenic lipids that enable the cellular uptake and endosomal release of the particle's nucleic acid payload, WO 2009/149418, describing neutral phospho lipid-oil-RNAi emulsions, WO 2007/121947, describing the use of a delivery vehicle based on lipoplex, WO 2009/132131, describing the use of novel lipids and nucleic acid-lipid particles that provide efficient encapsulation and efficient delivery of the encapsulated nucleic acid to cells, WO2004/091578 and WO2004/064805 describing cochleate technology of alternating layers of lipids that spiral around a nucleic acid molecule, WO2003/047494 and WO2003/047493 describing reverse micelles incorporating nucleic acids for oral and mucosal delivery, WO 2008/156702, describing bacteria and bacterial therapeutic particle (BTP), including oligonucleotides for as delivery vehicle to cells. Each of the formulations referred to or disclosed in these publications is encompassed by the present invention.

A variety of compounds have been attached to the ends of oligonucleotides to facilitate their transport across cell membranes. Short signal peptides found in the HIV TAT, HSV VP22, Drosphila antennapedia, and other proteins have been found to enable the rapid transfer of biomolecules across membranes (reviewed by Schwarze 2000). These signal peptides, referred to as Protein Transduction Domains (PTDs), have been attached to oligonucleotides to facilitate their delivery into cultured cells (Eguchi A, Dowdy S F, Trends Pharmacol Sci., 2009, 7:341-5). Cholesterols have been conjugated to oligonucleotides to improve their uptake into cells in animals (MacKellar 1992). The terminal cholesterol groups apparently interact with receptors or lipids on the surfaces of cells and facilitate the internalization of the modified oligonucleotides. Likewise, poly-L-lysine has been conjugated to oligonucleotides to decrease the net negative charge and improve uptake into cells (Leonetti 1990).

A variety of compounds have been developed that complex with nucleic acids, deliver them to surfaces of cells, and facilitate their uptake in and release from endosomes. Among these are: (1) a variety of lipids such as DOTAP (or other cationic lipid), DDAB, DHDEAB, and DOPE and (2) non-lipid-based polymers like polyethylenimine, polyamidoamine, and dendrimers of these and other polymers. In certain of these embodiments a combination of lipids is employed such as DOTAP and cholesterol or a cholesterol derivative (U.S. Pat. No. 6,770,291, which is hereby incorporated by reference). Several of these reagents have been shown to facilitate nucleic acid uptake in animals.

The cellular components involved in the miRNA pathway are becoming known. Proteins that stabilize and/or transport miRNAs within cells might enhance the stability and activity of miRNAs because they should protect and guide the bound miRNAs once they are in cells. Mixtures of miRNA-transporter proteins and miRNAs could enhance the efficacy of miRNA-based therapeutics. RNAs are hydrophilic molecules by virtue of their anionic phosphate and sugar backbone. Although the nucleobases are hydrophobic, hydrophilicity dominates owing to the extensive hydrogen bonding resulting from the phosphate and sugar residues. The hydrophilic character and anionic backbone reduces cellular permeation. Conjugation of lipophilic groups like cholesterol (Manoharan, 2002) and lauric and lithocholic acid derivatives with C32 functionality (Lorenz et al, 2004), have been shown to improve cellular uptake. Moreover binding of steroid conjugated oligonucleotides to different lipoproteins in the bloodstream, such as LDL, protect their integrity and govern their biodistribution (Rump et al, 2000). Cholesterol attached to anti-sense molecules (Bijsterbosch et al., 2001) and aptamers (Rusconi et al., 2004) has also been shown to stabilize oligonucleotides by allowing binding to lipoproteins. Cholesterol has been demonstrated to enhance uptake and serum stability of siRNAs in vitro (Lorenz et al., 2004) and in vivo (Soutschek et al., 2004). Additionally, a number of small molecules like SB-435495 (Blackie et al, (2002), Isradipine (Oravcova et al, 1994), amlodipine (Oravcova et al, 1994) and 2,2',4,4',5,5'-hexachlorobiphenyl (Borlakoglu et al, 1990) could enhance cellular uptake, and improve nuclease resistance by promoting lipoprotein association.

The efficacy of different therapeutic drugs is altered by miRNAs according to the present invention. Moreover, it has been described that tumor cells with BRAF mutations may become resistant to chemo- and immunotherapy (Abrams S. L. et al., Cell cycle 9:1781, 2010, McCubrey J. A. et al., Adv. Enzyme Regul. 46: 249, 2006). Therefore, miRNA based drugs that affect the active BRAF pathway may enhance susceptibility to e.g. chemo- and immunotherapy. Such therapeutic drugs include, but are not limited to, chemotherapeutic drugs. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Below, we provide a list of cancer drugs that corresponds to the second list of compounds according to the invention (i.e. first list of compound present in said second combination being a miRNA-3157 molecule, equivalent, mimic, isomer or source thereof). This list below comprises suitable chemotherapeutics and other types of cancer drugs as RNR inhibitors and AURKB inhibitors.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma and calicheamicin omega); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholmo-doxorubicm, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; amino levulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-I1); topoisomerase inhibitor RFS 2000; difluorometlhylornithine (DMFO); retinoids such as retinoic acid; capecitabine; gefitinib and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY1 17018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-α, Raf and H-Ras; ribozymes such as a VEGF expression inhibitor and a HER2 expression inhibitor; vaccines such as gene therapy vaccines and pharmaceutically acceptable salts, acids or derivatives of any of the above. A list of U.S. FDA approved oncology drags with their approved indications can be found on the World Wide Web at accessdata.fda.gov/scripts/cder/onctools/druglist.cfm. A suitable RNR inhibitor is selected from the group consisting of gemcitabine, hydroxyurea, clolar, clofarabine, and triapine. A suitable AURKB inhibitor is selected from the group consisting of: AZD1152, VX-680, MLN8054, MLN8237, PHA680632, PH739358, Hesperidin, ZM447439, JNJ770621, SU6668, CCT129202, AT9283, MP529, SNS314, R763, ENMD2076, XL228, TTP687, PF03814735 and CYC116. Another suitable anticancer drug is gefitinib.

Moreover, it is contemplated that samples that have differences in the activity of certain pathways may also be compared. Such cellular pathways include but are not limited to the following: any adhesion or motility pathway including but not limited to those involving cyclic AMP, protein kinase A, G-protein couple receptors, adenylyl cyclase, L-selectin, E-selectin, PECAM, VCAM-I, α-actinin, paxillin, cadherins, AKT, integrin-α, integrin-β, RAF-I, ERK, PI-3 kinase, vinculin, matrix metalloproteinases, Rho GTPases, p85, trefoil factors, profilin, FAK, MAP kinase, Ras, caveolin, calpain-1, calpain-2, epidermal growth factor receptor, ICAM-1, ICAM-2, cofilin, actin, gelsolin, Rho A, Rac, myosin light chain kinase, platelet-derived growth factor receptor or ezrin; any apoptosis pathway including but not limited to those involving AKT, Fas ligand, NFKB, caspase-9, PB kinase, caspase-3, caspase-7, ICAD, CAD, EndoG, Granzyme B, Bad, Bax, Bid, Bak, APAF-I, cytochrome C, p53, ATM, Bcl-2, PARP, Chk1, Chk2, Rho-21, c-Jun, Rho73, Rad51, Mdm2, Rad50, c-Abl, BRCA-I, perforin, caspase-4, caspase-8, caspase-6, caspase-1, caspase-2, caspase-10, Rho, Jun kinase, Jun kinase kinase, Rip2, lamin-A, lamin-B1, lamin-B2, Fas receptor, H2O2, Granzyme A, NADPH oxidase, HMG2, CD4, CD28, CD3, TRADD, IKK, FADD, GADD45, DR3 death receptor, DR4/5 death receptor, FLIPs, APO-3, GRB2, SHC, ERK, MEK, RAF-1, cyclic AMP, protein kinase A, E2F, retinoblastoma protein, Smac/Diablo, ACH receptor, 14-3-3, FAK, SODD, TNF receptor, RTP, cyclin-D1, PCNA, Bcl-XL, PIP2, PIP3, PTEN, ATM, Cdc2, protein kinase C, calcineurin, IKKα, IKKβ, IKKy, SOS-I, c-FOS, Traf-1, Traf-2, IKBβ or the proteasome; any cell activation pathway including but not limited to those involving protein kinase A, nitric oxide, caveolin-1, actin, calcium, protein kinase C, Cdc2, cyclin B, Cdc25, GRB2, SRC protein kinase, ADP-ribosylation factors (ARFs), phospholipase D, AKAP95, p68, Aurora B, CDKI, Eg7, histone H3, PKAc, CD80, PI3 kinase, WASP, Arp2, Arp3, p34, p20, PP2A, angiotensin, angiotensin-converting enzyme, protease-activated receptor-1, protease-activated receptor-4, Ras, RAF-I, PLCβ, PLCγ, COX-I, G-protein-coupled receptors, phospholipase A2, IP3, SUMO1, SUMO 2/3, ubiquitin, Ran, Ran-GAP, Ran-GEF, p53, glucocorticoids, glucocorticoid receptor, components of the SWI/SNF complex, RanBP1, RanBP2, importins, exportins, RCCl, CD40, CD40 ligand, p38, DCKα, IKKβ, NFKB, TRAF2, TRAF3, TRAF5, TRAF6, IL-4, IL-4 receptor, CDK5, AP-I transcription factor, CD45, CD4, T cell receptors, MAP kinase, nerve growth factor, nerve growth factor receptor, c-Jun, c-Fos, Jun kinase, GRB2, SOS-I, ERK-I, ERK, JAK2, STAT4, IL-12, IL-12 receptor, nitric oxide synthase, TYK2, IFNγ, elastase, IL-8, epithelins, IL-2, IL-2 receptor, CD28, SMAD3, SMAD4, TGFβ or TGFβ receptor; any cell cycle regulation, signaling or differentiation pathway including but not limited to those involving TNFs, SRC protein kinase, Cdc2, cyclin B, Grb2, Sos-1, SHC, p68, Aurora kinases, protein kinase A, protein kinase C, Eg7, p53, cyclins, cyclin-dependent kinases, neural growth factor, epidermal growth factor, retinoblastoma protein, ATF-2, ATM, ATR, AKT, CHK1, CHK2, 14-3-3, WEE1, CDC25 CDC6, Origin Recognition Complex proteins, p15, p16, p27, p21, ABL, c-ABL, SMADs, ubiquitin, SUMO, heat shock proteins, Wnt, GSK-3, angiotensin, p73 any PPAR, TGFα, Taβ, p300, MDM2, GADD45, Notch, cdc34, BRCA-I, BRCA-2, SKP1, the proteasome, CUL1, E2F, pi 07, steroid hormones, steroid hormone receptors, IκBα, IκBβ, Sin3A, heat shock proteins, Ras, Rho, ERKs, IKKs, PI3 kinase, Bcl-2, Bax, PCNA, MAP kinases, dynein, RhoA, PKAc, cyclin AMP, FAK, PIP2, PIP3, integrins, thrombopoietin, Fas, Fas ligand, PLK3, MEKs, JAKs, STATs, acetylcholine, paxillin calcineurin, p38, importins, exportins, Ran, Rad50, Rad51, DNA polymerase, RNA polymerase, Ran-GAP, Ran-GEF, NuMA, Tpx2, RCC1, Sonic Hedgehog, Crm1, Patched (Ptc-1), MPF, CaM kinases, tubulin, actin, kinetochore-associated proteins, centromere-binding proteins, telomerase, TERT, PP2A, c-MYC, insulin, T cell receptors, B cell receptors, CBP, 1 KB, NFKB, RAC1, RAF1, EPO, diacylglycerol, c-Jun, c-Fos, Jun kinase, hypoxia-inducible factors, GATA4, β-catenin, α-catenin, calcium, arrestin, survivin, caspases, procaspases, CREB, CREM, cadherins, PECAMs, corticosteroids, colony-stimulating factors, calpains, adenylyl cyclase, growth factors, nitric oxide, transmembrane receptors, retinoids, G-proteins, ion channels, transcriptional activators, transcriptional coactivators, transcriptional repressors, interleukins, vitamins, interferons, transcriptional corepressors, the nuclear pore, nitrogen, toxins, proteolysis, or phosphorylation; or any metabolic pathway including but not limited to those involving the biosynthesis of amino acids, oxidation of fatty acids, biosynthesis of neurotransmitters and other cell signaling molecules, biosynthesis of polyamines, biosynthesis of lipids and sphingolipids, catabolism of amino acids and nutrients, nucleotide synthesis, eicosanoids, electron transport reactions, ER-associated degradation, glycolysis, fibrinolysis, formation of ketone bodies, formation of phagosomes, cholesterol metabolism, regulation of food intake, energy homeostasis, prothrombin activation, synthesis of lactose and other sugars, multi-drug resistance, biosynthesis of phosphatidylcholine, the proteasome, amyloid precursor protein, Rab GTPases, starch synthesis, glycosylation, synthesis of phosphoglycerides, vitamins, the citric acid cycle, IGF-I receptor, the urea cycle, vesicular transport, or salvage pathways. It is further contemplated that nucleic acids molecules of the invention can be employed in diagnostic and therapeutic methods with respect to any of the above pathways or factors. Thus, in some embodiments of the invention, a miRNA inhibits, eliminate, activates, induces, increases, or otherwise modulates one or more of the above pathways or factors is contemplated as part of methods of the invention. The nucleic acid can be used to diagnosis a disease or condition based on the relation of that miRNA to any of the pathways described above.

Other Assays

In addition to the use of arrays and microarrays, it is contemplated that a number of difference assays could be employed to analyze miRNAs, their activities and their effects. Such assays include, but are not limited to, RT-PCR, in situ hybridization, hybridization protection assay (HPA) (GenProbe), branched DNA (bDNA) assay (Collins, M. L. et al. (1997). Nucleic Acids Research 25: 2979-2984), rolling circle amplification (RCA), single molecule hybridization detection (US Genomics), Invader assay (ThirdWave Technologies), and Bridge Litigation Assay (Qiagen). It is contemplated that such methods may be used in the context of arrays, as well as in the context of diagnostic assays.

Therapeutic Application miRNAs that affect phenotypic traits provide intervention points for therapeutic application. It is specifically contemplated that RNA molecules of the present invention can be used to treat any of the diseases or conditions discussed in the previous section. Moreover, any of the methods described above can also be employed with respect to therapeutic aspect of the invention. In therapeutic applications, an effective amount of the miRNAs of the present invention is administered to a cell, which may or may not be in an animal. In some embodiments, a therapeutically effective amount of the miRNAs of the present invention is administered to an individual for the treatment of disease or condition. The term "effective amount" as used herein is defined as the amount of the molecules of the present invention that are necessary to result in the desired physiological change in the cell or tissue to which it is administered. The term "therapeutically effective amount" as used herein is defined as the amount of the molecules of the present invention that achieves a desired effect with respect to a disease or condition associated with a melanoma as earlier defined herein. A skilled artisan readily recognizes that in many cases the molecules may not provide a cure but may provide a partial benefit, such as alleviation or improvement of at least one symptom. In some embodiments, a physiological change having some benefit is also considered therapeutically beneficial. Thus, in some embodiments, an amount of molecules that provides a physiological change is considered an "effective amount" or a "therapeutically effective amount."

In some embodiments the molecule has a sequence that corresponds to the miRNA sequence from that particular animal, as opposed to from another animal. Thus, in some embodiments, a human sequence is utilized in the RNA molecules of the present invention.

Modes of Administration and Formulations

Each compound of the first or second combination may be present in a composition, preferably a pharmaceutical composition. It is further preferred that a first or second combination is a single composition or a single pharmaceutical composition comprising the at least one compound of the first list and the at least one compound of the second list as defined herein. Each nucleic acid molecules (i.e. miRNA, equivalent or sources thereof) of the invention may be administered to a subject alone or in the form of a composition or pharmaceutical composition for the treatment of a condition or disease. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen. For topical administration the proteins of the invention may be formulated as solutions, gels, ointments, creams, suspensions, etc. as are well-known in the art. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration. For injection, the nucleic acids of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the nucleic acid molecules may be in powder form for constitution with a suitable vehicle, e.g., sterile pyrogen-free water, before use. For transmucosal administration, penetrants appropriate to the barrier to be permeated are used in the formulation. Such penetrants are generally known in the art. For oral administration, the nucleic acids can be readily formulated by combining the molecules with pharmaceutically acceptable carriers well known in the art. Such carriers enable the nucleic acids of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropyl-methyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. For oral liquid preparations such as, for example, suspensions, elixirs and solutions, suitable carriers, excipients or diluents include water, glycols, oils, alcohols, etc. Additionally, flavoring agents, preservatives, coloring agents and the like may be added. For buccal administration, the molecules may take the form of tablets, lozenges, etc. formulated in conventional manner. For administration by inhalation, the molecules for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the nucleic acids and a suitable powder base such as lactose or starch. The RNA molecules may also be formulated in rectal or vaginal compositions such as suppositories or retention enemas, e.g., containing conventional suppository bases such as cocoa butter or other glycerides.

In addition to the formulations described previously, the molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt. Alternatively, other pharmaceutical delivery systems may be employed.

Liposomes and emulsions are well-known examples of delivery vehicles that may be used to deliver nucleic acids of the invention. A compound from the second list (i.e. a B-raf and/or MEK inhibitor) may be administered orally. All details of oral administration provided above for a compound of the first list also apply for the compound of the second list. The same holds for each compound of the second combination as defined herein and for each other compound defined herein (i.e. "a miRNA-518b-based compound" and a "stand alone therapy using miRNA-3157").

A nucleic acid of the invention may be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP; cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844, 107, 5,877,302, 6,008,336, 6,077,835, 5,972,901, 6,200,801, and 5,972,900, which are incorporated by reference for those aspects. The nucleic acids may also be administered in combination with a cationic amine such as poly-L-lysine.

Nucleic acids may also be conjugated to a chemical moiety, such as transferrin and cholesteryls. In addition, oligonucleotides may be targeted to certain organelles by linking specific chemical groups to the oligonucleotide. For example, linking the oligonucleotide to a suitable array of mannose residues will target the oligonucleotide to the liver. Other targeting ligands are described in Liu B., Brief Funct. Genomic Proteomic 6:112-119, 2007. Additional examples are carbohydrate sugars such as galactose, N-acetylgalactosamine, mannose; vitamins such as folates; small molecules including naproxen, ibuprofen or other known protein-binding molecules, cyclodextrin, which targets the transferrin receptor (Hu-Lieskovan et al., 2005), PEI (RGD-targeted PEG-PEI, Schiffelers et al. 2004), anisamide, RGD-peptide or RGD mimics, poly-arginin, anti-TM single chain antibody fragment/TfRscFv, Annexin A5 (targeting phophatidylserine exposing membranes, Garnier B. et al., Bioconjug Chem., 2009, 11:2114-22), WO 2009/126933 describing compositions and methods for site-specific delivery of nucleic acids by combining them with targeting ligands and endosomolytic components. Targeting ligands that are preferentially suitable are tumor associated cell surface proteins, more preferably prostate tumor associated cell surface proteins. Targeting of nucleic acids may also be accomplished by using aptamer technology as described in WO2005/111238. Moreover, additional lipid moieties, such as PEG-lipids, cholesterol, endosomolytic helper lipids or peptides (WO2009/046220) or the overall morphology of the generated nanoparticles (characterized by charge and particle size) to the above mentioned delivery vehicles may confer targeting specificity to either cancer cells and/or tumor vasculature.

Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Alternatively, the molecules may be delivered using a coordination chemistry based delivery system as described in WO2007011217, which is specifically incorporated herein by reference.

Nucleic acids may be included in any of the above-described formulations as the free acids or bases or as pharmaceutically acceptable salts. Pharmaceutically acceptable salts are those salts that substantially retain the biological activity of the free bases and which are prepared by reaction with inorganic acids. Pharmaceutical salts tend to be more soluble in aqueous and other protic solvents than are the corresponding free base forms.

Pharmaceutical compositions of the present invention comprise an effective amount of one or more miRNA molecules dissolved or dispersed in a pharmaceutically acceptable carrier. The phrases "pharmaceutical or pharmacologically acceptable" refers to molecular entities and compositions that do not produce or produce acceptable adverse, allergic or other untoward reaction when administered to an animal, such as, for example, a human, as appropriate. Whether certain adverse effects are acceptable is determined based on the severity of the disease. The preparation of an pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The chimeric molecules may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal or a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. In other non-limiting examples, a dose may also comprise less than 1 microgram/kg/body weight, or 1 microgram/kg/body weight, from 5 microgram/kg/body weight, 10 microgram/kg/body weight, 50 microgram/kg/body weight, 100 microgram/kg/body weight, 200 microgram/kg/body weight, 350 microgram/kg/body weight, 500 microgram/kg/body weight, 1 milligram/kg/body weight, 5 milligram/kg/body weight, 10 milligram/kg/body weight, 50 milligram/kg/body weight, 100 milligram/kg/body weight, 200 milligram/kg/body weight, 350 milligram/kg/body weight, or 500 milligram/kg/body weight, to 1000 mg/kg/body weight or more per administration, and any range derivable therein. In non-limiting examples of a derivable range from the numbers listed herein, a range of 5 mg/kg/body weight to 100 mg/kg/body weight, 5 microgram/kg/body weight to 500 milligram/kg/body weight, etc., can be administered, based on the numbers described above.

Usually vemurafnib may be used 960 mg twice daily, which may be 12.8 mg/kg body weight twice daily.

Usually an AURKB inhibitor may be used at a does of 250 mg per day.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compound may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines. In certain embodiments, the molecules are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, *acacia*, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. or combinations of the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Any embodiment discussed above with respect to delivery or transport to cells can also be employed with respect to implementing delivery of medicinal compounds discussed in this section.

Effective Dosages

The molecules of the invention will generally be used in an amount effective to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms, or prolong the survival of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the EC50 as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from 0.01 to 0.1 mg/kg/day, or from 0.1 to 5 mg/kg/day, preferably from 0.5 to 1 mg/kg/day or more. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs or treatment (including surgery).

Toxicity

Preferably, a therapeutically effective dose of the molecules described herein will provide therapeutic benefit without causing substantial toxicity. Toxicity of the molecules described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al, 1975, In: The Pharmacological Basis of Therapeutics, Ch. 1, p. 1).

Pendant Groups

A "pendant group" may be attached or conjugated to the nucleic acid. Pendant groups may increase cellular uptake of the nucleic acid. Pendant groups can be linked to any portion of the nucleic acid but are commonly linked to the end(s) of the oligonucleotide chain. Examples of pendant groups include, but are not limited to: acridine derivatives (i.e. 2-methoxy-6-chloro-9-ammoacridine); cross-linkers such as psoralen derivatives, azidophenacyl, proflavin, and azidoproflavin; artificial endonucleases; metal complexes such as EDTA-Fe(II), o-phenanthroline-Cu(I), and porphyrin-Fe (II); alkylating moieties; nucleases such as amino-1-hexanolstaphylococcal nuclease and alkaline phosphatase; terminal transferases; abzymes; cholesteryl moieties; lipophilic carriers; peptide conjugates; long chain alcohols; phosphate esters; amino; mercapto groups; radioactive markers; nonradioactive markers such as dyes; and polylysine or other polyamines. In one example, the nucleic acid is conjugated to a carbohydrate, sulfated carbohydrate, or glycan.

Sequence Identity

"Sequence identity" is herein defined as a relationship between two or more nucleic acid (nucleotide, polynucleotide, RNA, DNA) sequences, as determined by comparing the sequences. In the art, "identity" also means the degree of sequence relatedness between nucleic acid sequences, as the case may be, as determined by the match between strings of such sequences. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a miRNA, an equivalent, a mimic, an isomiR or an antagomir or a source thereof or a composition or a combination as defined herein may comprise additional component(s) than the ones specifically identified, said additional component(s) not altering the unique characteristic of the invention. In addition the verb "to consist" may be replaced by "to consist essentially of" meaning that a method as defined herein may comprise additional step(s) than the ones specifically identified, said additional step(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

Figure 1B:
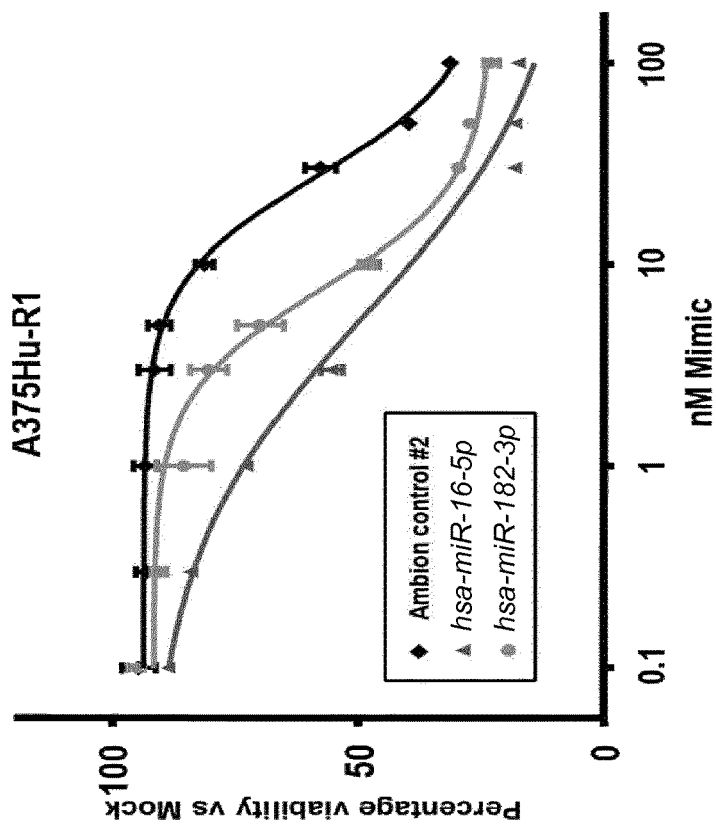
FIG. 1:
Anti-proliferative effect of miRNA's in A375Hu-R1. The vemurafenib resistant clone of A375Hu melanoma cells, A375Hu-R1 was transfected with 0.1-100 nM miRNA mimic and control and cell viability was measured 72 h later. Cell viability inhibition was normalized against Mock transfection and GraphPad Prism was used to fit the curve.
Figure 1A:
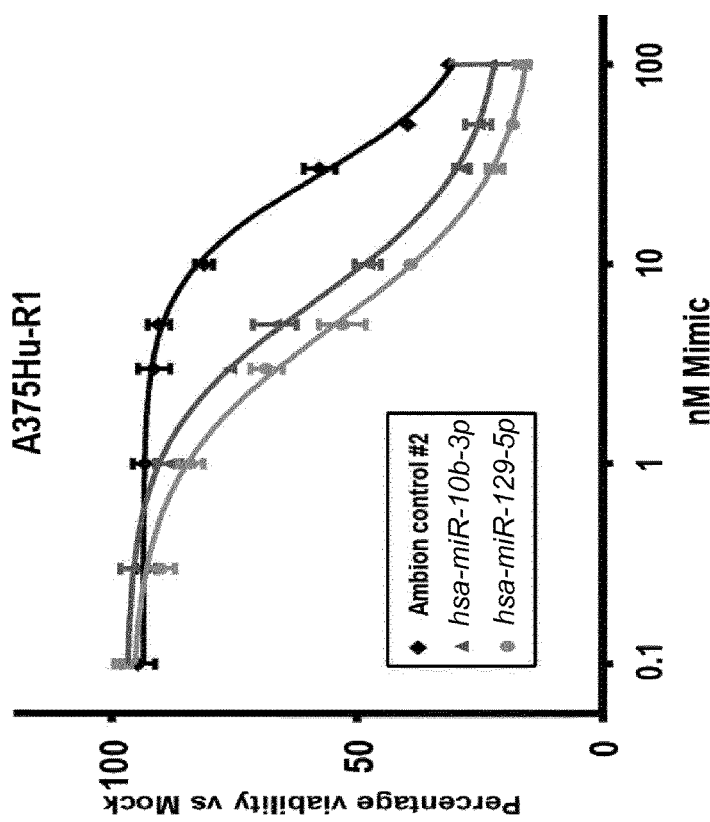
Figure 1D:
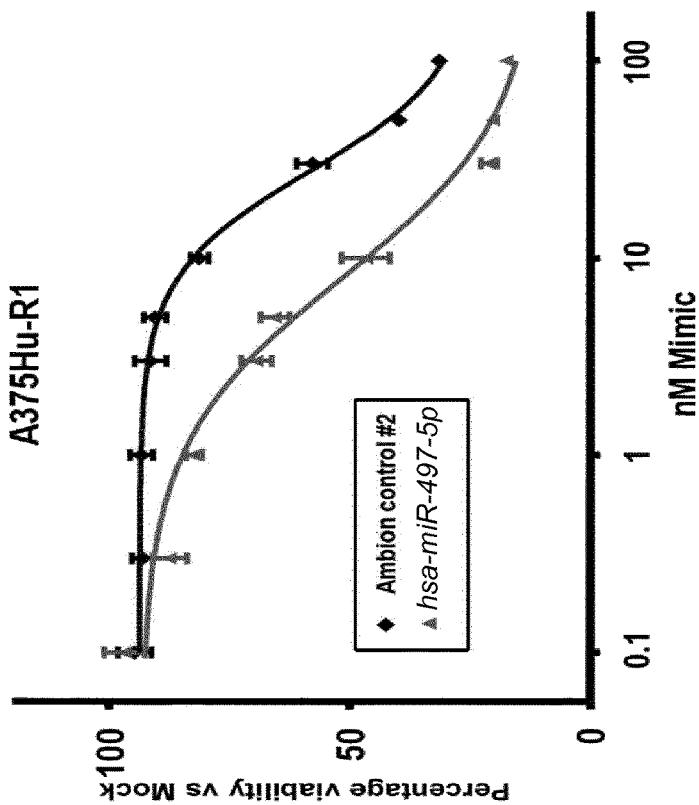
Figure 1C:
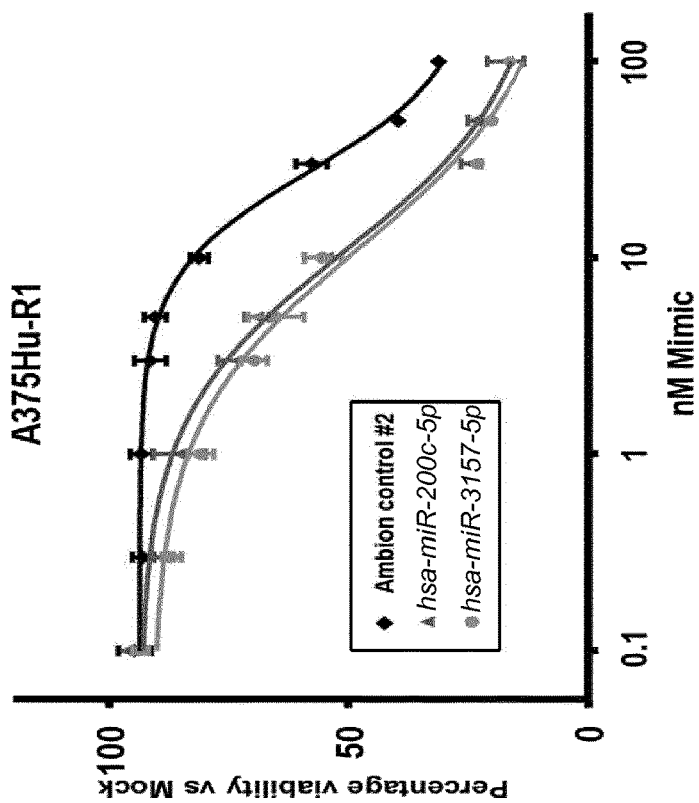
Figure 1E:
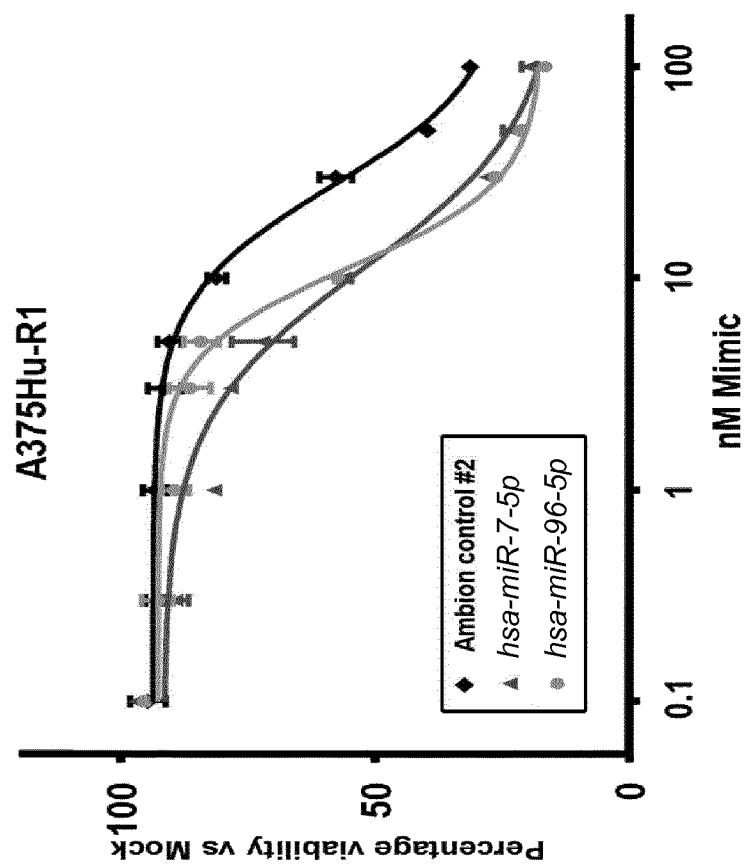
Figure 2A:
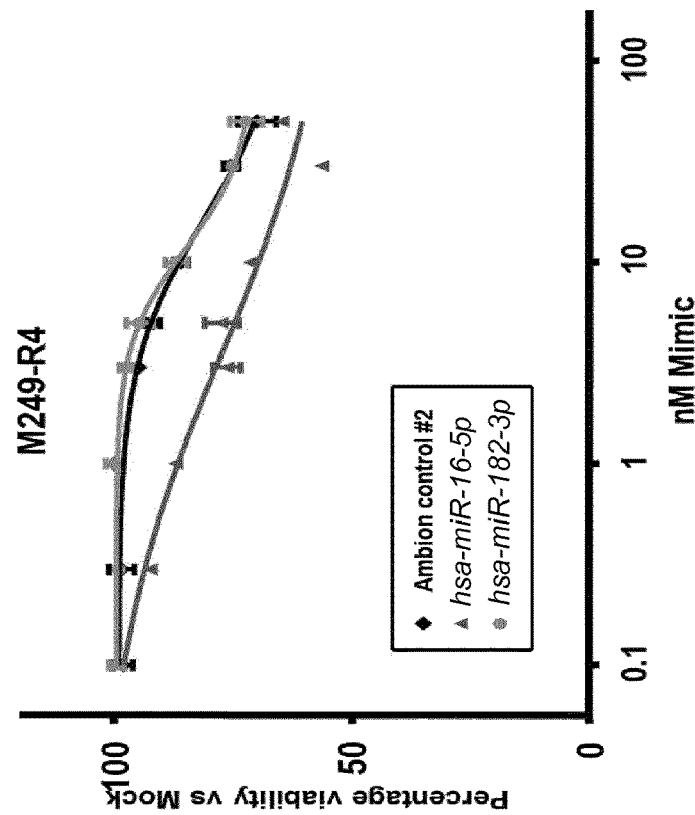
FIG. 2:
Anti-proliferative effect of miRNA's in M249-R4. The vemurafenib resistant melanoma cell line M249-R4 was transfected with 0.1-100 nM miRNA mimic and control and cell viability was measured 72 h later. Cell viability inhibition was normalized against Mock transfection and GraphPad Prism was used to fit the curve.
Figure 2B:
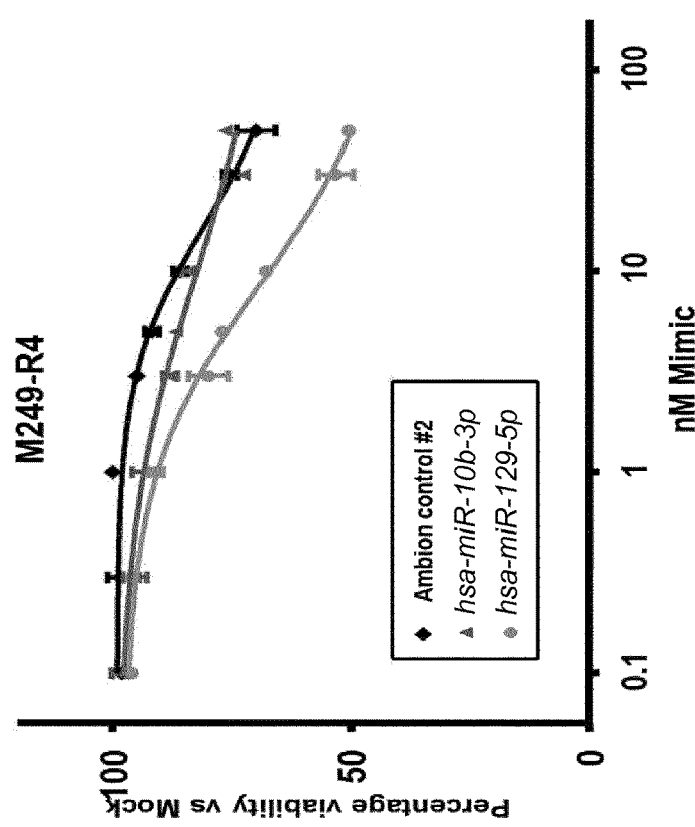
Figure 2C:
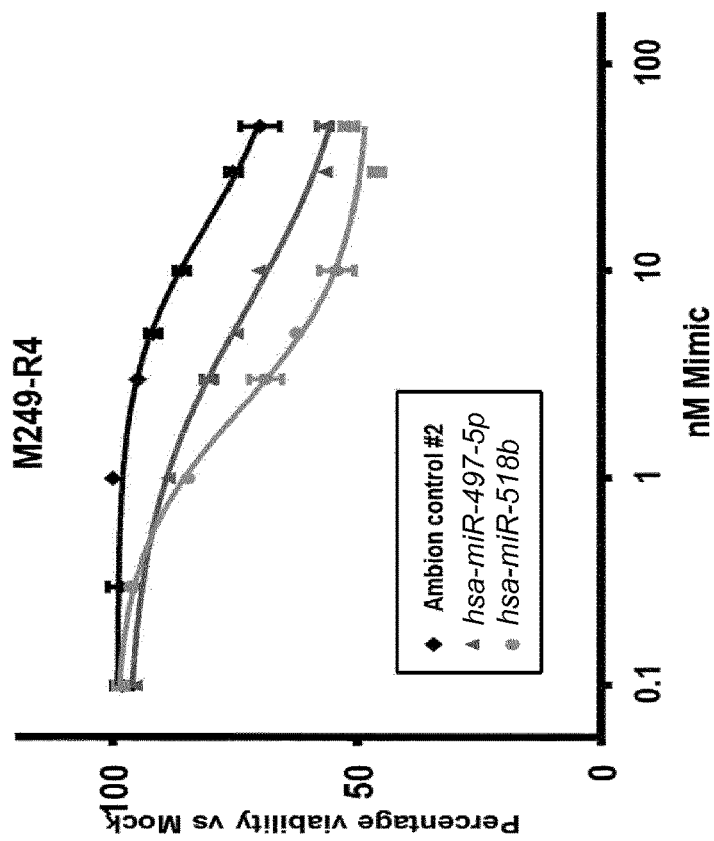
Figure 2D:
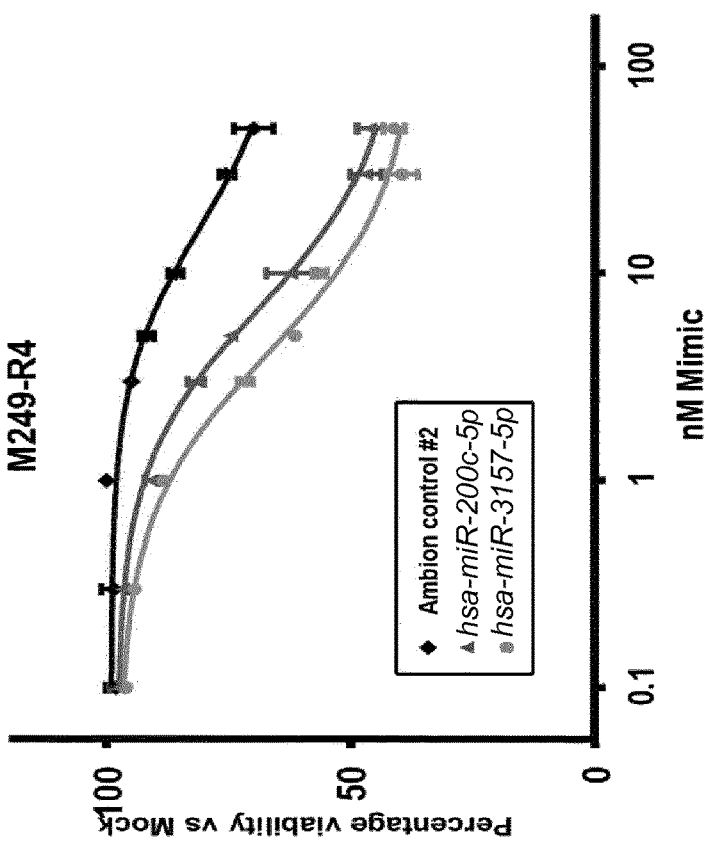
Figure 2E:
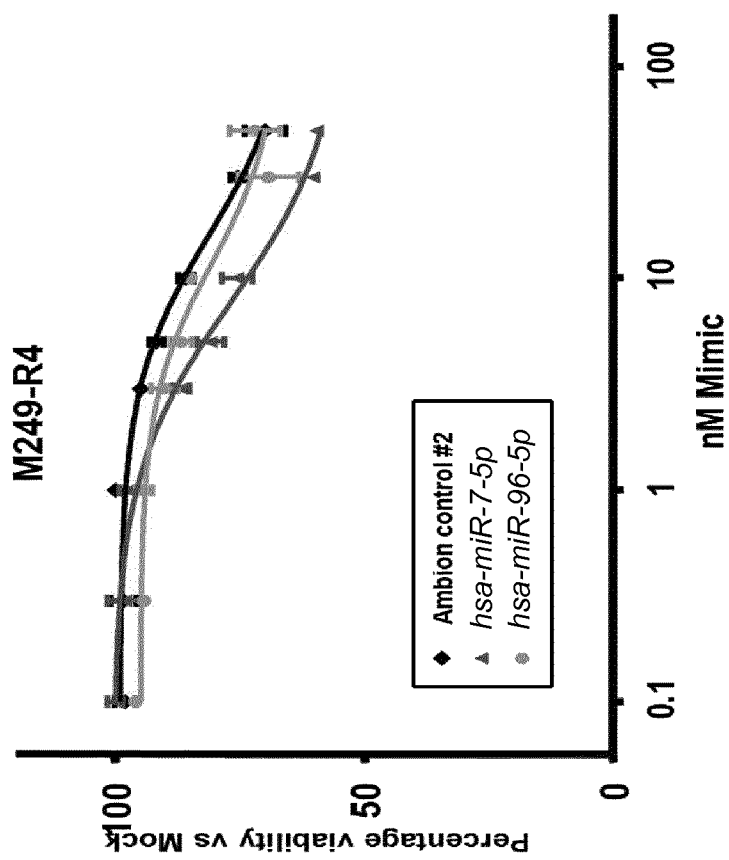
Figure 3A:
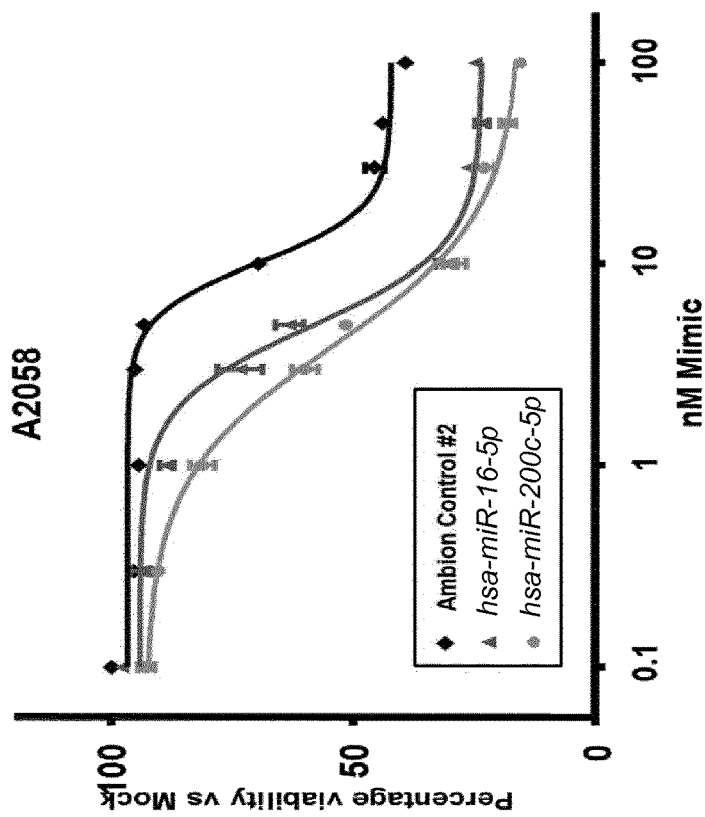
FIG. 3:
Anti-proliferative effect of miRNA's in A2058. The vemurafenib resistant melanoma cell line A2058 was transfected with 0.1-100 nM miRNA mimic and control and cell viability was measured 72 h later. Cell viability inhibition was normalized against Mock transfection and GraphPad Prism was used to fit the curve.
Figure 3B:
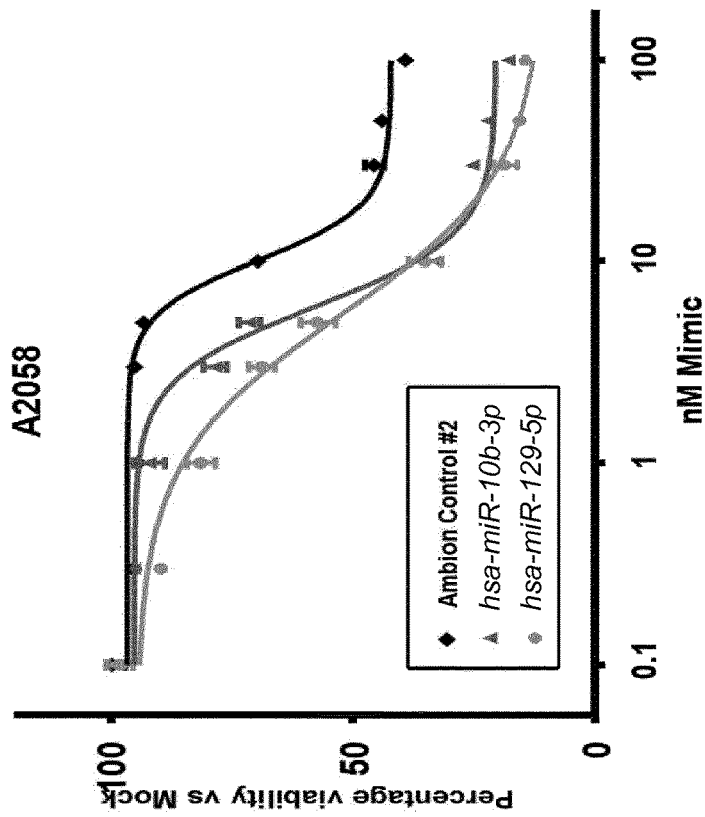
Figure 3C:
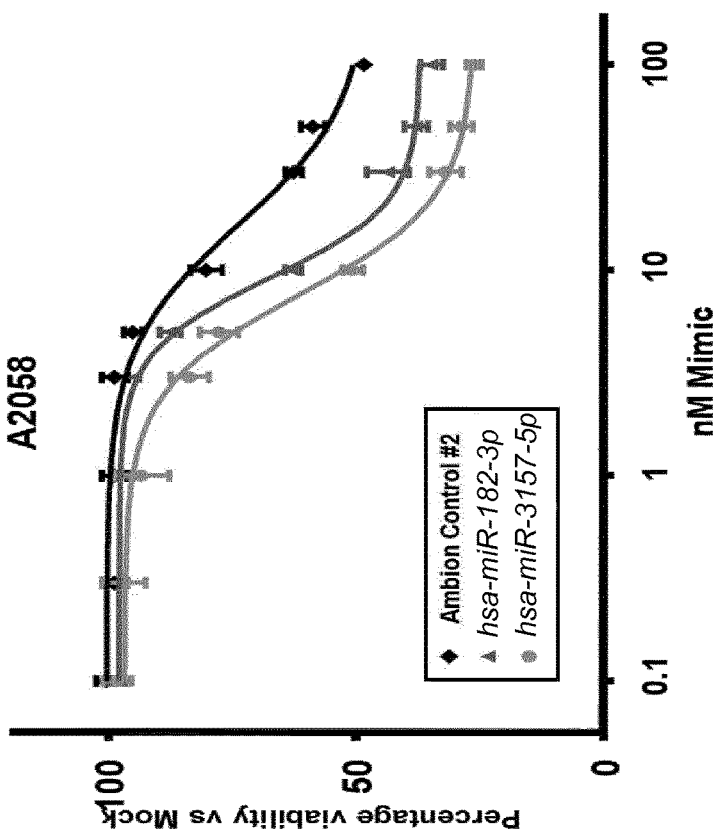
Figure 3D:
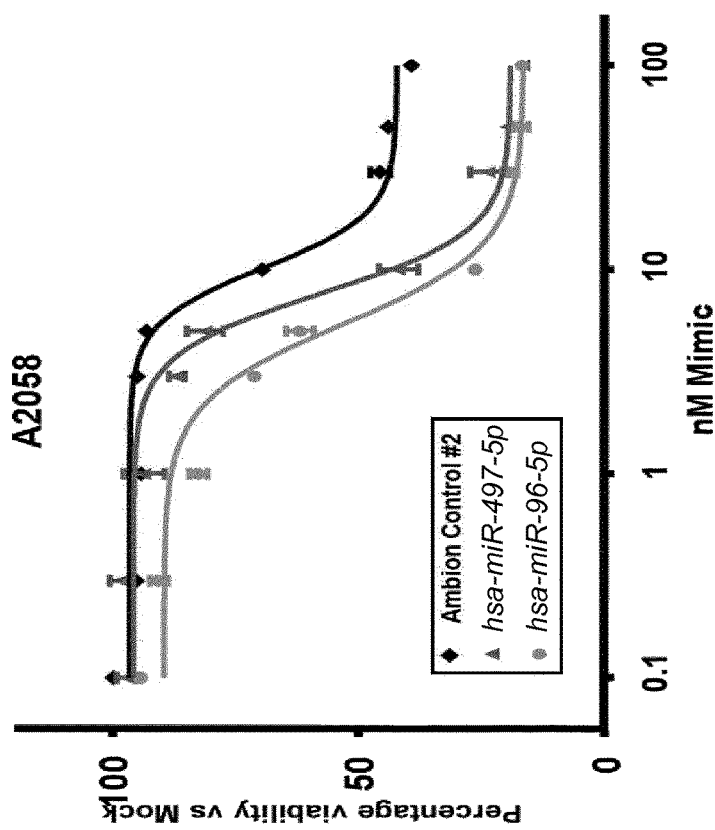
Figure 3E:
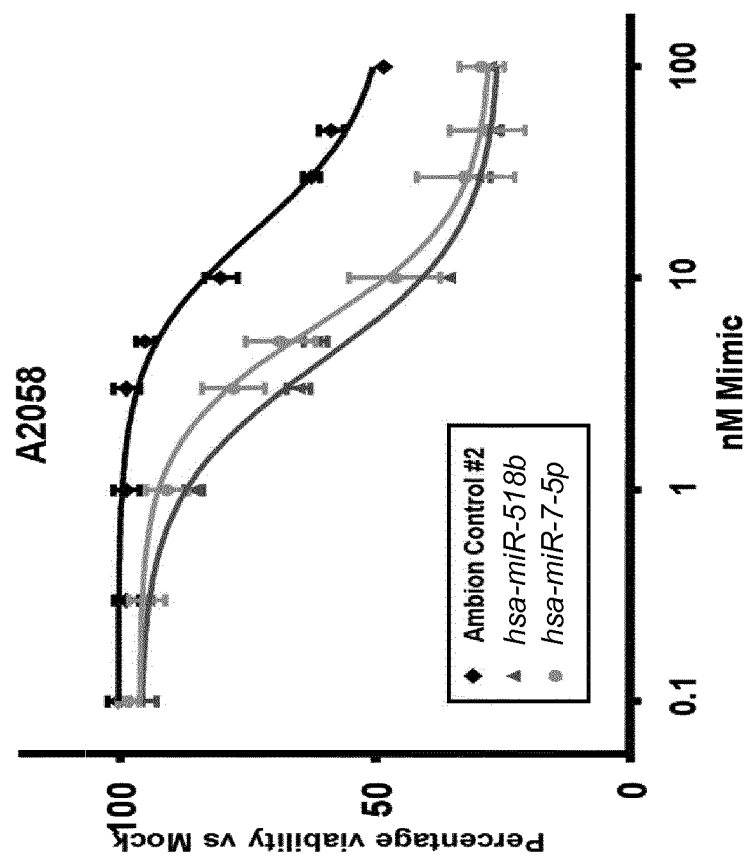
Figure 4A:
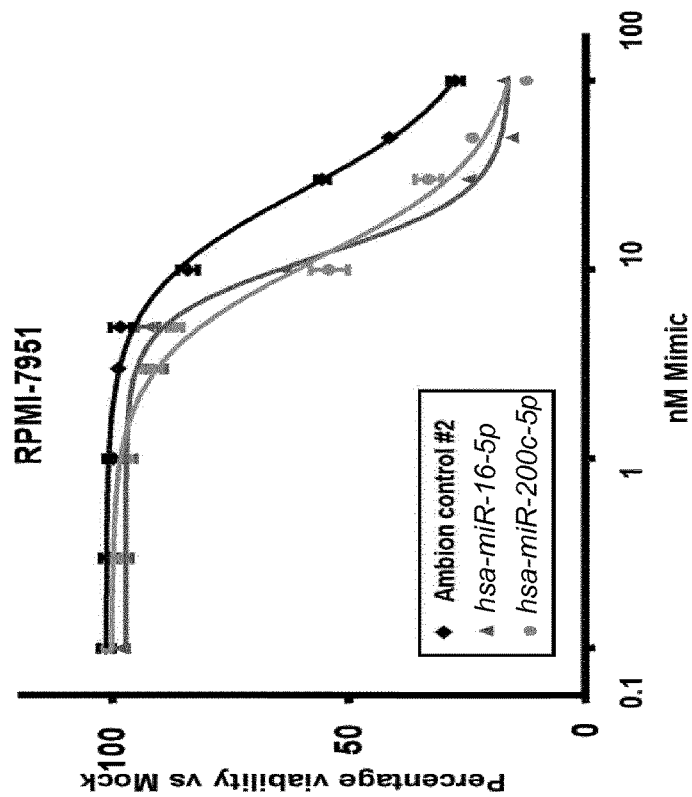
FIG. 4:
Anti-proliferative effect of miRNA's in RPMI-7951. The vemurafenib resistant melanoma cell line RPMI-7951 was transfected with 0.1-100 nM miRNA mimic and control and cell viability was measured 72 h later. Cell viability inhibition was normalized against Mock transfection and GraphPad Prism was used to fit the curve.
Figure 4B:
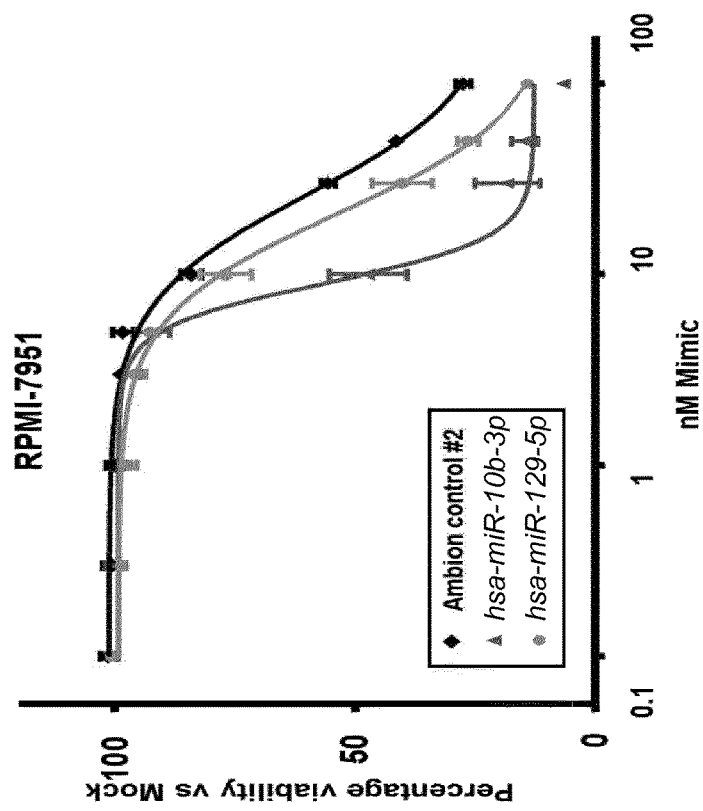
Figure 4D:
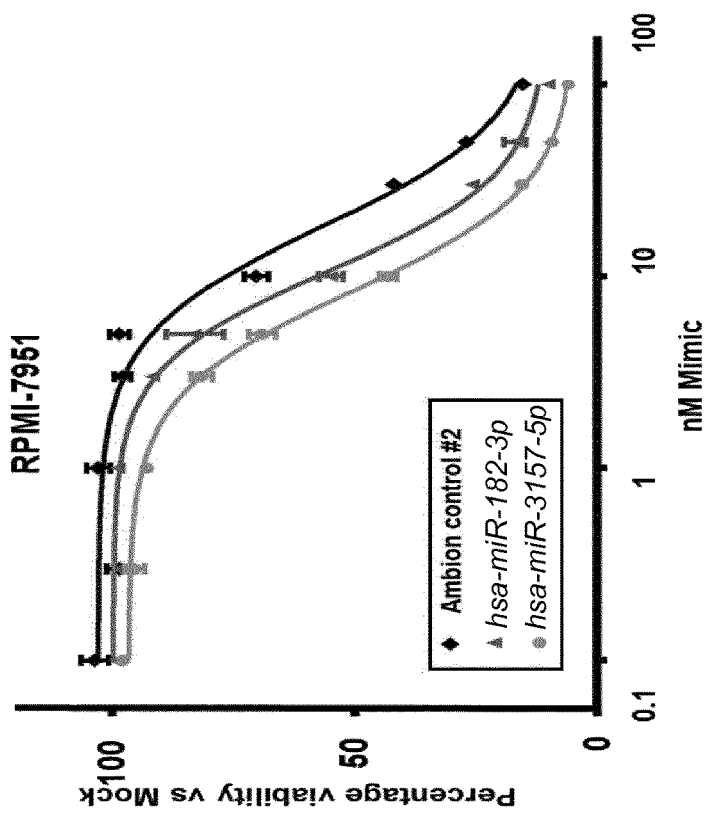
Figure 4C:
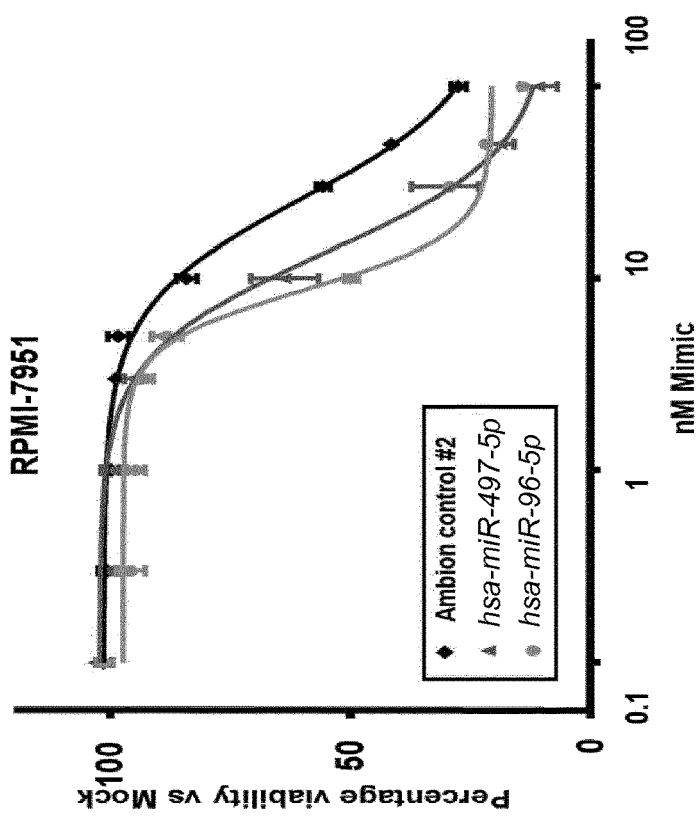
Figure 4E:
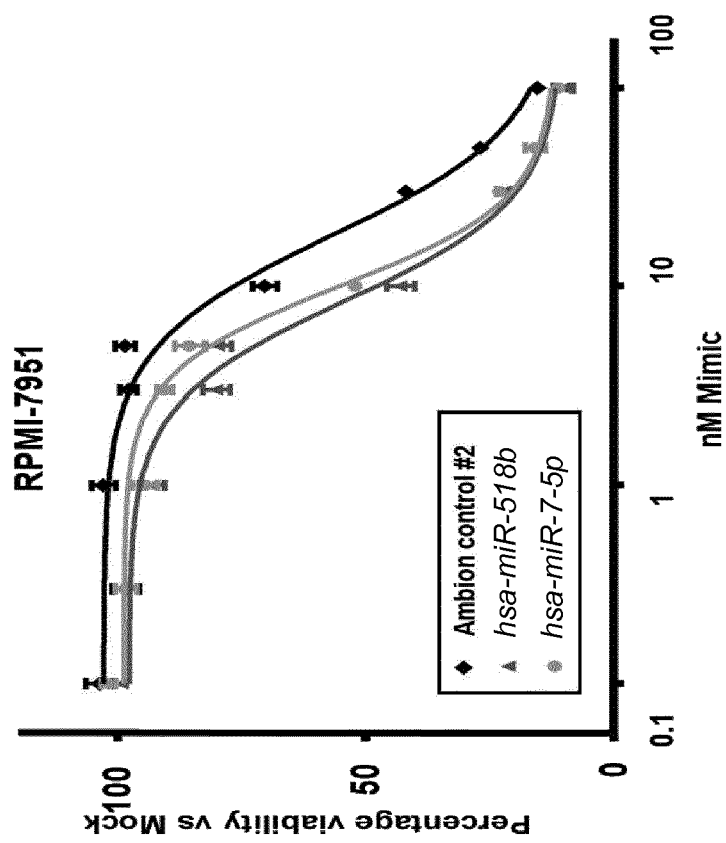

miR-3157 broadly affects melanoma cell line viability. Melanoma cell lines were divided into those that have the BRAFV600E mutation and are sensitive (a), intrinsically resistant (b) or acquired resistance to vemurafenib (c). Cell lines were transfected in triplicate with control miRNA or miR-3157 mimics (10 nM; n=2). Mock is transfectant only. Cell viability was determined using the MTS assay and calculated relative to mock transfected cells.

FIG. 12:

Identification of direct miR-3157 target genes. (a) Transcriptome analysis of A375 cells transfected with miR-3157 or control mimic. Waterfall plots depict differentially expressed genes (expression+/−60%, p<10-5) in miR-3157 transfected A375 cells (left panel), and the predicted miR-3157 targets among the differentially expressed genes (right panel). (b) A375 cells were transfected with miR-3157 or control mimics (10 nM) and monitored for mRNA levels of the indicated genes (identified in (a)) by qPCR. HPRT1 was used for normalization, and mRNA knockdown was calculated relative to the mRNA levels in control transfected cells. (c) A375 cells were transfected with increasing concentrations of miR-3157 or control mimics ('C', 30 nM), and monitored for protein levels of the indicated genes by Western blotting. Tubulin was used as loading control.

FIG. 13:

MiR-3157 directly targets ERK1, AURKB and RRM2. (a) Alignments of the 3'UTRs of ERK1 (TargetScan), RRM2 and AURKB (both microRNA.org) with miR-3157. Underlined nucleotides were mutated (UG→AC, not depicted) for testing the specificity of miR-3157 binding to the selected 3'UTRs in the 3'UTR Luciferase assay. (b) HELA cells were transfected with the psiCHECK2-3'UTR constructs containing unmodified 3'UTR sequence ('WT'), or the 3'UTR sequence with the mutated miR-3157 binding site ('Mu'), together with control ('C') or miR-3157 mimics. Transfections were in duplo, and each experiment was repeated twice.

FIG. 14:

MiR-3157 downregulates targets in vemurafenib-resistant cells. (a) Western blot analysis of the indicated genes for A2058, M249, M249-AR4 and M376 melanoma cells transfected with increasing concentrations of miR-3157 or control mimics (30 nM; 'C'). (b) Western blot analysis of the indicated genes for A375, A2058, M249, M249-AR4 and M376 cells incubated with 1 µM vemurafenib ('VEM') or DMSO ('C') for 24 hrs. Tubulin was used as loading control.

FIG. 15:

Hsa-miR-16-5p and hsa-miR-10-3p in combination with vemurafenib improves inhibition of cell viability of vemurafenib resistant cell line. (a) Vemurafenib concentration dependent inhibition of cell viability of the vemurafenib-resistant cell line RPMI-7951. (b) RPMI-7951 cells were transfected in triplicate with 10 nM control miRNA, control siRNA, siBRAF, hsa-miR-16-5p or hsa-miR-10-3p in the absence and in the presence of vemurafenib (3 µM, N=2). Cell viability was determined using the MTS assay and calculated relative to siRNA scrambled transfected cells. (c) Simulation of concentration dependent inhibition of cell viability with a miRNA characterized by a $GI_{50}$ of 10 nM (50% inhibition of cell viability at 10 nM) in combination with 3 uM vemurafenib (80% inhibition of cell viability).

EXAMPLES

Example 1: Properties of Melanoma Cell Lines

Vemurafenib, a V600E BRAF oral inhibitor approved in August of 2011 for metastatic melanoma patients who are V600E BRAF-positive, is now considered standard of care for the approximately 40% of metastatic melanoma who harbor a BRAF mutation. Approximately 50% of these BRAF-treated patients become resistant to vemurafenib treatment and have documented progressive disease within 6 or 7 months of the start of treatment. The other 50% of BRAF-treated patients do not respond to vemurafenib and are intrinsically resistant to the drug. These patient populations (acquired and intrinsic resistant) are mimicked by (1) vemurafenib sensitive cell lines that have been continuously treated with vemurafenib and became resistant to vemurafenib and (2) melanoma cell lines that are intrinsically resistant to vemurafenib.

Material and Methods

The anti-proliferative effect of small molecules in melanoma cell lines was determined with V600E BRAF inhibitor, vemurafenib (PLX-4032, 51267, Selleck) and MEK inhibitor, selumetinib (AZD-6244, S1008, Selleck). For each cell line optimal growth conditions were determined prior to the experiment. Cells were plated in a 96-well plate at 3000 cells per well (100 uL) and were grown at 37 C, 5% CO2. Small molecule mix (50 uL per well) was made for each concentration in medium. Cells were treated in triplicate 24 hours after plating. After 72 hours medium was replaced and viability was measured with the MTS assay (Promega) according to manufacturer's instructions. Cell viability inhibition is normalized against loading control (0.1% DMSO) and GraphPad Prism was used to fit the curve and calculate $GI_{50}$ values.

The A375Hu melanoma cell line was used to make a vemurafenib (PLX-4032) resistant sub line. A375Hu cells were plated at low density in 96-well plates and exposed to 1 uM PLX-4032. Cell growth was monitored until clonal growth was observed. Wells with clonal growth (approximately 5%) were replated in a 96-well plate and exposed to 1 uM PLX-4032. The 10 best growing clones were replated in 6-well plates in 1 uM PLX-4032 and the three best growing clones were used for further culturing. Clone number 1 (A375Hu-R1) grew best with 1 uM PLX-4032 and was chosen for additional experiments.

Results

Table 6 summarizes the genetic properties of BRAF sensitive, BRAF acquired resistant and BRAF intrinsic resistant cell lines. The A375Hu vemurafenib sensitive cell line was made resistant as described above, while the other cell lines were purchased from ATCC (A2058 and RPMI-7951) or obtained through collaboration with experts in the field (M249 and M249-R4, Nazarian et al. Nature 2010). The genetic properties have been extracted from literature and the Sanger mutation database (http://www.sanger.ac.uk/resources/databases/, Nazarian R., et al, and Atefi M., et al). The $GI_{50}$ concentration, i.e. the concentration that is required for 50% inhibition of cell growth, of the V600E BRAF inhibitor (vemurafenib (PLX-4032) or MEK inhibitor (selumetinib (AZD-6244)) was measured and is listed in Table 6. All resistant cell lines are resistant against inhibition of cell growth by vemurafenib or selumetinib, but the M249-R4 cell line is somewhat less resistant against the selumetinib MEK inhibitor compared to the other cell lines.

Example 2: Inhibition of Cell Viability

Through a functional screen of a lentiviral miRNA expression library in V600E BRAF inhibitor sensitive human A375Hu melanoma cells, a set of 19 miRNA hairpins were discovered that inhibit cell viability of V600E BRAF sensitive melanoma cells (WO2012/005572, Poell et al,). This set of 19 hairpin miRNAs was translated in a set of 27 mature miRNAs that was used to explore their anti-proliferative activity in BRAF inhibitor resistant cell lines. Five mature miRNAs were added to the set of 27 mature miRNAs based on their original activity in the lentiviral miRNA screen to complete the set to a total of 32 mature miRNAs.
Material and Methods The anti-proliferative effect of miRNA's in melanoma cell lines was determined with mature miRNA mimics from Ambion. For each cell line optimal growth and transfection conditions were determined prior to the experiment. Cells were plated in a 96-well plate at 3000 cells per well (100 uL) and were grown at 37 C, 5% CO2. Transfection mix (20 uL per well) was made for each miRNA mimic concentration with 0.3 uL (M249, M249-R4) or 0.5 uL (A375Hu, A375Hu-R1, A2058, RPMI-7951) X-TremeGene (Roche) per well (according to manufacturer's instructions) in Optimem (Invitrogen). Cells were transfected 24 hours after plating in triplicate. Medium was replaced 48 hours after transfection with fresh medium. 72 hours after transfection medium was again replaced and cell viability was measured with the MTS assay (Promega) according to manufacturer's instructions. miRNA's which gave more than 20% inhibition compared to the negative mimic control were considered an hit.
Results Table 7 shows the percentage of cell viability of V600E BRAF inhibitor resistant cells that have been treated with the 32 individual mature miRNAs. Four resistant cell lines were tested, two intrinsically resistant cell lines (RPMI-7951, A2058) and two acquired resistant cell lines (M249-R4, A375Hu-R1). MiRNAs that inhibit cell viability of a resistant cell line by more than 20% compared to the miR-scrambled control have been highlighted in grey in Table 7. Based on this selection criterion and based on the criterion that this selection criterion needs to be met in three out of four resistant cell lines, a set of 10 miRNAs was identified that inhibit cell viability of acquired BRAF resistant cell lines and intrinsic BRAF resistant cell lines. These miRNAs are of interest to treat melanoma patients that carry the V600E BRAF mutation and have been treated with V600E BRAF inhibitor (e.g. vemurafenib or dabrafenib) but did not respond or relapsed after several months.

The 10 miRNAs of interest are: hsa-miR-10b-3p, hsa-miR-129-5p, hsa-miR-16-5p, hsa-miR-182-3p, hsa-miR-200c-5p, hsa-miR-3157-5p, hsa-miR-497-5p, hsa-miR-518b, hsa-miR-7-5p and hsa-miR-96-5p, respectively (using the nomenclature of miRBase Release 19, August 2012). "hsa" means *homo sapiens*.

FIGS. 1-4 show the dose response curve of the mature miRNAs in the four resistant cell lines, i.e. A375Hu-R1, M249-R4, A2058, RPMI-7951, respectively. The figures corroborate the data that are summarized in Table 7 and show that the miRNAs inhibit cell viability significantly better than a miRNA with random sequence (miR-Scr, (Ambion Control)) with potencies ranging between 3 and 10 nM. Comparison of the figures and averaging of the $GI_{50}$ values of the curves results in the following ranking of the miRNAs: hsa-miR-3157-5p, hsa-miR-497-5p, hsa-miR-129-5p, hsa-miR-518b, hsa-miR-200c-5p, hsa-miR-16-5p, hsa-miR-10b-3p, hsa-miR-96-5p, hsa-miR-7-5p, hsa-miR-182-3p.

Example 3: Down-Regulation of Multiple Pathways by miRNA

Figure 5:
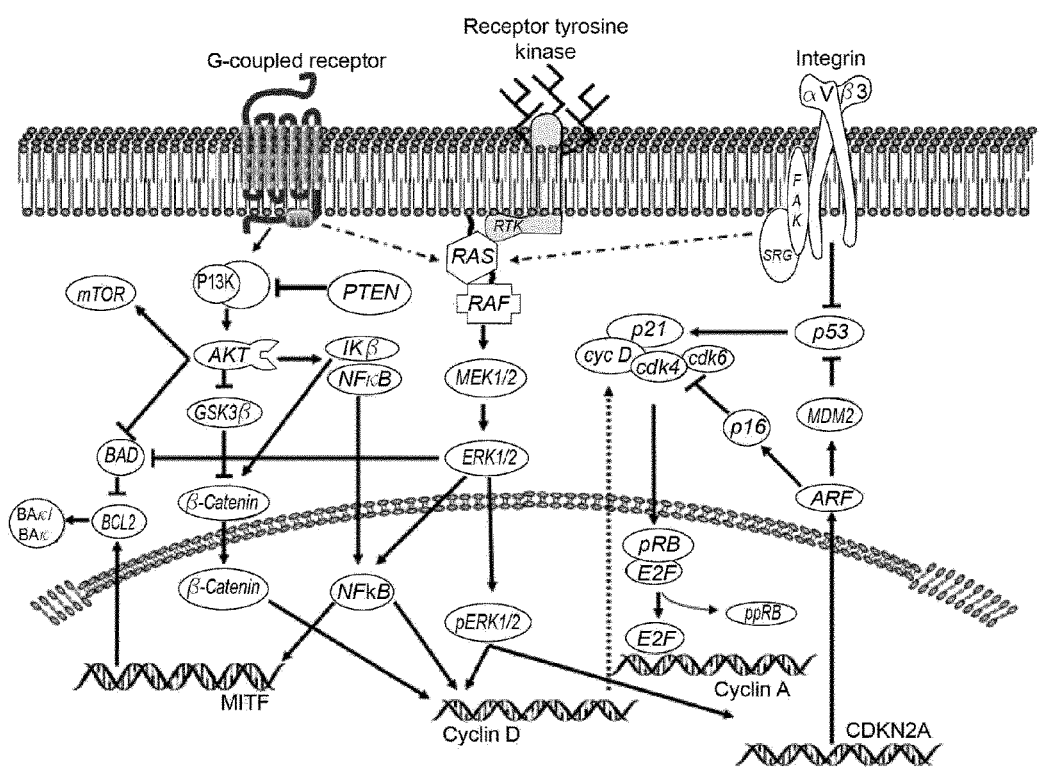
FIG. 5: Schematic overview of three main pathways in melanoma, i.e. the BRAF pathway, the integrin receptor pathway and the PI3K pathway (Villanueva, J. and Herlyn, M. 2009. Melanoma. eLS, modified by addition of CDK6 in the cell cycle complex in the integrin receptor pathway).

A key advantage of therapeutic miRNAs is the intrinsic property of miRNA to down-regulate multiple genes in multiple pathways, while single drug targets inhibit only one pathway. As depicted in Table 7, many of the miRNAs that are active in BRAF resistant cell lines are also active in the BRAF sensitive cell lines. In the BRAF sensitive cell lines, cell proliferation is driven by the activated BRAF pathway. Treatment of these cells with siRNA against BRAF or a BRAF inhibitor such as vemurafenib or dabrafenib or MEK inhibitor such as selumetinib or trametinib results in cell death. This indicates that the BRAF pathway is the main driver of cell proliferation in these cells. The observation that miRNAs are able to inhibit both BRAF sensitive and BRAF resistant cell lines indicates that the miRNA down-regulates pathways other than BRAF that are equally important for cell survival in BRAF sensitive cell line and BRAF resistant cell lines. To exemplify this, we analysed miRNA and siBRAF treated samples for down-regulation of various pathways based on literature. FIG. 5 depicts various pathways in melanoma that lead to enhanced cell proliferation of melanoma cell lines (reproduced from). Roughly three main pathways are depicted, i.e. the activated BRAF pathway, the integrin receptor pathway and the PI3K pathway. The down-regulation of various proteins in these three pathways was investigated in BRAF sensitive and BRAF resistant cell lines.
Material and Methods
A. Knock-Down of CDK6 by hsa-miR-129-5p A375Hu cells were seeded in 6-well plates and transfected with different concentrations (10, 50 and 100 nM) of synthetic hsa-miR-129-5p or BRAF siRNA (100 nM) using RNAiMAX (7.5 µl/well). As control a scrambled miRNA and a non-targeting siRNA pool were included. Proteins were harvested 72 hrs post transfection using RIPA buffer supplemented with HALT™ Phosphatase Inhibitor (Thermo Scientific) and Protease Inhibitor Cocktail (Sigma). Fifteen µg protein was loaded on 7.5% TGX acrylamide gels (Bio-Rad) and subsequently transferred to PVDF membranes. The membranes were blocked in 5% milk in TBS-T and incubated O/N at 4° C. with primary antibodies to bRAF, phosphoERK1/2, CDK6, and tubulin (Santa Cruz). After incubation with secondary goat-anti-mouse antibodies (Santa Cruz), membranes were developed using ECL (Pierce).
B. Knock-Down of CDK4 and BCL2 by hsa-miR-3157-5p A375Hu cells were seeded in 6-well plates and transfected with different concentrations (1, 10 and 100 nM) of synthetic hsa-miR-3157 or BRAF siRNA (100 nM) using RNAiMAX (7.5 µl/well). As control a scrambled miRNA and a non-targeting siRNA pool were included. Proteins were harvested 72 hrs post transfection using RIPA buffer supplemented with HALT™ Phosphatase Inhibitor (Thermo Scientific) and Protease Inhibitor Cocktail (Sigma). Fifteen µg protein was loaded on 7.5% TGX acrylamide gels (Bio-Rad) and subsequently transferred to PVDF membranes. The membranes were blocked in 5% milk in TBS-T and incubated O/N at 4° C. with primary antibodies to bRAF, total ERK1/2, phosphoERK1/2, CDK4, BCL2 and tubulin (Santa Cruz). After incubation with secondary goat-anti-mouse antibodies (Santa Cruz), membranes were developed using ECL (Pierce).

A375Hu cells were seeded in 6-well plates and transfected with different concentrations of vemurafenib (PLX-4032, 0.01, 0.1, 1 uM). Proteins were harvested 72 hrs post transfection using RIPA buffer supplemented with HALT™ Phosphatase Inhibitor (Thermo Scientific) and Protease Inhibitor Cocktail (Sigma). Fifteen µg protein was loaded on 7.5% TGX acrylamide gels (Bio-Rad) and subsequently transferred to PVDF membranes. The membranes were blocked in 5% milk in TBS-T and incubated O/N at 4° C. with primary antibodies to bRAF, total ERK1/2, phosphoERK1/2, CDK4, BCL2 and tubulin (Santa Cruz). After incubation with secondary goat-anti-mouse antibodies (Santa Cruz), membranes were developed using ECL (Pierce).

A2058 cells were seeded in 6-well plates and transfected with different concentrations (1, 10 and 100 nM) of synthetic hsa-miR-3157-5p or BRAF siRNA using X-TremeGene (Roche, 15 µl/well). As control a scrambled miRNA was included. Proteins were harvested 72 hrs post transfection using RIPA buffer supplemented with HALT™ Phosphatase Inhibitor (Thermo Scientific) and Protease Inhibitor Cocktail (Sigma). Fifteen µg protein was loaded on 10% TGX acrylamide gels (Bio-Rad) and subsequently transferred to PVDF membranes. The membranes were blocked in 5% milk in TBS-T and incubated O/N at 4° C. with primary antibodies to bRAF, total ERK1/2, phosphoERK1/2, BCL2, CDK4 and tubulin (Santa Cruz). After incubation with secondary goat-anti-mouse antibodies (Santa Cruz), membranes were developed using ECL (Pierce).

Results

A. Knock-Down of CDK6 by hsa-miR-129-5p

Figure 6:
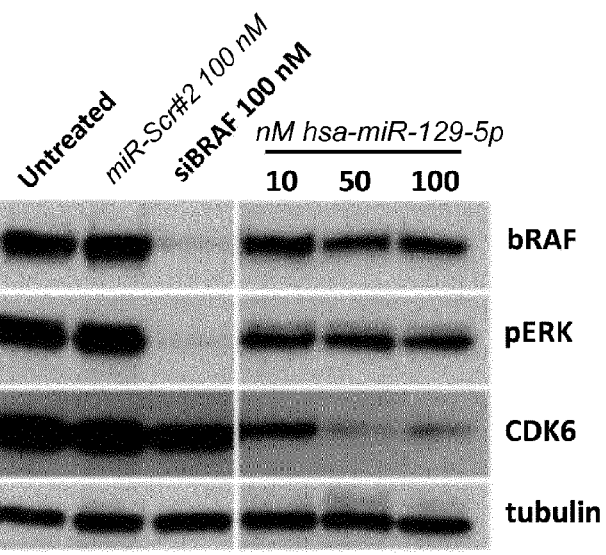
FIG. 6. Overexpression of hsa-miR-129-5p affects CDK6 protein levels in A375Hu cells. Synthetic hsa-miR-129-5p mimic, siRNA BRAF and a control non-targeting miRNA were transfected into A375Hu cells and the effect on CDK6 protein levels was determined by Western immunoblotting. A significant reduction in CDK6 protein abundance was observed in cells transfected with hsa-miR-129-5p. Transfection with siRNA BRAF results in down regulation of BRAF and phospho-ERK1/2 protein levels, but not in reduction of CDK6 protein levels. Tubulin served as protein loading control.

FIG. 6 shows the Western Blot of protein samples extracted from A375Hu cells that were transfected with 10, 50 or 100 nM hsa-miR-129-5p, 100 nM miR-scrambled or 100 nM siBRAF. As expected inhibition of the activated BRAF pathway with siBRAF results in down-regulation of bRAF and pERK. In contrast, hsa-miR-129-5p treatment does not result in pERK down-regulation, while cell viability is significantly inhibited (Table 7). This indicates that another pathway must be down-regulated. In literature CDK6 is described as potential target of hsa-miR-129-5p (Wu J. et al). Therefore CDK6 was selected as interesting target in the integrin receptor pathway (see FIG. 5). FIG. 6 shows that hsa-miR-129-5p down-regulates the cell cycle protein CDK6, while this protein is not down-regulated upon treatment of cells by siBRAF. This indicates that hsa-miR-129-5p regulates cell viability through other pathways, than the main activated BRAF pathway, in this case through the integrin receptor pathway.

B. Knock-Down of CDK4 and BCL2 by hsa-miR-3157-5p

Figure 7:
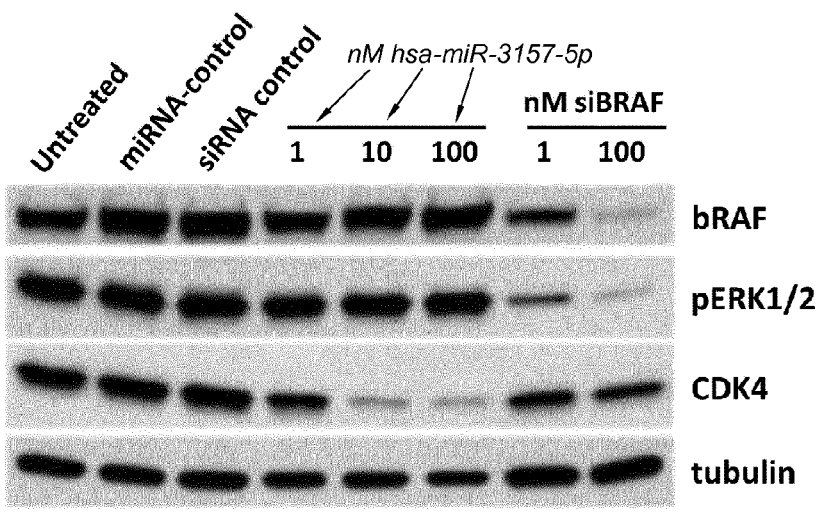
FIG. 7: Overexpression of hsa-miR-3157-5p in A375Hu cells affects CDK4 protein levels. Synthetic hsa-miR-3157-5p mimic, siRNA BRAF, control non-targeting siRNA and a control non-targeting miRNA were transfected into A375Hu cells and the effect on CDK4 protein levels was determined by Western immunoblotting. A significant reduction in CDK4 protein levels was observed in cells transfected with hsa-miR-3157-5p. Transfection with siRNA BRAF results in down regulation of BRAF and phospho-ERK1/2 protein levels, but not in reduction of CDK4 protein levels. Tubulin served as protein loading control.

Along the same line of reasoning, CDK4, a protein involved in melanoma progression (Jalili A., et al) was profiled to be down-regulated by hsa-miR-3157-5p. FIG. 7 shows that CDK4 is down-regulated in A375Hu cells treated with hsa-miR-3157-5p, while this protein is not down-regulated upon treatment of cells with siBRAF. Moreover, hsa-miR-3157-5p 7 does not down-regulate pERK1/2 suggesting that the inhibition of cell viability by hsa-miR-3157-5p acts through inhibition of the integrin receptor pathway and counteract the activated BRAF pathway with equal potency as siBRAF.

Figure 8:
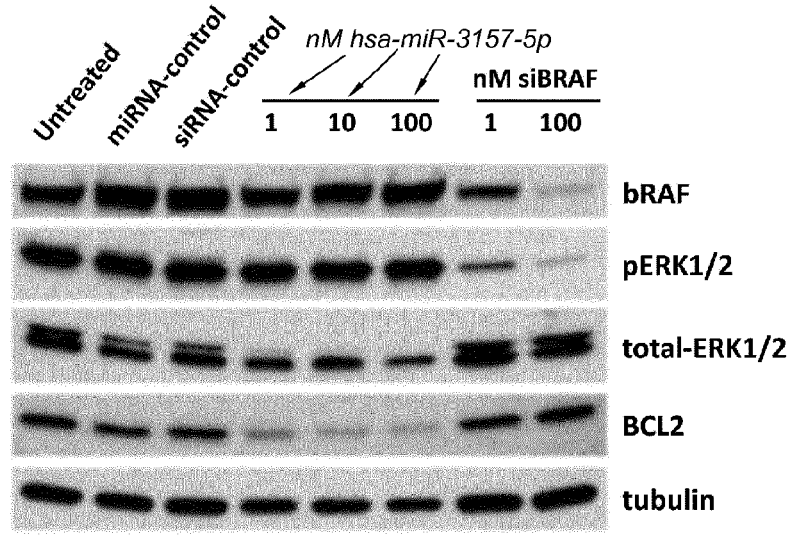
FIG. 8: Overexpression of hsa-miR-3157-5p in A375Hu cells affects BCL2 protein levels. Synthetic hsa-miR-3157-5p mimic, siRNA BRAF, control non-targeting siRNA and a control non-targeting miRNA were transfected into A375Hu cells and the effect on BCL2 protein levels was determined by Western immunoblotting. A significant reduction in BCL2 protein levels was observed in cells transfected with hsa-miR-3157-5p. Transfection with siRNA BRAF results in down regulation of BRAF and phospho-ERK1/2 protein levels, but not in reduction of BCL2 protein levels. Tubulin served as protein loading control.

Another pathway that is involved in melanoma cell proliferation is the PI3K pathway. FIG. 5 indicates that this pathway is, amongst others, characterized by down-regulation of BCL2, a well known cell apoptosis marker. Comparison of BCL2 protein levels in A375Hu cells treated with either miR-3157 or siBRAF shows that BCL2 is down-regulated upon treatment with hsa-miR-3157-5p but not upon treatment with siBRAF (FIG. 8). Similarly pERK1/2 levels are not affected upon treatment with hsa-miR-3157-5p, suggesting that hsa-miR-3157-5p also counteracts the activated BRAF pathway by inhibition of the PI3K pathway.

Figure 9:
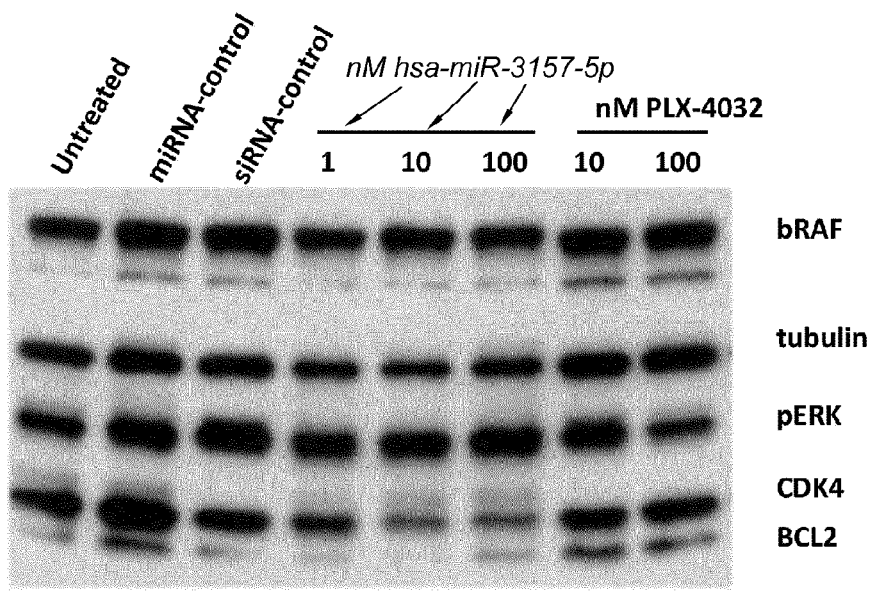
FIG. 9: Synthetic hsa-miR-3157-5p mimic, control non-targeting siRNA and a control non-targeting miRNA were transfected into A375Hu cells or cells were treated with the BRAF inhibitor vemurafenib (PLX-4032). The effect on CDK4 and BCL2 protein levels was determined by Western immunoblotting. A significant reduction in CDK4 and BCL2 protein levels was observed in cells transfected with hsa-miR-3157-5p. Treatment with PLX-4032 results in down regulation of phospho-ERK1/2 protein levels, but not in reduction of CDK4 and BCL2 protein levels. Tubulin served as protein loading control.

Thus far the activated BRAF pathway was inhibited by treatment of cells by siBRAF. Patients are treated with vemurafenib and therefore the same comparison of down-regulation of pathways was performed by comparing A375Hu samples treated with hsa-miR-3157-5p or vemurafenib (PLX-4032). FIG. 9 shows that vemurafenib inhibits pERK, but not CDK4 or BCL2, corroborating the observation that hsa-miR-3157-5p is counteracting activated BRAF pathway through other pathways than vemurafenib. This suggests that the resistance of melanoma cells to vemurafenib can be counteracted by inhibition of other activated pathways in melanoma cells.

Figure 10:
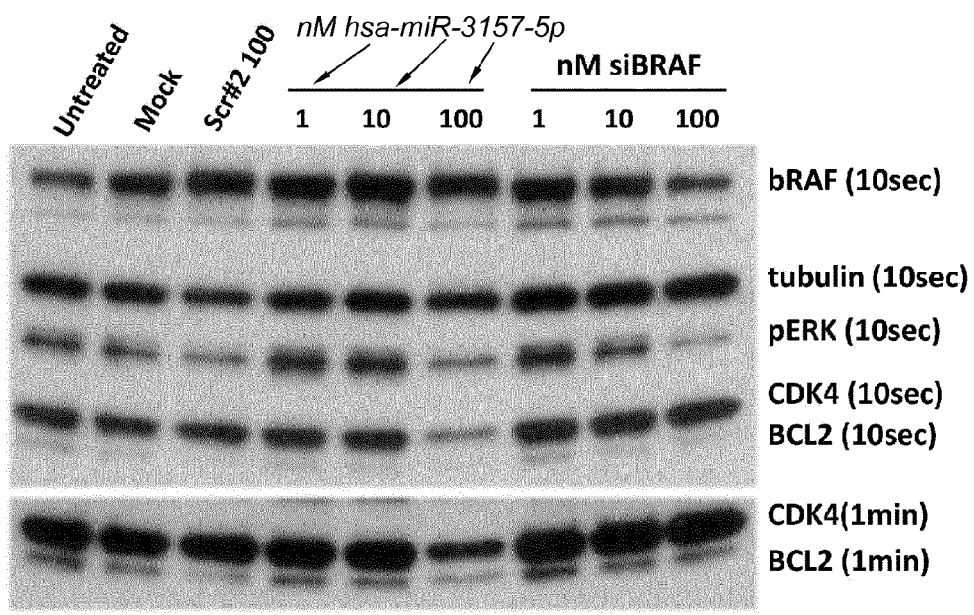
FIG. 10: Overexpression of hsa-miR-3157-5p in A2058 cells affects CDK4 and BCL2 protein levels. Synthetic hsa-miR-3157-5p mimic, siRNA BRAF and a control non-targeting miRNA were transfected into A2058 cells and the effect on CDK4 and BCL2 protein levels was determined by Western immunoblotting. A reduction in CDK4 and BCL2 protein levels was observed in cells transfected with hsa-miR-3157-5p. Transfection with siRNA BRAF results in down regulation of BRAF and phospho-ERK1/2 protein levels, but not in reduction of CDK4 or BCL2 protein levels. Tubulin served as protein loading control.

The above shows that hsa-miR-3157-5p acts through two other pathways than the activated BRAF pathway, i.e. the integrin receptor pathway (CDK4) and the PI3K pathway (BCL2), exemplifying the multiple pathway approach of miRNA drugs and suggesting a smaller change on drug resistance. It was therefore investigated whether hsa-miR-3157-5p inhibits these proteins also in a vemurafenib resistant cell line, A2058. FIG. 10 shows that both CDK4 and BCL2 are down-regulated by hsa-miR-3157-5p, while pERK1/2 is not down-regulated. This suggests that hsa-miR-3157-5p is able to down-regulated proteins through similar mechanism in both BRAF sensitive and BRAF resistant cell lines.

Example 4: miR-3157 Reduces Cell Viability of a Broad Panel of Vemurafenib-Sensitive and Vemurafenib-Resistant Cell Lines The data described in Example 2 and 3 suggest that hsa-miR-3157-5p inhibits melanoma cell viability in vemurafenib-sensitive and vemurafenib-resistant cell lines through down-regulation of CDK4 and BCL2. These proteins are involved in cell cycle and apoptosis and part of the integrin receptor and PI3K pathway, respectively (FIG. 5). To explore the multiple pathway regulation of hsa-miR-3157 in more detail, we first set out to test the effect of hsa-miR-3157-5p overexpression on the viability of a broader panel of vemurafenib-sensitive and vemurafenib-resistant melanoma cell lines using the MTS assay (expansion of the panel described in Example 1 by four cell lines described in the bottom rows of Table 8). For clarity, we note that in Example 4 compound names miR-3157 and hsa-miR-3157 refer to the same compound.

Material and Methods

Cell Culture and Reagents

A375 cells were obtained from the Hubrecht Institute (Utrecht, The Netherlands); SKMEL-28, A2058 and RPMI-7951 were from the ATCC; SKMEL-57 was a gift from Dr. Patricia Groenen (Radboud University Nijmegen Medical Centre, The Netherlands); for cell line characteristics of M249, M249-AR4, M233 and M376 see (Atefi et al. 2011). A375-R, with in vitro acquired resistance to vemurafenib, was established in our lab by clonal selection of cells continually exposed to 1 µM vemurafenib. A375, A375-R, SKMEL-28, A2058 and SKMEL-57 were grown in DMEM GlutaMAX™-I (Gibco®), all other cell lines in RPMI-1640 (Gibco®). Media was supplemented with 10% FBS (Sigma), and cells were maintained in a humidified 37° C. incubator (Thermo Scientific) with 5% $CO_2$. Vemurafenib (PLX4032; Selleck Chemicals) was diluted in DMSO to a stock concentration of 10 mM.

Transfections

Transfections were performed with X-tremeGENE siRNA Transfection Reagent (Roche) or Lipofectamine™ RNAiMAX (Invitrogen), according to the manufacturer's instructions. Synthetic miRNA-3157-5p mimics (Pre-miR™ miRNA Precursors), and the control miRNA Pre-miR™ Negative Control #2 were obtained from Life Technologies (Ambion®). For each construct/condition, transfections in a 96-well format were performed in triplicate.

MTS Assay

Cells were seeded in 96-well plates and transfected the next day. To determine cell viability, cells were incubated with MTS (CellTiter 96® AQueous One Solution Cell Proliferation Assay, Promega), according to manufacturer's instructions. Read-out was performed at 490 nm on a Multiskan FC plate reader (Thermo Scientific) at 72 hours post transfection.

Results

Figure 11A:
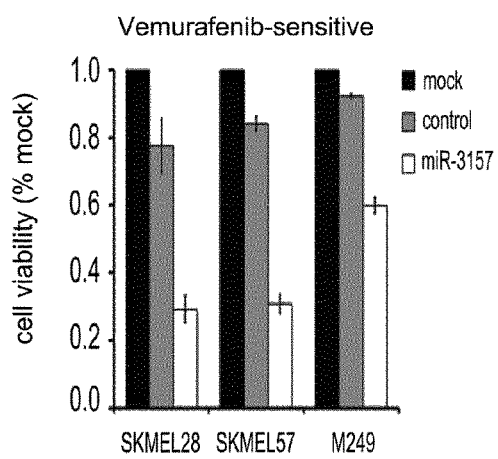
FIG. 11.

We first focused on the effect of miR-3157 on the viability of cell lines that are sensitive to treatment with vemurafenib (for $GI_{50}$ values see Table 8). The $BRAF^{V600E}$ mutant A375 cell line is highly sensitive to vemurafenib ($GI_{50} \approx 0.1$ µM), and was also shown to be sensitive to treatment with miR-3157 (Table 7). $BRAF^{V600E}$ mutant melanoma cell lines SKMEL-28, SKMEL-57 and M249 are all sensitive to treatment with vemurafenib ($GI_{50} \approx 0.6$, 0.8 and 0.3 µM resp.). Transfection of these cell lines with miR-3157 mimic strongly reduced cell viability (FIG. 11a), indicating that melanoma BRAF mutant cell lines sensitive to treatment with vemurafenib show reduced cell viability upon ectopic miR-3157 expression.

Figure 11B:
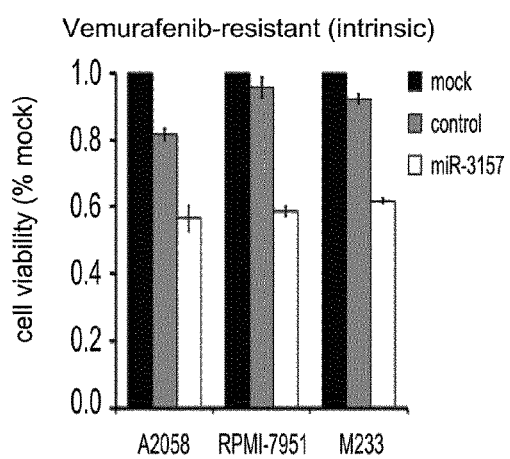

Treatment with BRAF inhibitors targeting $BRAF^{V600E}$ has shown that a number of patients does not respond, and thus are intrinsically resistant to these drugs. We tested the effect of miR-3157 on $BRAF^{V600E}$ mutant melanoma cell lines A2058, RPMI-7951 and M233, which are intrinsically resistant to vemurafenib ($GI_{50} > 10$ µM). While vemurafenib treatment of these cell lines has no effect, their viability was reduced after transfection with miR-3157 mimics (FIG. 11b). This suggests that miR-3157 targets genes that are important for survival in $BRAF^{V600E}$ mutant melanoma cells with intrinsic resistance to BRAF inhibitors.

Figure 11C:
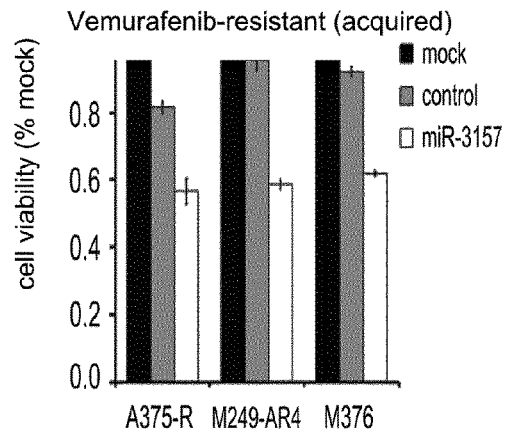

Development of resistance to BRAF inhibitors during the treatment of patients with BRAF mutant melanoma is an eminent problem. Therefore, we investigated the capability of miR-3157 to affect the viability of cell lines that have acquired resistance to $BRAF^{V600E}$ inhibition. Two cell lines, A375-R and M249-AR4, acquired resistance after continuous exposure to vemurafenib in vitro, while M376 was derived from a tumor from a patient that acquired resistance during treatment. Although insensitive to vemurafenib ($GI_{50} > 10$ µM), these cell lines showed reduced viability when transfected with miR-3157 mimics (FIG. 11c). Thus, miR-3157 also appears to regulate genes that are important for survival of melanoma cells that acquired resistance to $BRAF^{V600E}$ inhibition.

Example 5: MiRNA-3157 Targets ERK1, RRM2 and AURKB and is a Candidate Therapeutic Agent for the Treatment of Vemurafenib-Resistant Melanoma To elucidate the mechanism through which hsa-miR-3157-5p regulates multiple pathways, we transfected A375Hu cells with hsa-miR-3157-5p mimics and profiled the effects on the transcriptome using RNA deep sequencing (RNAseq). Based on the overlay of downregulated genes involved in cancer-related pathways and genes predicted as hsa-miR-3157-5p target gene, putative target genes were selected and validated as hsa-miR-3157-5p target gene by qPCR, western blotting and 3'UTR assays. For clarity, we note that in Example 5 the compound names miR-3157 and hsa-miR-3157 refer to the same compound.

Material and Methods miR-3157 Stem-Loop RT-PCR, cDNA Synthesis and Quantitative Real-Time PCR Total RNA was isolated using TRI Reagent® (Sigma). To detect miR-3157 and U6 (small nuclear RNA RNU6-1) by qPCR, first 100 ng total RNA was mixed with 50 nM of a miR-3157 specific stem-loop (SL) primer or a U6 Reverse Transcriptase (RT) primer (Table 9), 33 µM dNTPs and 50 units M-MLV Reverse Transcriptase (RT) enzyme (Promega) in a 15 µl SL-RT reaction, and incubated for 30 min at 16° C., 30 min at 42° C. and 5 min at 85° C. For cDNA synthesis of total RNA, 1 µg RNA was mixed with 50 units M-MLV RT enzyme, 0.4 µg random hexamers (Qiagen) and 1 mM dNTPs in a 20 µl cDNA synthesis reaction, and incubated 10 min at 25° C., 120 min at 37° C. and 5 min at 85° C. For miR-3157 and U6 quantification, one µl SL-RT product was used for quantification in a single 20 µl qPCR reaction, using iQ™ SYBR® Green (Bio-Rad), and 0.625 µM forward and reverse primer (Table 9). The PCR protocol was 5 min 95° C. (1×), 10 s 95° C./20 s 60° C./10 s 72° C. (×45). For mRNA quantification, 1 µl cDNA was incubated with 1.25 µM gene-specific forward and reverse primers (Table 10) and iQ™ SYBR® Green in a 20 µl qPCR reaction for 5 min at 95° C. (1×), 15 s 95° C./30 s 60° C./30 s 72° C. (×45). PCR amplification was performed on a CFX96 Touch™ Real-Time PCR Detection System (Bio-Rad).

RNA Sequencing

A375 cells were plated in duplo in a 6-well plate at $1.5 \times 10^5$ cells/well. The next day, cells were transfected with 100 nM miR-3157 or Negative Control #2 mimics, using 15 µl X-tremeGENE. This procedure (plating and transfection) was repeated three times to generate biological replicates. After 72 hrs, total RNA was isolated using TRI reagent (Sigma-Aldrich) according to the manufacturer's protocol. From 30 µg total RNA, the mRNA was isolated using the MicroPoly(A)Purist kit (Ambion), and the mRNA-ONLY Eukaryotic mRNA Isolation Kit (Epicenter). RNAseq libraries were further prepared using the SOLiD™ Total RNA-Seq Kit (Life Technologies (LT)). Fragmentation of the isolated mRNA was performed by incubation in 20 µl 3 mM MgCl/10 mM Tris pH8, for 15 minutes at 95° C. The fragmented mRNA was incubated with SOLiD™ Adapter mix (LT) in STAR hybridization solution (LT), and incubated for 5 minutes at 65° C. After incubation on ice, adapter ligation was performed according to the STAR protocol (LT). The samples were run on a 10% denaturing polyacrylamide gel, and fragments from 180-300 nucleotides were excised. Reverse transcription and PCR amplification of the libraries was performed according to the STAR protocol, followed by excision of 200 to 300 nucleotide fragments from a 6% native polyacrylamide gel. Sequencing of the fragments was performed on the SOLiD™ System (LT). Differentially expressed genes were selected using a +/−change in expression of at least 60%, and a cut-off p-value of $<10^{-5}$.

Target Prediction miRWalk (Dweep et al. 2011), miRmap (Vejnar et al. 2012), miRanda, miRDB, DIANAmT and Targetscan were used to predict putative targets of miR-3157. Genes which were predicted by four or more databases were selected for further analysis. Pathway analysis (Ingenuity) and literature were used to select predicted putative targets in cancer related pathways.

Western Blotting

Transfection was performed as described in Example 4 in 6-well format. Proteins were isolated using RIPA buffer (50 mM Tris pH 8.0, 150 mM NaCL, 1% NP-40, 0.5% Sodium deoxycholate, 0.1% SDS), supplemented with Protease Inhibitor Cocktail (Sigma) and Halt™ Phosphatase Inhibitor Cocktail (Pierce/Thermo Scientific). Fifteen μg protein was loaded on a 12% Mini-PROTEAN® TGX™ Precast Gel (Bio-Rad), and proteins were transferred to Immun-Blot PVDF Membrane (Bio-Rad). Membranes were blocked in 5% milk or 5% BSA in TBS-T, and incubated O/N at 4° C. with primary antibodies against α-tubulin (1:5000), BRAF, pERK1/2, CDK4, RRM2 (all 1:1000), BCL-2 (1:500) (Santa Cruz), total-ERK1/2 (1:2000), BIRC5, AURKB (1:1000) (Cell Signaling), ERK1 (1:2000) (GeneTex). After incubation with appropriate secondary antibodies and western blot chemiluminescence substrate ECL (Pierce/Thermo Scientific), membranes were exposed to CL-XPosure Film (Pierce/Thermo Scientific).

3'UTR Luciferase Assay

The 3'UTR sequences (Table 11) were synthesized by IDT Technologies, and cloned into psiCHECK™-2 (Promega). HeLa cells ($5\times10^4$) were seeded in 24-well plates, and the next day transfected with 100 ng/well 3'UTR psi-CHECK™-2 construct and 10 nM miR-3157 mimics, or control miRNA using Lipofectamine 2000 Transfection Reagent (Invitrogen). After 24 hrs cells were lysed using Passive Lysis Buffer and luciferase activity was measured using the Dual-Luciferase Reporter Assay System (Promega) and the Glomax-Multi Detection system (Promega) in a 96-well format according to the manufacturer's protocol. The Renilla luciferase signal was normalized to background Firefly luciferase, and changes in Renilla luciferase activity in the miR-3157 transfected cells calculated relative to the Renilla signal in control mimic transfected cells.

Results miR-3157 Target Identification

Figure 12:
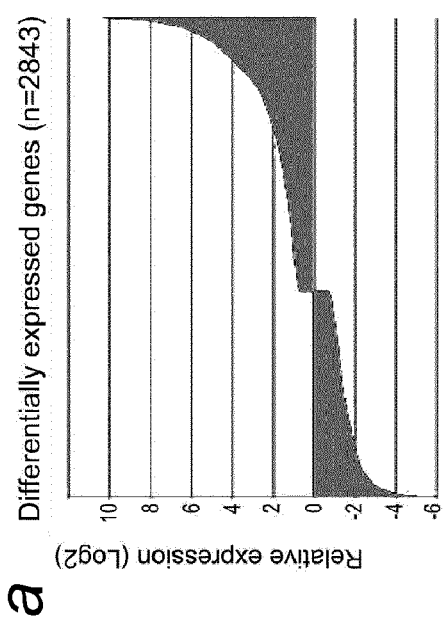
Figure 12:
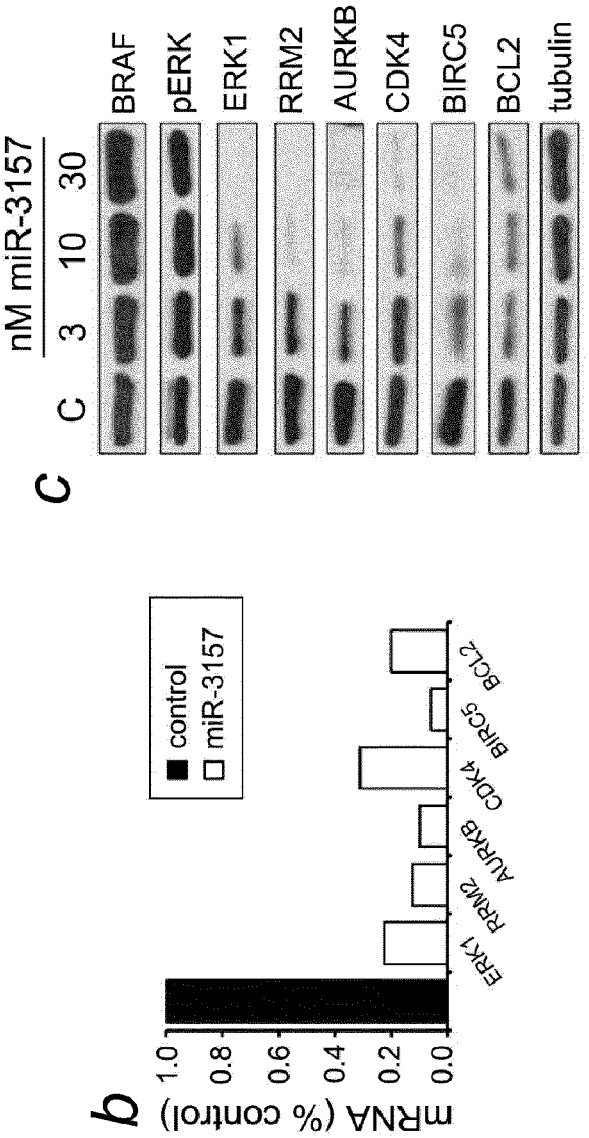

We used a change in expression of at least 60% and a p-value $<10^{-5}$ to identify genes that are differentially expressed (up- or downregulated) between miRNA control or miR-3157 transfected cells (FIG. 12a, left panel). An enrichment of downregulated genes was observed when we employed in silico target prediction analysis for hsa-miR-3157-5p for the pool of differentially expressed genes (FIG. 12a, right panel). Of the predicted targets, 145 genes showed reduced mRNA levels. The presence of predicted targets in the pool of upregulated genes is probably the result of incorrect predictions, or may be caused by other, direct or indirect, effects of miR-3157.

A number of the top predicted genes with strongly reduced mRNA levels in the RNAseq analysis, extracellular signal-regulated kinase 1 (ERK1/MAPK3), ribonucleotide reductase M2 (RRM2) and aurora B kinase (AURKB), was selected for confirmation by quantitative real-time PCR (qPCR). We also selected cyclin-dependent kinase 4 (CDK4), B-cell CLL/lymphoma 2 (BCL2) and baculoviral IAP repeat-containing protein 5 (BIRC5/Survivin), genes with well established roles in cancer, which were not predicted as miR-3157 targets but showed strongly decreased mRNA levels (60%) in the RNAseq analysis. For all genes, reduced mRNA levels were detected by qPCR in A375 cells transfected with miR-3157 compared to miRNA control transfected cells (FIG. 12b). To see if the reduced mRNA levels of these genes correlated with a reduction in their protein levels, we transfected A375 cells with increasing concentrations of miR-3157 and monitored for protein levels by Western blotting. A strong reduction in protein levels was noted for all genes, and most pronounced for ERK1, RRM2, AURKB and BIRC5 (FIG. 12c).

Figure 13:
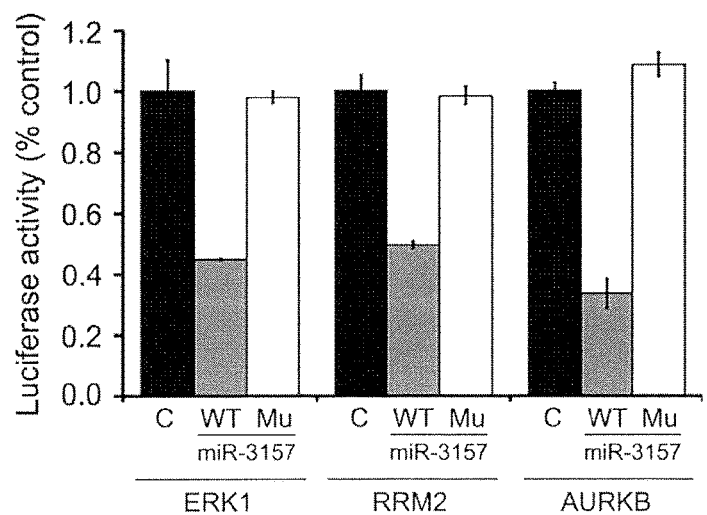

Next, we employed 3'UTR Luciferase-based assays to investigate if the predicted targets ERK1, RRM2 and AURKB are indeed direct targets of miR-3157 (FIG. 13). Alignments between miR-3157 and the 3'UTRs of the putative targets, as obtained from TargetScan (ERK1) and microRNA.org (RRM2, AURKB), show single binding sites (FIG. 13a). The 3'UTR sequences (AURKB: full length; RRM2 and ERK1: partial) were cloned into psiCHECK-2, and transfected into HeLa cells simultaneously with miR-3157 or control mimics. The results show reduced luciferase activity for all three targets (FIG. 13b). To investigate the specificity of miR-3157 binding, we mutated the miR-3157 binding sites of the three targets in an identical manner (FIG. 13a, underlined nucleotides). As expected, Luciferase activity remained unaffected (FIG. 13b). The data suggest that miR-3157 exerts its effect, in part, by directly regulating ERK1, RRM2 and AURKB.

MiR-3157 Downregulates its Targets in Vemurafenib-Resistant Melanoma Cells

Figure 14:
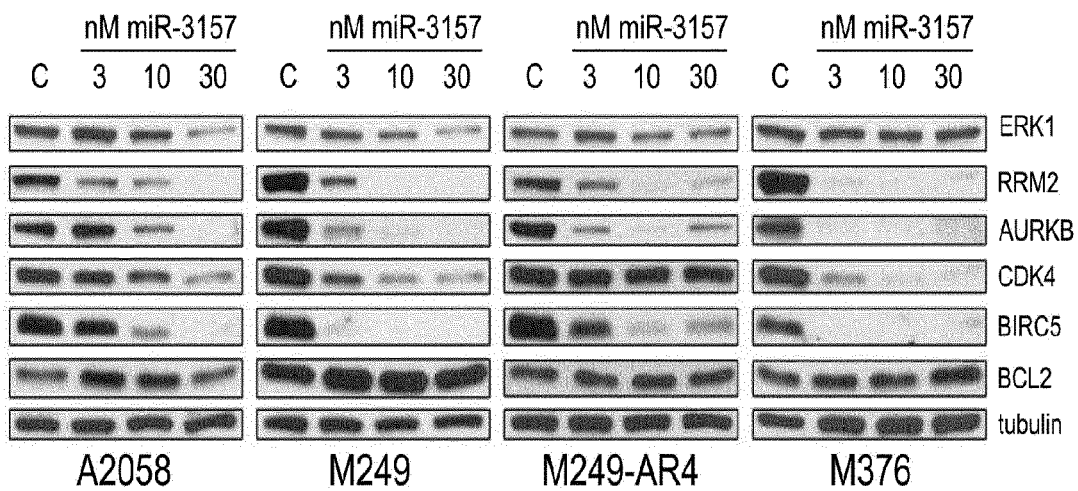
Figure 14:
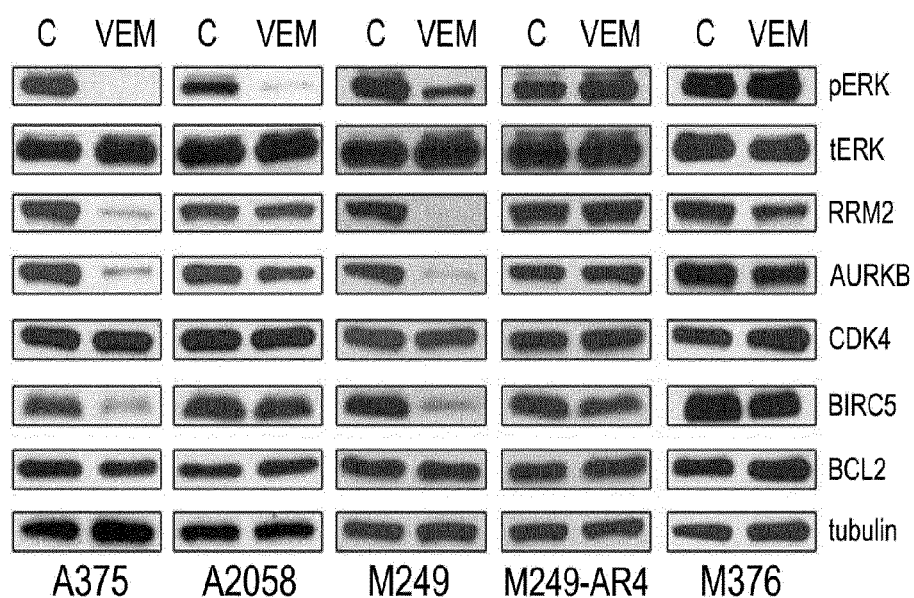

The genes that we identified as, direct or indirect, targets of miR-3157 in A375 cells are involved in cell proliferation and apoptosis, which provides a biological explanation for the effect of miR-3157 on A375 cell viability. We also show that miR-3157 reduces cell viability of various other melanoma cell lines (Table 7 and FIG. 11). We were interested if miR-3157 also downregulates the direct, and indirect, targets in a number of these melanoma cell lines, particularly in a vemurafenib-resistant context. We transfected A2058 (intrinsically resistant), M249 (sensitive), M249-AR4 (acquired resistance in vitro) and M376 (acquired resistance in vivo) with increasing concentrations of miR-3157, and the effect on protein levels was monitored by Western blotting. As expected, the direct targets RRM2 and AURKB were strongly downregulated in all cell lines, with slight differences per cell line (FIG. 14a). Surprisingly, ERK1 protein levels were not very strongly affected in these cell lines, which is in contrast to what was observed for A375 (FIG. 12c). The indirect targets CDK4, BIRC5 and BCL2, show clear variations, with no effect of miR-3157 on BCL2 protein levels in any of the cell lines. CDK4 shows large variations in regulation by miR-3157, with no effect in M249-AR4, a mild effect in A2058 and a strong downregulation in M249 and M376. The effect of miR-3157 on BIRC5 protein levels, however, is highly similar to its effect on the direct targets RRM2 and AURKB, with strong downregulation in all cell lines. The data suggest that the effect of miR-3157 on BRAF-mutant melanoma can largely be explained by strong downregulation of its direct targets RRM2 and AURKB, and in part by differential regulation of other genes, in both a vemurafenib-sensitive and -resistant environment.

Since miR-3157 downregulates genes in BRAF-mutant melanoma cells that are vemurafenib-resistant, we wondered how vemurafenib affects the protein levels of these genes. We incubated A375 cells, and the melanoma cell lines used in FIG. 14a, with vemurafenib and investigated protein levels of the miR-3157 direct and indirect targets by Western blotting. We included phospho-ERK in the analysis as control for vemurafenib functionality, because it downregulates pERK in A375, A2058 and M249, but not in M249-

AR4 and M376 (Atefi et al. 2011, Nazarian et al. 2010). In the vemurafenib-sensitive cell lines A375 and M249, vemurafenib downregulated the miR-3157 direct targets RRM2 and AURKB, as well as BIRC5 (FIG. 14b). Interestingly, in the vemurafenib-resistant cell lines A2058, M249-AR4 and M376, these genes showed protein levels similar to control-treated cells (FIG. 14b). These results show that vemurafenib has lost the ability to repress the genes targeted by miR-3157 in a vemurafenib-resistant environment.

Our data show that miR-3157 direct targets AURKB and RRM2, and secondary target BIRC5, are repressed in vemurafenib-sensitive BRAF-mutant melanoma cells when treated with vemurafenib. However, the ability of vemurafenib to repress these genes when cells are resistant appears to be lost. Previous studies have linked AURKB and BIRC5 to vemurafenib-resistance (Bonet et al. 2012, Ji et al. 2013). A role for RRM2 in BRAF-inhibitor resistance has not been shown previously.

Recent studies show that vemurafenib treatment (Haferkamp et al. 2013), or RRM2 silencing (Aird et al. 2013) both induce melanoma cell senescence. Low RRM2 expression correlates with increased senescence in nevi and melanoma tumors with mutant BRAF, and high expression with reduced patient survival (Aird et al. 2013). Our data show that vemurafenib lost its ability to repress RRM2 expression in vemurafenib-resistant melanoma cells, suggesting these cells have overcome their block in cell cycle arrest. Therefore, RRM2 suppression, as conferred by miR-3157, seems advantageous in the treatment of vemurafenib-resistant melanoma.

One of the characteristics of melanoma that hampers patient treatment is its heterogeneous nature and inherent ability to circumvent single-gene targeted drug treatments, as evidenced by the use of BRAT-inhibitors like vemurafenib. It requires a drug to target multiple genes in order to elicit a durable effect and prevent the occurrence of resistance, hence the start of clinical trials using drug combinations. We show that miR-3157 is capable of reducing viability of various $BRAF^{V600E}$ melanoma cell lines that are sensitive or resistant to vemurafenib, which appears the consequence of targeting a number of genes generally important for the survival of BRAF-mutant melanoma cells.

Example 6: Improvement of the Inhibition of Cell Viability of Vemurafenib-Resistant Cells by Treatment of Cells with a Combination of Vemurafenib and hsa-miR-16-5p or Hsa-miR-10b-3p Material and Methods The inhibitory potency of hsa-miR-16-5p and hsa-miR-10b-3p on cell viability of RPMI-7951 cells was determined with mature miRNA mimics from Ambion in combination with $BRAF^{V600E}$ inhibitor, vemurafenib (PLX-4032, 51267, Selleck). The control miRNA with a scrambled sequence (Pre-miR™ Negative Control #2) was obtained from Ambion, while the additional controls, siBRAF and scrambled siRNA, were obtained from Dharmacon. Vemurafenib (dissolved in DMSO) was added to medium to a concentration of 9 µM and added to empty plates (96 well plate, 50 uL per well). Cells were seeded at 3000 cells per well (100 uL) to a total volume of 150 uL (3 µM vemurafenib final concentration) and were grown at 37 C, 5% CO2. Transfection mix (20 uL per well) was made for each miRNA mimic concentration with 0.5 uL X-TremeGene (Roche) per well (according to manufacturer's instructions) in Optimem (Invitrogen). Cells were transfected 24 hours after plating. Each transfection was performed in triplicate. Medium was replaced 48 hours after transfection with fresh medium containing 3 uM vemurafenib. 72 hours after transfection medium was again replaced and cell viability was measured with the MTS assay (Promega) according to manufacturer's instructions.

Results

Figure 15:
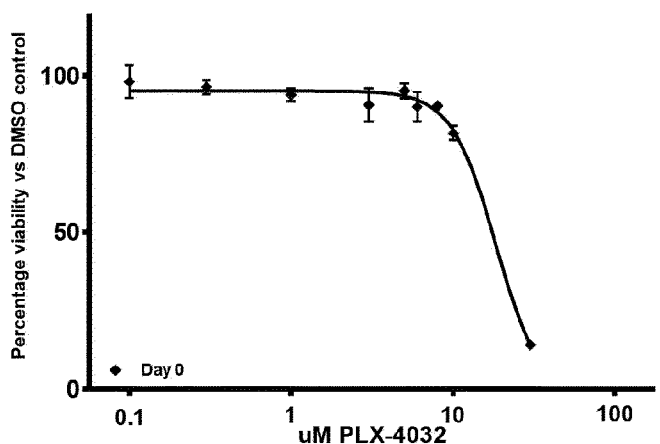
Figure 15:
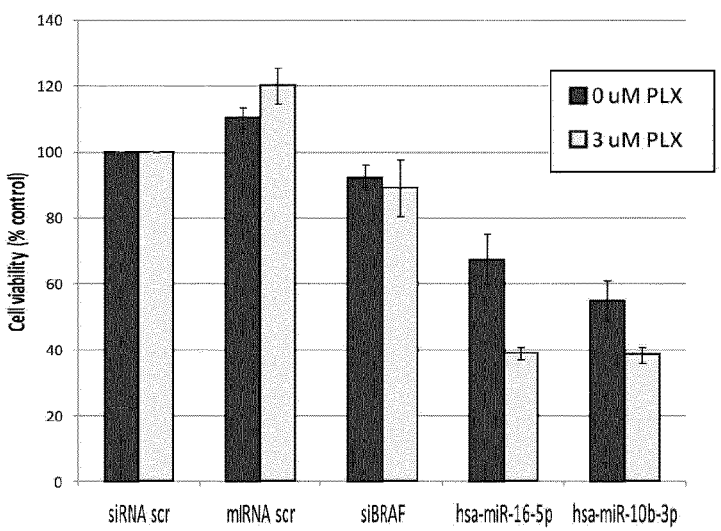
Figure 15:
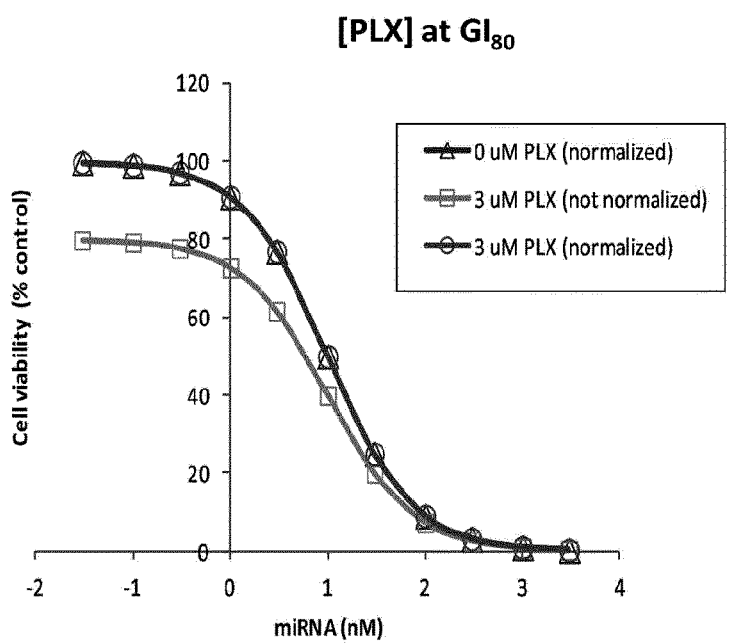

Concentration dependent treatment of RMPI-7951 cells with vemurafenib shows that the $GI_{50}$ (the concentration leading to a reduction in cell viability of 50%) is larger than 10 µM (Table 8 and FIG. 15a). At a concentration of 3 µM, the RPMI-7951 cell viability is starting to be affected by vemurafenib, i.e. reduction of cell viability by approximately 20% ($GI_{80}$, see FIG. 15a). We tested hsa-miR-10b-3p and hsa-miR-16-5p at a concentration of 10 nM in combination with 3 µM vemurafenib. On day 1 cells were transfected with miRNA or siRNA and miRNA controls. On day 2 cells were washed and new medium containing 3 uM vemurafenib was added. Cell viability was measured on day 4. Cell viability was normalized to the effect of siRNA scrambled control sequence. Theoretically, if there is no combinatorial effect of 10 nM miRNA and 3 uM vemurafenib, the inhibition of cell viability is not improved, because cell viability is normalized to siRNA scrambled (FIG. 15c). We observed an approximately 30-40% better inhibition of cell viability when vemurafenib was combined with hsa-miR-16-5p or hsa-miR-10b-3p (FIG. 15b), indicating that the observed improvement of inhibition of cell viability by combining 10 nM hsa-miR-16-5p and hsa-miR-10b-3p with 3 µM vemurafenib is due to the combination of the two compounds.

TABLE 1

Mature sequences of miRNAs precursor (hairpin).
List of mature miRNA sequences 5' to 3' direction)
processed from miRNA precursor hairpins. All
sequence designations were obtained from miRBase
(release 19: August 2012; www.mirbase.org).

| miRNA precursor | Mature miRNA | Seq ID | Sequence mature miRNA |
|---|---|---|---|
| hsa-mir-7-1 | hsa-miR-7-5p | 1 | UGGAAGACUAGUGAUUUUGUUGU |
| hsa-mir-7-2 | hsa-miR-7-5p | 1 | UGGAAGACUAGUGAUUUUGUUGU |
| hsa-mir-7-3 | hsa-miR-7-5p | 1 | UGGAAGACUAGUGAUUUUGUUGU |
| hsa-mir-10b | hsa-miR-10b-3p | 2 | ACAGAUUCGAUUCUAGGGGAAU |
| hsa-mir-96 | hsa-miR-96-5p | 3 | UUUGGCACUAGCACAUUUUUGCU |
| hsa-mir-129-1 | hsa-miR-129-5p | 4 | CUUUUUGCGGUCUGGGCUUGC |
| hsa-mir-129-2 | hsa-miR-129-5p | 4 | CUUUUUGCGGUCUGGGCUUGC |
| hsa-mir-518b | hsa-miR-518b | 5 | CAAAGCGCUCCCCUUUAGAGGU |
| hsa-mir-3157 | hsa-miR-31517-5p | 6 | UUCAGCCAGGCUAGUGCAGUCU |
| hsa-mir-16-1 | hsa-miR-16-5p | 7 | UAGCAGCACGUAAAUAUUGGCG |

TABLE 1-continued

Mature sequences of miRNAs precursor (hairpin).
List of mature miRNA sequences 5' to 3' direction)
processed from miRNA precursor hairpins. All
sequence designations were obtained from miRBase
(release 19: August 2012; www.mirbase.org).

| miRNA precursor | Mature miRNA | Seq ID | Sequence mature miRNA |
|---|---|---|---|
| hsa-mir-16-2 | hsa-miR-16-5p | 7 | UAGCAGCACGUAAAUAUUGGCG |
| hsa-mir-497 | hsa-miR-497-5p | 8 | CAGCAGCACACUGUGGUUUGU |
| hsa-mir-200c | hsa-miR-200c-5p | 9 | CGUCUUACCCAGCAGUGUUUGG |
| hsa-mir-182 | hsa-miR-182-3p | 10 | UGGUUCUAGACUUGCCAACUA |

TABLE 2

Precursor sequences of miRNAs
List of miRNA precursor sequences
(5' to 3' direction). All sequence designations
were obtained from miRBase
(release 19: August 2012; www.mirbase.org).

| SEQ ID NO | miRNA precursor | Precursor sequence |
|---|---|---|
| 11 | hsa-mir-7-1 | UUGGAUGUUGGCCUAGUUCUGUGUGGAAG ACUAGUGAUUUUGUUGUUUUUAGAUAACU AAAUCGACAACAAAUCACAGUCUGCCAUAU GGCACAGGCCAUGCCUCUACAG |
| 12 | hsa-mir-7-2 | CUGGAUACAGAGUGGACCGGCUGGCCCCAU CUGGAAGACUAGUGAUUUUGUUGUUGUCU UACUGCGCUCAACAACAAAUCCCAGUCUAC CUAAUGGUGCCAGCCAUCGCA |
| 13 | hsa-mir-7-3 | AGAUUAGAGUGGCUGUGGGUCUAGUGCUGU GUGGAAGACUAGUGAUUUUGUUGUUCUGA UGUACUACGACAACAAGUCACAGCCGGCCU CAUAGCGCAGACUCCCUUCGAC |
| 14 | hsa-mir-10b | CCAGAGGUUGUAACGUUGUCUAUAUAUAC CCUGUAGAACCGAAUUUGUGUGGUAUCCG UAUAGUCACAGAUUCGAUUCUAGGGGAAU AUAUGGUCGAUGCAAAAACUUCA |
| 15 | hsa-mir-96 | UGGCCGAUUUUGGCACUAGCACAUUUUUG CUUGUGUCUCUCCGCUCUGAGCAAUCAUGU GCAGUGCCAAUAUGGGAAA |
| 16 | hsa-mir-129-1 | GGAUCUUUUUGCGGUCUGGGCUUGCUGUU CCUCUCAACAGUAGUCAGGAAGCCCUUACC CCAAAAAGUAUCU |
| 17 | hsa-mir-129-2 | UGCCCUUCGCGAAUCUUUUUGCGGUCUGGG CUUGCUGUACAUAACUCAAUAGCCGGAAGC CCUUACCCCAAAAAGCAUUUGCGGAGGGCG |
| 18 | hsa-mir-518b | UCAUGCUGUGGCCCUCCAGAGGGAAGCGCU UUCUGUUGUCUGAAAGAAAACAAAGCGCU CCCCUUUAGAGGUUUACGGUUUGA |
| 19 | hsa-mir-3157 | GGGAAGGGCUUCAGCCAGGCUAGUGCAGU CUGCUUUGUGCCAACACUGGGGUGAUGAC UGCCCUAGUCUAGCUGAAGCUUUUCCC |
| 20 | hsa-mir-16-1 | GUCAGCAGUGCCUUAGCAGCACGUAAAUA UUGGCGUUAAGAUUCUAAAAUUAUCUCCA GUAUUAACUGUGCUGCUGAAGUAAGGUUG AC |

TABLE 2-continued

Precursor sequences of miRNAs
List of miRNA precursor sequences
(5' to 3' direction). All sequence designations
were obtained from miRBase
(release 19: August 2012; www.mirbase.org).

| SEQ ID NO | miRNA precursor | Precursor sequence |
|---|---|---|
| 21 | hsa-mir-16-2 | GUUCCACUCUAGCAGCACGUAAAUAUUGGC GUAGUGAAAUAUAUAUUAAACACCAAUAU UACUGUGCUGCUUUAGUGUGAC |
| 22 | hsa-mir-497 | CCACCCCGGUCCUGCUCCCGCCCCAGCAGC ACACUGUGGUUUGUACGGCACUGUGGCCAC GUCCAAACCACACUGUGGUGUUAGAGCGA GGGUGGGGGAGGCACCGCCGAGG |
| 23 | hsa-mir-200c | CCCUCGUCUUACCCAGCAGUGUUUGGGUGC GGUUGGGAGUCUCUAAUACUGCCGGGUAA UGAUGGAGG |
| 24 | hsa-mir-182 | GAGCUGCUUGCCUCCCCCCGUUUUUGGCAA UGGUAGAACUCACACUGGUGAGGUAACAG GAUCCGGUGGUUCUAGACUUGCCAACUAU GGGGCGAGGACUCAGCCGGCAC |

TABLE 3

Sequences of miRNAs as cloned in lentiviral vectors

| SEQ ID NO | miRNA | Cloned sequence in lentiviral vector |
|---|---|---|
| 25 | hsa-miR-7-1 | GCCTTAACCAAGCAAACTTCT-CATTTCTCTGG TGAAAACTGCTGCCAAAACCACTTGTTAAAA ATTGTACAGAGCCTGTAGAAAATATAGAAGA TTCATTGGATGTTGGCCTAGTTCTGTGTG-GAA GACTAGTGATTTTGTTGTTTTTAGA-TAACTAA ATCGACAACAAATCACAGTCTGCCATATGGC ACAGGCCATGCCTCTACAGGACAAATGATTG GTGCTGTAAAATGCAGCATTTCACACCT-TACT AGC |
| 26 | hsa-miR-7-2 | TGAAGGAGCATCCAGACCGCTGACCTGGTGG CGAGGGGAGGGGGTGGTCCTCGAACGCCTT GCAGAACTGGCCTGGATACAGAGTGGACCGG CTGGCCCCATCTGGAAGACTAGTGATTTT-GTT GTTGTCTTACTGCGCTCAACAACAAATC-CCAG TCTACCTAATGGTGCCAGCCATCGCAGCGGG GTGCAGGAAATGGGGGCAGCCCCCCTTTTTG GCTATCCTTCCACGTGTTCT |
| 27 | hsa-miR-7-3 | TCATAGCTTGGCTCAGGTGAGAAGGAGGAGC TGGGCAGGGGTCTCAGACATGGGCAGAGGG TGGTGAAGAAGATTAGAGTGGCTGTGGTCTA GTGCTGTGTGGAAGACTAGTGATTTTGTT-GTT CTGATGTACTACGACAACAAGTCACAGCCGG CCTCATAGCGCAGACTCCCTTCGACCT-TCGCC TTCAATGGGCTGGCCAGTGGGGGAGAACCGG GGAGGTCGGGGAAGAATCGCTTCCACTCGGA GTGGGGGGCTGGCTCACTCCAGGCGATACA G |
| 28 | hsa-miR-10b | TGGCTCAGAGGAAGAGATTGGGGCCGGCAGC GACCTAGGTACCTCACTCTGGGTGGGACCCA GAGGTTGTAACGTTGTCTATATATACCCT-GTA GAACCGAATTTGTGTGGTATCCGTATAGT-CAC |

TABLE 3-continued

Sequences of miRNAs as cloned in lentiviral vectors

| SEQ ID NO | miRNA | Cloned sequence in lentiviral vector |
|---|---|---|
| 29 | hsa-miR-96 | AGATTCGATTCTAGGGGAATATATGGTC-GATG CAAAAACTTCACGTTTCTTCGGAATAGC-CAGA GACCAAAGTGCGACATGGAGACTAGAAGCA CTCCTAGACGTCGGAAACAGGCTGCTTCCAA GGGTGCAGGGATGCAAGGCCCCTCGTCCAGT GTGTCCCCAGAGAGCCCGCACCCAGTGC-CATCT GCTTGGCCGATTTTGGCACTAGCA-CATTTTTG CTTGTGTCTCTCCGCTCTGAGCAATCAT-GTGC AGTGCCAATATGGGAAAAGCAGGACCCGCAG CTGCCGTCCGCCTCCCCTGCATCCTTGT-GTCAG G |
| 30 | hsa-miR-129-1 | GTACCAGCTAAGCCCTGGAGGGGCCACAGCC TCCCCTCCAGCCCCCCTGCCATGGGATG-GCTG CTGTCTCCTTTGGATCTTTTTGCG-GTCTGGGCT TGCTGTTCCTCTCAACAGTAGTCAG-GAAGCCC TTACCCCAAAAAGTATCTGCGGGAGGCCT-TGT CCACAGGGGAGGCTGCCCCAAGGGCTCCAGG TGAGTCACAGCAAACCCAAG |
| 31 | hsa-miR-129-2 | GAGACATCCTGGGCTGAAGGCGGCGGCGAAC CGAAGAAGCCGGCATATTCTGCCCTTCGCGA ATCTTTTTGCGGTCTGGGCTTGCTGTA-CATAA CTCAATAGCCGGAAGCCCTTACCCCAAAAAG CATTTGCGGAGGGCGCACTCGTCGAGAAGAC GGCAGCCATCCAGCGATCGCCGAAGCCCGCA CCTTCCCGAAGCTGCTCCATCCGAGCCT-TACC |
| 32 | hsa-miR-518b | GCAAACAGGGCAAATAAATGCATCTTT-ATTTT GTGTCCATTTTAACCTGGTCAAGGAAAAT-TCC AACAGCAACATCAAAAAACCAGTGTTGGAGC AAGAATATGTCATGCTGTGGCCCTCCAGAGG GAAGCGCTTTCTGTTGTCTGAAAGAAAACAA AGCGCTCCCCTTTAGAGGTTTACGGTTT-GAGT AAAGCAGCGTTGAAGTTGATGCTGATCT-TGGT AATACATTTGCAGAGCGTGCTTATCATCAG |
| 33 | hsa-miR-3157 | ACAACTTCTCAATGAGTCTGCCCTCACT-GTCC AACAATTGAGCTGAGAATATAAGAAGGGAAG GGCTTCAGCCAGGCTAGTGCAGTCT-GCTTTGT GCCAACACTGGGGTGATGACTGC-CCTAGTCTA GCTGAAGCTTTTCCCTTCTTTCTACACCCA-GCT CAAGTCCCAGGTCCATAAAACCTTTA-GAAACT CTTCAGAAACTCTTTAGAGCTTCA-GAAGCTCT TGAGAATTGGAAGATG |
| 34 | hsa-miR-16-1 | TTGTGGATTTTGAAAAGGTGCAGGCCAT-ATTG TGCTGCCTCAAAAATACAAGGATCT-GATCTTC TGAAGAAAATATATTTCTTTTTAT-TCATAGCT CTTATGATAGCAATGTCAGCAGTGCCT-TAGCA GCACGTAAATATTGGCGTTAAGAT-TCTAAAAT TATCTCCAGTATTAACTGTGCTGCTGAAG-TAA GGTTGACCATACTCTACAGTTGTGTTT-TAATG TATATTAATGTTACTAATGTGTTTTCA-GTTTTA TTGA |
| 35 | hsa-miR-16-2 | TTTCATCATCAGATGTTCGTTTTATGTTTG-GAT GAACTGACATACTTGTTCCACTCTAGCAG-CAC GTAAATATTGGCGTAGTGAAATATATAT-TAAA CACCAATATTACTGTGCTGCTTTAGTGT-GACA GGGATACAGCAACTATTTTATCAATT-GTTTGT ATTTCCCTTTAAGG |
| 36 | hsa-miR-497 | TCCCAGCACTGCTATGTGCTCTCTTC-CTTTCAA CCCACCCCGGTCCTGCTCCCGCCCCAGCA-GCA CACTGTGGTTTGTACGGCACTGTGGC-CACGTC CAAACCACACTGTGGTGTTAGAGCGAGGGTG GGGGAGGCACCGCCGAGGCTTGGCCCTGGGA GGCATCCTGGAGAAGTGACACA |
| 37 | hsa-miR-200c | AAGCTGCCTGACCCAAGGTGGGCGGGCTGGG CGGGGGCCCTCGTCTTACCCAGCAGT-GTTTGG GTGCGGTTGGGAGTCTCTAATACTGC-CGGGTA ATGATGGAGGCCCCTGTCCCTGTGTCAG-CAAC ATCCATCGCCTCA |
| 38 | hsa-miR-182 | CTGTCTCTTCCTCAGCACAGACCGAGGC-CTCC CCAGCTCCTGGGGGAGCTGCTTGCCTC-CCCC CGTTTTTGGCAATGGTAGAACTCACACTG-GTG AGGTAACAGGATCCGGTGGTTCTAGACTT-GCC AACTATGGGGCGAGGACTCAGCCGGCACCCT GTGCACAGCCAGCGAGGGAAGGGCCGGCCAT GCTGGACCTGCTGTTCTCC |

TABLE 4

Seed sequences of miRNAs
List of miRNA seed sequences (5' to 3' direction). Seed sequence is defined as nucleotide 2-8 (5' to 3' direction) of the mature miRNA sequence processed from miRNA precursor hairpins. All sequence designations were obtained from miRBase (release 19: August 2012; www.mirbase.org). The seed sequences of the mature miRNAs listed in Table 1 are enclosed in this Table.

| miRNA precursor | Mature miRNA | Seq ID | Seed sequence mature miRNA |
|---|---|---|---|
| hsa-mir-7-1 | hsa-miR-7-5p | 39 | GGAAGAC |
| hsa-mir-7-2 | hsa-miR-7-5p | 39 | GGAAGAC |
| hsa-mir-7-3 | hsa-miR-7-5p | 39 | GGAAGAC |
| hsa-mir-10b | hsa-miR-10b-3p | 40 | CAGAUUC |

TABLE 4-continued

Seed sequences of miRNAs
List of miRNA seed sequences (5' to 3' direction). Seed sequence is defined as nucleotide 2-8 (5' to 3' direction) of the mature miRNA sequence processed from miRNA precursor hairpins. All sequence designations were obtained from miRBase (release 19: August 2012; www.mirbase.org). The seed sequences of the mature miRNAs listed in Table 1 are enclosed in this Table.

| miRNA precursor | Mature miRNA | Seq ID | Seed sequence mature miRNA |
|---|---|---|---|
| hsa-mir-96 | hsa-miR-96-5p | 41 | UUGGCAC |
| hsa-mir-129-1 | hsa-miR-129-5p | 42 | UUUUUGC |
| hsa-mir-129-2 | hsa-miR-129-5p | 42 | UUUUUGC |
| hsa-mir-518b | hsa-miR-518b | 43 | AAAGCGC |
| hsa-mir-3157 | hsa-miR-3157-5p | 44 | UCAGCCA |
| hsa-mir-16-1 | hsa-miR-16-5p | 45 | AGCAGCA |
| hsa-mir-16-2 | hsa-miR-16-5p | 45 | AGCAGCA |
| hsa-mir-497 | hsa-miR-497-5p | 46 | AGCAGCA |
| hsa-mir-200c | hsa-miR-200c-5p | 47 | GUCUUAC |
| hsa-mir-182 | hsa-miR-182-3p | 48 | GGUUCUA |

TABLE 5

IsomiR and seed sequences of miRNAs referred to in the application. These isomiR sequences have been derived from small RNA high-throughput deep sequencing analyses, and were obtained after combining the data of 87 human tissue samples.

| Mature miRNA | Seed (SEQ ID NO) | IsomiR sequence (SEQ ID NO) |
|---|---|---|
| hsa-miR-7-5p | GGAAGAC (49) | UGGAAGACUAGUGAUUUUGUUGUU (96) |
|  | GAAGACU (50) | UGGAAGACUAGUGAUUUUGUUG (97) |
|  | AAGACUA (51) | UGGAAGACUAGUGAUUUUGU (98) |
|  | AGACUAG (52) | UGGAAGACUAGUGAUUUUGUUGUUU (99) |
|  | GACUAGU (53) | UGGAAGACUAGUGAUUUUGUU (100) |
|  | ACUAGUG (54) | GGAAGACUAGUGAUUUUGUUGUU (101) |
|  | CUAGUGA (55) | GGAAGACUAGUGAUUUUGUUGU (102) |
|  | UGGAAGA (56) | UGGAAGACUAGUGAUUUUG (103) |
|  | GUGGAAG (57) | UGGAAGACUAGUGAUUUUGUUGUUC (104) |
|  |  | UGGAAGACUAGUGAUUUU (105) |
|  |  | GAAGACUAGUGAUUUUGUUGUU (106) |
|  |  | GAAGACUAGUGAUUUUGUUGU (107) |
|  |  | UGGAAGACUAGUGAUUUUGUUGUUUU (108) |
|  |  | GGAAGACUAGUGAUUUUGUUGUUU (109) |
|  |  | GAAGACUAGUGAUUUUGUUGUUG (110) |
|  |  | AAGACUAGUGAUUUUGUUGUU (111) |
|  |  | AGACUAGUGAUUUUGUUGUU (112) |
|  |  | AAGACUAGUGAUUUUGUUGU (113) |
|  |  | GACUAGUGAUUUUGUUGUUUU (114) |
|  |  | GACUAGUGAUUUUGUUGUU (115) |
|  |  | GGAAGACUAGUGAUUUUGUUG (116) |
|  |  | UGGAAGACUAGUGAUUUUGUUGUUGU (117) |
|  |  | UGGAAGACUAGUGAUUUUGUUGUUCUG (118) |
|  |  | UGGAAGACUAGUGAUUUUGUUGUUCUGA (119) |
|  |  | AGACUAGUGAUUUUGUUGU (120) |
|  |  | GGAAGACUAGUGAUUUUGUU (121) |
|  |  | GACUAGUGAUUUUGUUGUUUUA (122) |
|  |  | GACUAGUGAUUUUGUUGU (123) |
|  |  | GACUAGUGAUUUUGUUGUUU (124) |
|  |  | GUGGAAGACUAGUGAUUUUGUU (125) |
|  |  | GAAGACUAGUGAUUUUGUUGUUU (126) |
|  |  | GUGGAAGACUAGUGAUUUUGUUGUU (127) |
|  |  | GACUAGUGAUUUUGUUGUUUU (128) |
|  |  | AAGACUAGUGAUUUUGUUGUUU (129) |
|  |  | AACAAAUCACAGUCUGCCAU (130) |
|  |  | GUGGAAGACUAGUGAUUUUGUUGU (131) |
|  |  | UGGAAGACUAGUGAUUUUGUUGUUUUU (132) |
|  |  | AAGACUAGUGAUUUUGUUGUUUU (133) |
|  |  | ACUAGUGAUUUUGUUGUU (134) |
|  |  | GGAAGACUAGUGAUUUUGUUGUUG (135) |
|  |  | GAAGACUAGUGAUUUUGUUG (136) |
|  |  | AAGACUAGUGAUUUUGUUGUUG (137) |
|  |  | UGUGGAAGACUAGUGAUUUUGUUGU (138) |

TABLE 5-continued

IsomiR and seed sequences of miRNAs referred to in the application.
These isomiR sequences have been derived from small RNA high-throughput deep
sequencing analyses, and were obtained after combining the data of 87
human tissue samples.

| Mature miRNA | Seed (SEQ ID NO) | IsomiR sequence (SEQ ID NO) |
|---|---|---|
| | | UGUGGAAGACUAGUGAUUUUGU (139) |
| | | CUGGAAGACUAGUGAUUUUGUUGU (140) |
| | | GGAAGACUAGUGAUUUUGUUGUUUU (141) |
| | | GGAAGACUAGUGAUUUUGU (142) |
| | | GAAGACUAGUGAUUUUGUUGUUUU (143) |
| | | AGACUAGUGAUUUUGUUG (144) |
| | | AAGACUAGUGAUUUUGUUGUUUU (145) |
| | | AGACUAGUGAUUUUGUUGUUU (146) |
| hsa-miR-10b-3p | AGAUUCG (58) | CAGAUUCGAUUCUAGGGGAAU (147) |
| | GAUUCGA (59) | AGAUUCGAUUCUAGGGGAAU (148) |
| | CAGAUUC (60) | AGAUUCGAUUCUAGGGGAAUAU (149) |
| | ACAGAUU (61) | CAGAUUCGAUUCUAGGGGAA (150) |
| | | CAGAUUCGAUUCUAGGGGAAUA (151) |
| | | AGAUUCGAUUCUAGGGGAA (152) |
| | | ACAGAUUCGAUUCUAGGGGAA (153) |
| | | CACAGAUUCGAUUCUAGGGGAA (154) |
| | | ACAGAUUCGAUUCUAGGGG (155) |
| | | AGAUUCGAUUCUAGGGGAAUA (156) |
| | | ACAGAUUCGAUUCUAGGGGAAUAU (157) |
| | | ACAGAUUCGAUUCUAGGGGAAUA (158) |
| hsa-miR-96-5p | UUGGCAC (62) | UUUGGCACUAGCACAUUUUUG (159) |
| | UGGCACU (63) | UUUGGCACUAGCACAUUUUUGC (160) |
| | GGCACUA (64) | UUUGGCACUAGCACAUUUUU (161) |
| | GCACUAG (65) | UUGGCACUAGCACAUUUUUGCU (162) |
| | ACUAGCA (66) | UUUGGCACUAGCACAUUUUUGCUU (163) |
| | UUUGGCA (67) | UUUGGCACUAGCACAUUUU (164) |
| | | UGGCACUAGCACAUUUUUGCU (165) |
| | | GGCACUAGCACAUUUUUGCU (166) |
| | | UUGGCACUAGCACAUUUUUGC (167) |
| | | UUGGCACUAGCACAUUU (168) |
| | | UGGCACUAGCACAUUUUUGC (169) |
| | | UUUGGCACUAGCACAUUUUG (170) |
| | | UUGGCACUAGCACAUUUUUGCUU (171) |
| | | GGCACUAGCACAUUUUUGC (172) |
| | | CACUAGCACAUUUUUGCU (173) |
| | | UUUUGGCACUAGCACAUUUUUGC (174) |
| hsa-miR-129- | UUUUUGC (68) | CUUUUUGCGGUCUGGGCUUG (175) |
| | UUUUGCG (69) | CUUUUUGCGGUCUGGGCUU (176) |
| | UUUGCGG (70) | CUUUUUGCGGUCUGGGCU (177) |
| | UCUUUUU (71) | CUUUUUGCGGUCUGGGCUUGCU (178) |
| | CUUUUUG (72) | CUUUUUGCGGUCUGGGCUUGCUG (179) |
| | | UUUUUGCGGUCUGGGCUUG (180) |
| | | UUUUUGCGGUCUGGGCUUGC (181) |
| | | CUUUUUGCGGUCUGGGCUUGCUGU (182) |
| | | UUUUGCGGUCUGGGCUUGCUG (183) |
| | | UUUUGCGGUCUGGGCUUG (184) |
| | | AUCUUUUUGCGGUCUGGGCUU (185) |
| | | UCUUUUUGCGGUCUGGGCUUG (186) |
| hsa-miR-518b | AAAGCGC (73) | CAAAGCGCUCCCCUUUAGAGGUU (187) |
| | AAGCGCU (74) | CAAAGCGCUCCCCUUUAGAGG (188) |
| | | CAAAGCGCUCCCC UUUAGAG (189) |
| | | AAAGCGCUCCCCUUUAGAGGUU (190) |
| | | CAAAGCGCUCCCCUUUAGAGGUUU (191) |
| hsa-miR-3157- | UCAGCCA (75) | UUCAGCCAGGCUAGUGCAG (192) |
| | UUCAGCC (76) | CUUCAGCCAGGCUAGUGCAGU (193) |
| | | UUCAGCCAGGCUAGUGCAGUC (194) |
| hsa-miR-16-5p | AGCAGCA (77) | UAGCAGCACGUAAAUAUUGGCGU (195) |
| | GCAGCAC (78) | UAGCAGCACGUAAAUAUUGG (196) |
| | CAGCACG (79) | UAGCAGCACGUAAAUAUUGGC (197) |
| | AGCACGU (80) | AGCAGCACGUAAAUAUUGGCG (198) |
| | GCACGUA (81) | UAGCAGCACGUAAAUAUUG (199) |
| | UAGCAGC (82) | GCAGCACGUAAAUAUUGGCG (200) |
| | AGCACGU (83) | UAGCAGCACGUAAAUAUUGGCGUA (201) |
| | CGUAAAU (84) | AGCAGCACGUAAAUAUUGGCGU (202) |
| | ACGUAAA (85) | AGCAGCACGUAAAUAUUGGC (203) |
| | CUAGCAG (86) | UAGCAGCACGUAAAUAUU (204) |

TABLE 5-continued

IsomiR and seed sequences of miRNAs referred to in the application. These isomiR sequences have been derived from small RNA high-throughput deep sequencing analyses, and were obtained after combining the data of 87 human tissue samples.

| Mature miRNA | Seed (SEQ ID NO) | IsomiR sequence (SEQ ID NO) |
|---|---|---|
| | | GCAGCACGUAAAUAUUGGCGU (205) |
| | | CAGCACGUAAAUAUUGGCG (206) |
| | | AGCAGCACGUAAAUAUUGG (207) |
| | | AGCACGUAAAUAUUGGCG (208) |
| | | GCAGCACGUAAAUAUUGGC (209) |
| | | UAGCAGCACGUAAAUAUUGGCGUAG (210) |
| | | CUAGCAGCACGUAAAUAUUGG (211) |
| | | CAGCACGUAAAUAUUGGCGUAG (212) |
| | | AGCAGCACGUAAAUAUUGGCGUA (213) |
| | | GCAGCACGUAAAUAUUGGCGUA (214) |
| | | CAGCACGUAAAUAUUGGCGU (215) |
| | | CUAGCAGCACGUAAAUAUUGGCG (216) |
| | | GCAGCACGUAAAUAUUGG (217) |
| | | AGCACGUAAAUAUUGGCGU (218) |
| | | CAGCACGUAAAUAUUGGCGUA (219) |
| | | CAGCACGUAAAUAUUGGC (220) |
| | | AGCACGUAAAUAUUG (221) |
| | | CUAGCAGCACGUAAAUAUUGGCGU (222) |
| | | GCACGUAAAUAUUGGCGU (223) |
| | | AGCAGCACGUAAAUAUUGGCGUAG (224) |
| | | ACGUAAAUAUUGGCGUAGUGAA (225) |
| | | CACGUAAAUAUUGGCGUA (226) |
| | | UAGCAGCACGUAAAUAUUGGCG (227) |
| | | UAGCAGCACGUAAAUAUUGGCGUU (228) |
| | | UAGCAGCACGUAAAUAUUGGCGUUA (229) |
| | | AGCAGCACGUAAAUAUUGGCGUU (230) |
| | | UUAGCAGCACGUAAAUAUUGGCG (231) |
| | | GCAGCACGUAAAUAUUGGCGUUA (232) |
| | | GCAGCACGUAAAUAUUGGCGUU (233) |
| | | UAGCAGCACGUAAAUAUUGGCGUUAAG (234) |
| | | UAGCAGCACGUAAAUAUUGGCGUUAA (235) |
| | | UUAGCAGCACGUAAAUAUUGGC (236) |
| | | UUAGCAGCACGUAAAUAUUGGCGU (237) |
| | | UUAGCAGCACGUAAAUAUUG (238) |
| | | AGCAGCACGUAAAUAUUGGCGUUA (239) |
| | | ACGUAAAUAUUGGCGUAGUG (240) |
| | | UCUAGCAGCACGUAAAUAUUGGCG (241) |
| hsa-miR-497- | AGCAGCA (87) GCAGCAC (88) CAGCACA (89) AGCACAC (90) CAGCAGC (91) | CAGCAGCACACUGUGGUUUGUA (242) AGCAGCACACUGUGGUUUGU (243) AGCAGCACACUGUGGUUUGUAC (244) CAGCAGCACACUGUGGUUUG (245) AGCAGCACACUGUGGUUUGUA (246) CAGCAGCACACUGUGGUUU (247) CAGCAGCACACUGUGGUUUGUAC (248) AGCAGCACACUGUGGUUUG (249) GCAGCACACUGUGGUUUGU (250) AGCAGCACACUGUGGUUU (251) AGCAGCACACUGUGGUUUGUACG (252) CAGCAGCACACUGUGGUU (253) GCAGCACACUGUGGUUUGUAC (254) CAGCACACUGUGGUUUGUA (255) CAGCACACUGUGGUUUGUAC (256) GCAGCACACUGUGGUUUGUA (257) AGCAGCACACUGUGGUUUGUACGG (258) CAGCACACUGUGGUUUGU (259) CCAGCAGCACACUGUGGUUUG (260) CAGCAGCACACUGUGGUUUGUACG (261) CCAGCAGCACACUGUGGUUUGU (262) CAGCACACUGUGGUUUGUACGGCAC (263) CAGCAGCACACUGUGGUUUGUACGG (264) |
| hsa-miR-200c- | GUCUUAC (92) | CGUCUUACCCAGCAGUGUUUG (265) CGUCUUACCCAGCAGUGUUU (266) |
| hsa-miR-182- | GUGGUUC (93) GGUUCUA (94) UGGUUCU (95) | GGUGGUUCUAGACUUGCCAACU (267) UGGUUCUAGACUUGCCAACU (268) GGUGGUUCUAGACUUGCCAACUA (269) GUGGUUCUAGACUUGCCAACU (270) GGUGGUUCUAGACUUGCCAA (271) |

TABLE 6

Properties of BRAF inhibitor sensitive, BRAF inhibitor acquired resistant and BRAF inhibitor instrinsic resistant cell lines.

| Cell line Name | Type Vemurafenib type | Resistance | Mutational status BRAF | KRAS | NRAS | PTEN | Drugs ($GI_{50}$ in µM) Vemurafenib BRAFV600E inhibitor PLX-4032 | Selumetinib MEK-inhibitor AZD-6244 |
|---|---|---|---|---|---|---|---|---|
| A375Hu | Sensitive | | V600E | WT | WT | | 0.10 | 0.05 |
| M249[1] | Sensitive | | V600E/WT[1] | WT | WT[2] | del/del[1] | 0.30 | 0.10 |
| A375Hu-R1 | Resistant | In vitro acquired | V600E | WT | WT | | >10 | >10 |
| M249-R4 | Resistant | In vitro acquired | V600E/WT[1] | WT | Q61K[2] | del/del[1] | >10 | 2.91 |
| RPMI-7951 | Resistant | In vitro intrinsic | V600E/WT | | | | >10 | >10 |
| A2058 | Resistant | In vitro intrinsic | V600E | WT | WT | | >10 | >10 |

[1] Atefi M. et al. PLoS ONE 6(12): e28973 (2011)
[2] Nazarian R. et al. Nature 468(7326): 973-977 (2010),

TABLE 7

Percentage viable cells after treatment of different cell lines with mature miRNA mimic. Nomenclature of miRNA mimic according to miRBase Release 19.

| | A2058 % Viability 10 nM | RPMI-7951 % Viability 10 nM | M249-AR % Viability 30 nM | A375Hu-R1 % Viability 10 nM | A375Hu % Viability 10 nM | M249 % Viability 5 nM |
|---|---|---|---|---|---|---|
| siRNA Contol | 100 | 100 | 100 | 100 | 100 | 100 |
| siRNA Control | 100 | 100 | | | 100 | |
| Ambion Ctrl #2- | 87 | 90 | 90 | 97 | 93 | 90 |
| Ambion Ctrl #2- | 99 | 87 | | | 89 | |
| siRNA Pool | 49 | 71 | 79 | 88 | 27 | 30 |
| siRNA Pool | 59 | 64 | | | 19 | 20 |
| siRNA Pool | 6 | 18 | 31 | 37 | 22 | 20 |
| siRNA Pool | 6 | 12 | — | — | 17 | — |
| hsa-miR-10b-5p | 61 | 72 | 86 | 55 | 61 | 76 |
| hsa-miR-10b-3p | 42 | 51 | 86 | 59 | 71 | 82 |
| hsa-miR-128 | 77 | 54 | 81 | | 74 | 80 |
| hsa-miR-129-3p | 59 | 80 | 77 | 63 | 65 | 73 |
| hsa-miR-1295 | 82 | 69 | 60 | | 63 | 62 |
| hsa-miR-129-5p | 44 | 82 | 64 | 48 | 59 | 47 |
| hsa-miR-133a- | 71 | 80 | 73 | | 55 | 79 |
| hsa-miR-141-5p | 93 | 82 | 94 | | 92 | 96 |
| hsa-miR-141-3p | 54 | 72 | 67 | | 66 | 73 |
| hsa-miR-16-5p | 39 | 68 | 68 | 57 | 62 | 27 |
| hsa-miR-182-5p | 72 | 64 | 75 | 81 | 71 | 71 |
| hsa-miR-182-3p | 77 | 68 | 83 | 59 | | 71 |
| hsa-miR-184 | 73 | 74 | 74 | 62 | 49 | 67 |
| hsa-miR-18b-5p | 74 | 64 | 85 | | 90 | 91 |
| hsa-miR-18b-3p | 85 | 60 | 85 | | 95 | 90 |
| hsa-miR-190b | 63 | 57 | 75 | | 48 | 76 |
| hsa-miR-193a-3p | 54 | 83 | 71 | 63 | 38 | 67 |
| hsa-miR-193a-5p | 44 | 69 | 83 | 98 | 87 | 87 |
| hsa-miR-200a-5p | 79 | 68 | 90 | | 82 | 107 |
| hsa-miR-200c-3p | 56 | 57 | 85 | 82 | 80 | 79 |
| hsa-miR-200c-5p | 37 | 58 | 58 | 66 | 43 | 44 |
| hsa-miR-203a | 56 | 76 | 88 | 78 | 57 | 74 |
| hsa-miR-3157-5p | 43 | 26 | 53 | 67 | 42 | 42 |
| hsa-miR-497-5p | 53 | 68 | 68 | 57 | 45 | 29 |
| hsa-miR-497-3p | 89 | 86 | 101 | 118 | 101 | 103 |
| hsa-miR-509-3p | 59 | 57 | 75 | | 75 | 66 |
| hsa-miR-509-5p | 75 | 59 | 74 | | 61 | 65 |
| hsa-miR-518b | 44 | 53 | 53 | | 66 | 50 |
| hsa-miR-610 | 75 | 79 | 73 | | 79 | 67 |
| hsa-miR-7-5p | 51 | 65 | 67 | 68 | 58 | 48 |
| hsa-miR-95 | 65 | 56 | 77 | | 57 | 83 |
| hsa-miR-96-5p | 33 | 53 | 82 | 69 | 73 | 64 |

TABLE 8

Properties of BRAF inhibitor sensitive, BRAF inhibitor acquired resistant and BRAF inhibitor instrinsic resistant cell lines.

| Cell line Name | Type Vemurafenib type | Resistance | Mutational status BRAF | KRAS | NRAS | PTEN | Drugs (GI$_{50}$ in µM) Vemurafenib BRAFV600E inhibitor PLX-4032 | Selumetinib MEK-inhibitor AZD-6244 |
|---|---|---|---|---|---|---|---|---|
| A375Hu (A375) | Sensitive | | V600E | WT | WT | | 0.10 | 0.05 |
| M249[1)] | Sensitive | | V600E/WT[1)] | WT | WT[2)] | del/del[1)] | 0.30 | 0.10 |
| A375Hu-R1(A375-R) | Resistant | In vitro acquired | V600E | WT | WT | | >10 | >10 |
| M249-R4 (M249-AR4) | Resistant | In vitro acquired | V600E/WT[1)] | WT | Q61K[2)] | del/del[1)] | >10 | 2.91 |
| RPMI-7951 | Resistant | In vitro intrinsic | V600E/WT | | | | >10 | >10 |
| A2058 | Resistant | In vitro intrinsic | V600E | WT | WT | | >10 | >10 |
| SKMEL-28 | Sensitive | | V600E | WT | WT | | 0.6 | n. a. |
| SKMEL-57 | Sensitive | | V600E | WT | WT | | 0.8 | 0.7 |
| M233 | Resistant | In vitro acquired | V600E | WT | WT | | >10 | >10[1)] |
| M376 | Resistant | In vivo acquired | V600E | WT | Q61K[2)] | | >10 | 1.0[1)] |

[1)]Atefi M. et al. PLoS ONE 6(12): e28973 (2011)
[2)]Nazarian R. et al. Nature 468(7326): 973-977 (2010)

TABLE 9

Sequences of the primers used for the detection of miR-3157 and U6

| Primer | Sequence (5'-3') |
|---|---|
| miR-3157 Stem-loop RT | GTCGTATCCAGTGCAGGGTCCGAGGTAATTCGCACTGGATACGACAGACTG (SEQ ID NO: 274) |
| miR-3157 qPCR-forward | TGCCAGTTCAGCCAGGCTAGTGCA (SEQ ID NO: 275) |
| miR-3157 qPCR-reverse | GTGCAGGGTCCGAGGT (SEQ ID NO: 276) |
| U6 RT | GTCATCCTTGCGCAGG (SEQ ID NO: 277) |
| U6 qPCR forward | CGCTTCGGCAGCACATATAC (SEQ ID NO: 278) |
| U6 qPCR reverse | AGGGGCCATGCTAATCTTCT (SEQ ID NO: 279) |

TABLE 10

Sequences of the primers used for mRNA quantification by qPCR

| Primer | Sequence (5'-3') |
|---|---|
| HPRT1-Fwd | CCTGGCGTCGTGATTAGTGAT (SEQ ID NO: 280) |
| HPRT1-Rev | AGACGTTCAGTCCTGTCCATAA (SEQ ID NO: 281) |
| MAPK3- | CTACACGCAGTTGCAGTACAT (SEQ ID NO: 282) |
| MAPK3-Rev | CAGCAGGATCTGGATCTCCC (SEQ ID NO: 283) |
| RRM2-Fwd | GTGGAGCGATTTAGCCAAGAA (SEQ ID NO: 284) |
| RRM2-Rev | CACAAGGCATCGTTTCAATGG (SEQ ID NO: 285) |
| AURKB- | CGCAGAGAGATCGAAATCCAG (SEQ ID NO: 286) |
| AURKB-Rev | AGATCCTCCTCCGGTCATAAAA (SEQ ID NO: 287) |
| CDK4-Fwd | CTGGTGTTTGAGCATGTAGACC (SEQ ID NO: 288) |
| CDK4-Rev | GATCCTTGATCGTTTCGGCTG (SEQ ID NO: 289) |
| BIRC5-Fwd | AGGACCACCGCATCTCTACAT (SEQ ID NO: 290) |
| BIRC5-Rev | AAGTCTGGCTCGTTCTCAGTG (SEQ ID NO: 291) |
| BCL2-Fwd | GCCTTCTTTGAGTTCGGTGG (SEQ ID NO: 292) |
| BCL2-Rev | ATCTCCCGGTTGACGCTCT (SEQ ID NO: 293) |

TABLE 11

Sequences of ERK1, RRM2 and AURKB, as used in the 3'UTR luciferase assay. The seed sequence of the miR-3157 binding site is underlined.

| Gene | 3'UTR sequence |
|---|---|
| ERK1 | CGTGGAGAGCCCGGCGCCCCTGCCACCTCCCTGACCCGTCTAATATATAAATATAGAGATGTGTCTA<u>TGGCTGAAA</u> (SEQ ID NO: 294) |
| RRM2 | TCAGAGGATGGGAGTGATGTCAAGTCCAACAGAGAATTCTTTTACCTTGGATGCTGACTTCTAAATGAACTGAAGATGTGCCCTTA |

TABLE 11-continued

Sequences of ERK1, RRM2 and AURKB, as used in the 3'UTR luciferase assay. The seed sequence of the miR-3157 binding site is underlined.

| Gene | 3'UTR sequence |
|---|---|
|  | CTTGGCTGATTTTT<br>(SEQ ID NO: 295) |
| AURKB | TGGTCCCTGTCATTCACTCGGGTGCGTGTGTTTGTATGTCTG<br>TGTATGTATAGGGGAAAGAAGGGATCCCTAACTGTTCCCTTA<br>TCTGTTTTCTACCTCCTCCTTTGTTTAATAAAGGCTGAAGCT<br>TTTTGTACTCATGAA<br>(SEQ ID NO: 296) |

REFERENCE LIST

Aird K. M. et al. Cell reports. 2013; 3:1252-65. Atefi M. et al., PLoS ONE 6(12):e28973 (2011).
Balch C. M. et al., J. Clin. Oncol., (2001).
Bonet C. et al. J Biol Chem. 2012; 287:29887-98. Dassie, J. P. et al., Nat. Biotechnol. 27:839-849, (2009).
Davies, H. et al., Nature 417: 949, (2002).
Dhomen N. et al., Hematol. Oncol. Clin. North Am., 23: 529, (2009).
Duxbury M S. et al., Oncogene. 23:1539-48, (2004).
Dweep H. et al. J Biomed Inform. 2011; 44:839-47.
Felicetti F., Oncogene 23: 4567, (2004).
Felicetti F. et al., Cancer Res. 68:2745, (2008).
Haferkamp S. et al. J Invest Dermatol. 2013; 133:1601-9. Houben, R. at al. J. Carcinog. 3: 6, (2004).
Garbe C. and Leiter U., Clin. Dermatol. 27: 3, (2009).
Garnett M. J. et al., Cancer Cell, (2004).
Ikenoue, T. et al., Cancer res. 63: 8132, (2003).
Hingorani, S. R., et al., Cancer res. 63: 5198, (2003).
Jalili A. et al. J. Nat. Cancer Inst. E-pub ahead of print (2012).
Ji Z. et al. Clin Cancer Res. 2013; 19:4383-91. Karasarides, M. et al. Oncogene 23: 6292, (2004).
Madhunapantula S. V. et al., Pigment Cell Melanoma Res. 22:400-19, (2009).
Nazarian R. et al. Nature 468(7326):973-977 (2010).
Mraz-Gernhard S. et al., Arch. Dermatol., (1998).
Obad S. et al, Nature Genetics, on line, 20 March (2011), 43: 371-37.
Oshie S. et al., J. Cut. Pathol. 35: 433, (2008).
Parkin D. M. et al., Cancer J. Clin. 55: 74, (2005).
Poell et al. J. PLoS ONE 7(8):e43569 (2012).
Scherr M et al., Nucleic Acids Res. 2007; 35(22):e149. Epub (2007) November 19.
Schutters K. et al., Apoptosis 2010 and de Saint-Hubert M. et al., Methods 48: 178, (2009).
Scolyer R. A. et al., Am. J. Surg. Pathol. (2003).
Steeper J. R. et al., Anal Biochem. 34:123-30 (1970).
Steffen P., et al., Bioinformatics, 22:500, (2006).
Urdziel E, et al., M. Methods Mol Biol. (2010); 667:237-48.
Vejnar C. E. et al. Nucleic Acids Res. 2012; 40:11673-83.
Villanueva, J. and Herlyn, M. (2009). Melanoma. eLS.
Wan P. T. et al., Cell 116: 855, (2004).
Wong K. K., (2009), 4, 28-35.
Wu J. et al. Cell Cycle (9):1809-1818 (2010).
Xu N. et al. Acta Pharmacol Sin. 33:675-81 (2012).
Zhou B., et al, (2013), Cancer Research, 73(21): 6484-6493.

ABBREVIATIONS miR, miRNA—microRNA
hsa-miR—*Homo sapiens* miR
MOI—multiplicity of infection
MTT—(3-(4,5-Dimethylthiazol-2-yl)-2,5-diphenyltetrazolium bromide
qPCR—quantitative PCR
CGH—Comparative Genomic Hybridization
PVDF—Polyvinylidene difluoride
HUVEC—Human umbilical vein endothelial cells

The invention claimed is:

1. A synergistic combination of at least two compounds, at least one compound being taken from the first list and at least one compound being taken from the second list:
   a) at least one of a miRNA-3157-5p, miRNA-10b-3p, miRNA-129-5p, miRNA-96-5p, miRNA-200c-5p, miRNA-182-3p, miRNA-16-5p, miRNA-497-5p, miRNA-518b and/or a miRNA-7-5p molecule, an equivalent or a precursor thereof, or a composition comprising said at least one miRNA, equivalent or precursor thereof, and
   b) at least one B-raf and/or MEK inhibitor, or a composition comprising said at least one B-raf and/or MEK inhibitor, wherein the combination provides for a synergistic effect on inhibition of the proliferation of melanoma cells or cells harboring an activated B-raf pathway that are resistant to said B-raf and/or MEK inhibitor.

2. The combination according to claim 1, wherein said at least one B-raf inhibitor is vemurafenib or dabrafenib, and/or wherein said at least one MEK inhibitor is trametinib or selumetinib.

3. The combination according to claim 1, wherein:
   a) said at least one compound from the first list is a miRNA-3157-5p, and/or an equivalent and/or a precursor thereof or a composition comprising said miRNA-3157-5p, and/or an equivalent and/or a precursor thereof and
   b) said at least one compound from the second list is at least one B-raf and/or MEK inhibitor.

4. The combination according to claim 1, further comprising another miRNA molecule, equivalent or precursor thereof, or a composition comprising said miRNA molecule, and/or an equivalent and/or a precursor thereof selected from:
   a) at least one of miRNA-13, Let-7 and Let-7a and/or an equivalent or a precursor thereof and/or,
   b) at least one antagomir of miRNA-221 and miRNA-222 and/or an equivalent or a precursor thereof.

5. The combination according to claim 1, wherein said at least one compound from the first list and said at least one compound from the second list are:

(i) combined in a single composition; or
(ii) present in a kit of parts comprising at least two separate compositions for sequential or simultaneous administration to a subject.

6. A method for inhibiting growth and/or reducing viability of melanoma cells or of cells containing an activating BRAF mutation by administering a synergistic combination as defined in claim 1 to a subject in need thereof.

7. The method according to claim 6, wherein sensitization of the subject to a B-raf and/or MEK inhibitor is promoted.

8. The combination according to claim 3, wherein said at least one B-raf inhibitor is vemurafenib or dabrafenib, and/or wherein said at least one MEK inhibitor is trametinib or selumetinib.

9. The combination according to claim 1, wherein the combination provides for a synergistic effect on inhibition of the proliferation of melanoma cells resistant to vemurafenib.

10. The combination according to claim 3, wherein said at least one compound from the second list is vemurafenib.

* * * * *

SEQUENCE LISTING

```
<160> NUMBER OF SEQ ID NOS: 299

<210> SEQ ID NO 1
<211> LENGTH: 23
<212> TYPE: RNA
<213> ORGANISM: Artificial
<220> FEATURE:
<223> OTHER INFORMATION: Mature miRNA sequence of hsa-miR-7-5p

<400> SEQUENCE: 1
uggaagacua gugauuuugu ugu                                              23

<210> SEQ ID NO 2
<211> LENGTH: 22
<212> TYPE: RNA
<213> ORGANISM: Artificial
<220> FEATURE:
<223> OTHER INFORMATION: Mature miRNA sequence of hsa-miR-10b-3p

<400> SEQUENCE: 2
acagauucga uucuagggga au                                               22

<210> SEQ ID NO 3
<211> LENGTH: 23
<212> TYPE: RNA
<213> ORGANISM: Artificial
<220> FEATURE:
```

<223> OTHER INFORMATION: Mature miRNA sequence of hsa-miR-96-5p

<400> SEQUENCE: 3
uuuggcacua gcacauuuuu gcu                                           23

<210> SEQ ID NO 4
<211> LENGTH: 21
<212> TYPE: RNA
<213> ORGANISM: Artificial
<220> FEATURE:
<223> OTHER INFORMATION: Mature miRNA sequence of hsa-miR-129-5p

<400> SEQUENCE: 4
cuuuuugcgg ucugggcuug c                                             21

<210> SEQ ID NO 5
<211> LENGTH: 22
<212> TYPE: RNA
<213> ORGANISM: Artificial
<220> FEATURE:
<223> OTHER INFORMATION: Mature miRNA sequence of hsa-miR-518b

<400> SEQUENCE: 5
caaagcgcuc cccuuuagag gu                                            22

<210> SEQ ID NO 6
<211> LENGTH: 22
<212> TYPE: RNA
<213> ORGANISM: Artificial
<220> FEATURE:
<223> OTHER INFORMATION: Mature miRNA sequence of hsa-miR-3157-5p

<400> SEQUENCE: 6
uucagccagg cuagugcagu cu                                            22

<210> SEQ ID NO 7
<211> LENGTH: 22
<212> TYPE: RNA
<213> ORGANISM: Artificial
<220> FEATURE:
<223> OTHER INFORMATION: Mature miRNA sequence of hsa-miR-16-5p

<400> SEQUENCE: 7
uagcagcacg uaaauauugg cg                                            22

<210> SEQ ID NO 8
<211> LENGTH: 21
<212> TYPE: RNA
<213> ORGANISM: Artificial
<220> FEATURE:
<223> OTHER INFORMATION: Mature miRNA sequence of hsa-miR-497-5p

<400> SEQUENCE: 8
cagcagcaca cugugguuug u                                             21

<210> SEQ ID NO 9
<211> LENGTH: 22
<212> TYPE: RNA
<213> ORGANISM: Artificial
<220> FEATURE:
<223> OTHER INFORMATION: Mature miRNA sequence of hsa-miR-200c-5p

<400> SEQUENCE: 9
cgucuuaccc agcaguguuu gg                                            22

```
<210> SEQ ID NO 10
<211> LENGTH: 21
<212> TYPE: RNA
<213> ORGANISM: Artificial
<220> FEATURE:
<223> OTHER INFORMATION: Mature miRNA sequence of hsa-miR-182-3p

<400> SEQUENCE: 10
ugguucuaga cuugccaacu a                                              21

<210> SEQ ID NO 11
<211> LENGTH: 110
<212> TYPE: RNA
<213> ORGANISM: Artificial
<220> FEATURE:
<223> OTHER INFORMATION: Precursor sequence of hsa-mir-7-1

<400> SEQUENCE: 11
uuggauguug gccuaguucu guguggaaga cuagugauuu uguuguuuuu agauaacuaa     60
aucgacaaca aaucacaguc ugccauaugg cacaggccau gccucuacag              110

<210> SEQ ID NO 12
<211> LENGTH: 110
<212> TYPE: RNA
<213> ORGANISM: Artificial
<220> FEATURE:
<223> OTHER INFORMATION: Precursor sequence of hsa-mir-7-2

<400> SEQUENCE: 12
cuggauacag aguggaccgg cuggccccau cuggaagacu agugauuuug uuguugucuu     60
acugcgcuca acaacaaauc ccagucuacc uaauggugcc agccaucgca              110

<210> SEQ ID NO 13
<211> LENGTH: 110
<212> TYPE: RNA
<213> ORGANISM: Artificial
<220> FEATURE:
<223> OTHER INFORMATION: Precursor sequence of hsa-mir-7-3

<400> SEQUENCE: 13
agauuagagu ggcugugguc uagugcugug uggaagacua gugauuuugu uguucugaug     60
uacuacgaca acaagucaca gccggccuca uagcgcagac ucccuucgac              110

<210> SEQ ID NO 14
<211> LENGTH: 110
<212> TYPE: RNA
<213> ORGANISM: Artificial
<220> FEATURE:
<223> OTHER INFORMATION: Precursor sequence of hsa-mir-10b

<400> SEQUENCE: 14
ccagagguug uaacguuguc uauauauacc cuguagaacc gaauuugugu gguauccgua     60
uagucacaga uucgauucua ggggaauaua uggucgaugc aaaaacuuca              110

<210> SEQ ID NO 15
<211> LENGTH: 78
<212> TYPE: RNA
<213> ORGANISM: Artificial
<220> FEATURE:
<223> OTHER INFORMATION: Precursor sequence of hsa-mir-96

<400> SEQUENCE: 15
uggccgauuu uggcacuagc acauuuugc uugugucucu ccgcucugag caaucaugug      60
```

```
cagugccaau augggaaa                                              78

<210> SEQ ID NO 16
<211> LENGTH: 72
<212> TYPE: RNA
<213> ORGANISM: Artificial
<220> FEATURE:
<223> OTHER INFORMATION: Precursor sequence of hsa-mir-129-1

<400> SEQUENCE: 16
ggaucuuuuu gcggucuggg cuugcuguuc cucucaacag uagucaggaa gcccuuaccc   60
caaaaaguau cu                                                     72

<210> SEQ ID NO 17
<211> LENGTH: 180
<212> TYPE: RNA
<213> ORGANISM: Artificial
<220> FEATURE:
<223> OTHER INFORMATION: Precursor sequence of hsa-mir-129-2

<400> SEQUENCE: 17
ugcccuuugc ccuucgcgaa ucuuuuugcg gucgggcuu gcuuacaua acucaauagc    60 cggaagcccu uacccaaaaa agcauuugcg gagggcgcgc gaaucuuuuu gcggucuggg 120
cuugcuguac auaacucaau agccggaagc ccuuacccca aaaagcauuu gcggagggcg 180

<210> SEQ ID NO 18
<211> LENGTH: 83
<212> TYPE: RNA
<213> ORGANISM: Artificial
<220> FEATURE:
<223> OTHER INFORMATION: Precursor sequence of hsa-mir-518b

<400> SEQUENCE: 18
ucaugcugug gcccuccaga gggaagcgcu uucuguuguc ugaagaaaa caaagcgcuc   60 cccuuuagag guuuacgguu uga                                         83

<210> SEQ ID NO 19
<211> LENGTH: 85
<212> TYPE: RNA
<213> ORGANISM: Artificial
<220> FEATURE:
<223> OTHER INFORMATION: Precursor sequence of hsa-mir-3157

<400> SEQUENCE: 19
gggaagggcu ucagccaggc uagugcaguc ugcuuuguge caacacuggg gugaugacug   60
cccuagucua gcugaagcuu uuccc                                       85

<210> SEQ ID NO 20
<211> LENGTH: 89
<212> TYPE: RNA
<213> ORGANISM: Artificial
<220> FEATURE:
<223> OTHER INFORMATION: Precursor sequence of hsa-mir-16-1

<400> SEQUENCE: 20
gucagcagug ccuuagcagc acguaaauau uggcguuaag auucuaaaau uaucuccagu   60
auuaacugug cugcugaagu aagguugac                                   89

<210> SEQ ID NO 21
<211> LENGTH: 81
<212> TYPE: RNA
<213> ORGANISM: Artificial
```

```
<220> FEATURE:
<223> OTHER INFORMATION: Precursor sequence of hsa-mir-16-2

<400> SEQUENCE: 21
guuccacucu agcagcacgu aaauauuggc guagugaaau auauauuaaa caccaauauu    60
acugugcugc uuuagugugu c                                              81

<210> SEQ ID NO 22
<211> LENGTH: 112
<212> TYPE: RNA
<213> ORGANISM: Artificial
<220> FEATURE:
<223> OTHER INFORMATION: Precursor sequence of hsa-mir-497

<400> SEQUENCE: 22
ccaccccggu ccugcucccg ccccagcagc acacuguggu uuguacggca cuguggccac    60
guccaaacca cacuguggug uuagagcgag ggugggggag gcaccgccga gg           112

<210> SEQ ID NO 23
<211> LENGTH: 68
<212> TYPE: RNA
<213> ORGANISM: Artificial
<220> FEATURE:
<223> OTHER INFORMATION: Precursor sequence of hsa-mir-200c

<400> SEQUENCE: 23
cccucgucuu acccagcagu guuuggugc gguugggagu cucuaauacu gccgggauaau    60 gauggagg                                                             68

<210> SEQ ID NO 24
<211> LENGTH: 110
<212> TYPE: RNA
<213> ORGANISM: Artificial
<220> FEATURE:
<223> OTHER INFORMATION: Precursor sequence of hsa-mir-182

<400> SEQUENCE: 24
gagcugcuug ccucccccg uuuuuggcaa ugguagaacu cacacuggug agguaacagg    60 auccggguggu ucuagacuug ccaacuaugg ggcgaggacu cagccggcac            110

<210> SEQ ID NO 25
<211> LENGTH: 255
<212> TYPE: DNA
<213> ORGANISM: Artificial
<220> FEATURE:
<223> OTHER INFORMATION: Sequence of hsa- miR-7-1 cloned in lenti vector

<400> SEQUENCE: 25
gccttaacca agcaaacttc tcatttctct ggtgaaaact gctgccaaaa ccacttgtta    60
aaaattgtac agagcctgta gaaaatatag aagattcatt ggatgttggc ctagttctgt   120
gtggaagact agtgattttg ttgttttag ataactaaat cgacaacaaa tcacagtctg    180
ccatatggca caggccatgc ctctacagga caaatgattg gtgctgtaaa atgcagcatt   240
tcacacctta ctagc                                                    255

<210> SEQ ID NO 26
<211> LENGTH: 239
<212> TYPE: DNA
<213> ORGANISM: Artificial
<220> FEATURE:
<223> OTHER INFORMATION: Sequence of hsa- miR-7-2 cloned in lenti vector
```

<400> SEQUENCE: 26

```
tgaaggagca tccagaccgc tgacctggtg gcgaggggag ggggtggtc ctcgaacgcc      60 ttgcagaact ggcctggata cagagtggac cggctggccc catctggaag actagtgatt    120
ttgttgttgt cttactgcgc tcaacaacaa atcccagtct acctaatggt gccagccatc    180
gcagcggggt gcaggaaatg ggggcagccc ccttttttgg ctatccttcc acgtgttct     239
```

<210> SEQ ID NO 27
<211> LENGTH: 282
<212> TYPE: DNA
<213> ORGANISM: Artificial
<220> FEATURE:
<223> OTHER INFORMATION: Sequence of hsa- miR-7-3 cloned in lenti vector

<400> SEQUENCE: 27

```
tcatagcttg gctcaggtga aaggaggag ctgggcaggg gtctcagaca tggggcagag      60
ggtggtgaag aagattagag tggctgtggt ctagtgctgt gtggaagact agtgattttg    120
ttgttctgat gtactacgac aacaagtcac agccggcctc atagcgcaga ctcccttcga    180
ccttcgcctt caatgggctg ccagtgggg gagaaccggg gaggtcgggg aagaatcgct     240
tccactcgga gtgggggggc tggctcactc caggcgatac ag                       282
```

<210> SEQ ID NO 28
<211> LENGTH: 220
<212> TYPE: DNA
<213> ORGANISM: Artificial
<220> FEATURE:
<223> OTHER INFORMATION: Sequence of hsa-miR-10b cloned in lenti vector

<400> SEQUENCE: 28

```
tggctcagag gaagagattg gggccggcag cgacctaggt acctcactct gggtgggacc     60
cagaggttgt aacgttgtct atatataccc tgtagaaccg aatttgtgtg gtatccgtat    120
agtcacagat tcgattctag ggaatatat ggtcgatgca aaaacttcac gtttcttcgg    180
aatagccaga gaccaaagtg cgacatggag actagaagca                          220
```

<210> SEQ ID NO 29
<211> LENGTH: 222
<212> TYPE: DNA
<213> ORGANISM: Artificial
<220> FEATURE:
<223> OTHER INFORMATION: Sequence of hsa- miR-96 cloned in lenti vector

<400> SEQUENCE: 29

```
ctcctagacg tcggaaacag gctgcttcca agggtgcagg gatgcaaggc ccctcgtcca     60
gtgtgtcccc agagagcccg caccagtgcc atctgcttgg ccgatttgg cactagcaca    120 tttttgcttg tgtctctccg ctctgagcaa tcatgtgcag tgccaatatg ggaaaagcag    180
gacccgcagc tgcgtccgcc tcccctgcat ccttgtgtca gg                       222
```

<210> SEQ ID NO 30
<211> LENGTH: 211
<212> TYPE: DNA
<213> ORGANISM: Artificial
<220> FEATURE:
<223> OTHER INFORMATION: Sequence of hsa-miR-129-1 cloned in lenti
      vector

<400> SEQUENCE: 30

```
gtaccagcta agccctggag gggccacagc ctcccctcca gccccctgc catgggatgg      60
```
ctgctgtctc ctttggatct ttttgcggtc tgggcttgct gttcctctca acagtagtca    120
ggaagccctt accccaaaaa gtatctgcgg gaggccttgt ccacagggga ggctgcccca    180
agggctccag gtgagtcaca gcaaacccaa g                                   211

<210> SEQ ID NO 31
<211> LENGTH: 219
<212> TYPE: DNA
<213> ORGANISM: Artificial
<220> FEATURE:
<223> OTHER INFORMATION: Sequence of hsa-miR-129-2 cloned in lenti
      vector

<400> SEQUENCE: 31
gagacatcct gggctgaagg cggcggcgaa ccgaagaagc cggcatattc tgcccttcgc    60
gaatcttttt gcggtctggg cttgctgtac ataactcaat agccggaagc ccttacccca   120
aaaagcattt gcggagggcg cactcgtcga aagacggca gccatccagc gatcgccgaa    180
gcccgcacct tcccgaagct gctccatccg agccttacc                          219

<210> SEQ ID NO 32
<211> LENGTH: 251
<212> TYPE: DNA
<213> ORGANISM: Artificial
<220> FEATURE:
<223> OTHER INFORMATION: Sequence of hsa-miR-518b cloned in lenti vector

<400> SEQUENCE: 32
gcaaacaggg caaataaatg catctttatt ttgtgtccat tttaacctgg tcaaggaaaa    60
ttccaacagc aacatcaaaa accagtgtt ggagcaagaa tatgtcatgc tgtggccctc    120
cagagggaag cgctttctgt tgtctgaaag aaaacaaagc gctccccttt agaggtttac   180
ggtttgagta aagcagcgtt gaagttgatg ctgatcttgg taatacattt gcagagcgtg   240
cttatcatca g                                                        251

<210> SEQ ID NO 33
<211> LENGTH: 240
<212> TYPE: DNA
<213> ORGANISM: Artificial
<220> FEATURE:
<223> OTHER INFORMATION: Sequence of hsa-miR-3157 cloned in lenti vector

<400> SEQUENCE: 33
acaacttctc aatgagtctg ccctcactgt ccaacaattg agctgagaat ataagaaggg    60
aagggcttca gccaggctag tgcagtctgc tttgtgccaa cactggggtg atgactgccc   120
tagtctagct gaagctttc ccttctttct acacccagct caagtcccag gtccataaaa    180
cctttagaaa ctcttcagaa actctttaga gcttcagaag ctcttgagaa ttggaagatg   240

<210> SEQ ID NO 34
<211> LENGTH: 261
<212> TYPE: DNA
<213> ORGANISM: Artificial
<220> FEATURE:
<223> OTHER INFORMATION: Sequence of hsa-miR-16-1 cloned in lenti vector

<400> SEQUENCE: 34
ttgtggattt tgaaaaggtg caggccatat tgtgctgcct caaaaataca aggatctgat    60
cttctgaaga aaatatattt cttttattc atagctctta tgatagcaat gtcagcagtg   120
ccttagcagc acgtaaatat tggcgttaag attctaaaat tatctccagt attaactgtg   180
ctgctgaagt aaggttgacc atactctaca gttgtgtttt aatgtatatt aatgttacta    240
atgtgttttc agttttattg a    261

<210> SEQ ID NO 35
<211> LENGTH: 175
<212> TYPE: DNA
<213> ORGANISM: Artificial
<220> FEATURE:
<223> OTHER INFORMATION: Sequence of hsa-miR-16-2 cloned in lenti vector

<400> SEQUENCE: 35
tttcatcatc agatgttcgt tttatgtttg gatgaactga catacttgtt ccactctagc    60
agcacgtaaa tattggcgta gtgaaatata tattaaacac caatattact gtgctgcttt    120
agtgtgacag ggatacagca actattttat caattgtttg tatttcccct taagg    175

<210> SEQ ID NO 36
<211> LENGTH: 182
<212> TYPE: DNA
<213> ORGANISM: Artificial
<220> FEATURE:
<223> OTHER INFORMATION: Sequence of hsa-miR-497 cloned in lenti vector

<400> SEQUENCE: 36
tcccagcact gctatgtgct ctcttccttt caacccaccc cggtcctgct cccgccccag    60
cagcacactg tggtttgtac ggcactgtgg ccacgtccaa accacactgt ggtgttagag    120
cgagggtggg ggaggcaccg ccgaggcttg ccctgggag gccatcctgg agaagtgaca    180
ca    182

<210> SEQ ID NO 37
<211> LENGTH: 140
<212> TYPE: DNA
<213> ORGANISM: Artificial
<220> FEATURE:
<223> OTHER INFORMATION: Sequence of hsa-miR-200c cloned in lenti vector

<400> SEQUENCE: 37
aagctgcctg acccaaggtg ggcgggctgg gcggggggccc tcgtcttacc cagcagtgtt    60
tgggtgcggt tgggagtctc taatactgcc gggtaatgat ggaggcccct gtccctgtgt    120
cagcaacatc catcgcctca    140

<210> SEQ ID NO 38
<211> LENGTH: 209
<212> TYPE: DNA
<213> ORGANISM: Artificial
<220> FEATURE:
<223> OTHER INFORMATION: Sequence of hsa-miR-182 cloned in lenti vector

<400> SEQUENCE: 38
ctgtctcttc ctcagcacag accgaggcct ccccagctcc tgggggagc tgcttgcctc    60 cccccgtttt tggcaatggt agaactcaca ctggtgaggt aacaggatcc ggtggttcta    120
gacttgccaa ctatggggcg aggactcagc cggcaccctg tgcacagcca gcgagggaag    180
ggccggccat gctggacctg ctgttctcc    209

<210> SEQ ID NO 39
<211> LENGTH: 7
<212> TYPE: RNA
<213> ORGANISM: Artificial
<220> FEATURE:
<223> OTHER INFORMATION: hsa-miR-7-5p seed sequence

```
<400> SEQUENCE: 39 ggaagac                                                             7

<210> SEQ ID NO 40
<211> LENGTH: 7
<212> TYPE: RNA
<213> ORGANISM: Artificial
<220> FEATURE:
<223> OTHER INFORMATION: hsa-miR-10b-3p seed sequence

<400> SEQUENCE: 40 cagauuc                                                             7

<210> SEQ ID NO 41
<211> LENGTH: 7
<212> TYPE: RNA
<213> ORGANISM: Artificial
<220> FEATURE:
<223> OTHER INFORMATION: hsa-miR-96-5p seed sequence

<400> SEQUENCE: 41 uuggcac                                                             7

<210> SEQ ID NO 42
<211> LENGTH: 7
<212> TYPE: RNA
<213> ORGANISM: Artificial
<220> FEATURE:
<223> OTHER INFORMATION: hsa-miR-129-5p seed sequence

<400> SEQUENCE: 42 uuuuugc                                                             7

<210> SEQ ID NO 43
<211> LENGTH: 7
<212> TYPE: RNA
<213> ORGANISM: Artificial
<220> FEATURE:
<223> OTHER INFORMATION: hsa-miR-518b seed sequence

<400> SEQUENCE: 43 aaagcgc                                                             7

<210> SEQ ID NO 44
<211> LENGTH: 7
<212> TYPE: RNA
<213> ORGANISM: Artificial
<220> FEATURE:
<223> OTHER INFORMATION: hsa-miR-3157-5p seed sequence

<400> SEQUENCE: 44 ucagcca                                                             7

<210> SEQ ID NO 45
<211> LENGTH: 7
<212> TYPE: RNA
<213> ORGANISM: Artificial
<220> FEATURE:
<223> OTHER INFORMATION: hsa-miR-16-5p seed sequence

<400> SEQUENCE: 45 agcagca                                                             7

<210> SEQ ID NO 46
```

```
<211> LENGTH: 7
<212> TYPE: RNA
<213> ORGANISM: Artificial
<220> FEATURE:
<223> OTHER INFORMATION: hsa-miR-497-5p seed sequence

<400> SEQUENCE: 46 agcagca                                                                    7

<210> SEQ ID NO 47
<211> LENGTH: 7
<212> TYPE: RNA
<213> ORGANISM: Artificial
<220> FEATURE:
<223> OTHER INFORMATION: hsa-miR-200c-5p seed sequence

<400> SEQUENCE: 47 gucuuac                                                                    7

<210> SEQ ID NO 48
<211> LENGTH: 7
<212> TYPE: RNA
<213> ORGANISM: Artificial
<220> FEATURE:
<223> OTHER INFORMATION: hsa-miR-182-3p seed sequence

<400> SEQUENCE: 48 gguucua                                                                    7

<210> SEQ ID NO 49
<211> LENGTH: 7
<212> TYPE: RNA
<213> ORGANISM: Artificial
<220> FEATURE:
<223> OTHER INFORMATION: hsa-miR-7-5p seed sequence

<400> SEQUENCE: 49 ggaagac                                                                    7

<210> SEQ ID NO 50
<211> LENGTH: 7
<212> TYPE: RNA
<213> ORGANISM: Artificial
<220> FEATURE:
<223> OTHER INFORMATION: hsa-miR-7-5p seed sequence

<400> SEQUENCE: 50 gaagacu                                                                    7

<210> SEQ ID NO 51
<211> LENGTH: 7
<212> TYPE: RNA
<213> ORGANISM: Artificial
<220> FEATURE:
<223> OTHER INFORMATION: hsa-miR-7-5p seed sequence

<400> SEQUENCE: 51 aagacua                                                                    7

<210> SEQ ID NO 52
<211> LENGTH: 7
<212> TYPE: RNA
<213> ORGANISM: Artificial
<220> FEATURE:
<223> OTHER INFORMATION: hsa-miR-7-5p seed sequence

<400> SEQUENCE: 52
``` agacuag                                                                 7

<210> SEQ ID NO 53
<211> LENGTH: 7
<212> TYPE: RNA
<213> ORGANISM: Artificial
<220> FEATURE:
<223> OTHER INFORMATION: hsa-miR-7-5p seed sequence

<400> SEQUENCE: 53 gacuagu                                                                 7

<210> SEQ ID NO 54
<211> LENGTH: 7
<212> TYPE: RNA
<213> ORGANISM: Artificial
<220> FEATURE:
<223> OTHER INFORMATION: hsa-miR-7-5p seed sequence

<400> SEQUENCE: 54 acuagug                                                                 7

<210> SEQ ID NO 55
<211> LENGTH: 7
<212> TYPE: RNA
<213> ORGANISM: Artificial
<220> FEATURE:
<223> OTHER INFORMATION: hsa-miR-7-5p seed sequence

<400> SEQUENCE: 55 cuaguga                                                                 7

<210> SEQ ID NO 56
<211> LENGTH: 7
<212> TYPE: RNA
<213> ORGANISM: Artificial
<220> FEATURE:
<223> OTHER INFORMATION: hsa-miR-7-5p seed sequence

<400> SEQUENCE: 56 uggaaga                                                                 7

<210> SEQ ID NO 57
<211> LENGTH: 7
<212> TYPE: RNA
<213> ORGANISM: Artificial
<220> FEATURE:
<223> OTHER INFORMATION: hsa-miR-7-5p seed sequence

<400> SEQUENCE: 57 guggaag                                                                 7

<210> SEQ ID NO 58
<211> LENGTH: 7
<212> TYPE: RNA
<213> ORGANISM: Artificial
<220> FEATURE:
<223> OTHER INFORMATION: hsa-miR-10b-3p seed sequence

<400> SEQUENCE: 58 agauucg                                                                 7

<210> SEQ ID NO 59
<211> LENGTH: 7
<212> TYPE: RNA

```
<213> ORGANISM: Artificial
<220> FEATURE:
<223> OTHER INFORMATION: hsa-miR-10b-3p seed sequence

<400> SEQUENCE: 59 gauucga                                                              7

<210> SEQ ID NO 60
<211> LENGTH: 7
<212> TYPE: RNA
<213> ORGANISM: Artificial
<220> FEATURE:
<223> OTHER INFORMATION: hsa-miR-10b-3p seed sequence

<400> SEQUENCE: 60 cagauuc                                                              7

<210> SEQ ID NO 61
<211> LENGTH: 7
<212> TYPE: RNA
<213> ORGANISM: Artificial
<220> FEATURE:
<223> OTHER INFORMATION: hsa-miR-10b-3p seed sequence

<400> SEQUENCE: 61 acagauu                                                              7

<210> SEQ ID NO 62
<211> LENGTH: 7
<212> TYPE: RNA
<213> ORGANISM: Artificial
<220> FEATURE:
<223> OTHER INFORMATION: hsa-miR-96-5p seed sequence

<400> SEQUENCE: 62 uuggcac                                                              7

<210> SEQ ID NO 63
<211> LENGTH: 7
<212> TYPE: RNA
<213> ORGANISM: Artificial
<220> FEATURE:
<223> OTHER INFORMATION: hsa-miR-96-5p seed sequence

<400> SEQUENCE: 63 uggcacu                                                              7

<210> SEQ ID NO 64
<211> LENGTH: 7
<212> TYPE: RNA
<213> ORGANISM: Artificial
<220> FEATURE:
<223> OTHER INFORMATION: hsa-miR-96-5p seed sequence

<400> SEQUENCE: 64 ggcacua                                                              7

<210> SEQ ID NO 65
<211> LENGTH: 7
<212> TYPE: RNA
<213> ORGANISM: Artificial
<220> FEATURE:
<223> OTHER INFORMATION: hsa-miR-96-5p seed sequence

<400> SEQUENCE: 65 gcacuag                                                              7
```

```
<210> SEQ ID NO 66
<211> LENGTH: 7
<212> TYPE: RNA
<213> ORGANISM: Artificial
<220> FEATURE:
<223> OTHER INFORMATION: hsa-miR-96-5p seed sequence

<400> SEQUENCE: 66 acuagca                                                              7

<210> SEQ ID NO 67
<211> LENGTH: 7
<212> TYPE: RNA
<213> ORGANISM: Artificial
<220> FEATURE:
<223> OTHER INFORMATION: hsa-miR-96-5p seed sequence

<400> SEQUENCE: 67 uuuggca                                                              7

<210> SEQ ID NO 68
<211> LENGTH: 7
<212> TYPE: RNA
<213> ORGANISM: Artificial
<220> FEATURE:
<223> OTHER INFORMATION: hsa-miR-129-5p seed sequence

<400> SEQUENCE: 68 uuuuugc                                                              7

<210> SEQ ID NO 69
<211> LENGTH: 7
<212> TYPE: RNA
<213> ORGANISM: Artificial
<220> FEATURE:
<223> OTHER INFORMATION: hsa-miR-129-5p seed sequence

<400> SEQUENCE: 69 uuuugcg                                                              7

<210> SEQ ID NO 70
<211> LENGTH: 7
<212> TYPE: RNA
<213> ORGANISM: Artificial
<220> FEATURE:
<223> OTHER INFORMATION: hsa-miR-129-5p seed sequence

<400> SEQUENCE: 70 uuugcgg                                                              7

<210> SEQ ID NO 71
<211> LENGTH: 7
<212> TYPE: RNA
<213> ORGANISM: Artificial
<220> FEATURE:
<223> OTHER INFORMATION: hsa-miR-129-5p seed sequence

<400> SEQUENCE: 71 ucuuuuu                                                              7

<210> SEQ ID NO 72
<211> LENGTH: 7
<212> TYPE: RNA
<213> ORGANISM: Artificial
<220> FEATURE:
```

```
<223> OTHER INFORMATION: hsa-miR-129-5p seed sequence

<400> SEQUENCE: 72 cuuuuug                                                                  7

<210> SEQ ID NO 73
<211> LENGTH: 7
<212> TYPE: RNA
<213> ORGANISM: Artificial
<220> FEATURE:
<223> OTHER INFORMATION: hsa-miR-518b seed sequence

<400> SEQUENCE: 73 aaagcgc                                                                  7

<210> SEQ ID NO 74
<211> LENGTH: 7
<212> TYPE: RNA
<213> ORGANISM: Artificial
<220> FEATURE:
<223> OTHER INFORMATION: hsa-miR-518b seed sequence

<400> SEQUENCE: 74 aagcgcu                                                                  7

<210> SEQ ID NO 75
<211> LENGTH: 7
<212> TYPE: RNA
<213> ORGANISM: Artificial
<220> FEATURE:
<223> OTHER INFORMATION: hsa-miR-3157-5p seed sequence

<400> SEQUENCE: 75 ucagcca                                                                  7

<210> SEQ ID NO 76
<211> LENGTH: 7
<212> TYPE: RNA
<213> ORGANISM: Artificial
<220> FEATURE:
<223> OTHER INFORMATION: hsa-miR-3157-5p seed sequence

<400> SEQUENCE: 76 uucagcc                                                                  7

<210> SEQ ID NO 77
<211> LENGTH: 7
<212> TYPE: RNA
<213> ORGANISM: Artificial
<220> FEATURE:
<223> OTHER INFORMATION: hsa-miR-16-5p seed sequence

<400> SEQUENCE: 77 agcagca                                                                  7

<210> SEQ ID NO 78
<211> LENGTH: 7
<212> TYPE: RNA
<213> ORGANISM: Artificial
<220> FEATURE:
<223> OTHER INFORMATION: hsa-miR-16-5p seed sequence

<400> SEQUENCE: 78 gcagcac                                                                  7
```

```
<210> SEQ ID NO 79
<211> LENGTH: 7
<212> TYPE: RNA
<213> ORGANISM: Artificial
<220> FEATURE:
<223> OTHER INFORMATION: hsa-miR-16-5p seed sequence

<400> SEQUENCE: 79 cagcacg                                                                    7

<210> SEQ ID NO 80
<211> LENGTH: 7
<212> TYPE: RNA
<213> ORGANISM: Artificial
<220> FEATURE:
<223> OTHER INFORMATION: hsa-miR-16-5p seed sequence

<400> SEQUENCE: 80 agcacgu                                                                    7

<210> SEQ ID NO 81
<211> LENGTH: 7
<212> TYPE: RNA
<213> ORGANISM: Artificial
<220> FEATURE:
<223> OTHER INFORMATION: hsa-miR-16-5p seed sequence

<400> SEQUENCE: 81 gcacgua                                                                    7

<210> SEQ ID NO 82
<211> LENGTH: 7
<212> TYPE: RNA
<213> ORGANISM: Artificial
<220> FEATURE:
<223> OTHER INFORMATION: hsa-miR-16-5p seed sequence

<400> SEQUENCE: 82 uagcagc                                                                    7

<210> SEQ ID NO 83
<211> LENGTH: 7
<212> TYPE: RNA
<213> ORGANISM: Artificial
<220> FEATURE:
<223> OTHER INFORMATION: hsa-miR-16-5p seed sequence

<400> SEQUENCE: 83 agcacgu                                                                    7

<210> SEQ ID NO 84
<211> LENGTH: 7
<212> TYPE: RNA
<213> ORGANISM: Artificial
<220> FEATURE:
<223> OTHER INFORMATION: hsa-miR-16-5p seed sequence

<400> SEQUENCE: 84 cguaaau                                                                    7

<210> SEQ ID NO 85
<211> LENGTH: 7
<212> TYPE: RNA
<213> ORGANISM: Artificial
<220> FEATURE:
<223> OTHER INFORMATION: hsa-miR-16-5p seed sequence
```

```
<400> SEQUENCE: 85 acguaaa                                                              7

<210> SEQ ID NO 86
<211> LENGTH: 7
<212> TYPE: RNA
<213> ORGANISM: Artificial
<220> FEATURE:
<223> OTHER INFORMATION: hsa-miR-16-5p seed sequence

<400> SEQUENCE: 86 cuagcag                                                              7

<210> SEQ ID NO 87
<211> LENGTH: 7
<212> TYPE: RNA
<213> ORGANISM: Artificial
<220> FEATURE:
<223> OTHER INFORMATION: hsa-miR-497-5p seed sequence

<400> SEQUENCE: 87 agcagca                                                              7

<210> SEQ ID NO 88
<211> LENGTH: 7
<212> TYPE: RNA
<213> ORGANISM: Artificial
<220> FEATURE:
<223> OTHER INFORMATION: hsa-miR-497-5p seed sequence

<400> SEQUENCE: 88 gcagcac                                                              7

<210> SEQ ID NO 89
<211> LENGTH: 7
<212> TYPE: RNA
<213> ORGANISM: Artificial
<220> FEATURE:
<223> OTHER INFORMATION: hsa-miR-497-5p seed sequence

<400> SEQUENCE: 89 cagcaca                                                              7

<210> SEQ ID NO 90
<211> LENGTH: 7
<212> TYPE: RNA
<213> ORGANISM: Artificial
<220> FEATURE:
<223> OTHER INFORMATION: hsa-miR-497-5p seed sequence

<400> SEQUENCE: 90 agcacac                                                              7

<210> SEQ ID NO 91
<211> LENGTH: 7
<212> TYPE: RNA
<213> ORGANISM: Artificial
<220> FEATURE:
<223> OTHER INFORMATION: hsa-miR-497-5p seed sequence

<400> SEQUENCE: 91 cagcagc                                                              7

<210> SEQ ID NO 92
<211> LENGTH: 7
```

```
<212> TYPE: DNA
<213> ORGANISM: Artificial
<220> FEATURE:
<223> OTHER INFORMATION: hsa-miR-200c-5p seed sequence

<400> SEQUENCE: 92 gtcttac                                                                    7

<210> SEQ ID NO 93
<211> LENGTH: 7
<212> TYPE: RNA
<213> ORGANISM: Artificial
<220> FEATURE:
<223> OTHER INFORMATION: hsa-miR-182-3p seed sequence

<400> SEQUENCE: 93 gugguuc                                                                    7

<210> SEQ ID NO 94
<211> LENGTH: 7
<212> TYPE: RNA
<213> ORGANISM: Artificial
<220> FEATURE:
<223> OTHER INFORMATION: hsa-miR-182-3p seed sequence

<400> SEQUENCE: 94 gguucua                                                                    7

<210> SEQ ID NO 95
<211> LENGTH: 7
<212> TYPE: RNA
<213> ORGANISM: Artificial
<220> FEATURE:
<223> OTHER INFORMATION: hsa-miR-182-3p seed sequence

<400> SEQUENCE: 95 ugguucu                                                                    7

<210> SEQ ID NO 96
<211> LENGTH: 24
<212> TYPE: RNA
<213> ORGANISM: Artificial
<220> FEATURE:
<223> OTHER INFORMATION: hsa-miR-7-5p isomiR sequence

<400> SEQUENCE: 96
uggaagacua gugauuuugu uguu                                                 24

<210> SEQ ID NO 97
<211> LENGTH: 22
<212> TYPE: RNA
<213> ORGANISM: Artificial
<220> FEATURE:
<223> OTHER INFORMATION: hsa-miR-7-5p isomiR sequence

<400> SEQUENCE: 97
uggaagacua gugauuuugu ug                                                   22

<210> SEQ ID NO 98
<211> LENGTH: 20
<212> TYPE: RNA
<213> ORGANISM: Artificial
<220> FEATURE:
<223> OTHER INFORMATION: hsa-miR-7-5p isomiR sequence

<400> SEQUENCE: 98
```
uggaagacua gugauuuugu     20

<210> SEQ ID NO 99
<211> LENGTH: 25
<212> TYPE: RNA
<213> ORGANISM: Artificial
<220> FEATURE:
<223> OTHER INFORMATION: hsa-miR-7-5p isomiR sequence

<400> SEQUENCE: 99
uggaagacua gugauuuugu uguuu     25

<210> SEQ ID NO 100
<211> LENGTH: 21
<212> TYPE: RNA
<213> ORGANISM: Artificial
<220> FEATURE:
<223> OTHER INFORMATION: hsa-miR-7-5p isomiR sequence

<400> SEQUENCE: 100
uggaagacua gugauuuugu u     21

<210> SEQ ID NO 101
<211> LENGTH: 23
<212> TYPE: RNA
<213> ORGANISM: Artificial
<220> FEATURE:
<223> OTHER INFORMATION: hsa-miR-7-5p isomiR sequence

<400> SEQUENCE: 101
ggaagacuag ugauuuuguu guu     23

<210> SEQ ID NO 102
<211> LENGTH: 22
<212> TYPE: RNA
<213> ORGANISM: Artificial
<220> FEATURE:
<223> OTHER INFORMATION: hsa-miR-7-5p isomiR sequence

<400> SEQUENCE: 102
ggaagacuag ugauuuuguu gu     22

<210> SEQ ID NO 103
<211> LENGTH: 19
<212> TYPE: RNA
<213> ORGANISM: Artificial
<220> FEATURE:
<223> OTHER INFORMATION: hsa-miR-7-5p isomiR sequence

<400> SEQUENCE: 103
uggaagacua gugauuuug     19

<210> SEQ ID NO 104
<211> LENGTH: 25
<212> TYPE: RNA
<213> ORGANISM: Artificial
<220> FEATURE:
<223> OTHER INFORMATION: hsa-miR-7-5p isomiR sequence

<400> SEQUENCE: 104
uggaagacua gugauuuugu uguuc     25

<210> SEQ ID NO 105
<211> LENGTH: 18
<212> TYPE: RNA
<213> ORGANISM: Artificial

```
<220> FEATURE:
<223> OTHER INFORMATION: hsa-miR-7-5p isomiR sequence

<400> SEQUENCE: 105
uggaagacua gugauuuu                                                    18

<210> SEQ ID NO 106
<211> LENGTH: 22
<212> TYPE: RNA
<213> ORGANISM: Artificial
<220> FEATURE:
<223> OTHER INFORMATION: hsa-miR-7-5p isomiR sequence

<400> SEQUENCE: 106
gaagacuagu gauuuuguug uu                                               22

<210> SEQ ID NO 107
<211> LENGTH: 21
<212> TYPE: RNA
<213> ORGANISM: Artificial
<220> FEATURE:
<223> OTHER INFORMATION: hsa-miR-7-5p isomiR sequence

<400> SEQUENCE: 107
gaagacuagu gauuuuguug u                                                21

<210> SEQ ID NO 108
<211> LENGTH: 26
<212> TYPE: RNA
<213> ORGANISM: Artificial
<220> FEATURE:
<223> OTHER INFORMATION: hsa-miR-7-5p isomiR sequence

<400> SEQUENCE: 108
uggaagacua gugauuuugu uguuuu                                           26

<210> SEQ ID NO 109
<211> LENGTH: 24
<212> TYPE: RNA
<213> ORGANISM: Artificial
<220> FEATURE:
<223> OTHER INFORMATION: hsa-miR-7-5p isomiR sequence

<400> SEQUENCE: 109
ggaagacuag ugauuuuguu guuu                                             24

<210> SEQ ID NO 110
<211> LENGTH: 23
<212> TYPE: RNA
<213> ORGANISM: Artificial
<220> FEATURE:
<223> OTHER INFORMATION: hsa-miR-7-5p isomiR sequence

<400> SEQUENCE: 110
gaagacuagu gauuuuguug uug                                              23

<210> SEQ ID NO 111
<211> LENGTH: 21
<212> TYPE: RNA
<213> ORGANISM: Artificial
<220> FEATURE:
<223> OTHER INFORMATION: hsa-miR-7-5p isomiR sequence

<400> SEQUENCE: 111
aagacuagug auuuuguugu u                                                21
```

```
<210> SEQ ID NO 112
<211> LENGTH: 20
<212> TYPE: RNA
<213> ORGANISM: Artificial
<220> FEATURE:
<223> OTHER INFORMATION: hsa-miR-7-5p isomiR sequence

<400> SEQUENCE: 112
agacuaguga uuuuguuguu                                             20

<210> SEQ ID NO 113
<211> LENGTH: 20
<212> TYPE: RNA
<213> ORGANISM: Artificial
<220> FEATURE:
<223> OTHER INFORMATION: hsa-miR-7-5p isomiR sequence

<400> SEQUENCE: 113
aagacuagug auuuuguugu                                             20

<210> SEQ ID NO 114
<211> LENGTH: 22
<212> TYPE: RNA
<213> ORGANISM: Artificial
<220> FEATURE:
<223> OTHER INFORMATION: hsa-miR-7-5p isomiR sequence

<400> SEQUENCE: 114
gacuagugau uuuguuguuu uu                                          22

<210> SEQ ID NO 115
<211> LENGTH: 19
<212> TYPE: RNA
<213> ORGANISM: Artificial
<220> FEATURE:
<223> OTHER INFORMATION: hsa-miR-7-5p isomiR sequence

<400> SEQUENCE: 115
gacuagugau uuuguuguu                                              19

<210> SEQ ID NO 116
<211> LENGTH: 21
<212> TYPE: RNA
<213> ORGANISM: Artificial
<220> FEATURE:
<223> OTHER INFORMATION: hsa-miR-7-5p isomiR sequence

<400> SEQUENCE: 116
ggaagacuag ugauuuuguu g                                           21

<210> SEQ ID NO 117
<211> LENGTH: 26
<212> TYPE: RNA
<213> ORGANISM: Artificial
<220> FEATURE:
<223> OTHER INFORMATION: hsa-miR-7-5p isomiR sequence

<400> SEQUENCE: 117
uggaagacua gugauuuugu uguugu                                      26

<210> SEQ ID NO 118
<211> LENGTH: 27
<212> TYPE: RNA
<213> ORGANISM: Artificial
<220> FEATURE:
<223> OTHER INFORMATION: hsa-miR-7-5p isomiR sequence
```

<400> SEQUENCE: 118
uggaagacua gugauuuugu uguucug                                27

<210> SEQ ID NO 119
<211> LENGTH: 28
<212> TYPE: RNA
<213> ORGANISM: Artificial
<220> FEATURE:
<223> OTHER INFORMATION: hsa-miR-7-5p isomiR sequence

<400> SEQUENCE: 119
uggaagacua gugauuuugu uguucuga                               28

<210> SEQ ID NO 120
<211> LENGTH: 19
<212> TYPE: RNA
<213> ORGANISM: Artificial
<220> FEATURE:
<223> OTHER INFORMATION: hsa-miR-7-5p isomiR sequence

<400> SEQUENCE: 120
agacuaguga uuuuguugu                                         19

<210> SEQ ID NO 121
<211> LENGTH: 20
<212> TYPE: RNA
<213> ORGANISM: Artificial
<220> FEATURE:
<223> OTHER INFORMATION: hsa-miR-7-5p isomiR sequence

<400> SEQUENCE: 121
ggaagacuag ugauuuuguu                                        20

<210> SEQ ID NO 122
<211> LENGTH: 23
<212> TYPE: RNA
<213> ORGANISM: Artificial
<220> FEATURE:
<223> OTHER INFORMATION: hsa-miR-7-5p isomiR sequence

<400> SEQUENCE: 122
gacuagugau uuuguuguuu uua                                    23

<210> SEQ ID NO 123
<211> LENGTH: 18
<212> TYPE: RNA
<213> ORGANISM: Artificial
<220> FEATURE:
<223> OTHER INFORMATION: hsa-miR-7-5p isomiR sequence

<400> SEQUENCE: 123
gacuagugau uuuguugu                                          18

<210> SEQ ID NO 124
<211> LENGTH: 20
<212> TYPE: RNA
<213> ORGANISM: Artificial
<220> FEATURE:
<223> OTHER INFORMATION: hsa-miR-7-5p isomiR sequence

<400> SEQUENCE: 124
gacuagugau uuuguuguuu                                        20

<210> SEQ ID NO 125

```
<211> LENGTH: 22
<212> TYPE: RNA
<213> ORGANISM: Artificial
<220> FEATURE:
<223> OTHER INFORMATION: hsa-miR-7-5p isomiR sequence

<400> SEQUENCE: 125
guggaagacu agugauuuug uu                                               22

<210> SEQ ID NO 126
<211> LENGTH: 23
<212> TYPE: RNA
<213> ORGANISM: Artificial
<220> FEATURE:
<223> OTHER INFORMATION: hsa-miR-7-5p isomiR sequence

<400> SEQUENCE: 126
gaagacuagu gauuuuguug uuu                                              23

<210> SEQ ID NO 127
<211> LENGTH: 25
<212> TYPE: RNA
<213> ORGANISM: Artificial
<220> FEATURE:
<223> OTHER INFORMATION: hsa-miR-7-5p isomiR sequence

<400> SEQUENCE: 127
guggaagacu agugauuuug uuguu                                            25

<210> SEQ ID NO 128
<211> LENGTH: 21
<212> TYPE: RNA
<213> ORGANISM: Artificial
<220> FEATURE:
<223> OTHER INFORMATION: hsa-miR-7-5p isomiR sequence

<400> SEQUENCE: 128
gacuagugau uuuguuguuu u                                                21

<210> SEQ ID NO 129
<211> LENGTH: 22
<212> TYPE: RNA
<213> ORGANISM: Artificial
<220> FEATURE:
<223> OTHER INFORMATION: hsa-miR-7-5p isomiR sequence

<400> SEQUENCE: 129
aagacuagug auuuuguugu uu                                               22

<210> SEQ ID NO 130
<211> LENGTH: 20
<212> TYPE: RNA
<213> ORGANISM: Artificial
<220> FEATURE:
<223> OTHER INFORMATION: hsa-miR-7-5p isomiR sequence

<400> SEQUENCE: 130
aacaaaucac agucugccau                                                  20

<210> SEQ ID NO 131
<211> LENGTH: 24
<212> TYPE: RNA
<213> ORGANISM: Artificial
<220> FEATURE:
<223> OTHER INFORMATION: hsa-miR-7-5p isomiR sequence

<400> SEQUENCE: 131
```

```
guggaagacu agugauuuug uugu                                        24

<210> SEQ ID NO 132
<211> LENGTH: 27
<212> TYPE: RNA
<213> ORGANISM: Artificial
<220> FEATURE:
<223> OTHER INFORMATION: hsa-miR-7-5p isomiR sequence

<400> SEQUENCE: 132
uggaagacua gugauuugu uguuuuu                                      27

<210> SEQ ID NO 133
<211> LENGTH: 23
<212> TYPE: RNA
<213> ORGANISM: Artificial
<220> FEATURE:
<223> OTHER INFORMATION: hsa-miR-7-5p isomiR sequence

<400> SEQUENCE: 133
aagacuagug auuuuguugu uuu                                         23

<210> SEQ ID NO 134
<211> LENGTH: 18
<212> TYPE: RNA
<213> ORGANISM: Artificial
<220> FEATURE:
<223> OTHER INFORMATION: hsa-miR-7-5p isomiR sequence

<400> SEQUENCE: 134
acuagugauu uuguuguu                                               18

<210> SEQ ID NO 135
<211> LENGTH: 24
<212> TYPE: RNA
<213> ORGANISM: Artificial
<220> FEATURE:
<223> OTHER INFORMATION: hsa-miR-7-5p isomiR sequence

<400> SEQUENCE: 135
ggaagacuag ugauuuuguu guug                                        24

<210> SEQ ID NO 136
<211> LENGTH: 20
<212> TYPE: RNA
<213> ORGANISM: Artificial
<220> FEATURE:
<223> OTHER INFORMATION: hsa-miR-7-5p isomiR sequence

<400> SEQUENCE: 136
gaagacuagu gauuuuguug                                             20

<210> SEQ ID NO 137
<211> LENGTH: 22
<212> TYPE: RNA
<213> ORGANISM: Artificial
<220> FEATURE:
<223> OTHER INFORMATION: hsa-miR-7-5p isomiR sequence

<400> SEQUENCE: 137
aagacuagug auuuuguugu ug                                          22

<210> SEQ ID NO 138
<211> LENGTH: 25
<212> TYPE: RNA
```

```
<213> ORGANISM: Artificial
<220> FEATURE:
<223> OTHER INFORMATION: hsa-miR-7-5p isomiR sequence

<400> SEQUENCE: 138
uguggaagac uagugauuuu guugu                                       25

<210> SEQ ID NO 139
<211> LENGTH: 22
<212> TYPE: RNA
<213> ORGANISM: Artificial
<220> FEATURE:
<223> OTHER INFORMATION: hsa-miR-7-5p isomiR sequence

<400> SEQUENCE: 139
uguggaagac uagugauuuu gu                                          22

<210> SEQ ID NO 140
<211> LENGTH: 24
<212> TYPE: RNA
<213> ORGANISM: Artificial
<220> FEATURE:
<223> OTHER INFORMATION: hsa-miR-7-5p isomiR sequence

<400> SEQUENCE: 140
cuggaagacu agugauuuug uugu                                        24

<210> SEQ ID NO 141
<211> LENGTH: 25
<212> TYPE: RNA
<213> ORGANISM: Artificial
<220> FEATURE:
<223> OTHER INFORMATION: hsa-miR-7-5p isomiR sequence

<400> SEQUENCE: 141
ggaagacuag ugauuuuguu guuuu                                       25

<210> SEQ ID NO 142
<211> LENGTH: 19
<212> TYPE: RNA
<213> ORGANISM: Artificial
<220> FEATURE:
<223> OTHER INFORMATION: hsa-miR-7-5p isomiR sequence

<400> SEQUENCE: 142
ggaagacuag ugauuuugu                                              19

<210> SEQ ID NO 143
<211> LENGTH: 24
<212> TYPE: RNA
<213> ORGANISM: Artificial
<220> FEATURE:
<223> OTHER INFORMATION: hsa-miR-7-5p isomiR sequence

<400> SEQUENCE: 143
gaagacuagu gauuuuguug uuuu                                        24

<210> SEQ ID NO 144
<211> LENGTH: 18
<212> TYPE: RNA
<213> ORGANISM: Artificial
<220> FEATURE:
<223> OTHER INFORMATION: hsa-miR-7-5p isomiR sequence

<400> SEQUENCE: 144
agacuaguga uuuuguug                                               18
```

```
<210> SEQ ID NO 145
<211> LENGTH: 24
<212> TYPE: RNA
<213> ORGANISM: Artificial
<220> FEATURE:
<223> OTHER INFORMATION: hsa-miR-7-5p isomiR sequence

<400> SEQUENCE: 145
aagacuagug auuuuguugu uuuu                                              24

<210> SEQ ID NO 146
<211> LENGTH: 21
<212> TYPE: RNA
<213> ORGANISM: Artificial
<220> FEATURE:
<223> OTHER INFORMATION: hsa-miR-7-5p isomiR sequence

<400> SEQUENCE: 146
agacuaguga uuuuguuguu u                                                 21

<210> SEQ ID NO 147
<211> LENGTH: 21
<212> TYPE: RNA
<213> ORGANISM: Artificial
<220> FEATURE:
<223> OTHER INFORMATION: hsa-miR-10b-3p isomiR sequence

<400> SEQUENCE: 147
cagauucgau ucuaggggaa u                                                 21

<210> SEQ ID NO 148
<211> LENGTH: 20
<212> TYPE: RNA
<213> ORGANISM: Artificial
<220> FEATURE:
<223> OTHER INFORMATION: hsa-miR-10b-3p isomiR sequence

<400> SEQUENCE: 148
agauucgauu cuaggggaau                                                   20

<210> SEQ ID NO 149
<211> LENGTH: 22
<212> TYPE: RNA
<213> ORGANISM: Artificial
<220> FEATURE:
<223> OTHER INFORMATION: hsa-miR-10b-3p isomiR sequence

<400> SEQUENCE: 149
agauucgauu cuaggggaau au                                                22

<210> SEQ ID NO 150
<211> LENGTH: 20
<212> TYPE: RNA
<213> ORGANISM: Artificial
<220> FEATURE:
<223> OTHER INFORMATION: hsa-miR-10b-3p isomiR sequence

<400> SEQUENCE: 150
cagauucgau ucuaggggaa                                                   20

<210> SEQ ID NO 151
<211> LENGTH: 22
<212> TYPE: RNA
<213> ORGANISM: Artificial
<220> FEATURE:
```

```
<223> OTHER INFORMATION: hsa-miR-10b-3p isomiR sequence

<400> SEQUENCE: 151
cagauucgau ucuagggaa ua                                                   22

<210> SEQ ID NO 152
<211> LENGTH: 19
<212> TYPE: RNA
<213> ORGANISM: Artificial
<220> FEATURE:
<223> OTHER INFORMATION: hsa-miR-10b-3p isomiR sequence

<400> SEQUENCE: 152
agauucgauu cuagggaa                                                       19

<210> SEQ ID NO 153
<211> LENGTH: 21
<212> TYPE: RNA
<213> ORGANISM: Artificial
<220> FEATURE:
<223> OTHER INFORMATION: hsa-miR-10b-3p isomiR sequence

<400> SEQUENCE: 153
acagauucga uucuagggga a                                                   21

<210> SEQ ID NO 154
<211> LENGTH: 22
<212> TYPE: RNA
<213> ORGANISM: Artificial
<220> FEATURE:
<223> OTHER INFORMATION: hsa-miR-10b-3p isomiR sequence

<400> SEQUENCE: 154
cacagauucg auucuagggg aa                                                  22

<210> SEQ ID NO 155
<211> LENGTH: 19
<212> TYPE: RNA
<213> ORGANISM: Artificial
<220> FEATURE:
<223> OTHER INFORMATION: hsa-miR-10b-3p isomiR sequence

<400> SEQUENCE: 155
acagauucga uucuagggg                                                      19

<210> SEQ ID NO 156
<211> LENGTH: 21
<212> TYPE: RNA
<213> ORGANISM: Artificial
<220> FEATURE:
<223> OTHER INFORMATION: hsa-miR-10b-3p isomiR sequence

<400> SEQUENCE: 156
agauucgauu cuagggaau a                                                    21

<210> SEQ ID NO 157
<211> LENGTH: 24
<212> TYPE: RNA
<213> ORGANISM: Artificial
<220> FEATURE:
<223> OTHER INFORMATION: hsa-miR-10b-3p isomiR sequence

<400> SEQUENCE: 157
acagauucga uucuagggga auau                                                24
```

```
<210> SEQ ID NO 158
<211> LENGTH: 23
<212> TYPE: RNA
<213> ORGANISM: Artificial
<220> FEATURE:
<223> OTHER INFORMATION: hsa-miR-10b-3p isomiR sequence

<400> SEQUENCE: 158
acagauucga uucuagggga aua                                              23

<210> SEQ ID NO 159
<211> LENGTH: 21
<212> TYPE: RNA
<213> ORGANISM: Artificial
<220> FEATURE:
<223> OTHER INFORMATION: hsa-miR-96-5p isomiR sequence

<400> SEQUENCE: 159
uuuggcacua gcacauuuuu g                                                21

<210> SEQ ID NO 160
<211> LENGTH: 22
<212> TYPE: RNA
<213> ORGANISM: Artificial
<220> FEATURE:
<223> OTHER INFORMATION: hsa-miR-96-5p isomiR sequence

<400> SEQUENCE: 160
uuuggcacua gcacauuuuu gc                                               22

<210> SEQ ID NO 161
<211> LENGTH: 20
<212> TYPE: RNA
<213> ORGANISM: Artificial
<220> FEATURE:
<223> OTHER INFORMATION: hsa-miR-96-5p isomiR sequence

<400> SEQUENCE: 161
uuuggcacua gcacauuuuu                                                  20

<210> SEQ ID NO 162
<211> LENGTH: 22
<212> TYPE: RNA
<213> ORGANISM: Artificial
<220> FEATURE:
<223> OTHER INFORMATION: hsa-miR-96-5p isomiR sequence

<400> SEQUENCE: 162
uuggcacuag cacauuuuug cu                                               22

<210> SEQ ID NO 163
<211> LENGTH: 24
<212> TYPE: RNA
<213> ORGANISM: Artificial
<220> FEATURE:
<223> OTHER INFORMATION: hsa-miR-96-5p isomiR sequence

<400> SEQUENCE: 163
uuuggcacua gcacauuuuu gcuu                                             24

<210> SEQ ID NO 164
<211> LENGTH: 19
<212> TYPE: RNA
<213> ORGANISM: Artificial
<220> FEATURE:
<223> OTHER INFORMATION: hsa-miR-96-5p isomiR sequence
```

-continued

<400> SEQUENCE: 164
uuuggcacua gcacauuuu                                                19

<210> SEQ ID NO 165
<211> LENGTH: 21
<212> TYPE: RNA
<213> ORGANISM: Artificial
<220> FEATURE:
<223> OTHER INFORMATION: hsa-miR-96-5p isomiR sequence

<400> SEQUENCE: 165
uggcacuagc acauuuugc u                                              21

<210> SEQ ID NO 166
<211> LENGTH: 20
<212> TYPE: RNA
<213> ORGANISM: Artificial
<220> FEATURE:
<223> OTHER INFORMATION: hsa-miR-96-5p isomiR sequence

<400> SEQUENCE: 166
ggcacuagca cauuuugcu                                                20

<210> SEQ ID NO 167
<211> LENGTH: 21
<212> TYPE: RNA
<213> ORGANISM: Artificial
<220> FEATURE:
<223> OTHER INFORMATION: hsa-miR-96-5p isomiR sequence

<400> SEQUENCE: 167
uuggcacuag cacauuuug c                                              21

<210> SEQ ID NO 168
<211> LENGTH: 18
<212> TYPE: RNA
<213> ORGANISM: Artificial
<220> FEATURE:
<223> OTHER INFORMATION: hsa-miR-96-5p isomiR sequence

<400> SEQUENCE: 168
uuuggcacua gcacauuu                                                 18

<210> SEQ ID NO 169
<211> LENGTH: 20
<212> TYPE: RNA
<213> ORGANISM: Artificial
<220> FEATURE:
<223> OTHER INFORMATION: hsa-miR-96-5p isomiR sequence

<400> SEQUENCE: 169
uggcacuagc acauuuugc                                                20

<210> SEQ ID NO 170
<211> LENGTH: 20
<212> TYPE: RNA
<213> ORGANISM: Artificial
<220> FEATURE:
<223> OTHER INFORMATION: hsa-miR-96-5p isomiR sequence

<400> SEQUENCE: 170
uuggcacuag cacauuuug                                                20

<210> SEQ ID NO 171
<211> LENGTH: 23

```
<212> TYPE: RNA
<213> ORGANISM: Artificial
<220> FEATURE:
<223> OTHER INFORMATION: hsa-miR-96-5p isomiR sequence

<400> SEQUENCE: 171
uuggcacuag cacauuuuug cuu                                        23

<210> SEQ ID NO 172
<211> LENGTH: 19
<212> TYPE: RNA
<213> ORGANISM: Artificial
<220> FEATURE:
<223> OTHER INFORMATION: hsa-miR-96-5p isomiR sequence

<400> SEQUENCE: 172
ggcacuagca cauuuuugc                                             19

<210> SEQ ID NO 173
<211> LENGTH: 18
<212> TYPE: RNA
<213> ORGANISM: Artificial
<220> FEATURE:
<223> OTHER INFORMATION: hsa-miR-96-5p isomiR sequence

<400> SEQUENCE: 173
cacuagcaca uuuugcu                                               18

<210> SEQ ID NO 174
<211> LENGTH: 23
<212> TYPE: RNA
<213> ORGANISM: Artificial
<220> FEATURE:
<223> OTHER INFORMATION: hsa-miR-96-5p isomiR sequence

<400> SEQUENCE: 174
uuuuggcacu agcacauuuu ugc                                        23

<210> SEQ ID NO 175
<211> LENGTH: 20
<212> TYPE: RNA
<213> ORGANISM: Artificial
<220> FEATURE:
<223> OTHER INFORMATION: hsa-miR-129-5p isomiR sequence

<400> SEQUENCE: 175
cuuuuugcgg ucugggcuug                                            20

<210> SEQ ID NO 176
<211> LENGTH: 19
<212> TYPE: RNA
<213> ORGANISM: Artificial
<220> FEATURE:
<223> OTHER INFORMATION: hsa-miR-129-5p isomiR sequence

<400> SEQUENCE: 176
cuuuuugcgg ucugggcuu                                             19

<210> SEQ ID NO 177
<211> LENGTH: 18
<212> TYPE: RNA
<213> ORGANISM: Artificial
<220> FEATURE:
<223> OTHER INFORMATION: hsa-miR-129-5p isomiR sequence

<400> SEQUENCE: 177
```
cuuuuugcgg ucugggcu                                              18

<210> SEQ ID NO 178
<211> LENGTH: 22
<212> TYPE: RNA
<213> ORGANISM: Artificial
<220> FEATURE:
<223> OTHER INFORMATION: hsa-miR-129-5p isomiR sequence

<400> SEQUENCE: 178
cuuuuugcgg ucugggcuug cu                                         22

<210> SEQ ID NO 179
<211> LENGTH: 23
<212> TYPE: RNA
<213> ORGANISM: Artificial
<220> FEATURE:
<223> OTHER INFORMATION: hsa-miR-129-5p isomiR sequence

<400> SEQUENCE: 179
cuuuuugcgg ucugggcuug cug                                        23

<210> SEQ ID NO 180
<211> LENGTH: 19
<212> TYPE: RNA
<213> ORGANISM: Artificial
<220> FEATURE:
<223> OTHER INFORMATION: hsa-miR-129-5p isomiR sequence

<400> SEQUENCE: 180
uuuuugcggu cugggcuug                                             19

<210> SEQ ID NO 181
<211> LENGTH: 20
<212> TYPE: RNA
<213> ORGANISM: Artificial
<220> FEATURE:
<223> OTHER INFORMATION: hsa-miR-129-5p isomiR sequence

<400> SEQUENCE: 181
uuuuugcggu cugggcuugc                                            20

<210> SEQ ID NO 182
<211> LENGTH: 24
<212> TYPE: RNA
<213> ORGANISM: Artificial
<220> FEATURE:
<223> OTHER INFORMATION: hsa-miR-129-5p isomiR sequence

<400> SEQUENCE: 182
cuuuuugcgg ucugggcuug cugu                                       24

<210> SEQ ID NO 183
<211> LENGTH: 21
<212> TYPE: RNA
<213> ORGANISM: Artificial
<220> FEATURE:
<223> OTHER INFORMATION: hsa-miR-129-5p isomiR sequence

<400> SEQUENCE: 183
uuuugcgguc ugggcuugcu g                                          21

<210> SEQ ID NO 184
<211> LENGTH: 18
<212> TYPE: RNA
<213> ORGANISM: Artificial

```
<220> FEATURE:
<223> OTHER INFORMATION: hsa-miR-129-5p isomiR sequence

<400> SEQUENCE: 184
uuuugcgguc ugggcuug                                                 18

<210> SEQ ID NO 185
<211> LENGTH: 21
<212> TYPE: RNA
<213> ORGANISM: Artificial
<220> FEATURE:
<223> OTHER INFORMATION: hsa-miR-129-5p isomiR sequence

<400> SEQUENCE: 185 aucuuuugc ggucugggcu u                                              21

<210> SEQ ID NO 186
<211> LENGTH: 21
<212> TYPE: RNA
<213> ORGANISM: Artificial
<220> FEATURE:
<223> OTHER INFORMATION: hsa-miR-129-5p isomiR sequence

<400> SEQUENCE: 186
ucuuuuugcg gucugggcuu g                                             21

<210> SEQ ID NO 187
<211> LENGTH: 23
<212> TYPE: RNA
<213> ORGANISM: Artificial
<220> FEATURE:
<223> OTHER INFORMATION: hsa-miR-518b isomiR sequence

<400> SEQUENCE: 187
caaagcgcuc cccuuuagag guu                                           23

<210> SEQ ID NO 188
<211> LENGTH: 21
<212> TYPE: RNA
<213> ORGANISM: Artificial
<220> FEATURE:
<223> OTHER INFORMATION: hsa-miR-518b isomiR sequence

<400> SEQUENCE: 188
caaagcgcuc cccuuuagag g                                             21

<210> SEQ ID NO 189
<211> LENGTH: 20
<212> TYPE: RNA
<213> ORGANISM: Artificial
<220> FEATURE:
<223> OTHER INFORMATION: hsa-miR-518b isomiR sequence

<400> SEQUENCE: 189
caaagcgcuc cccuuuagag                                               20

<210> SEQ ID NO 190
<211> LENGTH: 22
<212> TYPE: RNA
<213> ORGANISM: Artificial
<220> FEATURE:
<223> OTHER INFORMATION: hsa-miR-518b isomiR sequence

<400> SEQUENCE: 190
aaagcgcucc ccuuuagagg uu                                            22
```

-continued

```
<210> SEQ ID NO 191
<211> LENGTH: 24
<212> TYPE: RNA
<213> ORGANISM: Artificial
<220> FEATURE:
<223> OTHER INFORMATION: hsa-miR-518b isomiR sequence

<400> SEQUENCE: 191
caaagcgcuc cccuuuagag guuu                                               24

<210> SEQ ID NO 192
<211> LENGTH: 19
<212> TYPE: RNA
<213> ORGANISM: Artificial
<220> FEATURE:
<223> OTHER INFORMATION: hsa-miR-3157-5p isomiR sequence

<400> SEQUENCE: 192
uucagccagg cuagugcag                                                     19

<210> SEQ ID NO 193
<211> LENGTH: 21
<212> TYPE: RNA
<213> ORGANISM: Artificial
<220> FEATURE:
<223> OTHER INFORMATION: hsa-miR-3157-5p isomiR sequence

<400> SEQUENCE: 193
cuucagccag gcuagugcag u                                                  21

<210> SEQ ID NO 194
<211> LENGTH: 21
<212> TYPE: RNA
<213> ORGANISM: Artificial
<220> FEATURE:
<223> OTHER INFORMATION: hsa-miR-3157-5p isomiR sequence

<400> SEQUENCE: 194
uucagccagg cuagugcagu c                                                  21

<210> SEQ ID NO 195
<211> LENGTH: 23
<212> TYPE: RNA
<213> ORGANISM: Artificial
<220> FEATURE:
<223> OTHER INFORMATION: hsa-miR-16-5p isomiR sequence

<400> SEQUENCE: 195
uagcagcacg uaaauauugg cgu                                                23

<210> SEQ ID NO 196
<211> LENGTH: 20
<212> TYPE: RNA
<213> ORGANISM: Artificial
<220> FEATURE:
<223> OTHER INFORMATION: hsa-miR-16-5p isomiR sequence

<400> SEQUENCE: 196
uagcagcacg uaaauauugg                                                    20

<210> SEQ ID NO 197
<211> LENGTH: 21
<212> TYPE: RNA
<213> ORGANISM: Artificial
<220> FEATURE:
<223> OTHER INFORMATION: hsa-miR-16-5p isomiR sequence
```

```
<400> SEQUENCE: 197
uagcagcacg uaaauauugg c                                              21

<210> SEQ ID NO 198
<211> LENGTH: 21
<212> TYPE: RNA
<213> ORGANISM: Artificial
<220> FEATURE:
<223> OTHER INFORMATION: hsa-miR-16-5p isomiR sequence

<400> SEQUENCE: 198
agcagcacgu aaauauuggc g                                              21

<210> SEQ ID NO 199
<211> LENGTH: 19
<212> TYPE: RNA
<213> ORGANISM: Artificial
<220> FEATURE:
<223> OTHER INFORMATION: hsa-miR-16-5p isomiR sequence

<400> SEQUENCE: 199
uagcagcacg uaaauauug                                                 19

<210> SEQ ID NO 200
<211> LENGTH: 20
<212> TYPE: RNA
<213> ORGANISM: Artificial
<220> FEATURE:
<223> OTHER INFORMATION: hsa-miR-16-5p isomiR sequence

<400> SEQUENCE: 200
gcagcacgua aauauuggcg                                                20

<210> SEQ ID NO 201
<211> LENGTH: 24
<212> TYPE: RNA
<213> ORGANISM: Artificial
<220> FEATURE:
<223> OTHER INFORMATION: hsa-miR-16-5p isomiR sequence

<400> SEQUENCE: 201
uagcagcacg uaaauauugg cgua                                           24

<210> SEQ ID NO 202
<211> LENGTH: 22
<212> TYPE: RNA
<213> ORGANISM: Artificial
<220> FEATURE:
<223> OTHER INFORMATION: hsa-miR-16-5p isomiR sequence

<400> SEQUENCE: 202
agcagcacgu aaauauuggc gu                                             22

<210> SEQ ID NO 203
<211> LENGTH: 20
<212> TYPE: RNA
<213> ORGANISM: Artificial
<220> FEATURE:
<223> OTHER INFORMATION: hsa-miR-16-5p isomiR sequence

<400> SEQUENCE: 203
agcagcacgu aaauauuggc                                                20

<210> SEQ ID NO 204
```

-continued

```
<211> LENGTH: 18
<212> TYPE: RNA
<213> ORGANISM: Artificial
<220> FEATURE:
<223> OTHER INFORMATION: hsa-miR-16-5p isomiR sequence

<400> SEQUENCE: 204
uagcagcacg uaaauauu                                                 18

<210> SEQ ID NO 205
<211> LENGTH: 21
<212> TYPE: RNA
<213> ORGANISM: Artificial
<220> FEATURE:
<223> OTHER INFORMATION: hsa-miR-16-5p isomiR sequence

<400> SEQUENCE: 205
gcagcacgua aauauuggcg u                                             21

<210> SEQ ID NO 206
<211> LENGTH: 19
<212> TYPE: RNA
<213> ORGANISM: Artificial
<220> FEATURE:
<223> OTHER INFORMATION: hsa-miR-16-5p isomiR sequence

<400> SEQUENCE: 206
cagcacguaa auauuggcg                                                19

<210> SEQ ID NO 207
<211> LENGTH: 19
<212> TYPE: RNA
<213> ORGANISM: Artificial
<220> FEATURE:
<223> OTHER INFORMATION: hsa-miR-16-5p isomiR sequence

<400> SEQUENCE: 207
agcagcacgu aaauauugg                                                19

<210> SEQ ID NO 208
<211> LENGTH: 18
<212> TYPE: RNA
<213> ORGANISM: Artificial
<220> FEATURE:
<223> OTHER INFORMATION: hsa-miR-16-5p isomiR sequence

<400> SEQUENCE: 208
agcacguaaa uauuggcg                                                 18

<210> SEQ ID NO 209
<211> LENGTH: 19
<212> TYPE: RNA
<213> ORGANISM: Artificial
<220> FEATURE:
<223> OTHER INFORMATION: hsa-miR-16-5p isomiR sequence

<400> SEQUENCE: 209
gcagcacgua aauauuggc                                                19

<210> SEQ ID NO 210
<211> LENGTH: 25
<212> TYPE: RNA
<213> ORGANISM: Artificial
<220> FEATURE:
<223> OTHER INFORMATION: hsa-miR-16-5p isomiR sequence

<400> SEQUENCE: 210
```
uagcagcacg uaaauauugg cguag                            25

<210> SEQ ID NO 211
<211> LENGTH: 21
<212> TYPE: RNA
<213> ORGANISM: Artificial
<220> FEATURE:
<223> OTHER INFORMATION: hsa-miR-16-5p isomiR sequence

<400> SEQUENCE: 211
cuagcagcac guaaauauug g                                21

<210> SEQ ID NO 212
<211> LENGTH: 22
<212> TYPE: RNA
<213> ORGANISM: Artificial
<220> FEATURE:
<223> OTHER INFORMATION: hsa-miR-16-5p isomiR sequence

<400> SEQUENCE: 212
cagcacguaa auauuggcgu ag                               22

<210> SEQ ID NO 213
<211> LENGTH: 23
<212> TYPE: RNA
<213> ORGANISM: Artificial
<220> FEATURE:
<223> OTHER INFORMATION: hsa-miR-16-5p isomiR sequence

<400> SEQUENCE: 213
agcagcacgu aaauauuggc gua                              23

<210> SEQ ID NO 214
<211> LENGTH: 22
<212> TYPE: RNA
<213> ORGANISM: Artificial
<220> FEATURE:
<223> OTHER INFORMATION: hsa-miR-16-5p isomiR sequence

<400> SEQUENCE: 214
gcagcacgua aauauuggcg ua                               22

<210> SEQ ID NO 215
<211> LENGTH: 20
<212> TYPE: RNA
<213> ORGANISM: Artificial
<220> FEATURE:
<223> OTHER INFORMATION: hsa-miR-16-5p isomiR sequence

<400> SEQUENCE: 215
cagcacguaa auauuggcgu                                  20

<210> SEQ ID NO 216
<211> LENGTH: 23
<212> TYPE: RNA
<213> ORGANISM: Artificial
<220> FEATURE:
<223> OTHER INFORMATION: hsa-miR-16-5p isomiR sequence

<400> SEQUENCE: 216
cuagcagcac guaaauauug gcg                              23

<210> SEQ ID NO 217
<211> LENGTH: 18
<212> TYPE: RNA

<213> ORGANISM: Artificial
<220> FEATURE:
<223> OTHER INFORMATION: hsa-miR-16-5p isomiR sequence

<400> SEQUENCE: 217
gcagcacgua aauauugg                                                    18

<210> SEQ ID NO 218
<211> LENGTH: 19
<212> TYPE: RNA
<213> ORGANISM: Artificial
<220> FEATURE:
<223> OTHER INFORMATION: hsa-miR-16-5p isomiR sequence

<400> SEQUENCE: 218
agcacguaaa uauuggcgu                                                   19

<210> SEQ ID NO 219
<211> LENGTH: 21
<212> TYPE: RNA
<213> ORGANISM: Artificial
<220> FEATURE:
<223> OTHER INFORMATION: hsa-miR-16-5p isomiR sequence

<400> SEQUENCE: 219
cagcacguaa auauuggcgu a                                                21

<210> SEQ ID NO 220
<211> LENGTH: 18
<212> TYPE: RNA
<213> ORGANISM: Artificial
<220> FEATURE:
<223> OTHER INFORMATION: hsa-miR-16-5p isomiR sequence

<400> SEQUENCE: 220
cagcacguaa auauuggc                                                    18

<210> SEQ ID NO 221
<211> LENGTH: 18
<212> TYPE: RNA
<213> ORGANISM: Artificial
<220> FEATURE:
<223> OTHER INFORMATION: hsa-miR-16-5p isomiR sequence

<400> SEQUENCE: 221
agcagcacgu aaauauug                                                    18

<210> SEQ ID NO 222
<211> LENGTH: 24
<212> TYPE: RNA
<213> ORGANISM: Artificial
<220> FEATURE:
<223> OTHER INFORMATION: hsa-miR-16-5p isomiR sequence

<400> SEQUENCE: 222
cuagcagcac guaaauauug gcgu                                             24

<210> SEQ ID NO 223
<211> LENGTH: 18
<212> TYPE: RNA
<213> ORGANISM: Artificial
<220> FEATURE:
<223> OTHER INFORMATION: hsa-miR-16-5p isomiR sequence

<400> SEQUENCE: 223
gcacguaaau auuggcgu                                                    18

```
<210> SEQ ID NO 224
<211> LENGTH: 24
<212> TYPE: RNA
<213> ORGANISM: Artificial
<220> FEATURE:
<223> OTHER INFORMATION: hsa-miR-16-5p isomiR sequence

<400> SEQUENCE: 224
agcagcacgu aaauauuggc guag                                          24

<210> SEQ ID NO 225
<211> LENGTH: 22
<212> TYPE: RNA
<213> ORGANISM: Artificial
<220> FEATURE:
<223> OTHER INFORMATION: hsa-miR-16-5p isomiR sequence

<400> SEQUENCE: 225
acguaaauau uggcguagug aa                                            22

<210> SEQ ID NO 226
<211> LENGTH: 18
<212> TYPE: RNA
<213> ORGANISM: Artificial
<220> FEATURE:
<223> OTHER INFORMATION: hsa-miR-16-5p isomiR sequence

<400> SEQUENCE: 226
cacguaaaua uuggcgua                                                 18

<210> SEQ ID NO 227
<211> LENGTH: 22
<212> TYPE: RNA
<213> ORGANISM: Artificial
<220> FEATURE:
<223> OTHER INFORMATION: hsa-miR-16-5p isomiR sequence

<400> SEQUENCE: 227
uagcagcacg uaaauauugg cg                                            22

<210> SEQ ID NO 228
<211> LENGTH: 24
<212> TYPE: RNA
<213> ORGANISM: Artificial
<220> FEATURE:
<223> OTHER INFORMATION: hsa-miR-16-5p isomiR sequence

<400> SEQUENCE: 228
uagcagcacg uaaauauugg cguu                                          24

<210> SEQ ID NO 229
<211> LENGTH: 25
<212> TYPE: RNA
<213> ORGANISM: Artificial
<220> FEATURE:
<223> OTHER INFORMATION: hsa-miR-16-5p isomiR sequence

<400> SEQUENCE: 229
uagcagcacg uaaauauugg cguua                                         25

<210> SEQ ID NO 230
<211> LENGTH: 23
<212> TYPE: RNA
<213> ORGANISM: Artificial
<220> FEATURE:
```

<223> OTHER INFORMATION: hsa-miR-16-5p isomiR sequence

<400> SEQUENCE: 230
agcagcacgu aaauauuggc guu                                        23

<210> SEQ ID NO 231
<211> LENGTH: 23
<212> TYPE: RNA
<213> ORGANISM: Artificial
<220> FEATURE:
<223> OTHER INFORMATION: hsa-miR-16-5p isomiR sequence

<400> SEQUENCE: 231
uuagcagcac guaaauauug gcg                                        23

<210> SEQ ID NO 232
<211> LENGTH: 23
<212> TYPE: RNA
<213> ORGANISM: Artificial
<220> FEATURE:
<223> OTHER INFORMATION: hsa-miR-16-5p isomiR sequence

<400> SEQUENCE: 232
gcagcacgua aauauuggcg uua                                        23

<210> SEQ ID NO 233
<211> LENGTH: 22
<212> TYPE: RNA
<213> ORGANISM: Artificial
<220> FEATURE:
<223> OTHER INFORMATION: hsa-miR-16-5p isomiR sequence

<400> SEQUENCE: 233
gcagcacgua aauauuggcg uu                                         22

<210> SEQ ID NO 234
<211> LENGTH: 27
<212> TYPE: RNA
<213> ORGANISM: Artificial
<220> FEATURE:
<223> OTHER INFORMATION: hsa-miR-16-5p isomiR sequence

<400> SEQUENCE: 234
uagcagcacg uaaauauugg cguuaag                                    27

<210> SEQ ID NO 235
<211> LENGTH: 26
<212> TYPE: RNA
<213> ORGANISM: Artificial
<220> FEATURE:
<223> OTHER INFORMATION: hsa-miR-16-5p isomiR sequence

<400> SEQUENCE: 235
uagcagcacg uaaauauugg cguuaa                                     26

<210> SEQ ID NO 236
<211> LENGTH: 22
<212> TYPE: RNA
<213> ORGANISM: Artificial
<220> FEATURE:
<223> OTHER INFORMATION: hsa-miR-16-5p isomiR sequence

<400> SEQUENCE: 236
uuagcagcac guaaauauug gc                                         22

```
<210> SEQ ID NO 237
<211> LENGTH: 24
<212> TYPE: RNA
<213> ORGANISM: Artificial
<220> FEATURE:
<223> OTHER INFORMATION: hsa-miR-16-5p isomiR sequence

<400> SEQUENCE: 237
uuagcagcac guaaauauug gcgu                                          24

<210> SEQ ID NO 238
<211> LENGTH: 20
<212> TYPE: RNA
<213> ORGANISM: Artificial
<220> FEATURE:
<223> OTHER INFORMATION: hsa-miR-16-5p isomiR sequence

<400> SEQUENCE: 238
uuagcagcac guaaauauug                                               20

<210> SEQ ID NO 239
<211> LENGTH: 24
<212> TYPE: RNA
<213> ORGANISM: Artificial
<220> FEATURE:
<223> OTHER INFORMATION: hsa-miR-16-5p isomiR sequence

<400> SEQUENCE: 239
agcagcacgu aaauauuggc guua                                          24

<210> SEQ ID NO 240
<211> LENGTH: 20
<212> TYPE: RNA
<213> ORGANISM: Artificial
<220> FEATURE:
<223> OTHER INFORMATION: hsa-miR-3157-5p isomiR sequence

<400> SEQUENCE: 240
acguaaauau uggcguagug                                               20

<210> SEQ ID NO 241
<211> LENGTH: 24
<212> TYPE: RNA
<213> ORGANISM: Artificial
<220> FEATURE:
<223> OTHER INFORMATION: hsa-miR-16-5p isomiR sequence

<400> SEQUENCE: 241
ucuagcagca cguaaauauu ggcg                                          24

<210> SEQ ID NO 242
<211> LENGTH: 22
<212> TYPE: RNA
<213> ORGANISM: Artificial
<220> FEATURE:
<223> OTHER INFORMATION: hsa-miR-497-5p isomiR sequence

<400> SEQUENCE: 242
cagcagcaca cuguggutuug ua                                           22

<210> SEQ ID NO 243
<211> LENGTH: 20
<212> TYPE: RNA
<213> ORGANISM: Artificial
<220> FEATURE:
<223> OTHER INFORMATION: hsa-miR-497-5p isomiR sequence
```

```
<400> SEQUENCE: 243
agcagcacac ugugguuugu                                             20

<210> SEQ ID NO 244
<211> LENGTH: 22
<212> TYPE: RNA
<213> ORGANISM: Artificial
<220> FEATURE:
<223> OTHER INFORMATION: hsa-miR-497-5p isomiR sequence

<400> SEQUENCE: 244
agcagcacac ugugguuugu ac                                          22

<210> SEQ ID NO 245
<211> LENGTH: 20
<212> TYPE: RNA
<213> ORGANISM: Artificial
<220> FEATURE:
<223> OTHER INFORMATION: hsa-miR-497-5p isomiR sequence

<400> SEQUENCE: 245
cagcagcaca cugugguuug                                             20

<210> SEQ ID NO 246
<211> LENGTH: 21
<212> TYPE: RNA
<213> ORGANISM: Artificial
<220> FEATURE:
<223> OTHER INFORMATION: hsa-miR-497-5p isomiR sequence

<400> SEQUENCE: 246
agcagcacac ugugguuugu a                                           21

<210> SEQ ID NO 247
<211> LENGTH: 19
<212> TYPE: RNA
<213> ORGANISM: Artificial
<220> FEATURE:
<223> OTHER INFORMATION: hsa-miR-497-5p isomiR sequence

<400> SEQUENCE: 247
cagcagcaca cugugguuu                                              19

<210> SEQ ID NO 248
<211> LENGTH: 23
<212> TYPE: RNA
<213> ORGANISM: Artificial
<220> FEATURE:
<223> OTHER INFORMATION: hsa-miR-497-5p isomiR sequence

<400> SEQUENCE: 248
cagcagcaca cugugguuug uac                                         23

<210> SEQ ID NO 249
<211> LENGTH: 19
<212> TYPE: RNA
<213> ORGANISM: Artificial
<220> FEATURE:
<223> OTHER INFORMATION: hsa-miR-497-5p isomiR sequence

<400> SEQUENCE: 249
agcagcacac ugugguuug                                              19

<210> SEQ ID NO 250
<211> LENGTH: 19
```

```
<212> TYPE: RNA
<213> ORGANISM: Artificial
<220> FEATURE:
<223> OTHER INFORMATION: hsa-miR-497-5p isomiR sequence

<400> SEQUENCE: 250
gcagcacacu gugguuugu                                                  19

<210> SEQ ID NO 251
<211> LENGTH: 18
<212> TYPE: RNA
<213> ORGANISM: Artificial
<220> FEATURE:
<223> OTHER INFORMATION: hsa-miR-497-5p isomiR sequence

<400> SEQUENCE: 251
agcagcacac ugugguuu                                                   18

<210> SEQ ID NO 252
<211> LENGTH: 23
<212> TYPE: RNA
<213> ORGANISM: Artificial
<220> FEATURE:
<223> OTHER INFORMATION: hsa-miR-497-5p isomiR sequence

<400> SEQUENCE: 252
agcagcacac ugugguuugu acg                                             23

<210> SEQ ID NO 253
<211> LENGTH: 18
<212> TYPE: RNA
<213> ORGANISM: Artificial
<220> FEATURE:
<223> OTHER INFORMATION: hsa-miR-497-5p isomiR sequence

<400> SEQUENCE: 253
cagcagcaca cugugguu                                                   18

<210> SEQ ID NO 254
<211> LENGTH: 21
<212> TYPE: RNA
<213> ORGANISM: Artificial
<220> FEATURE:
<223> OTHER INFORMATION: hsa-miR-497-5p isomiR sequence

<400> SEQUENCE: 254
gcagcacacu gugguuugua c                                               21

<210> SEQ ID NO 255
<211> LENGTH: 19
<212> TYPE: RNA
<213> ORGANISM: Artificial
<220> FEATURE:
<223> OTHER INFORMATION: hsa-miR-497-5p isomiR sequence

<400> SEQUENCE: 255
cagcacacug ugguuugua                                                  19

<210> SEQ ID NO 256
<211> LENGTH: 20
<212> TYPE: RNA
<213> ORGANISM: Artificial
<220> FEATURE:
<223> OTHER INFORMATION: hsa-miR-497-5p isomiR sequence

<400> SEQUENCE: 256
```

-continued cagcacacug ugguuuguac                             20

<210> SEQ ID NO 257
<211> LENGTH: 20
<212> TYPE: RNA
<213> ORGANISM: Artificial
<220> FEATURE:
<223> OTHER INFORMATION: hsa-miR-497-5p isomiR sequence

<400> SEQUENCE: 257
gcagcacacu ugguuugua                              20

<210> SEQ ID NO 258
<211> LENGTH: 24
<212> TYPE: RNA
<213> ORGANISM: Artificial
<220> FEATURE:
<223> OTHER INFORMATION: hsa-miR-497-5p isomiR sequence

<400> SEQUENCE: 258
agcagcacac ugugguuugu acgg                        24

<210> SEQ ID NO 259
<211> LENGTH: 18
<212> TYPE: RNA
<213> ORGANISM: Artificial
<220> FEATURE:
<223> OTHER INFORMATION: hsa-miR-497-5p isomiR sequence

<400> SEQUENCE: 259
cagcacacug ugguuugu                               18

<210> SEQ ID NO 260
<211> LENGTH: 21
<212> TYPE: RNA
<213> ORGANISM: Artificial
<220> FEATURE:
<223> OTHER INFORMATION: hsa-miR-497-5p isomiR sequence

<400> SEQUENCE: 260
ccagcagcac acugggguuu g                           21

<210> SEQ ID NO 261
<211> LENGTH: 24
<212> TYPE: RNA
<213> ORGANISM: Artificial
<220> FEATURE:
<223> OTHER INFORMATION: hsa-miR-497-5p isomiR sequence

<400> SEQUENCE: 261
cagcagcaca cugggguuug uacg                        24

<210> SEQ ID NO 262
<211> LENGTH: 22
<212> TYPE: RNA
<213> ORGANISM: Artificial
<220> FEATURE:
<223> OTHER INFORMATION: hsa-miR-497-5p isomiR sequence

<400> SEQUENCE: 262
ccagcagcac acugggguuu gu                          22

<210> SEQ ID NO 263
<211> LENGTH: 25
<212> TYPE: RNA
<213> ORGANISM: Artificial

```
<220> FEATURE:
<223> OTHER INFORMATION: hsa-miR-497-5p isomiR sequence

<400> SEQUENCE: 263
cagcacacug ugguuuguac ggcac                                        25

<210> SEQ ID NO 264
<211> LENGTH: 25
<212> TYPE: RNA
<213> ORGANISM: Artificial
<220> FEATURE:
<223> OTHER INFORMATION: hsa-miR-497-5p isomiR sequence

<400> SEQUENCE: 264
cagcagcaca cugugguuug uacgg                                        25

<210> SEQ ID NO 265
<211> LENGTH: 21
<212> TYPE: DNA
<213> ORGANISM: Artificial
<220> FEATURE:
<223> OTHER INFORMATION: hsa-miR-200c-5p isomiR sequence

<400> SEQUENCE: 265
cgtcttaccc agcagtgttt g                                            21

<210> SEQ ID NO 266
<211> LENGTH: 20
<212> TYPE: DNA
<213> ORGANISM: Artificial
<220> FEATURE:
<223> OTHER INFORMATION: hsa-miR-200c-5p isomiR sequence

<400> SEQUENCE: 266
cgtcttaccc agcagtgttt                                              20

<210> SEQ ID NO 267
<211> LENGTH: 22
<212> TYPE: RNA
<213> ORGANISM: Artificial
<220> FEATURE:
<223> OTHER INFORMATION: hsa-miR-182-3p isomiR sequence

<400> SEQUENCE: 267 gguguucua gacuugccaa cu                                            22

<210> SEQ ID NO 268
<211> LENGTH: 20
<212> TYPE: RNA
<213> ORGANISM: Artificial
<220> FEATURE:
<223> OTHER INFORMATION: hsa-miR-182-3p isomiR sequence

<400> SEQUENCE: 268
ugguucuaga cuugccaacu                                              20

<210> SEQ ID NO 269
<211> LENGTH: 23
<212> TYPE: RNA
<213> ORGANISM: Artificial
<220> FEATURE:
<223> OTHER INFORMATION: hsa-miR-182-3p isomiR sequence

<400> SEQUENCE: 269 gguguucua gacuugccaa cua                                           23
```

<210> SEQ ID NO 270
<211> LENGTH: 21
<212> TYPE: RNA
<213> ORGANISM: Artificial
<220> FEATURE:
<223> OTHER INFORMATION: hsa-miR-182-3p isomiR sequence

<400> SEQUENCE: 270
gugguucuag acuugccaac u                                              21

<210> SEQ ID NO 271
<211> LENGTH: 20
<212> TYPE: RNA
<213> ORGANISM: Artificial
<220> FEATURE:
<223> OTHER INFORMATION: hsa-miR-182-3p isomiR sequence

<400> SEQUENCE: 271
ggugguucua gacuugccaa                                                20

<210> SEQ ID NO 272
<211> LENGTH: 23
<212> TYPE: RNA
<213> ORGANISM: Artificial
<220> FEATURE:
<223> OTHER INFORMATION: antagomir of miRNA-221

<400> SEQUENCE: 272
gaaacccagc agacaaugua gcu                                            23

<210> SEQ ID NO 273
<211> LENGTH: 24
<212> TYPE: RNA
<213> ORGANISM: Artificial
<220> FEATURE:
<223> OTHER INFORMATION: antagomir of miRNA-222

<400> SEQUENCE: 273
gagacccagu agccagaugu agcu                                           24

<210> SEQ ID NO 274
<211> LENGTH: 51
<212> TYPE: DNA
<213> ORGANISM: Artificial
<220> FEATURE:
<223> OTHER INFORMATION: miR-3157 Stem-loop RT primer

<400> SEQUENCE: 274
gtcgtatcca gtgcagggtc cgaggtaatt cgcactggat acgacagact g            51

<210> SEQ ID NO 275
<211> LENGTH: 24
<212> TYPE: DNA
<213> ORGANISM: Artificial
<220> FEATURE:
<223> OTHER INFORMATION: miR-3157 qPCR-forward primer

<400> SEQUENCE: 275
tgccagttca gccaggctag tgca                                           24

<210> SEQ ID NO 276
<211> LENGTH: 16
<212> TYPE: DNA
<213> ORGANISM: Artificial
<220> FEATURE:
<223> OTHER INFORMATION: miR-3157 qPCR-reverse primer

<400> SEQUENCE: 276
gtgcagggtc cgaggt                                                    16

<210> SEQ ID NO 277
<211> LENGTH: 16
<212> TYPE: DNA
<213> ORGANISM: Artificial
<220> FEATURE:
<223> OTHER INFORMATION: U6 RT primer

<400> SEQUENCE: 277
gtcatccttg cgcagg                                                    16

<210> SEQ ID NO 278
<211> LENGTH: 20
<212> TYPE: DNA
<213> ORGANISM: Artificial
<220> FEATURE:
<223> OTHER INFORMATION: U6 qPCR forward primer

<400> SEQUENCE: 278
cgcttcggca gcacatatac                                                20

<210> SEQ ID NO 279
<211> LENGTH: 20
<212> TYPE: DNA
<213> ORGANISM: Artificial
<220> FEATURE:
<223> OTHER INFORMATION: U6 qPCR reverse primer

<400> SEQUENCE: 279
aggggccatg ctaatcttct                                                20

<210> SEQ ID NO 280
<211> LENGTH: 21
<212> TYPE: DNA
<213> ORGANISM: Artificial
<220> FEATURE:
<223> OTHER INFORMATION: HPRT1-Fwd primer

<400> SEQUENCE: 280
cctggcgtcg tgattagtga t                                              21

<210> SEQ ID NO 281
<211> LENGTH: 22
<212> TYPE: DNA
<213> ORGANISM: Artificial
<220> FEATURE:
<223> OTHER INFORMATION: HPRT1-Rev primer

<400> SEQUENCE: 281
agacgttcag tcctgtccat aa                                             22

<210> SEQ ID NO 282
<211> LENGTH: 21
<212> TYPE: DNA
<213> ORGANISM: Artificial
<220> FEATURE:
<223> OTHER INFORMATION: MAPK3-Fwd primer

<400> SEQUENCE: 282
ctacacgcag ttgcagtaca t                                              21

<210> SEQ ID NO 283

```
<211> LENGTH: 20
<212> TYPE: DNA
<213> ORGANISM: Artificial
<220> FEATURE:
<223> OTHER INFORMATION: MAPK3-Rev primer

<400> SEQUENCE: 283
cagcaggatc tggatctccc                                              20

<210> SEQ ID NO 284
<211> LENGTH: 21
<212> TYPE: DNA
<213> ORGANISM: Artificial
<220> FEATURE:
<223> OTHER INFORMATION: RRM2-Fwd primer

<400> SEQUENCE: 284
gtggagcgat ttagccaaga a                                            21

<210> SEQ ID NO 285
<211> LENGTH: 21
<212> TYPE: DNA
<213> ORGANISM: Artificial
<220> FEATURE:
<223> OTHER INFORMATION: RRM2-Rev primer

<400> SEQUENCE: 285
cacaaggcat cgtttcaatg g                                            21

<210> SEQ ID NO 286
<211> LENGTH: 21
<212> TYPE: DNA
<213> ORGANISM: Artificial
<220> FEATURE:
<223> OTHER INFORMATION: AURKB-Fwd primer

<400> SEQUENCE: 286
cgcagagaga tcgaaatcca g                                            21

<210> SEQ ID NO 287
<211> LENGTH: 22
<212> TYPE: DNA
<213> ORGANISM: Artificial
<220> FEATURE:
<223> OTHER INFORMATION: AURKB-Rev primer

<400> SEQUENCE: 287
agatcctcct ccggtcataa aa                                           22

<210> SEQ ID NO 288
<211> LENGTH: 22
<212> TYPE: DNA
<213> ORGANISM: Artificial
<220> FEATURE:
<223> OTHER INFORMATION: CDK4-Fwd primer

<400> SEQUENCE: 288
ctggtgtttg agcatgtaga cc                                           22

<210> SEQ ID NO 289
<211> LENGTH: 21
<212> TYPE: DNA
<213> ORGANISM: Artificial
<220> FEATURE:
<223> OTHER INFORMATION: CDK4-Rev primer

<400> SEQUENCE: 289
```

```
gatccttgat cgtttcggct g                                              21

<210> SEQ ID NO 290
<211> LENGTH: 21
<212> TYPE: DNA
<213> ORGANISM: Artificial
<220> FEATURE:
<223> OTHER INFORMATION: BIRC5-Fwd primer

<400> SEQUENCE: 290
aggaccaccg catctctaca t                                              21

<210> SEQ ID NO 291
<211> LENGTH: 21
<212> TYPE: DNA
<213> ORGANISM: Artificial
<220> FEATURE:
<223> OTHER INFORMATION: BIRC5-Rev primer

<400> SEQUENCE: 291
aagtctggct cgttctcagt g                                              21

<210> SEQ ID NO 292
<211> LENGTH: 20
<212> TYPE: DNA
<213> ORGANISM: Artificial
<220> FEATURE:
<223> OTHER INFORMATION: BCL2-Fwd primer

<400> SEQUENCE: 292
gccttctttg agttcggtgg                                                20

<210> SEQ ID NO 293
<211> LENGTH: 19
<212> TYPE: DNA
<213> ORGANISM: Artificial
<220> FEATURE:
<223> OTHER INFORMATION: BCL2-Rev primer

<400> SEQUENCE: 293
atctcccggt tgacgctct                                                 19

<210> SEQ ID NO 294
<211> LENGTH: 76
<212> TYPE: DNA
<213> ORGANISM: Artificial
<220> FEATURE:
<223> OTHER INFORMATION: ERK1 3'UTR sequence

<400> SEQUENCE: 294
cgtggagagc ccggcgcccc tgccacctcc ctgacccgtc taatatataa atatagagat    60
gtgtctatgg ctgaaa                                                    76

<210> SEQ ID NO 295
<211> LENGTH: 100
<212> TYPE: DNA
<213> ORGANISM: Artificial
<220> FEATURE:
<223> OTHER INFORMATION: RRM2 3'UTR sequence

<400> SEQUENCE: 295
tcagaggatg ggagtgatgt caagtccaac agagaattct tttaccttgg atgctgactt    60
ctaaatgaac tgaagatgtg cccttacttg gctgatttt                          100
```

```
<210> SEQ ID NO 296
<211> LENGTH: 141
<212> TYPE: DNA
<213> ORGANISM: Artificial
<220> FEATURE:
<223> OTHER INFORMATION: AURKB 3'UTR sequence

<400> SEQUENCE: 296
tggtccctgt cattcactcg ggtgcgtgtg tttgtatgtc tgtgtatgta taggggaaag      60
aagggatccc taactgttcc cttatctgtt ttctacctcc tcctttgttt aataaaggct    120
gaagcttttt gtactcatga a                                              141

<210> SEQ ID NO 297
<211> LENGTH: 22
<212> TYPE: DNA
<213> ORGANISM: Artificial
<220> FEATURE:
<223> OTHER INFORMATION: ERK1 3'UTR sequence

<400> SEQUENCE: 297
uagagaugug ucuauggcug aa                                              22

<210> SEQ ID NO 298
<211> LENGTH: 22
<212> TYPE: DNA
<213> ORGANISM: Artificial
<220> FEATURE:
<223> OTHER INFORMATION: RRM2 3'UTR sequence

<400> SEQUENCE: 298
gaugugcccu uacuuggcug au                                              22

<210> SEQ ID NO 299
<211> LENGTH: 22
<212> TYPE: DNA
<213> ORGANISM: Artificial
<220> FEATURE:
<223> OTHER INFORMATION: AURKB 3'UTR sequence

<400> SEQUENCE: 299
ccuuuguuua auaaaggcug aa                                              22
```